US011845979B2

(12) United States Patent
Engblom et al.

(10) Patent No.: US 11,845,979 B2
(45) Date of Patent: *Dec. 19, 2023

(54) SPATIAL TRANSCRIPTOMICS FOR ANTIGEN-RECEPTORS

(71) Applicant: 10x Genomics, Inc., Pleasanton, CA (US)

(72) Inventors: Camilla Engblom, Solna (SE); Kim Thrane, Stockholm (SE); Jeffrey Mold, Pleasanton, CA (US); Jonas Frisen, Stockholm (SE); Joakim Lundeberg, Stockholm (SE); Qirong Lin, Solna (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,289

(22) Filed: May 10, 2023

(65) Prior Publication Data

US 2023/0340577 A1 Oct. 26, 2023

Related U.S. Application Data

(63) Continuation of application No. 17/552,135, filed on Dec. 15, 2021, now Pat. No. 11,692,218, which is a continuation of application No. PCT/US2021/035242, filed on Jun. 1, 2021.

(60) Provisional application No. 63/033,568, filed on Jun. 2, 2020.

(51) Int. Cl.

| | |
|---|---|
| ***C12Q 1/6837*** | (2018.01) |
| ***C12Q 1/6881*** | (2018.01) |
| ***C12Q 1/6869*** | (2018.01) |

(52) U.S. Cl.
CPC ......... *C12Q 1/6837* (2013.01); *C12Q 1/6869* (2013.01); *C12Q 1/6881* (2013.01)

(58) Field of Classification Search
CPC .. C12Q 1/6869; C12Q 1/6881; C12Q 1/6806; C12Q 2525/179; C12Q 2563/179; C12Q 2565/514; C12Q 2565/518; C12Q 2565/537
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |

(Continued)

FOREIGN PATENT DOCUMENTS

| | | |
|---|---|---|
| CN | 1680604 | 10/2005 |
| CN | 108676814 | 10/2018 |

(Continued)

OTHER PUBLICATIONS

[No Author Listed], "Chromium Next GEM Single Cell 3' Reagent Kits v3.1—User Guide," 10x Genomics, Document No. CG000204, Nov. 2019, 58 pages.

(Continued)

*Primary Examiner* — Joseph G. Dauner
(74) *Attorney, Agent, or Firm* — Fish & Richardson P.C.

(57) ABSTRACT

Provided herein are methods, compositions, and kits for the detection of immune cell clonotypes and immune cell analytes within a biological sample.

30 Claims, 36 Drawing Sheets

Specification includes a Sequence Listing.

(56) References Cited

U.S. PATENT DOCUMENTS 5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,494,810 A 2/1996 Barany et al.
5,503,980 A 4/1996 Cantor
5,512,439 A 4/1996 Hornes
5,512,462 A 4/1996 Cheng
5,582,977 A 12/1996 Yue
5,599,675 A 2/1997 Brenner
5,641,658 A 6/1997 Adams
5,648,245 A 7/1997 Fire et al.
5,658,751 A 8/1997 Yue
5,750,341 A 5/1998 Macevicz
5,763,175 A 6/1998 Brenner
5,830,711 A 11/1998 Barany et al.
5,837,832 A 11/1998 Chee et al.
5,854,033 A 12/1998 Lizardi
5,863,753 A 1/1999 Haugland
5,871,921 A 2/1999 Landegren et al.
5,912,148 A 6/1999 Eggerding
6,013,440 A 1/2000 Lipshutz
6,027,889 A 2/2000 Barany et al.
6,060,240 A 5/2000 Kamb et al.
6,130,073 A 10/2000 Eggerding
6,143,496 A 11/2000 Brown
6,153,389 A 11/2000 Haarer
6,165,714 A 12/2000 Lane et al.
6,210,891 B1 4/2001 Nyren
6,210,894 B1 4/2001 Brennan
6,214,587 B1 4/2001 Dattagupta
6,258,568 B1 7/2001 Nyren
6,266,459 B1 7/2001 Walt
6,274,320 B1 8/2001 Rothberg
6,300,063 B1 10/2001 Lipshutz et al.
6,309,824 B1 10/2001 Drmanac
6,344,316 B1 2/2002 Lockhart
6,355,431 B1 3/2002 Chee
6,368,801 B1 4/2002 Faruqi
6,401,267 B1 6/2002 Drmanac
6,404,907 B1 6/2002 Gilchrist
6,432,360 B1 8/2002 Church et al.
6,503,713 B1 1/2003 Rana
6,506,561 B1 1/2003 Cheval et al.
6,544,732 B1 4/2003 Chee
6,620,584 B1 9/2003 Chee
6,632,641 B1 10/2003 Brennan
6,699,710 B1 3/2004 Kononen
6,737,236 B1 5/2004 Pieken et al.
6,770,441 B2 8/2004 Dickinson
6,773,886 B2 8/2004 Kaufman
6,787,308 B2 9/2004 Balasubramanian
6,800,453 B2 10/2004 Labaer
6,812,005 B2 11/2004 Fan et al.
6,828,100 B1 12/2004 Ronaghi
6,833,246 B2 12/2004 Balasubramanian
6,859,570 B2 2/2005 Walt
6,864,052 B1 3/2005 Drmanac
6,878,515 B1 4/2005 Landegren
6,897,023 B2 5/2005 Fu
6,942,968 B1 9/2005 Dickinson et al.
6,969,589 B2 11/2005 Patil
7,057,026 B2 6/2006 Barnes
7,115,400 B1 10/2006 Adessi
7,118,883 B2 10/2006 Inoue
7,166,431 B2 1/2007 Chee et al.
7,211,414 B2 5/2007 Hardin
7,255,994 B2 8/2007 Lao
7,258,976 B2 8/2007 Mitsuhashi
7,297,518 B2 11/2007 Quake
7,329,492 B2 2/2008 Hardin
7,361,488 B2 4/2008 Fan et al.
7,378,242 B2 5/2008 Hurt
7,393,665 B2 7/2008 Brenner
7,405,281 B2 7/2008 Xu
7,407,757 B2 8/2008 Brenner
7,537,897 B2 5/2009 Brenner
7,563,576 B2 7/2009 Chee
7,582,420 B2 9/2009 Oliphant et al.
7,601,498 B2 10/2009 Mao
7,635,566 B2 12/2009 Brenner
7,674,752 B2 3/2010 He
7,700,286 B2 4/2010 Stroun et al.
7,709,198 B2 5/2010 Luo et al.
7,776,567 B2 8/2010 Mao
7,803,943 B2 9/2010 Mao
7,910,304 B2 3/2011 Drmanac
7,955,794 B2 6/2011 Shen et al.
7,960,119 B2 6/2011 Chee
8,003,354 B2 8/2011 Shen et al.
8,148,068 B2 4/2012 Brenner
8,206,917 B2 6/2012 Chee
8,288,103 B2 10/2012 Oliphant
8,337,851 B2 12/2012 Aukerman
8,460,865 B2 6/2013 Chee
8,481,257 B2 7/2013 Van Eijk
RE44,596 E 11/2013 Stroun et al.
8,603,743 B2 12/2013 Liu et al.
8,604,182 B2 12/2013 Luo et al.
8,685,889 B2 4/2014 Van Eijk
8,748,103 B2 6/2014 Faham et al.
8,815,512 B2 8/2014 Van Eijk
8,835,358 B2 9/2014 Fodor
8,911,945 B2 12/2014 Van Eijk
8,951,726 B2 2/2015 Luo et al.
9,062,348 B1 6/2015 Van Eijk
9,121,069 B2 9/2015 Lo
9,194,001 B2 11/2015 Brenner
9,217,176 B2 12/2015 Faham
9,290,808 B2 3/2016 Fodor
9,290,809 B2 3/2016 Fodor
9,328,383 B2 5/2016 Van Eijk
9,334,536 B2 5/2016 Van Eijk
9,340,830 B2 5/2016 Lipson
9,371,598 B2 6/2016 Chee
9,506,061 B2 11/2016 Brown et al.
9,512,487 B2 12/2016 Faham et al.
9,593,365 B2 3/2017 Frisen et al.
9,644,204 B2 5/2017 Hindson et al.
9,694,361 B2 7/2017 Bharadwaj
9,702,004 B2 7/2017 Van Eijk
9,714,446 B2 7/2017 Webster et al.
9,727,810 B2 8/2017 Fodor et al.
9,777,324 B2 10/2017 Van Eijk
9,783,841 B2 10/2017 Nolan et al.
9,834,814 B2 12/2017 Peter et al.
9,850,536 B2 12/2017 Oliphant et al.
9,868,979 B2 1/2018 Chee et al.
9,879,313 B2 1/2018 Chee et al.
10,002,316 B2 6/2018 Fodor et al.
10,023,907 B2 7/2018 Van Eijk
10,030,261 B2 7/2018 Frisen et al.
10,041,949 B2 8/2018 Bendall et al.
10,049,770 B2 8/2018 Madabhushi et al.
10,059,990 B2 8/2018 Boyden et al.
10,078,895 B2 9/2018 Madabhushi et al.
10,196,691 B2 2/2019 Harkin et al.
10,208,982 B2 2/2019 Bannish et al.
10,221,461 B2 3/2019 Robins et al.
10,246,752 B2 4/2019 Faham et al.
10,273,541 B2 4/2019 Hindson et al.
10,357,771 B2 7/2019 Bharadwaj
10,472,669 B2 11/2019 Chee
10,480,022 B2 11/2019 Chee
10,480,029 B2 11/2019 Bent et al.
10,494,667 B2 12/2019 Chee
10,550,429 B2 2/2020 Harada et al.
10,590,244 B2 3/2020 Delaney et al.
10,633,648 B2 4/2020 Seelig et al.
10,724,078 B2 7/2020 Van Driel et al.
10,725,027 B2 7/2020 Bell

(56) References Cited

U.S. PATENT DOCUMENTS

| | | | |
|---|---|---|---|
| 10,774,372 | B2 | 9/2020 | Chee et al. |
| 10,774,374 | B2 | 9/2020 | Frisen et al. |
| 10,787,701 | B2 | 9/2020 | Chee |
| 10,858,702 | B2 | 12/2020 | Lucero et al. |
| 10,913,975 | B2 | 2/2021 | So et al. |
| 10,914,730 | B2 | 2/2021 | Chee et al. |
| 10,927,403 | B2 | 2/2021 | Chee et al. |
| 10,961,566 | B2 | 3/2021 | Chee |
| 11,008,607 | B2 | 5/2021 | Chee |
| 11,046,996 | B1 | 6/2021 | Chee et al. |
| 11,067,567 | B2 | 7/2021 | Chee |
| 11,156,603 | B2 | 10/2021 | Chee |
| 11,162,132 | B2 | 11/2021 | Frisen et al. |
| 11,208,684 | B2 | 12/2021 | Chee |
| 11,286,515 | B2 | 3/2022 | Chee et al. |
| 11,293,917 | B2 | 4/2022 | Chee |
| 11,299,774 | B2 | 4/2022 | Frisen et al. |
| 11,313,856 | B2 | 4/2022 | Chee |
| 11,332,790 | B2 | 5/2022 | Chell et al. |
| 11,352,659 | B2 | 6/2022 | Frisen et al. |
| 11,352,667 | B2 | 6/2022 | Hauling et al. |
| 11,359,228 | B2 | 6/2022 | Chee et al. |
| 11,365,442 | B2 | 6/2022 | Chee |
| 11,371,086 | B2 | 6/2022 | Chee |
| 11,384,386 | B2 | 7/2022 | Chee |
| 11,390,912 | B2 | 7/2022 | Frisen et al. |
| 11,401,545 | B2 | 8/2022 | Chee |
| 11,407,992 | B2 | 8/2022 | Dadhwal |
| 11,408,029 | B2 | 8/2022 | Katiraee et al. |
| 11,434,524 | B2 | 9/2022 | Ramachandran Iyer et al. |
| 11,479,809 | B2 | 10/2022 | Frisen et al. |
| 11,479,810 | B1 | 10/2022 | Chee |
| 11,492,612 | B1 | 11/2022 | Dadhwal |
| 11,505,828 | B2 | 11/2022 | Chell et al. |
| 11,512,308 | B2 | 11/2022 | Gallant et al. |
| 11,519,022 | B2 | 12/2022 | Chee |
| 11,519,033 | B2 | 12/2022 | Schnall-Levin et al. |
| 11,530,438 | B2 | 12/2022 | Persson et al. |
| 11,535,887 | B2 | 12/2022 | Gallant et al. |
| 11,542,543 | B2 | 1/2023 | Chee |
| 11,549,138 | B2 | 1/2023 | Chee |
| 11,560,587 | B2 | 1/2023 | Chee |
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,611,626 | B1 | 5/2023 | Katiraee et al. |
| 11,649,485 | B2 | 5/2023 | Yin et al. |
| 11,661,626 | B2 | 5/2023 | Katiraee et al. |
| 11,680,260 | B2 | 6/2023 | Kim et al. |
| 11,692,218 | B2 | 7/2023 | Engblom et al. |
| 11,702,693 | B2 | 7/2023 | Bharadwaj |
| 11,702,698 | B2 | 7/2023 | Stoeckius |
| 11,732,292 | B2 | 8/2023 | Chee |
| 11,732,299 | B2 | 8/2023 | Ramachandran Iyer |
| 11,732,300 | B2 | 8/2023 | Bava |
| 11,733,238 | B2 | 8/2023 | Chee |
| 11,739,372 | B2 | 8/2023 | Frisen et al. |
| 11,739,381 | B2 | 8/2023 | Chew et al. |
| 11,753,673 | B2 | 9/2023 | Chew et al. |
| 11,753,674 | B2 | 9/2023 | Chee et al. |
| 11,753,675 | B2 | 9/2023 | Ramachandran Iyer |
| 11,761,030 | B2 | 9/2023 | Chee |
| 11,761,038 | B1 | 9/2023 | Stoeckius |
| 2002/0006477 | A1 | 1/2002 | Shishido et al. |
| 2002/0040275 | A1 | 4/2002 | Cravatt |
| 2002/0132246 | A1 | 9/2002 | Kallioniemi et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0148335 | A1 | 8/2003 | Shen et al. |
| 2003/0162216 | A1 | 8/2003 | Gold |
| 2003/0170637 | A1 | 9/2003 | Pirrung et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2004/0002090 | A1 | 1/2004 | Mayer et al. |
| 2004/0019005 | A1 | 1/2004 | Van Ness |
| 2004/0033499 | A1 | 2/2004 | Ilsley et al. |
| 2004/0067492 | A1 | 4/2004 | Peng et al. |
| 2004/0067493 | A1 | 4/2004 | Matsuzaki |
| 2004/0096853 | A1 | 5/2004 | Mayer |
| 2004/0106110 | A1 | 6/2004 | Balasubramanian |
| 2005/0019776 | A1 | 1/2005 | Callow et al. |
| 2005/0026188 | A1 | 2/2005 | Van Kessel |
| 2005/0037362 | A1 | 2/2005 | Remacle et al. |
| 2005/0037393 | A1 | 2/2005 | Gunderson et al. |
| 2005/0048580 | A1 | 3/2005 | Labaer |
| 2005/0100900 | A1 | 5/2005 | Kawashima et al. |
| 2005/0130173 | A1 | 6/2005 | Leamon et al. |
| 2005/0136414 | A1 | 6/2005 | Gunderson et al. |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0260653 | A1 | 11/2005 | LaBaer |
| 2006/0110739 | A1 | 5/2006 | Heyduk |
| 2006/0188875 | A1 | 8/2006 | Cox et al. |
| 2006/0211001 | A1 | 9/2006 | Yu et al. |
| 2006/0216775 | A1 | 9/2006 | Burkart et al. |
| 2006/0228758 | A1 | 10/2006 | Muchhal et al. |
| 2006/0263789 | A1 | 11/2006 | Kincaid |
| 2007/0020640 | A1 | 1/2007 | McCloskey et al. |
| 2007/0054288 | A1 | 3/2007 | Su et al. |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0161029 | A1 | 7/2007 | Li et al. |
| 2007/0172873 | A1 | 7/2007 | Brenner et al. |
| 2007/0178503 | A1 | 8/2007 | Jiang |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0009420 | A1 | 1/2008 | Schroth et al. |
| 2008/0108804 | A1 | 5/2008 | Hayashizaki et al. |
| 2008/0153086 | A1 | 6/2008 | Wong |
| 2008/0160580 | A1 | 7/2008 | Adessi et al. |
| 2008/0220434 | A1 | 9/2008 | Thomas |
| 2008/0261204 | A1 | 10/2008 | Lexow |
| 2008/0286795 | A1 | 11/2008 | Kawashima et al. |
| 2009/0005252 | A1 | 1/2009 | Drmanac et al. |
| 2009/0006002 | A1 | 1/2009 | Honisch et al. |
| 2009/0018024 | A1 | 1/2009 | Church et al. |
| 2009/0026082 | A1 | 1/2009 | Rothberg et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0202998 | A1 | 8/2009 | Schlumpberger et al. |
| 2009/0215633 | A1 | 8/2009 | van Eijk et al. |
| 2009/0233802 | A1 | 9/2009 | Bignell et al. |
| 2009/0253581 | A1 | 10/2009 | van Eijk et al. |
| 2009/0291854 | A1 | 11/2009 | Weisinger-Mayr et al. |
| 2009/0312193 | A1 | 12/2009 | Kim et al. |
| 2010/0035249 | A1 | 2/2010 | Hayashizaki et al. |
| 2010/0120097 | A1 | 5/2010 | Matz et al. |
| 2010/0120098 | A1 | 5/2010 | Grunenwald et al. |
| 2010/0145037 | A1 | 6/2010 | Brive et al. |
| 2011/0028685 | A1 | 2/2011 | Purkayastha et al. |
| 2011/0059436 | A1 | 3/2011 | Hardin et al. |
| 2011/0111409 | A1 | 5/2011 | Sinicropi et al. |
| 2011/0207134 | A1 | 8/2011 | Faham et al. |
| 2011/0245111 | A1 | 10/2011 | Chee |
| 2012/0135871 | A1 | 5/2012 | van Eijk et al. |

(56) References Cited

U.S. PATENT DOCUMENTS

2012/0202698 A1 8/2012 van Eijk et al.
2012/0202704 A1 8/2012 Fan et al.
2012/0252702 A1 10/2012 Muratani et al.
2013/0065768 A1 3/2013 Zheng et al.
2013/0171621 A1 7/2013 Luo et al.
2013/0202718 A1 8/2013 Pepin et al.
2013/0302801 A1 11/2013 Asbury et al.
2014/0066318 A1 3/2014 Frisen et al.
2014/0080715 A1 3/2014 Lo et al.
2014/0270435 A1 9/2014 Dunn
2014/0274731 A1 9/2014 Raymond et al.
2014/0296081 A1 10/2014 Diehn et al.
2014/0323330 A1 10/2014 Glezer et al.
2014/0378350 A1 12/2014 Hindson et al.
2015/0000854 A1 1/2015 Gann-Fetter et al.
2015/0051085 A1 2/2015 Vogelstein et al.
2015/0292988 A1 10/2015 Bharadwaj et al.
2015/0344942 A1 12/2015 Frisen et al.
2016/0108458 A1 4/2016 Frei et al.
2016/0138091 A1 5/2016 Chee et al.
2016/0145677 A1 5/2016 Chee et al.
2016/0253584 A1 9/2016 Fodor et al.
2016/0289740 A1 10/2016 Fu et al.
2016/0298180 A1 10/2016 Chee
2017/0016053 A1 1/2017 Beechem et al.
2017/0029875 A1 2/2017 Zhang et al.
2017/0067096 A1 3/2017 Wassie et al.
2017/0089811 A1 3/2017 Tillberg et al.
2017/0220733 A1 8/2017 Zhuang et al.
2017/0241911 A1 8/2017 Rockel et al.
2017/0342405 A1 11/2017 Fu et al.
2018/0051322 A1 2/2018 Church et al.
2018/0057873 A1 3/2018 Zhou et al.
2018/0105808 A1 4/2018 Mikkelsen et al.
2018/0112209 A1 4/2018 Eshoo
2018/0112261 A1 4/2018 Van Driel et al.
2018/0156784 A1 6/2018 Usmani et al.
2018/0180601 A1 6/2018 Pedersen et al.
2018/0201980 A1 7/2018 Chee et al.
2018/0216161 A1 8/2018 Chen et al.
2018/0216162 A1 8/2018 Belhocine et al.
2018/0245142 A1 8/2018 So et al.
2018/0282803 A1 10/2018 Belgrader et al.
2018/0291439 A1 10/2018 van Eijk et al.
2018/0305681 A1 10/2018 Jovanovich et al.
2019/0055594 A1 2/2019 Samusik et al.
2019/0064173 A1 2/2019 Bharadwaj et al.
2019/0085383 A1 3/2019 Church et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0194709 A1 6/2019 Church et al.
2019/0203275 A1 7/2019 Frisen et al.
2019/0233878 A1 8/2019 Delaney et al.
2019/0249226 A1 8/2019 Bent et al.
2019/0262831 A1 8/2019 West et al.
2019/0264268 A1 8/2019 Frisen et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0330617 A1 10/2019 Church et al.
2019/0338353 A1 11/2019 Belgrader et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0024641 A1 1/2020 Nolan et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0080136 A1 3/2020 Zhang et al.
2020/0109443 A1 4/2020 Chee
2020/0173985 A1 6/2020 Dong et al.
2020/0224244 A1 7/2020 Nilsson et al.
2020/0239946 A1 7/2020 Dewal
2020/0256867 A1 8/2020 Hennek et al.
2020/0277663 A1 9/2020 Iyer
2020/0277664 A1 9/2020 Frenz
2020/0299757 A1 9/2020 Chee et al.
2020/0325531 A1 10/2020 Chee
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0095331 A1 4/2021 Fan et al.
2021/0123040 A1 4/2021 Macosko et al.
2021/0140982 A1 5/2021 Uytingco et al.
2021/0150707 A1 5/2021 Weisenfeld et al.
2021/0155982 A1 5/2021 Yin et al.
2021/0158522 A1 5/2021 Weisenfeld et al.
2021/0172007 A1 6/2021 Chee et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee
2021/0214785 A1 7/2021 Stoeckius
2021/0222235 A1 7/2021 Chee
2021/0222241 A1 7/2021 Bharadwaj
2021/0222242 A1 7/2021 Ramachandran Iyer
2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee
2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0317524 A1 10/2021 Lucero et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0064630 A1 3/2022 Bent et al.
2022/0081728 A1 3/2022 Williams
2022/0090058 A1 3/2022 Frisen et al.
2022/0090175 A1 3/2022 Uytingco et al.
2022/0090181 A1 3/2022 Gallant et al.
2022/0098576 A1 3/2022 Dadhwal
2022/0098661 A1 3/2022 Chew et al.

(56) References Cited

U.S. PATENT DOCUMENTS

| | | | |
|---|---|---|---|
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0334031 | A1 | 10/2022 | Delaney et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |
| 2022/0364163 | A1 | 11/2022 | Stahl et al. |
| 2022/0389491 | A1 | 12/2022 | Chee |
| 2022/0389503 | A1 | 12/2022 | Mikkelsen et al. |
| 2022/0389504 | A1 | 12/2022 | Chew et al. |
| 2022/0403455 | A1 | 12/2022 | Ramachandran Iyer et al. |
| 2022/0404245 | A1 | 12/2022 | Chell et al. |
| 2023/0002812 | A1 | 1/2023 | Stoeckius et al. |
| 2023/0014008 | A1 | 1/2023 | Shastry |
| 2023/0033960 | A1 | 2/2023 | Gallant et al. |
| 2023/0034039 | A1 | 2/2023 | Shahjamali |
| 2023/0034216 | A1 | 2/2023 | Bava |
| 2023/0040363 | A1 | 2/2023 | Chee |
| 2023/0042088 | A1 | 2/2023 | Chee |
| 2023/0042817 | A1 | 2/2023 | Mignardi |
| 2023/0047782 | A1 | 2/2023 | Tentori et al. |
| 2023/0056549 | A1 | 2/2023 | Dadhwal |
| 2023/0064372 | A1 | 3/2023 | Chell et al. |
| 2023/0069046 | A1 | 3/2023 | Chew et al. |
| 2023/0077364 | A1 | 3/2023 | Patterson et al. |
| 2023/0080543 | A1 | 3/2023 | Katiraee et al. |
| 2023/0081381 | A1 | 3/2023 | Chew et al. |
| 2023/0100497 | A1 | 3/2023 | Frisen et al. |
| 2023/0107023 | A1 | 4/2023 | Chee |
| 2023/0111225 | A1 | 4/2023 | Chew et al. |
| 2023/0113230 | A1 | 4/2023 | Kim et al. |
| 2023/0126825 | A1 | 4/2023 | Nagendran et al. |
| 2023/0129552 | A1 | 4/2023 | Ramachandran Iyer |
| 2023/0135010 | A1 | 5/2023 | Tentori et al. |
| 2023/0143569 | A1 | 5/2023 | Iyer et al. |
| 2023/0145575 | A1 | 5/2023 | Gallant et al. |
| 2023/0147726 | A1 | 5/2023 | Hadrup et al. |
| 2023/0151412 | A1 | 5/2023 | Chee |
| 2023/0159994 | A1 | 5/2023 | Chee |
| 2023/0159995 | A1 | 5/2023 | Iyer et al. |
| 2023/0160008 | A1 | 5/2023 | Chell et al. |
| 2023/0175045 | A1 | 6/2023 | Katsori et al. |
| 2023/0183785 | A1 | 6/2023 | Frisen et al. |
| 2023/0194469 | A1 | 6/2023 | Tentori et al. |
| 2023/0194470 | A1 | 6/2023 | Kim et al. |
| 2023/0203478 | A1 | 6/2023 | Kim et al. |
| 2023/0183684 | A1 | 7/2023 | Gallant et al. |
| 2023/0212650 | A1 | 7/2023 | Chew et al. |
| 2023/0212655 | A1 | 7/2023 | Chee |
| 2023/0220368 | A1 | 7/2023 | Kim |
| 2023/0220454 | A1 | 7/2023 | Bent et al. |
| 2023/0220455 | A1 | 7/2023 | Galonska et al. |
| 2023/0227811 | A1 | 7/2023 | Dadhwal |
| 2023/0228762 | A1 | 7/2023 | Uytingco et al. |
| 2023/0242973 | A1 | 8/2023 | Frisen et al. |
| 2023/0242976 | A1 | 8/2023 | Tentori et al. |
| 2023/0265488 | A1 | 8/2023 | Gohil et al. |
| 2023/0265489 | A1 | 8/2023 | Uytingco et al. |
| 2023/0265491 | A1 | 8/2023 | Tentori et al. |
| 2023/0279474 | A1 | 9/2023 | Katiraee |
| 2023/0279477 | A1 | 9/2023 | Kvastad et al. |
| 2023/0279481 | A1 | 9/2023 | Marrache et al. |
| 2023/0287399 | A1 | 9/2023 | Gallant et al. |
| 2023/0287475 | A1 | 9/2023 | Chell et al. |
| 2023/0287481 | A1 | 9/2023 | Katsori et al. |
| 2023/0295699 | A1 | 9/2023 | Sukovich et al. |
| 2023/0295722 | A1 | 9/2023 | Bharadwaj |
| 2023/0304078 | A1 | 9/2023 | Frisen et al. |
| 2023/0313279 | A1 | 10/2023 | Giacomello et al. |
| 2023/0323340 | A1 | 10/2023 | Dadhwal |
| 2023/0323434 | A1 | 10/2023 | Yin et al. |
| 2023/0323436 | A1 | 10/2023 | Chee |
| 2023/0323447 | A1 | 10/2023 | Schnall-Levin et al. |
| 2023/0323453 | A1 | 10/2023 | Stoeckius |

FOREIGN PATENT DOCUMENTS

| | | |
|---|---|---|
| EP | 1923471 | 5/2008 |
| EP | 2002017 | 12/2008 |
| EP | 2881465 | 6/2015 |
| EP | 3013984 | 5/2016 |
| EP | 3511423 | 7/2019 |
| EP | 3541956 | 9/2019 |
| RU | 2145635 | 2/2000 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2004/055159 | 7/2004 |
| WO | WO 2005/007814 | 1/2005 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2009/152928 | 12/2009 |
| WO | WO 2010/053587 | 5/2010 |
| WO | WO 2010/126614 | 11/2010 |
| WO | WO 2011/008502 | 1/2011 |
| WO | WO 2011/068088 | 6/2011 |
| WO | WO 2012/083225 | 6/2012 |
| WO | WO 2012/140224 | 10/2012 |
| WO | WO 2012/159089 | 11/2012 |
| WO | WO 2013/033271 | 3/2013 |
| WO | WO 2013/090390 | 6/2013 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2013/155119 | 10/2013 |
| WO | WO 2013/158936 | 10/2013 |
| WO | WO 2014/060483 | 4/2014 |
| WO | WO 2014/144713 | 9/2014 |
| WO | WO 2014/210223 | 12/2014 |
| WO | WO 2014/210225 | 12/2014 |
| WO | WO 2014/210353 | 12/2014 |
| WO | WO 2015/031691 | 3/2015 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2017/019456 | 2/2017 |
| WO | WO 2017/075293 | 5/2017 |
| WO | WO 2017/096158 | 7/2017 |
| WO | WO 2017/177308 | 10/2017 |

(56) References Cited

FOREIGN PATENT DOCUMENTS

| | | |
|---|---|---|
| WO | WO 2018/064640 | 4/2018 |
| WO | WO 2018/075693 | 4/2018 |
| WO | WO 2018/085599 | 5/2018 |
| WO | WO 2018/091676 | 5/2018 |
| WO | WO 2018/175779 | 9/2018 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047010 | 3/2020 |
| WO | WO 2020/053655 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/142490 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |

OTHER PUBLICATIONS

[No Author Listed], “Chromium Next GEM Single Cell 3' Reagent Kits v3.1 (Dual Index)—User Guide,” 10x Genomics, Mar. 2021, Document No. CG000315, 61 pages.

[No Author Listed], “HuSNP Mapping Assay User’s Manual,” Affymetrix Part No. 90094 (Affymetrix, Santa Clara, Calif.), GeneChip, 2000, 104 pages.

[No Author Listed], “Microarray technologies have excellent possibilities in genomics-related researches,” Science Tools From Amersham Pharmacia Biotech, 1998, 3(4): 8 pages (with English Translation).

10x Genomics, “Chromium Single Cell V(D)J Reagent Kits—User Guide,” 10x Genomics, 2018, CG000086 Rev J, 78 pages.

10x Genomics, “Chromium Single Cell V(D)J Solution,” 10x Genomics, May 2017, 38 pages.

10x Genomics, “Inside Visium Spatial Capture Technology,” 10x Genomics, 2021, 8 pages.

10xGenomics.com, [online], “Visium Spatial Gene Expression Reagent Kits—Tissue Optimization—User Guide,” Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.

10xGenomics.com, [online], “Visium Spatial Gene Expression Reagent Kits—Tissue Optimization,” Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.

10xGenomics.com, [online], “Visium Spatial Gene Expression Reagent Kits—Tissue Optimization,” Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.

10xGenomics.com, [online], “Visium Spatial Gene Expression Reagent Kits—User Guide,” Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.

10xGenomics.com, [online], “Visium Spatial Gene Expression Reagent Kits—User Guide,” Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Adessi et al., “Solid phase DNA amplification: characterisation of primer attachment and amplification mechanisms,” Nucl. Acids Res., 2000, 28(20):E87, 8 pages.

(56) References Cited

OTHER PUBLICATIONS

Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Akatsuka et al., "Rapid screening of T-cell receptor (TCR) variable gene usage by multiplex PCR: Application for assessment of clonal composition," Tissue Antigens, Jan. 5, 1999, 53:122-134.
Akatsuka et al., "T cell receptor clonal diversity following allogeneic marrow grafting," Human Immunology, Jun.-Jul. 1996, 48:125-134.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amgad et al., "Report on computational assessment of Tumor Infiltrating Lymphocytes from the International Immuno-Oncology Biomarker Working Group," Nature Partner Journals Breast Cancer, May 2020, 6:16, 13 pages.
Andresen et al., "Deciphering the Antibodyome—Peptide Arrays for Serum Antibody Biomarker Diagnostics," Current Proteomics, 6(1):1-12, 2009.
Armani et al, "2D-PCR: a method of mapping DNA in tissue sections," Lab Chip, 2009, 9(24):3526-34.
Asp et al., "Spatial detection of fetal marker genes expressed at low level in adult human heart tissue," Scientific Reports, 2017, 7(1):12941, 10 pages.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Bielas et al., "Human cancers express a mutator phenotype," Proc. Natl. Acad. Sci. USA, 2006, 103(48): 18238-18242.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blandini et al., "Animal models of Parkinson's disease," FEBS J., Apr. 2012, 279(7):1156-66.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Bowen et al., "Concurrent V(D)J recombination and DNA end instability increase interchromosomal trans-rearrangements in ATM-deficient thymocytes," Nucleic Acids Research, Apr. 1, 2013, 41(8):4535-4548.
Bowtell, "The genesis and evolution of high-grade serous ovarian cancer," Nat. Rev. Cancer, 2010, (11):803-808 Abstract.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein, " Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Cerutti et al., "Generation of sequence-specific, high affinity anti-DNA antibodies," Journal of Biological Chemistry, 2001, 276(16):12769-12773.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Codeluppi et al., "Spatial organization of the somatosensory cortex revealed by osmFISH," Nature Methods, Nov. 2018, 15:932-935.

(56) References Cited

OTHER PUBLICATIONS

Cole et al., "Complete characterization of the human immune cell transcriptome using accurate full-length cDNA sequencing," Genome Research, Apr. 2020, 30:589-601.
Constantine et al., "Use of genechip high-density oligonucleotide arrays for gene expression monitoring," Life Science News, Amersham Life Science, 1998, pp. 11-14.
Copeland et al., "Mitochondrial DNA Alterations in Cancer," Cancer Invest., 2002, 557-569.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Davis et al., "Recent progress in the analysis of αβ T cell and B cell receptor repertoires," Current Opinion in Immunology, Aug. 2019, 59:109-114.
Dawson et al., "Animal models of neurodegenerative diseases," Nat Neurosci., Oct. 2018, 21(10):1370-1379.
Dawson et al., "Genetic animal models of Parkinson's disease," Neuron, Jun. 2010, 66(5):646-661.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Drmanac et al., "Accurate sequencing by hybridization for DNA diagnostics and individual genomics," Nature Biotechnology, 16:54-58, 1998.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi-C," Trends in Biochemical Sciences, Jun. 2018, 43(6):469-478.
Efremova et al., "Immunology in the Era of Single-Cell Technologies," Annu Rev Immunol., Apr. 2020, 38:727-757.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Fan et al., "Single-cell RNA-seq and V(D)J profiling of immune cells in COVID-19 patients," medRxiv, May 27, 2020, 35 pages.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
FLUIDIGM, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
FLUIDIGM, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
FLUIDIGM, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.
FLUIDIGM, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy," BMC Biology, 15:50, 9 pages, 2017.
GenBank Accession No. M10098.1, "Human 18S rRNA gene, complete," Aug. 3, 1993, 2 pages.
GenBank Accession No. M11167.1, "Human 28S ribosomal RNA gene," Aug. 3, 1993, 2 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Giacomello et al., "Spatially resolved transcriptome profiling in model plant species", Nature Plants 3, 17061, 11 pages, 2017.
Gibson et al., "Enzymatic assembly of DNA molecules up to several hundred kilobases," Nat Methods., May 2009, 6(5):343-5.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gilles et al., "Single nucleotide polymorphic discrimination by an electronic dot blot assay on semiconductor microchips," Nat Biotechnol, Apr. 1999, 17(4):365-70.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging in Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-

(56) References Cited

OTHER PUBLICATIONS restriction analysis and for in vitro synthesis of DNA probes," Nucleic Acids Res., 1986, 14(22):9171-9191.
Goltsev et al., "Deep Profiling of Mouse Splenic Architecture with CODEX Multiplexed Imaging," Cell, 2018, 174(4):968-981.
Goransson et al., "A single molecule array for digital targeted molecular analyses," Nucleic Acids Res., Nov. 25, 2009, 37(1):e7, 9 pages.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadley et al., "Determining composition of micron-scale protein deposits in neurodegenerative disease by spatially targeted optical microproteomics," ELIFE, 2015, 4(e09579):21 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Han et al., "3C and 3C-based techniques: the powerful tools for spatial genome organization deciphering", Molecular Cytogenetics (2018) 11: 21, 10 pages, 2018.
Hayes et al., "Electrophoresis of proteins and nucleic acids: I—Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Heather et al., "High-throughput sequencing of the T-cell receptor repertoire: pitfalls and opportunities," Briefings in Bioinformatics, 2018, 19(4):554-565.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2): 119-25.
Hlubek et al, "Heterogeneous expression of Wnt/b-catenin target genes within colorectal cancer," 2007, Int. J. Cancer: 2017, 1941-1948.
Hou et al., "Basic research and clinical application of immune repertoire sequencing," Int J Clin Exp Med., Oct. 30, 2016, 9(10):18868-18882.
Hudson et al., "Localization of T cell clonotypes using the Visium spatial transcriptomics platform," STAR Protocols, Jun. 17, 2022, 3:101391, 14 pages.
Inoue and Wittbrodt, "One for All—A Highly Efficient and Versatile Method for Fluorescent Immunostaining in Fish Embryos," PLOS One 6, e19713, 2011.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kim et al., "Deep sequencing of B cell receptor repertoire," BMB Rep., Sep. 30, 2019, 52(9):540-547.
Kolovos et al., "Investigation of the spatial structure and interactions of the genome at sub-kilobasepair resolution using T2C," Nat. Protoc., 2018, 13:459-477.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kristensen et al., "High-Throughput Methods for Detection of Genetic Variation," BioTechniques, Feb. 2001, 30(2):318-332.
Kurz et al., "cDNA-protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array—CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Lassmann et al., A Novel Approach for Reliable Microarray Analysis of Microdissected Tumor Cells From Formalin-Fixed and Paraffin-Embedded Colorectal Cancer Resection Specimens, J Mol Med, 87, 211-224, 2009.
Lee et al., "Fluorescent in situ sequencing (FISSEQ) of RNA for gene expression profiling in intact cells and tissues," Nature Protocols, 2015, 10(3):442-458.
Lee et al., "Identifying T Cell Receptors from High-Throughput Sequencing: Dealing with Promiscuity in TCRα and TCRβ Pairing," PLoS Comput Biol., Jan. 2017, 13(1):e1005313, 25 pages.
Lein et al., "The promise of spatial transcriptomics for neuroscience in the era of molecular cell typing", Science 358, 64-69, 2017.
Leriche et al., "Cleavable linkers in chemical biology," Bioorganic & Medicinal Chemistry, 2012, 20:571-582.
Lewczuk et al., "Cerebrospinal fluid and blood biomarkers for neurodegenerative dementias: An update of the Consensus of the Task Force on Biological Markers in Psychiatry of the World Federation of Societies of Biological Psychiatry," World J Biol Psychiatry, Jun. 2018, 19(4):244-328.
Li et al., "RNase H-dependent PCR-enabled T-cell receptor sequencing for highly speci!c and ef!cient targeted sequencing of T-cell receptor mRNA for single-cell and repertoire analysis," Nature Protocols, Aug. 2019, 14:2571-2594.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lundberg et al., "Multiplexed homogeneous proximity ligation assays for high-throughput protein biomarker research in serological material," Mol Cell Proteomics, 2011, 10(4):M110.004978, 11 pages.
Luo et al., "Probing infectious disease by single-cell RNA sequencing: Progresses and perspectives," Computational and Structural Biotechnology Journal, Oct. 21, 2020, 18:2962-2971.
MacBeath et al., "Printing proteins as microarrays for high-throughput function determination," Science, Sep. 2000, 289(5485):1760-1763.
Maniatis et al., "Spatiotemporal Dynamics of Molecular Pathology in Amyotrophic Lateral Sclerosis", 54 pages, 2018.
Martin, "Cutadapt removes adapter sequences from high-throughput sequencing reads," EMBnet Journal, 2011, 17(1):10-12.

(56) References Cited

OTHER PUBLICATIONS

Marx, "Method of the Year: spatially resolved transcriptomics," Nature Methods, 2021, 18(1):9-14.
McKernan et al., "Sequence and structural variation in a human genome uncovered by short-read, massively parallel ligation sequencing using two-base encoding," Genome Res., 19: 1527-41, 2009.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Mulder et al., "CapTCR-seq: hybrid capture for T-cell receptor repertoire profiling," Blood Advances, Dec. 2018, 2(23):3506-3514.
Nagahara et al., "Neuroprotective effects of brain-derived neurotrophic factor in rodent and primate models of Alzheimer's disease," Nat Med., Mar. 2009, 15(3):331-337.
Nam et al., "Somatic mutations and cell identity linked by Genotyping of Transcriptomes," Nature, Jul. 2019, 571(7765):355-360.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
Park et al., "The Estimation of Breast Cancer Disease-Probability by Difference of Individual Susceptibility," Cancer Res. Treat., Feb. 2003, 35(1):35-51, Abstract.
Pasetto et al., "Single-Cell TCR and Transcriptome Analysis: An Indispensable Tool for Studying T-Cell Biology and Cancer Immunotherapy," Frontiers in Immunology, Jun. 7, 2021, 12:689091, 12 pages.
Paterson et al., "Cerebrospinal fluid in the differential diagnosis of Alzheimer's disease: clinical utility of an extended panel of biomarkers in a specialist cognitive clinic," Alzheimers Res Ther., Mar. 2018, 10(1):32, 11 pages.
PCT International Preliminary Report on Patentability in International Appln. No. PCT/US2021/035211, dated Dec. 6, 2022, 17 pages.
PCT International Preliminary Report on Patentability in International Appln. No. PCT/US2021/035242, dated Dec. 6, 2022, 7 pages.
PCT International Search Report and Written Opinion in International Appln. No. PCT/US2021/035211, dated Sep. 30, 2021, 27 pages.
PCT International Search Report and Written Opinion in International Appln. No. PCT/US2021/035242, dated Sep. 2, 2021, 13 pages.
PCT Invitation to Pay Additional Fees in International Appln. No. PCT/US2021/035211, dated Oct. 12, 2021, 17 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raj et al., "Imaging individual mRNA molecules using multiple singly labeled probes," Nature Methods, Oct. 2008, 5(10):877-879, 9 pages.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Ranzoni et al., "Application of single-cell RNA sequencing methodologies in understanding haematopoiesis and immunology," Essays in Biochemistry, Jul. 3, 2019, 63:217-225.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Robins et al., "Comprehensive assessment of T-cell receptor β-chain diversity in αβ T cells," Blood, Nov. 5, 2009, 114(19):4099-4107.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rubin et al., "Whole-genome resequencing reveals loci under selection during chicken domestication.," Nature, Mar. 2010, 464: 587-591.
Salmén et al., "Barcoded solid-phase RNA capture for Spatial Transcriptomics profiling in mammalian tissue sections," Nature Protocols, Oct. 2018, 13(11):2501-2534.
Salmen et al., "Multidimensional transcriptomics provides detailed information about immune cell distribution and identity in HER2+ breast tumors," bioRxiv, 2018, 41 pages.
Saxonov et al., "10x Genomics, Mastering Biology to Advance Human Health," PowerPoint, 10x, 2020, 41 pages.

(56) References Cited

OTHER PUBLICATIONS

Scheideler et al., "Recapitulating complex biological signaling environments using a multiplexed, DNA-patterning approach," Sci. Adv., 2020, 6:eay5696.
Schena et al., "Quantitative monitoring of gene expression patterns with a complementary DNA microarray," Science, Oct. 1995, 270(5235):467-470.
Schmitt et al., "Detection of ultra-rare mutations by next-generation sequencing," PNAS (2012) 109:14508-14523.
Schweitzer et al., "Immunoassays with rolling circle DNA amplification: A versatile platform for ultrasensitive antigen detection," Proc. Natl Acad. Sci. USA, May 22, 2000, 97:10113-119.
Segaliny et al., "Functional TCR T cell screening using single-cell droplet microfluidicst," Lab Chip, 2018, 3733-3749.
Sergeeva et al., "Display technologies: Application for the discovery of drug and gene delivery agents," Advanced Drug Delivery Reviews, 2006, 58(15):1622-1654.
Shalon et al., "A Dna microarray system for analyzing complex DNA samples using two-color fluorescent probe hybridization," Genome Res., Jul. 1996, 6(7):639-45.
Sheth et al., "Spatial metagenomic characterization of microbial biogeography in the gut," Nature Biotechnology, Aug. 2019, 37:877-883.
Shi, "Enabling large-scale pharmacogenetic studies by high-throughput mutation detection and genotyping technologies," Clin. Chem., Feb. 2001, 47(2):164-172.
Shoemaker et al., "Quantitative phenotypic analysis of yeast deletion mutants using a highly parallel molecular bar-coding strategy," Nature genetics (1996) 14:450-456.
Sievertzon et al., "Transcriptome analysis in primary neural stem cells using a tag cDNA amplification method," BMC Neuroscience, Dec. 2005, 6: 28.
Singh et al., "High-throughput targeted long-read single cell sequencing reveals the clonal and transcriptional landscape of lymphocytes," Nat Commun., Jul. 2019, 10(1):3120, 13 pages.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Strell et al., "Placing RNA in context and space—methods for spatially resolved transcriptomics," The FEBS Journal, 2019, 286(8):1468-1481.
Stuart et al., "Comprehensive Integration of Single-Cell Data," Cell, Jun. 2019, 177(7):1888-1902.
Stubbington et al., "T cell fate and clonality inference from single cell transcriptomes," Nature Methods, Apr. 2016, 13(4):329-332.
Sudmeier et al., "Distinct phenotypic states and spatial distribution of CD8+ T cell clonotypes in human brain metastases," Cell Reports Medicine, May 17, 2022, 3:100620, 22 pages.
Takei et al., "Integrated Spatial Genomics Reveals Global Architecture of Single Nuclei," Nature, Jan. 27, 2021, 590(7845):344-350, 53 pages.
Tegtmeyer et al., "Alternative Interactions of the SV40 A Protein with DNA," Virology, 1981, 115:75-87.
Teraguchi et al., "Methods for sequence and structural analysis of B and T cell receptor repertoires," Computational and Structural Biotechnology Journal, Jul. 17, 2020, 18:2000-2011.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tomita et al., "Attention-Based Deep Neural Networks for Detection of Cancerous and Precancerous Esophagus Tissue on Histopathological Slides," JAMA Network Open. Nov. 6, 2019, 2(11):e1914645, 13 pages.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Villa et al., "Partial V(D)J Recombination Activity Leads to Omenn Syndrome," Cell, May 29, 1998, 93:885-896.
Vogelstein et al., "Digital PCR," Proceedings of the National Academy of Sciences, Aug. 1999, 96(16):9236-9241.
Wade et al., "Genome sequence, comparative analysis, and population genetics of the domestic horse.," Science., 326: 865-7, 2009.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of IncRNA localization," Proc Natl Acad Sci USA, May 2019, 116(22):10842-10851.
Wang et al., "Molecular probes for enriching and detecting complex nucleic acid sequences," Nat Chem., Dec. 2017, 9(12):1222-1228.
Waxman et al., "De-regulation of common housekeeping genes in hepatocellular carcinoma," BMC Genomics, 2007, 1-9.
Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.
Worthington et al., "Cloning of random oligonucleotides to create single-insert plasmid libraries," Anal Biochem, 2001, 294(2):169-175.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Xiao et al., "Direct determination of haplotypes from single DNA molecules," Nature Methods, 2009, 6(3):199-01.
Yershov et al., "DNA analysis and diagnostics on oligonucleotide microchips," Proc. Natl. Acad. Sci. USA, May 1996, 93(10):4913-4918.
Zhang et al., "Single-base mutational analysis of cancer and genetic diseases using membrane bound modified oligonucleotides," Nucleic Acids Res., Jul. 1991, 19(14):3929-33.
Zhu et al., "Reverse transcriptase template switching: a SMART approach for full-length cDNA library construction," Biotechniques, Apr. 2001, 30(4):892-897.
Zilberman et al., "Genome-wide analysis of DNA methylation patterns," Development (2007) 134:3959-3965.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine, 2013 11(104):1-7.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.

(56) References Cited

OTHER PUBLICATIONS

Mamedov et al., "Preparing unbiased T-cell receptor and antibody cDNA libraries for the deep next generation sequencing profiling," Frontiers in Immunol., Dec. 23, 2013, 4(456):1-10.

SEQUENCE LISTING

```
Sequence total quantity: 640
SEQ ID NO: 1           moltype = DNA  length = 20
FEATURE                Location/Qualifiers
source                 1..20
                       mol_type = other DNA
                       organism = synthetic construct
SEQUENCE: 1
tctgatggct caaacacagc                                         20

SEQ ID NO: 2           moltype = DNA  length = 21
FEATURE                Location/Qualifiers
source                 1..21
                       mol_type = other DNA
                       organism = synthetic construct
SEQUENCE: 2
gccaggggga agaccgatgg g                                       21
```

-continued

```
SEQ ID NO: 3            moltype = DNA  length = 18
FEATURE                 Location/Qualifiers
source                  1..18
                        mol_type = other DNA
                        organism = synthetic construct
SEQUENCE: 3
cacgctgctc gtatccga                                                18

SEQ ID NO: 4            moltype = DNA  length = 27
FEATURE                 Location/Qualifiers
source                  1..27
                        mol_type = other DNA
                        organism = synthetic construct
SEQUENCE: 4
caacagggag aagaggatcc tcaggcc                                      27

SEQ ID NO: 5            moltype = DNA  length = 29
FEATURE                 Location/Qualifiers
source                  1..29
                        mol_type = other DNA
                        organism = synthetic construct
SEQUENCE: 5
ggacaaaaca ttgaccagcc cactgagat                                    29

SEQ ID NO: 6            moltype = DNA  length = 30
FEATURE                 Location/Qualifiers
source                  1..30
                        mol_type = other DNA
                        organism = synthetic construct
SEQUENCE: 6
aaaaaccaag tggagcagag tcctcagtcc                                   30

SEQ ID NO: 7            moltype = DNA  length = 25
FEATURE                 Location/Qualifiers
source                  1..25
                        mol_type = other DNA
                        organism = synthetic construct
SEQUENCE: 7
caacggaagg aggtggagca ggatc                                        25

SEQ ID NO: 8            moltype = DNA  length = 29
FEATURE                 Location/Qualifiers
source                  1..29
                        mol_type = other DNA
                        organism = synthetic construct
SEQUENCE: 8
caacagaagg aggtggagca gaattctgg                                    29

SEQ ID NO: 9            moltype = DNA  length = 27
FEATURE                 Location/Qualifiers
source                  1..27
                        mol_type = other DNA
                        organism = synthetic construct
SEQUENCE: 9
caacagaagg aggtggagca ggatcct                                      27

SEQ ID NO: 10           moltype = DNA  length = 27
FEATURE                 Location/Qualifiers
source                  1..27
                        mol_type = other DNA
                        organism = synthetic construct
SEQUENCE: 10
gagaatgtgg agcagcatcc ttcaacc                                      27

SEQ ID NO: 11           moltype = DNA  length = 27
FEATURE                 Location/Qualifiers
source                  1..27
                        mol_type = other DNA
                        organism = synthetic construct
SEQUENCE: 11
gagagtgtgg ggctgcatct tcctacc                                      27

SEQ ID NO: 12           moltype = DNA  length = 33
FEATURE                 Location/Qualifiers
source                  1..33
                        mol_type = other DNA
                        organism = synthetic construct
SEQUENCE: 12
```

```
cagaagataa ctcaaaccca accaggaatg ttc                            33

SEQ ID NO: 13          moltype = DNA  length = 27
FEATURE                Location/Qualifiers
source                 1..27
                       mol_type = other DNA
                       organism = synthetic construct
SEQUENCE: 13
cagagagtga ctcagcccga gaagctc                                   27

SEQ ID NO: 14          moltype = DNA  length = 26
FEATURE                Location/Qualifiers
source                 1..26
                       mol_type = other DNA
                       organism = synthetic construct
SEQUENCE: 14
gactcggtta cccagacaga aggccc                                    26

SEQ ID NO: 15          moltype = DNA  length = 33
FEATURE                Location/Qualifiers
source                 1..33
                       mol_type = other DNA
                       organism = synthetic construct
SEQUENCE: 15
cagaaggtaa ctcaagcgca gactgaaatt tct                            33

SEQ ID NO: 16          moltype = DNA  length = 30
FEATURE                Location/Qualifiers
source                 1..30
                       mol_type = other DNA
                       organism = synthetic construct
SEQUENCE: 16
aaggaccaag tgtttcagcc ttccacagtg                                30

SEQ ID NO: 17          moltype = DNA  length = 25
FEATURE                Location/Qualifiers
source                 1..25
                       mol_type = other DNA
                       organism = synthetic construct
SEQUENCE: 17
gaagaccagg tgacgcagag tcccg                                     25

SEQ ID NO: 18          moltype = DNA  length = 26
FEATURE                Location/Qualifiers
source                 1..26
                       mol_type = other DNA
                       organism = synthetic construct
SEQUENCE: 18
aaacaggagg tgacgcagat tcctgc                                    26

SEQ ID NO: 19          moltype = DNA  length = 31
FEATURE                Location/Qualifiers
source                 1..31
                       mol_type = other DNA
                       organism = synthetic construct
SEQUENCE: 19
atacaagtgg agcagagtcc tccagacctg a                              31

SEQ ID NO: 20          moltype = DNA  length = 29
FEATURE                Location/Qualifiers
source                 1..29
                       mol_type = other DNA
                       organism = synthetic construct
SEQUENCE: 20
caacagaagg agaaaagtga ccagcagca                                 29

SEQ ID NO: 21          moltype = DNA  length = 33
FEATURE                Location/Qualifiers
source                 1..33
                       mol_type = other DNA
                       organism = synthetic construct
SEQUENCE: 21
atactgaacg tggaacaaag tcctcagtca ctg                            33

SEQ ID NO: 22          moltype = DNA  length = 31
FEATURE                Location/Qualifiers
source                 1..31
                       mol_type = other DNA
                       organism = synthetic construct
```

-continued

```
SEQUENCE: 22
caacaggtaa tgcaaattcc tcagtaccag c                              31

SEQ ID NO: 23          moltype = DNA  length = 21
FEATURE                Location/Qualifiers
source                 1..21
                       mol_type = other DNA
                       organism = synthetic construct
SEQUENCE: 23
aagaccaccc agcccccctc c                                         21

SEQ ID NO: 24          moltype = DNA  length = 33
FEATURE                Location/Qualifiers
source                 1..33
                       mol_type = other DNA
                       organism = synthetic construct
SEQUENCE: 24
aagaccacac agccaaattc aatggagagt aac                            33

SEQ ID NO: 25          moltype = DNA  length = 25
FEATURE                Location/Qualifiers
source                 1..25
                       mol_type = other DNA
                       organism = synthetic construct
SEQUENCE: 25
cagctgctgg agcagagccc tcagt                                     25

SEQ ID NO: 26          moltype = DNA  length = 33
FEATURE                Location/Qualifiers
source                 1..33
                       mol_type = other DNA
                       organism = synthetic construct
SEQUENCE: 26
caacagaaga atgatgacca gcaagttaag caa                            33

SEQ ID NO: 27          moltype = DNA  length = 25
FEATURE                Location/Qualifiers
source                 1..25
                       mol_type = other DNA
                       organism = synthetic construct
SEQUENCE: 27
cagtcagtgg ctcagccgga agatc                                     25

SEQ ID NO: 28          moltype = DNA  length = 27
FEATURE                Location/Qualifiers
source                 1..27
                       mol_type = other DNA
                       organism = synthetic construct
SEQUENCE: 28
caacaaccag tgcagagtcc tcaagcc                                   27

SEQ ID NO: 29          moltype = DNA  length = 30
FEATURE                Location/Qualifiers
source                 1..30
                       mol_type = other DNA
                       organism = synthetic construct
SEQUENCE: 29
caagaactgg agcagagtcc tcagtccttg                                30

SEQ ID NO: 30          moltype = DNA  length = 36
FEATURE                Location/Qualifiers
source                 1..36
                       mol_type = other DNA
                       organism = synthetic construct
SEQUENCE: 30
caacagctga atcagagtcc tcaatctatg tttatc                         36

SEQ ID NO: 31          moltype = DNA  length = 33
FEATURE                Location/Qualifiers
source                 1..33
                       mol_type = other DNA
                       organism = synthetic construct
SEQUENCE: 31
gaagacaagg tggtacaaag ccctctatct ctg                            33

SEQ ID NO: 32          moltype = DNA  length = 33
FEATURE                Location/Qualifiers
source                 1..33
                       mol_type = other DNA
```

```
                      organism = synthetic construct
SEQUENCE: 32
cagacagtca ctcagtctca accagagatg tct                                33

SEQ ID NO: 33         moltype = DNA  length = 30
FEATURE               Location/Qualifiers
source                1..30
                      mol_type = other DNA
                      organism = synthetic construct
SEQUENCE: 33
gagctgaaag tggaacaaaa ccctctgttc                                    30

SEQ ID NO: 34         moltype = DNA  length = 24
FEATURE               Location/Qualifiers
source                1..24
                      mol_type = other DNA
                      organism = synthetic construct
SEQUENCE: 34
aagaccaccc agcccatctc catg                                          24

SEQ ID NO: 35         moltype = DNA  length = 29
FEATURE               Location/Qualifiers
source                1..29
                      mol_type = other DNA
                      organism = synthetic construct
SEQUENCE: 35
aattcagtca agcagacggg ccaaataac                                     29

SEQ ID NO: 36         moltype = DNA  length = 28
FEATURE               Location/Qualifiers
source                1..28
                      mol_type = other DNA
                      organism = synthetic construct
SEQUENCE: 36
gccaaaaatg aagtggagca gagtcctc                                      28

SEQ ID NO: 37         moltype = DNA  length = 31
FEATURE               Location/Qualifiers
source                1..31
                      mol_type = other DNA
                      organism = synthetic construct
SEQUENCE: 37
gaggatgtgg agcagagtct tttcctgagt g                                  31

SEQ ID NO: 38         moltype = DNA  length = 30
FEATURE               Location/Qualifiers
source                1..30
                      mol_type = other DNA
                      organism = synthetic construct
SEQUENCE: 38
caaaagatag aacagaattc cgaggccctg                                    30

SEQ ID NO: 39         moltype = DNA  length = 25
FEATURE               Location/Qualifiers
source                1..25
                      mol_type = other DNA
                      organism = synthetic construct
SEQUENCE: 39
gaaaaccagg tggagcacag ccctc                                         25

SEQ ID NO: 40         moltype = DNA  length = 27
FEATURE               Location/Qualifiers
source                1..27
                      mol_type = other DNA
                      organism = synthetic construct
SEQUENCE: 40
cagtctgtga gccagcataa ccaccac                                       27

SEQ ID NO: 41         moltype = DNA  length = 24
FEATURE               Location/Qualifiers
source                1..24
                      mol_type = other DNA
                      organism = synthetic construct
SEQUENCE: 41
cagtcggtga cccagcttga cagc                                          24

SEQ ID NO: 42         moltype = DNA  length = 27
FEATURE               Location/Qualifiers
source                1..27
```

```
                        mol_type = other DNA
                        organism = synthetic construct
SEQUENCE: 42
cagtcagtga cccagcctga catccac                                         27

SEQ ID NO: 43           moltype = DNA  length = 23
FEATURE                 Location/Qualifiers
source                  1..23
                        mol_type = other DNA
                        organism = synthetic construct
SEQUENCE: 43
cagtcggtga cccagcttgg cag                                             23

SEQ ID NO: 44           moltype = DNA  length = 26
FEATURE                 Location/Qualifiers
source                  1..26
                        mol_type = other DNA
                        organism = synthetic construct
SEQUENCE: 44
cagtctgtga cccagcttga cagcca                                          26

SEQ ID NO: 45           moltype = DNA  length = 24
FEATURE                 Location/Qualifiers
source                  1..24
                        mol_type = other DNA
                        organism = synthetic construct
SEQUENCE: 45
cagtcggtga cccagcttga tggc                                            24

SEQ ID NO: 46           moltype = DNA  length = 29
FEATURE                 Location/Qualifiers
source                  1..29
                        mol_type = other DNA
                        organism = synthetic construct
SEQUENCE: 46
gattcagtgg tccagacaga aggccaagt                                       29

SEQ ID NO: 47           moltype = DNA  length = 26
FEATURE                 Location/Qualifiers
source                  1..26
                        mol_type = other DNA
                        organism = synthetic construct
SEQUENCE: 47
aattcagtga cccagatgga agggcc                                          26

SEQ ID NO: 48           moltype = DNA  length = 27
FEATURE                 Location/Qualifiers
source                  1..27
                        mol_type = other DNA
                        organism = synthetic construct
SEQUENCE: 48
gaacctgaag tcacccagac tcccagc                                         27

SEQ ID NO: 49           moltype = DNA  length = 30
FEATURE                 Location/Qualifiers
source                  1..30
                        mol_type = other DNA
                        organism = synthetic construct
SEQUENCE: 49
gctgtttccc agactccaaa atacctggtc                                      30

SEQ ID NO: 50           moltype = DNA  length = 30
FEATURE                 Location/Qualifiers
source                  1..30
                        mol_type = other DNA
                        organism = synthetic construct
SEQUENCE: 50
gaagttaccc agacaccaaa acacctggtc                                      30

SEQ ID NO: 51           moltype = DNA  length = 35
FEATURE                 Location/Qualifiers
source                  1..35
                        mol_type = other DNA
                        organism = synthetic construct
SEQUENCE: 51
ggagtcactc aaactccaag atatctgatc aaaac                                35

SEQ ID NO: 52           moltype = DNA  length = 27
FEATURE                 Location/Qualifiers
```

-continued

```
source                 1..27
                       mol_type = other DNA
                       organism = synthetic construct
SEQUENCE: 52
ggtgtcactc agaccccaaa attccag                                        27

SEQ ID NO: 53          moltype = DNA  length = 28
FEATURE                Location/Qualifiers
source                 1..28
                       mol_type = other DNA
                       organism = synthetic construct
SEQUENCE: 53
ggagtctccc agtccctgag acacaagg                                       28

SEQ ID NO: 54          moltype = DNA  length = 28
FEATURE                Location/Qualifiers
source                 1..28
                       mol_type = other DNA
                       organism = synthetic construct
SEQUENCE: 54
ggagttacgc agacaccaag acacctgg                                       28

SEQ ID NO: 55          moltype = DNA  length = 26
FEATURE                Location/Qualifiers
source                 1..26
                       mol_type = other DNA
                       organism = synthetic construct
SEQUENCE: 55
ggtgtcactc agaccccaaa attccg                                         26

SEQ ID NO: 56          moltype = DNA  length = 27
FEATURE                Location/Qualifiers
source                 1..27
                       mol_type = other DNA
                       organism = synthetic construct
SEQUENCE: 56
ggagtctccc agtcccccag taacaag                                        27

SEQ ID NO: 57          moltype = DNA  length = 25
FEATURE                Location/Qualifiers
source                 1..25
                       mol_type = other DNA
                       organism = synthetic construct
SEQUENCE: 57
gggatcaccc aggcaccaac atctc                                          25

SEQ ID NO: 58          moltype = DNA  length = 27
FEATURE                Location/Qualifiers
source                 1..27
                       mol_type = other DNA
                       organism = synthetic construct
SEQUENCE: 58
ggagtctccc agacccccag taacaag                                        27

SEQ ID NO: 59          moltype = DNA  length = 26
FEATURE                Location/Qualifiers
source                 1..26
                       mol_type = other DNA
                       organism = synthetic construct
SEQUENCE: 59
ggagtcaccc aaagtcccac acacct                                         26

SEQ ID NO: 60          moltype = DNA  length = 26
FEATURE                Location/Qualifiers
source                 1..26
                       mol_type = other DNA
                       organism = synthetic construct
SEQUENCE: 60
ggagtcacac aaaccccaaa gcacct                                         26

SEQ ID NO: 61          moltype = DNA  length = 28
FEATURE                Location/Qualifiers
source                 1..28
                       mol_type = other DNA
                       organism = synthetic construct
SEQUENCE: 61
gaaatcaccc agagcccaag acacaaga                                       28

SEQ ID NO: 62          moltype = DNA  length = 31
```

```
FEATURE                Location/Qualifiers
source                 1..31
                       mol_type = other DNA
                       organism = synthetic construct
SEQUENCE: 62
gaagttgccc agtcccccag atataagatt a                                  31

SEQ ID NO: 63          moltype = DNA  length = 29
FEATURE                Location/Qualifiers
source                 1..29
                       mol_type = other DNA
                       organism = synthetic construct
SEQUENCE: 63
ggaatcaccc agagcccaag atacaagat                                     29

SEQ ID NO: 64          moltype = DNA  length = 36
FEATURE                Location/Qualifiers
source                 1..36
                       mol_type = other DNA
                       organism = synthetic construct
SEQUENCE: 64
ggagttgccc agtctcccag atataagatt atagag                             36

SEQ ID NO: 65          moltype = DNA  length = 28
FEATURE                Location/Qualifiers
source                 1..28
                       mol_type = other DNA
                       organism = synthetic construct
SEQUENCE: 65
ggagtctccc agtccccaag gtacaaag                                      28

SEQ ID NO: 66          moltype = DNA  length = 26
FEATURE                Location/Qualifiers
source                 1..26
                       mol_type = other DNA
                       organism = synthetic construct
SEQUENCE: 66
ggagtctccc agtccccaag gtacga                                        26

SEQ ID NO: 67          moltype = DNA  length = 27
FEATURE                Location/Qualifiers
source                 1..27
                       mol_type = other DNA
                       organism = synthetic construct
SEQUENCE: 67
ggtgtcactc agaccccaaa attccac                                       27

SEQ ID NO: 68          moltype = DNA  length = 30
FEATURE                Location/Qualifiers
source                 1..30
                       mol_type = other DNA
                       organism = synthetic construct
SEQUENCE: 68
ggagtctccc agtctcccag gtacaaagtc                                    30

SEQ ID NO: 69          moltype = DNA  length = 29
FEATURE                Location/Qualifiers
source                 1..29
                       mol_type = other DNA
                       organism = synthetic construct
SEQUENCE: 69
ggtgtcactc agaccccaaa attccacat                                     29

SEQ ID NO: 70          moltype = DNA  length = 30
FEATURE                Location/Qualifiers
source                 1..30
                       mol_type = other DNA
                       organism = synthetic construct
SEQUENCE: 70
ggagtctccc agtcccctag gtacaaagtc                                    30

SEQ ID NO: 71          moltype = DNA  length = 28
FEATURE                Location/Qualifiers
source                 1..28
                       mol_type = other DNA
                       organism = synthetic construct
SEQUENCE: 71
ggagtcacac aaagtcccac acacctga                                      28
```

```
SEQ ID NO: 72          moltype = DNA  length = 27
FEATURE                Location/Qualifiers
source                 1..27
                       mol_type = other DNA
                       organism = synthetic construct
SEQUENCE: 72
ggagtctccc agaaccccag acacaag                                    27

SEQ ID NO: 73          moltype = DNA  length = 29
FEATURE                Location/Qualifiers
source                 1..29
                       mol_type = other DNA
                       organism = synthetic construct
SEQUENCE: 73
ggagtcatcc agtccccaag acatctgat                                  29

SEQ ID NO: 74          moltype = DNA  length = 25
FEATURE                Location/Qualifiers
source                 1..25
                       mol_type = other DNA
                       organism = synthetic construct
SEQUENCE: 74
ggagttatcc agtcaccccg ccatg                                      25

SEQ ID NO: 75          moltype = DNA  length = 24
FEATURE                Location/Qualifiers
source                 1..24
                       mol_type = other DNA
                       organism = synthetic construct
SEQUENCE: 75
ggagttatcc agtcaccccg gcac                                       24

SEQ ID NO: 76          moltype = DNA  length = 27
FEATURE                Location/Qualifiers
source                 1..27
                       mol_type = other DNA
                       organism = synthetic construct
SEQUENCE: 76
agagtcaccc agacaccaag gcacaag                                    27

SEQ ID NO: 77          moltype = DNA  length = 27
FEATURE                Location/Qualifiers
source                 1..27
                       mol_type = other DNA
                       organism = synthetic construct
SEQUENCE: 77
ggagttactc agttccccag ccacagc                                    27

SEQ ID NO: 78          moltype = DNA  length = 30
FEATURE                Location/Qualifiers
source                 1..30
                       mol_type = other DNA
                       organism = synthetic construct
SEQUENCE: 78
atggtcatcc agaacccaag ataccaggtt                                 30

SEQ ID NO: 79          moltype = DNA  length = 23
FEATURE                Location/Qualifiers
source                 1..23
                       mol_type = other DNA
                       organism = synthetic construct
SEQUENCE: 79
gagcctggag tcagccagac ccc                                        23

SEQ ID NO: 80          moltype = DNA  length = 24
FEATURE                Location/Qualifiers
source                 1..24
                       mol_type = other DNA
                       organism = synthetic construct
SEQUENCE: 80
ggcgtcatgc agaacccaag acac                                       24

SEQ ID NO: 81          moltype = DNA  length = 31
FEATURE                Location/Qualifiers
source                 1..31
                       mol_type = other DNA
                       organism = synthetic construct
SEQUENCE: 81
ggaatcactc agtccccaaa gtacctgttc a                               31
```

-continued

```
SEQ ID NO: 82          moltype = DNA  length = 26
FEATURE                Location/Qualifiers
source                 1..26
                       mol_type = other DNA
                       organism = synthetic construct
SEQUENCE: 82
gctgtcgtct ctcaacatcc gagctg                                            26

SEQ ID NO: 83          moltype = DNA  length = 24
FEATURE                Location/Qualifiers
source                 1..24
                       mol_type = other DNA
                       organism = synthetic construct
SEQUENCE: 83
attccagctc actggggctg gatg                                              24

SEQ ID NO: 84          moltype = DNA  length = 31
FEATURE                Location/Qualifiers
source                 1..31
                       mol_type = other DNA
                       organism = synthetic construct
SEQUENCE: 84
aaagtcacac agactccagg acatttggtc a                                      31

SEQ ID NO: 85          moltype = DNA  length = 30
FEATURE                Location/Qualifiers
source                 1..30
                       mol_type = other DNA
                       organism = synthetic construct
SEQUENCE: 85
gatgttaccc agaccccaag gaataggatc                                        30

SEQ ID NO: 86          moltype = DNA  length = 35
FEATURE                Location/Qualifiers
source                 1..35
                       mol_type = other DNA
                       organism = synthetic construct
SEQUENCE: 86
gacatctacc agaccccaag ataccttgtt atagg                                  35

SEQ ID NO: 87          moltype = DNA  length = 35
FEATURE                Location/Qualifiers
source                 1..35
                       mol_type = other DNA
                       organism = synthetic construct
SEQUENCE: 87
gtagttacac aattcccaag acacagaatc attgg                                  35

SEQ ID NO: 88          moltype = DNA  length = 30
FEATURE                Location/Qualifiers
source                 1..30
                       mol_type = other DNA
                       organism = synthetic construct
SEQUENCE: 88
caagtgaccc agaacccaag atacctcatc                                        30

SEQ ID NO: 89          moltype = DNA  length = 27
FEATURE                Location/Qualifiers
source                 1..27
                       mol_type = other DNA
                       organism = synthetic construct
SEQUENCE: 89
ggtggcagca gtcacagatg cctactc                                           27

SEQ ID NO: 90          moltype = DNA  length = 27
FEATURE                Location/Qualifiers
source                 1..27
                       mol_type = other DNA
                       organism = synthetic construct
SEQUENCE: 90
ggtggcagca gccacaggtg cccactc                                           27

SEQ ID NO: 91          moltype = DNA  length = 27
FEATURE                Location/Qualifiers
source                 1..27
                       mol_type = other DNA
                       organism = synthetic construct
SEQUENCE: 91
```

```
ggtggcagca gctacaggtg tccagtc                                       27

SEQ ID NO: 92          moltype = DNA  length = 27
FEATURE                Location/Qualifiers
source                 1..27
                       mol_type = other DNA
                       organism = synthetic construct
SEQUENCE: 92
ggtggsagca gcaacargwg cccactc                                       27

SEQ ID NO: 93          moltype = DNA  length = 27
FEATURE                Location/Qualifiers
source                 1..27
                       mol_type = other DNA
                       organism = synthetic construct
SEQUENCE: 93
gctggctgta gctccaggtg ctcactc                                       27

SEQ ID NO: 94          moltype = DNA  length = 33
FEATURE                Location/Qualifiers
source                 1..33
                       mol_type = other DNA
                       organism = synthetic construct
SEQUENCE: 94
cctgctgctg accayccctt cmtgggtctt gtc                                33

SEQ ID NO: 95          moltype = DNA  length = 33
FEATURE                Location/Qualifiers
source                 1..33
                       mol_type = other DNA
                       organism = synthetic construct
SEQUENCE: 95
cctgctactg actgtcccgt cctgggtctt atc                                33

SEQ ID NO: 96          moltype = DNA  length = 37
FEATURE                Location/Qualifiers
source                 1..37
                       mol_type = other DNA
                       organism = synthetic construct
SEQUENCE: 96
gggttttcct cgttgctctt ttaagaggtg tccagtg                            37

SEQ ID NO: 97          moltype = DNA  length = 37
FEATURE                Location/Qualifiers
source                 1..37
                       mol_type = other DNA
                       organism = synthetic construct
SEQUENCE: 97
gggttttcct tgttgctatt ttaaaaggtg tccartg                            37

SEQ ID NO: 98          moltype = DNA  length = 37
FEATURE                Location/Qualifiers
source                 1..37
                       mol_type = other DNA
                       organism = synthetic construct
SEQUENCE: 98
ggattttcct tgctgctatt ttaaaaggtg tccagtg                            37

SEQ ID NO: 99          moltype = DNA  length = 37
FEATURE                Location/Qualifiers
source                 1..37
                       mol_type = other DNA
                       organism = synthetic construct
SEQUENCE: 99
gggttttcct tktkgctatw ttagaaggtg tccagtg                            37

SEQ ID NO: 100         moltype = DNA  length = 27
FEATURE                Location/Qualifiers
source                 1..27
                       mol_type = other DNA
                       organism = synthetic construct
SEQUENCE: 100
ggtggcrgct cccagatggg tcctgtc                                       27

SEQ ID NO: 101         moltype = DNA  length = 25
FEATURE                Location/Qualifiers
source                 1..25
                       mol_type = other DNA
                       organism = synthetic construct
```

```
SEQUENCE: 101
ctggctgttc tccaaggagt ctgtg                                          25

SEQ ID NO: 102          moltype = DNA  length = 23
FEATURE                 Location/Qualifiers
source                  1..23
                        mol_type = other DNA
                        organism = synthetic construct
SEQUENCE: 102
ggcctcccat ggggtgtcct gtc                                            23

SEQ ID NO: 103          moltype = DNA  length = 26
FEATURE                 Location/Qualifiers
source                  1..26
                        mol_type = other DNA
                        organism = synthetic construct
SEQUENCE: 103
ggtggcagca gcaacaggtg cccact                                         26

SEQ ID NO: 104          moltype = DNA  length = 28
FEATURE                 Location/Qualifiers
source                  1..28
                        mol_type = other DNA
                        organism = synthetic construct
SEQUENCE: 104
atggaactgg ggctccgctg ggttttcc                                       28

SEQ ID NO: 105          moltype = DNA  length = 27
FEATURE                 Location/Qualifiers
source                  1..27
                        mol_type = other DNA
                        organism = synthetic construct
SEQUENCE: 105
atggactgca cctggaggat cctcctc                                        27

SEQ ID NO: 106          moltype = DNA  length = 26
FEATURE                 Location/Qualifiers
source                  1..26
                        mol_type = other DNA
                        organism = synthetic construct
SEQUENCE: 106
tggctgagct gggtttycct tgttgc                                         26

SEQ ID NO: 107          moltype = DNA  length = 26
FEATURE                 Location/Qualifiers
source                  1..26
                        mol_type = other DNA
                        organism = synthetic construct
SEQUENCE: 107
ggagttkggg ctgmgctggg ttttcc                                         26

SEQ ID NO: 108          moltype = DNA  length = 28
FEATURE                 Location/Qualifiers
source                  1..28
                        mol_type = other DNA
                        organism = synthetic construct
SEQUENCE: 108
gcacctgtgg tttttcctcc tgctggtg                                       28

SEQ ID NO: 109          moltype = DNA  length = 25
FEATURE                 Location/Qualifiers
source                  1..25
                        mol_type = other DNA
                        organism = synthetic construct
SEQUENCE: 109
cacctgtggt tcttcctcct sctgg                                          25

SEQ ID NO: 110          moltype = DNA  length = 26
FEATURE                 Location/Qualifiers
source                  1..26
                        mol_type = other DNA
                        organism = synthetic construct
SEQUENCE: 110
ccaggatggg gtcaaccgcc atcctc                                         26

SEQ ID NO: 111          moltype = DNA  length = 30
FEATURE                 Location/Qualifiers
source                  1..30
                        mol_type = other DNA
```

```
                        organism = synthetic construct
SEQUENCE: 111
cagaggactc accatggagt ttgggctgag                                      30

SEQ ID NO: 112          moltype = DNA  length = 27
FEATURE                 Location/Qualifiers
source                  1..27
                        mol_type = other DNA
                        organism = synthetic construct
SEQUENCE: 112
ggactcacca tggagttggg actgagc                                         27

SEQ ID NO: 113          moltype = DNA  length = 26
FEATURE                 Location/Qualifiers
source                  1..26
                        mol_type = other DNA
                        organism = synthetic construct
SEQUENCE: 113
gggctgagct ggctttttct tgtggc                                          26

SEQ ID NO: 114          moltype = DNA  length = 30
FEATURE                 Location/Qualifiers
source                  1..30
                        mol_type = other DNA
                        organism = synthetic construct
SEQUENCE: 114
aagcagtggt atcaacgcag agtacatggg                                      30

SEQ ID NO: 115          moltype = DNA  length = 17
FEATURE                 Location/Qualifiers
source                  1..17
                        mol_type = other DNA
                        organism = synthetic construct
SEQUENCE: 115
tctgcgttga taccact                                                    17

SEQ ID NO: 116          moltype = DNA  length = 30
FEATURE                 Location/Qualifiers
source                  1..30
                        mol_type = genomic DNA
                        organism = Homo sapiens
SEQUENCE: 116
gaaggagctc cagatgaaag actctgcctc                                      30

SEQ ID NO: 117          moltype = DNA  length = 30
FEATURE                 Location/Qualifiers
source                  1..30
                        mol_type = genomic DNA
                        organism = Homo sapiens
SEQUENCE: 117
gttctcttca tcgctgctca tcctccaggt                                      30

SEQ ID NO: 118          moltype = DNA  length = 30
FEATURE                 Location/Qualifiers
source                  1..30
                        mol_type = genomic DNA
                        organism = Homo sapiens
SEQUENCE: 118
cttgtgagcg actccgcttt gtacttctgt                                      30

SEQ ID NO: 119          moltype = DNA  length = 30
FEATURE                 Location/Qualifiers
source                  1..30
                        mol_type = genomic DNA
                        organism = Homo sapiens
SEQUENCE: 119
ttatccctgc cgacagaaag tccagcactc                                      30

SEQ ID NO: 120          moltype = DNA  length = 31
FEATURE                 Location/Qualifiers
source                  1..31
                        mol_type = genomic DNA
                        organism = Homo sapiens
SEQUENCE: 120
aaggataaac atctgtctct gcgcattgca g                                    31

SEQ ID NO: 121          moltype = DNA  length = 30
FEATURE                 Location/Qualifiers
source                  1..30
```

```
                        mol_type = genomic DNA
                        organism = Homo sapiens
SEQUENCE: 121
ttgtttcata tcacagcctc ccagcctgca                                30

SEQ ID NO: 122          moltype = DNA  length = 31
FEATURE                 Location/Qualifiers
source                  1..31
                        mol_type = genomic DNA
                        organism = Homo sapiens
SEQUENCE: 122
tacattacag ccgtgcagcc tgaagattca g                              31

SEQ ID NO: 123          moltype = DNA  length = 30
FEATURE                 Location/Qualifiers
source                  1..30
                        mol_type = genomic DNA
                        organism = Homo sapiens
SEQUENCE: 123
aatctgagga aaccctctgt gcagtggagt                                30

SEQ ID NO: 124          moltype = DNA  length = 30
FEATURE                 Location/Qualifiers
source                  1..30
                        mol_type = genomic DNA
                        organism = Homo sapiens
SEQUENCE: 124
gaaacctcct tccacctgac gaaaccctca                                30

SEQ ID NO: 125          moltype = DNA  length = 30
FEATURE                 Location/Qualifiers
source                  1..30
                        mol_type = genomic DNA
                        organism = Homo sapiens
SEQUENCE: 125
caatctgagg aaaccctctg tgcattggag                                30

SEQ ID NO: 126          moltype = DNA  length = 30
FEATURE                 Location/Qualifiers
source                  1..30
                        mol_type = genomic DNA
                        organism = Homo sapiens
SEQUENCE: 126
cacctgacga aaccctcagc ccatatgagc                                30

SEQ ID NO: 127          moltype = DNA  length = 30
FEATURE                 Location/Qualifiers
source                  1..30
                        mol_type = genomic DNA
                        organism = Homo sapiens
SEQUENCE: 127
ggaaaccctc agtccatata agcgacacgg                                30

SEQ ID NO: 128          moltype = DNA  length = 30
FEATURE                 Location/Qualifiers
source                  1..30
                        mol_type = genomic DNA
                        organism = Homo sapiens
SEQUENCE: 128
gaggaaacca tcaacccatg tgagtgatgc                                30

SEQ ID NO: 129          moltype = DNA  length = 32
FEATURE                 Location/Qualifiers
source                  1..32
                        mol_type = genomic DNA
                        organism = Homo sapiens
SEQUENCE: 129
ggaaggaaca aaggttttga agccatgtac cg                             32

SEQ ID NO: 130          moltype = DNA  length = 30
FEATURE                 Location/Qualifiers
source                  1..30
                        mol_type = genomic DNA
                        organism = Homo sapiens
SEQUENCE: 130
tccacttgga gaaaggctca gttcaagtgt                                30

SEQ ID NO: 131          moltype = DNA  length = 30
FEATURE                 Location/Qualifiers
```

```
source                  1..30
                        mol_type = genomic DNA
                        organism = Homo sapiens
SEQUENCE: 131
gcagacacaa agcaaagctc tctgcacatc                                   30

SEQ ID NO: 132          moltype = DNA  length = 30
FEATURE                 Location/Qualifiers
source                  1..30
                        mol_type = genomic DNA
                        organism = Homo sapiens
SEQUENCE: 132
gccagccagt atatttccct gctcatcaga                                   30

SEQ ID NO: 133          moltype = DNA  length = 30
FEATURE                 Location/Qualifiers
source                  1..30
                        mol_type = genomic DNA
                        organism = Homo sapiens
SEQUENCE: 133
gccagccagt atgtttctct gctcatcaga                                   30

SEQ ID NO: 134          moltype = DNA  length = 30
FEATURE                 Location/Qualifiers
source                  1..30
                        mol_type = genomic DNA
                        organism = Homo sapiens
SEQUENCE: 134
ggtttacagc acaggtcgat aaatccagca                                   30

SEQ ID NO: 135          moltype = DNA  length = 30
FEATURE                 Location/Qualifiers
source                  1..30
                        mol_type = genomic DNA
                        organism = Homo sapiens
SEQUENCE: 135
gccaaacatt tctccctgca catcacagag                                   30

SEQ ID NO: 136          moltype = DNA  length = 30
FEATURE                 Location/Qualifiers
source                  1..30
                        mol_type = genomic DNA
                        organism = Homo sapiens
SEQUENCE: 136
tctgcaaatt gcagctactc aacctggaga                                   30

SEQ ID NO: 137          moltype = DNA  length = 30
FEATURE                 Location/Qualifiers
source                  1..30
                        mol_type = genomic DNA
                        organism = Homo sapiens
SEQUENCE: 137
gccaaccttg tcatctccgc ttcacaactg                                   30

SEQ ID NO: 138          moltype = DNA  length = 31
FEATURE                 Location/Qualifiers
source                  1..31
                        mol_type = genomic DNA
                        organism = Homo sapiens
SEQUENCE: 138
gaccttaaca aaggcgagac atctttccac c                                 31

SEQ ID NO: 139          moltype = DNA  length = 30
FEATURE                 Location/Qualifiers
source                  1..30
                        mol_type = genomic DNA
                        organism = Homo sapiens
SEQUENCE: 139
gtcacgcttg acacttccaa gaaaagcagt                                   30

SEQ ID NO: 140          moltype = DNA  length = 30
FEATURE                 Location/Qualifiers
source                  1..30
                        mol_type = genomic DNA
                        organism = Homo sapiens
SEQUENCE: 140
cctatcaaga gtgacagttc cttccacctg                                   30

SEQ ID NO: 141          moltype = DNA  length = 30
```

```
FEATURE                Location/Qualifiers
source                 1..30
                       mol_type = genomic DNA
                       organism = Homo sapiens
SEQUENCE: 141
ggaacttcca gaaatccacc agttccttca                                   30

SEQ ID NO: 142         moltype = DNA  length = 29
FEATURE                Location/Qualifiers
source                 1..29
                       mol_type = genomic DNA
                       organism = Homo sapiens
SEQUENCE: 142
agaaggaaag ctttctgcac atcacagcc                                    29

SEQ ID NO: 143         moltype = DNA  length = 30
FEATURE                Location/Qualifiers
source                 1..30
                       mol_type = genomic DNA
                       organism = Homo sapiens
SEQUENCE: 143
caagtggaag acttaatgcc tcgctggata                                   30

SEQ ID NO: 144         moltype = DNA  length = 30
FEATURE                Location/Qualifiers
source                 1..30
                       mol_type = genomic DNA
                       organism = Homo sapiens
SEQUENCE: 144
gactgtcgct acggaacgct acagcttatt                                   30

SEQ ID NO: 145         moltype = DNA  length = 30
FEATURE                Location/Qualifiers
source                 1..30
                       mol_type = genomic DNA
                       organism = Homo sapiens
SEQUENCE: 145
tgccaagcag ttctcatcgc atatcatgga                                   30

SEQ ID NO: 146         moltype = DNA  length = 30
FEATURE                Location/Qualifiers
source                 1..30
                       mol_type = genomic DNA
                       organism = Homo sapiens
SEQUENCE: 146
gccactctta ataccaagga gggttacagc                                   30

SEQ ID NO: 147         moltype = DNA  length = 30
FEATURE                Location/Qualifiers
source                 1..30
                       mol_type = genomic DNA
                       organism = Homo sapiens
SEQUENCE: 147
cacatcacag ccacccagac tacagatgta                                   30

SEQ ID NO: 148         moltype = DNA  length = 30
FEATURE                Location/Qualifiers
source                 1..30
                       mol_type = genomic DNA
                       organism = Homo sapiens
SEQUENCE: 148
tcatcacaga agacagaaag tccagcacct                                   30

SEQ ID NO: 149         moltype = DNA  length = 30
FEATURE                Location/Qualifiers
source                 1..30
                       mol_type = genomic DNA
                       organism = Homo sapiens
SEQUENCE: 149
agaaagtcca gtaccttgat cctgcaccgt                                   30

SEQ ID NO: 150         moltype = DNA  length = 30
FEATURE                Location/Qualifiers
source                 1..30
                       mol_type = genomic DNA
                       organism = Homo sapiens
SEQUENCE: 150
gttctctcca catcactgca gcccagactg                                   30
```

```
SEQ ID NO: 151         moltype = DNA  length = 30
FEATURE                Location/Qualifiers
source                 1..30
                       mol_type = genomic DNA
                       organism = Homo sapiens
SEQUENCE: 151
aaagtgccaa gcacctctct ctgcacattg                                   30

SEQ ID NO: 152         moltype = DNA  length = 30
FEATURE                Location/Qualifiers
source                 1..30
                       mol_type = genomic DNA
                       organism = Homo sapiens
SEQUENCE: 152
ctgtacctta cggcctccca gctcagttac                                   30

SEQ ID NO: 153         moltype = DNA  length = 30
FEATURE                Location/Qualifiers
source                 1..30
                       mol_type = genomic DNA
                       organism = Homo sapiens
SEQUENCE: 153
gccaagttgg atgagaaaaa gcagcaaagt                                   30

SEQ ID NO: 154         moltype = DNA  length = 30
FEATURE                Location/Qualifiers
source                 1..30
                       mol_type = genomic DNA
                       organism = Homo sapiens
SEQUENCE: 154
gacctcaaat ggaagactga ctgctcagtt                                   30

SEQ ID NO: 155         moltype = DNA  length = 30
FEATURE                Location/Qualifiers
source                 1..30
                       mol_type = genomic DNA
                       organism = Homo sapiens
SEQUENCE: 155
tttcagcatc ctgaacatca cagccaccca                                   30

SEQ ID NO: 156         moltype = DNA  length = 30
FEATURE                Location/Qualifiers
source                 1..30
                       mol_type = genomic DNA
                       organism = Homo sapiens
SEQUENCE: 156
ccttcagtct caagatctca gactcacagc                                   30

SEQ ID NO: 157         moltype = DNA  length = 29
FEATURE                Location/Qualifiers
source                 1..29
                       mol_type = genomic DNA
                       organism = Homo sapiens
SEQUENCE: 157
aatggcctca cttgatacca aagcccgtc                                    29

SEQ ID NO: 158         moltype = DNA  length = 30
FEATURE                Location/Qualifiers
source                 1..30
                       mol_type = genomic DNA
                       organism = Homo sapiens
SEQUENCE: 158
ctcccccatt gtgaaatatt cagtccaggt                                   30

SEQ ID NO: 159         moltype = DNA  length = 30
FEATURE                Location/Qualifiers
source                 1..30
                       mol_type = genomic DNA
                       organism = Homo sapiens
SEQUENCE: 159
catacaggaa aagcacagct ccctgcacat                                   30

SEQ ID NO: 160         moltype = DNA  length = 31
FEATURE                Location/Qualifiers
source                 1..31
                       mol_type = genomic DNA
                       organism = Homo sapiens
SEQUENCE: 160
atatcgcagc ctctcatctg ggagattcag c                                 31
```

-continued

```
SEQ ID NO: 161          moltype = DNA  length = 31
FEATURE                 Location/Qualifiers
source                  1..31
                        mol_type = genomic DNA
                        organism = Homo sapiens
SEQUENCE: 161
caggagctcc agatgaaaga ctctgcctct t                                 31

SEQ ID NO: 162          moltype = DNA  length = 32
FEATURE                 Location/Qualifiers
source                  1..32
                        mol_type = genomic DNA
                        organism = Homo sapiens
SEQUENCE: 162
acttccttcc acttgaggaa accctcagtc ca                                32

SEQ ID NO: 163          moltype = DNA  length = 64
FEATURE                 Location/Qualifiers
source                  1..64
                        mol_type = other DNA
                        organism = synthetic construct
SEQUENCE: 163
gtgactggag ttcagacgtg tgctcttccg atctgaagga gctccagatg aaagactctg  60
cctc                                                               64

SEQ ID NO: 164          moltype = DNA  length = 64
FEATURE                 Location/Qualifiers
source                  1..64
                        mol_type = other DNA
                        organism = synthetic construct
SEQUENCE: 164
gtgactggag ttcagacgtg tgctcttccg atctgttctc ttcatcgctg ctcatcctcc  60
aggt                                                               64

SEQ ID NO: 165          moltype = DNA  length = 64
FEATURE                 Location/Qualifiers
source                  1..64
                        mol_type = other DNA
                        organism = synthetic construct
SEQUENCE: 165
gtgactggag ttcagacgtg tgctcttccg atctcttgtg agcgactccg ctttgtactt  60
ctgt                                                               64

SEQ ID NO: 166          moltype = DNA  length = 64
FEATURE                 Location/Qualifiers
source                  1..64
                        mol_type = other DNA
                        organism = synthetic construct
SEQUENCE: 166
gtgactggag ttcagacgtg tgctcttccg atctttatcc ctgccgacag aaagtccagc  60
actc                                                               64

SEQ ID NO: 167          moltype = DNA  length = 65
FEATURE                 Location/Qualifiers
source                  1..65
                        mol_type = other DNA
                        organism = synthetic construct
SEQUENCE: 167
gtgactggag ttcagacgtg tgctcttccg atctaaggat aaacatctgt ctctgcgcat  60
tgcag                                                              65

SEQ ID NO: 168          moltype = DNA  length = 64
FEATURE                 Location/Qualifiers
source                  1..64
                        mol_type = other DNA
                        organism = synthetic construct
SEQUENCE: 168
gtgactggag ttcagacgtg tgctcttccg atctttgttt catatcacag cctcccagcc  60
tgca                                                               64

SEQ ID NO: 169          moltype = DNA  length = 65
FEATURE                 Location/Qualifiers
source                  1..65
                        mol_type = other DNA
                        organism = synthetic construct
SEQUENCE: 169
gtgactggag ttcagacgtg tgctcttccg atcttacatt acagccgtgc agcctgaaga  60
ttcag                                                              65
```

```
SEQ ID NO: 170          moltype = DNA  length = 64
FEATURE                 Location/Qualifiers
source                  1..64
                        mol_type = other DNA
                        organism = synthetic construct
SEQUENCE: 170
gtgactggag ttcagacgtg tgctcttccg atctaatctg aggaaaccct ctgtgcagtg  60
gagt                                                                64

SEQ ID NO: 171          moltype = DNA  length = 64
FEATURE                 Location/Qualifiers
source                  1..64
                        mol_type = other DNA
                        organism = synthetic construct
SEQUENCE: 171
gtgactggag ttcagacgtg tgctcttccg atctgaaacc tccttccacc tgacgaaacc  60
ctca                                                                64

SEQ ID NO: 172          moltype = DNA  length = 64
FEATURE                 Location/Qualifiers
source                  1..64
                        mol_type = other DNA
                        organism = synthetic construct
SEQUENCE: 172
gtgactggag ttcagacgtg tgctcttccg atctcaatct gaggaaaccc tctgtgcatt  60
ggag                                                                64

SEQ ID NO: 173          moltype = DNA  length = 64
FEATURE                 Location/Qualifiers
source                  1..64
                        mol_type = other DNA
                        organism = synthetic construct
SEQUENCE: 173
gtgactggag ttcagacgtg tgctcttccg atctcacctg acgaaaccct cagcccatat  60
gagc                                                                64

SEQ ID NO: 174          moltype = DNA  length = 64
FEATURE                 Location/Qualifiers
source                  1..64
                        mol_type = other DNA
                        organism = synthetic construct
SEQUENCE: 174
gtgactggag ttcagacgtg tgctcttccg atctggaaac cctcagtcca tataagcgac  60
acgg                                                                64

SEQ ID NO: 175          moltype = DNA  length = 64
FEATURE                 Location/Qualifiers
source                  1..64
                        mol_type = other DNA
                        organism = synthetic construct
SEQUENCE: 175
gtgactggag ttcagacgtg tgctcttccg atctgaggaa accatcaacc catgtgagtg  60
atgc                                                                64

SEQ ID NO: 176          moltype = DNA  length = 66
FEATURE                 Location/Qualifiers
source                  1..66
                        mol_type = other DNA
                        organism = synthetic construct
SEQUENCE: 176
gtgactggag ttcagacgtg tgctcttccg atctggaagg aacaaaggtt ttgaagccat  60
gtaccg                                                              66

SEQ ID NO: 177          moltype = DNA  length = 64
FEATURE                 Location/Qualifiers
source                  1..64
                        mol_type = other DNA
                        organism = synthetic construct
SEQUENCE: 177
gtgactggag ttcagacgtg tgctcttccg atcttccact tggagaaagg ctcagttcaa  60
gtgt                                                                64

SEQ ID NO: 178          moltype = DNA  length = 64
FEATURE                 Location/Qualifiers
source                  1..64
                        mol_type = other DNA
                        organism = synthetic construct
SEQUENCE: 178
```

```
gtgactggag ttcagacgtg tgctcttccg atctgcagac acaaagcaaa gctctctgca  60
catc                                                                64

SEQ ID NO: 179          moltype = DNA  length = 64
FEATURE                 Location/Qualifiers
source                  1..64
                        mol_type = other DNA
                        organism = synthetic construct
SEQUENCE: 179
gtgactggag ttcagacgtg tgctcttccg atctgccagc cagtatattt ccctgctcat  60
caga                                                                64

SEQ ID NO: 180          moltype = DNA  length = 64
FEATURE                 Location/Qualifiers
source                  1..64
                        mol_type = other DNA
                        organism = synthetic construct
SEQUENCE: 180
gtgactggag ttcagacgtg tgctcttccg atctgccagc cagtatgttt ctctgctcat  60
caga                                                                64

SEQ ID NO: 181          moltype = DNA  length = 64
FEATURE                 Location/Qualifiers
source                  1..64
                        mol_type = other DNA
                        organism = synthetic construct
SEQUENCE: 181
gtgactggag ttcagacgtg tgctcttccg atctggttta cagcacaggt cgataaatcc  60
agca                                                                64

SEQ ID NO: 182          moltype = DNA  length = 64
FEATURE                 Location/Qualifiers
source                  1..64
                        mol_type = other DNA
                        organism = synthetic construct
SEQUENCE: 182
gtgactggag ttcagacgtg tgctcttccg atctgccaaa catttctccc tgcacatcac  60
agag                                                                64

SEQ ID NO: 183          moltype = DNA  length = 64
FEATURE                 Location/Qualifiers
source                  1..64
                        mol_type = other DNA
                        organism = synthetic construct
SEQUENCE: 183
gtgactggag ttcagacgtg tgctcttccg atcttctgca aattgcagct actcaacctg  60
gaga                                                                64

SEQ ID NO: 184          moltype = DNA  length = 64
FEATURE                 Location/Qualifiers
source                  1..64
                        mol_type = other DNA
                        organism = synthetic construct
SEQUENCE: 184
gtgactggag ttcagacgtg tgctcttccg atctgccaac cttgtcatct ccgcttcaca  60
actg                                                                64

SEQ ID NO: 185          moltype = DNA  length = 65
FEATURE                 Location/Qualifiers
source                  1..65
                        mol_type = other DNA
                        organism = synthetic construct
SEQUENCE: 185
gtgactggag ttcagacgtg tgctcttccg atctgacctt aacaaaggcg agacatcttt  60
ccacc                                                               65

SEQ ID NO: 186          moltype = DNA  length = 64
FEATURE                 Location/Qualifiers
source                  1..64
                        mol_type = other DNA
                        organism = synthetic construct
SEQUENCE: 186
gtgactggag ttcagacgtg tgctcttccg atctgtcacg cttgacactt ccaagaaaag  60
cagt                                                                64

SEQ ID NO: 187          moltype = DNA  length = 64
FEATURE                 Location/Qualifiers
source                  1..64
                        mol_type = other DNA
```

```
                        organism = synthetic construct
SEQUENCE: 187
gtgactggag ttcagacgtg tgctcttccg atctcctatc aagagtgaca gttccttcca  60
cctg                                                               64

SEQ ID NO: 188          moltype = DNA  length = 64
FEATURE                 Location/Qualifiers
source                  1..64
                        mol_type = other DNA
                        organism = synthetic construct
SEQUENCE: 188
gtgactggag ttcagacgtg tgctcttccg atctggaact tccagaaatc caccagttcc  60
ttca                                                               64

SEQ ID NO: 189          moltype = DNA  length = 63
FEATURE                 Location/Qualifiers
source                  1..63
                        mol_type = other DNA
                        organism = synthetic construct
SEQUENCE: 189
gtgactggag ttcagacgtg tgctcttccg atctagaagg aaagctttct gcacatcaca  60
gcc                                                                63

SEQ ID NO: 190          moltype = DNA  length = 64
FEATURE                 Location/Qualifiers
source                  1..64
                        mol_type = other DNA
                        organism = synthetic construct
SEQUENCE: 190
gtgactggag ttcagacgtg tgctcttccg atctcaagtg gaagacttaa tgcctcgctg  60
gata                                                               64

SEQ ID NO: 191          moltype = DNA  length = 64
FEATURE                 Location/Qualifiers
source                  1..64
                        mol_type = other DNA
                        organism = synthetic construct
SEQUENCE: 191
gtgactggag ttcagacgtg tgctcttccg atctgactgt cgctacggaa cgctacagct  60
tatt                                                               64

SEQ ID NO: 192          moltype = DNA  length = 64
FEATURE                 Location/Qualifiers
source                  1..64
                        mol_type = other DNA
                        organism = synthetic construct
SEQUENCE: 192
gtgactggag ttcagacgtg tgctcttccg atcttgccaa gcagttctca tcgcatatca  60
tgga                                                               64

SEQ ID NO: 193          moltype = DNA  length = 64
FEATURE                 Location/Qualifiers
source                  1..64
                        mol_type = other DNA
                        organism = synthetic construct
SEQUENCE: 193
gtgactggag ttcagacgtg tgctcttccg atctgccact cttaatacca aggagggtta  60
cagc                                                               64

SEQ ID NO: 194          moltype = DNA  length = 64
FEATURE                 Location/Qualifiers
source                  1..64
                        mol_type = other DNA
                        organism = synthetic construct
SEQUENCE: 194
gtgactggag ttcagacgtg tgctcttccg atctcacatc acagccaccc agactacaga  60
tgta                                                               64

SEQ ID NO: 195          moltype = DNA  length = 64
FEATURE                 Location/Qualifiers
source                  1..64
                        mol_type = other DNA
                        organism = synthetic construct
SEQUENCE: 195
gtgactggag ttcagacgtg tgctcttccg atcttcatca cagaagacag aaagtccagc  60
acct                                                               64

SEQ ID NO: 196          moltype = DNA  length = 64
FEATURE                 Location/Qualifiers
```

```
source                  1..64
                        mol_type = other DNA
                        organism = synthetic construct
SEQUENCE: 196
gtgactggag ttcagacgtg tgctcttccg atctagaaag tccagtacct tgatcctgca  60
ccgt                                                               64

SEQ ID NO: 197          moltype = DNA  length = 64
FEATURE                 Location/Qualifiers
source                  1..64
                        mol_type = other DNA
                        organism = synthetic construct
SEQUENCE: 197
gtgactggag ttcagacgtg tgctcttccg atctgttctc tccacatcac tgcagcccag  60
actg                                                               64

SEQ ID NO: 198          moltype = DNA  length = 64
FEATURE                 Location/Qualifiers
source                  1..64
                        mol_type = other DNA
                        organism = synthetic construct
SEQUENCE: 198
gtgactggag ttcagacgtg tgctcttccg atctaaagtg ccaagcacct ctctctgcac  60
attg                                                               64

SEQ ID NO: 199          moltype = DNA  length = 64
FEATURE                 Location/Qualifiers
source                  1..64
                        mol_type = other DNA
                        organism = synthetic construct
SEQUENCE: 199
gtgactggag ttcagacgtg tgctcttccg atctctgtac cttacggcct cccagctcag  60
ttac                                                               64

SEQ ID NO: 200          moltype = DNA  length = 64
FEATURE                 Location/Qualifiers
source                  1..64
                        mol_type = other DNA
                        organism = synthetic construct
SEQUENCE: 200
gtgactggag ttcagacgtg tgctcttccg atctgccaag ttggatgaga aaaagcagca  60
aagt                                                               64

SEQ ID NO: 201          moltype = DNA  length = 64
FEATURE                 Location/Qualifiers
source                  1..64
                        mol_type = other DNA
                        organism = synthetic construct
SEQUENCE: 201
gtgactggag ttcagacgtg tgctcttccg atctgacctc aaatggaaga ctgactgctc  60
agtt                                                               64

SEQ ID NO: 202          moltype = DNA  length = 64
FEATURE                 Location/Qualifiers
source                  1..64
                        mol_type = other DNA
                        organism = synthetic construct
SEQUENCE: 202
gtgactggag ttcagacgtg tgctcttccg atcttttcag catcctgaac atcacagcca  60
ccca                                                               64

SEQ ID NO: 203          moltype = DNA  length = 64
FEATURE                 Location/Qualifiers
source                  1..64
                        mol_type = other DNA
                        organism = synthetic construct
SEQUENCE: 203
gtgactggag ttcagacgtg tgctcttccg atctccttca gtctcaagat ctcagactca  60
cagc                                                               64

SEQ ID NO: 204          moltype = DNA  length = 63
FEATURE                 Location/Qualifiers
source                  1..63
                        mol_type = other DNA
                        organism = synthetic construct
SEQUENCE: 204
gtgactggag ttcagacgtg tgctcttccg atctaatggc ctcacttgat accaaagccc  60
gtc                                                                63
```

```
SEQ ID NO: 205         moltype = DNA  length = 64
FEATURE                Location/Qualifiers
source                 1..64
                       mol_type = other DNA
                       organism = synthetic construct
SEQUENCE: 205
gtgactggag ttcagacgtg tgctcttccg atctctcccc cattgtgaaa tattcagtcc  60
aggt                                                               64

SEQ ID NO: 206         moltype = DNA  length = 64
FEATURE                Location/Qualifiers
source                 1..64
                       mol_type = other DNA
                       organism = synthetic construct
SEQUENCE: 206
gtgactggag ttcagacgtg tgctcttccg atctcataca ggaaaagcac agctccctgc  60
acat                                                               64

SEQ ID NO: 207         moltype = DNA  length = 65
FEATURE                Location/Qualifiers
source                 1..65
                       mol_type = other DNA
                       organism = synthetic construct
SEQUENCE: 207
gtgactggag ttcagacgtg tgctcttccg atctatatcg cagcctctca tctgggagat  60
tcagc                                                              65

SEQ ID NO: 208         moltype = DNA  length = 65
FEATURE                Location/Qualifiers
source                 1..65
                       mol_type = other DNA
                       organism = synthetic construct
SEQUENCE: 208
gtgactggag ttcagacgtg tgctcttccg atctcaggag ctccagatga aagactctgc  60
ctctt                                                              65

SEQ ID NO: 209         moltype = DNA  length = 66
FEATURE                Location/Qualifiers
source                 1..66
                       mol_type = other DNA
                       organism = synthetic construct
SEQUENCE: 209
gtgactggag ttcagacgtg tgctcttccg atctacttcc ttccacttga ggaaaccctc  60
agtcca                                                             66

SEQ ID NO: 210         moltype = DNA  length = 34
FEATURE                Location/Qualifiers
source                 1..34
                       mol_type = other DNA
                       organism = synthetic construct
SEQUENCE: 210
gtgactggag ttcagacgtg tgctcttccg atct                              34

SEQ ID NO: 211         moltype = DNA  length = 33
FEATURE                Location/Qualifiers
source                 1..33
                       mol_type = other DNA
                       organism = synthetic construct
SEQUENCE: 211
aaaaaccaag tggagcagag tcctcagtcc ctg                               33

SEQ ID NO: 212         moltype = DNA  length = 31
FEATURE                Location/Qualifiers
source                 1..31
                       mol_type = other DNA
                       organism = synthetic construct
SEQUENCE: 212
aaacaggagg tgacgcagat tcctgcagct c                                 31

SEQ ID NO: 213         moltype = DNA  length = 32
FEATURE                Location/Qualifiers
source                 1..32
                       mol_type = other DNA
                       organism = synthetic construct
SEQUENCE: 213
aaggaccaag tgtttcagcc ttccacagtg gc                                32

SEQ ID NO: 214         moltype = DNA  length = 28
FEATURE                Location/Qualifiers
```

```
source                  1..28
                        mol_type = other DNA
                        organism = synthetic construct
SEQUENCE: 214
acccagcttg acagccaagt ccctgtct                                      28

SEQ ID NO: 215          moltype = DNA  length = 30
FEATURE                 Location/Qualifiers
source                  1..30
                        mol_type = other DNA
                        organism = synthetic construct
SEQUENCE: 215
acccagcttg atggccacat cactgtctct                                    30

SEQ ID NO: 216          moltype = DNA  length = 25
FEATURE                 Location/Qualifiers
source                  1..25
                        mol_type = other DNA
                        organism = synthetic construct
SEQUENCE: 216
acccagcttg gcagccacgt ctctg                                         25

SEQ ID NO: 217          moltype = DNA  length = 31
FEATURE                 Location/Qualifiers
source                  1..31
                        mol_type = other DNA
                        organism = synthetic construct
SEQUENCE: 217
actcaagcgc agactgaaat ttctgtggtg g                                  31

SEQ ID NO: 218          moltype = DNA  length = 29
FEATURE                 Location/Qualifiers
source                  1..29
                        mol_type = other DNA
                        organism = synthetic construct
SEQUENCE: 218
agaaggaggt ggagcaggat cctggacca                                     29

SEQ ID NO: 219          moltype = DNA  length = 34
FEATURE                 Location/Qualifiers
source                  1..34
                        mol_type = other DNA
                        organism = synthetic construct
SEQUENCE: 219
agaattccga ggctctgaac attcaggagg gtaa                               34

SEQ ID NO: 220          moltype = DNA  length = 30
FEATURE                 Location/Qualifiers
source                  1..30
                        mol_type = other DNA
                        organism = synthetic construct
SEQUENCE: 220
agagagtgac tcagcccgag aagctcctct                                    30

SEQ ID NO: 221          moltype = DNA  length = 27
FEATURE                 Location/Qualifiers
source                  1..27
                        mol_type = other DNA
                        organism = synthetic construct
SEQUENCE: 221
agagcccagt cagtgaccca gcctgac                                       27

SEQ ID NO: 222          moltype = DNA  length = 27
FEATURE                 Location/Qualifiers
source                  1..27
                        mol_type = other DNA
                        organism = synthetic construct
SEQUENCE: 222
agagcccagt cagtgaccca gcctgac                                       27

SEQ ID NO: 223          moltype = DNA  length = 27
FEATURE                 Location/Qualifiers
source                  1..27
                        mol_type = other DNA
                        organism = synthetic construct
SEQUENCE: 223
agctgctgga gcagagccct cagtttc                                       27

SEQ ID NO: 224          moltype = DNA  length = 33
```

```
FEATURE                Location/Qualifiers
source                 1..33
                       mol_type = other DNA
                       organism = synthetic construct
SEQUENCE: 224
agtcaacagg gagaagagga tcctcaggcc ttg                              33

SEQ ID NO: 225         moltype = DNA  length = 31
FEATURE                Location/Qualifiers
source                 1..31
                       mol_type = other DNA
                       organism = synthetic construct
SEQUENCE: 225
agtggagact cggttaccca gacagaaggc c                                31

SEQ ID NO: 226         moltype = DNA  length = 31
FEATURE                Location/Qualifiers
source                 1..31
                       mol_type = other DNA
                       organism = synthetic construct
SEQUENCE: 226
agtggagcag agtcctccag acctgattct c                                31

SEQ ID NO: 227         moltype = DNA  length = 28
FEATURE                Location/Qualifiers
source                 1..28
                       mol_type = other DNA
                       organism = synthetic construct
SEQUENCE: 227
agtgtggggc tgcatcttcc taccctga                                    28

SEQ ID NO: 228         moltype = DNA  length = 37
FEATURE                Location/Qualifiers
source                 1..37
                       mol_type = other DNA
                       organism = synthetic construct
SEQUENCE: 228
atactgaacg tggaacaaag tcctcagtca ctgcatg                          37

SEQ ID NO: 229         moltype = DNA  length = 30
FEATURE                Location/Qualifiers
source                 1..30
                       mol_type = other DNA
                       organism = synthetic construct
SEQUENCE: 229
attcagtgac ccagatggaa gggccagtga                                  30

SEQ ID NO: 230         moltype = DNA  length = 29
FEATURE                Location/Qualifiers
source                 1..29
                       mol_type = other DNA
                       organism = synthetic construct
SEQUENCE: 230
attgatgcta agaccaccca gcccacctc                                   29

SEQ ID NO: 231         moltype = DNA  length = 31
FEATURE                Location/Qualifiers
source                 1..31
                       mol_type = other DNA
                       organism = synthetic construct
SEQUENCE: 231
cagaaggagg tggagcagaa ttctggaccc c                                31

SEQ ID NO: 232         moltype = DNA  length = 28
FEATURE                Location/Qualifiers
source                 1..28
                       mol_type = other DNA
                       organism = synthetic construct
SEQUENCE: 232
cagcaattca gtcaagcaga cgggccaa                                    28

SEQ ID NO: 233         moltype = DNA  length = 29
FEATURE                Location/Qualifiers
source                 1..29
                       mol_type = other DNA
                       organism = synthetic construct
SEQUENCE: 233
ccaacaacca gtgcagagtc ctcaagccg                                   29
```

-continued

```
SEQ ID NO: 234         moltype = DNA  length = 27
FEATURE                Location/Qualifiers
source                 1..27
                       mol_type = other DNA
                       organism = synthetic construct
SEQUENCE: 234
cggaaggagg tggagcagga tcctgga                                      27

SEQ ID NO: 235         moltype = DNA  length = 35
FEATURE                Location/Qualifiers
source                 1..35
                       mol_type = other DNA
                       organism = synthetic construct
SEQUENCE: 235
ctacatacgc cggagcagag tccttcattc ctgag                             35

SEQ ID NO: 236         moltype = DNA  length = 31
FEATURE                Location/Qualifiers
source                 1..31
                       mol_type = other DNA
                       organism = synthetic construct
SEQUENCE: 236
ctcaaaccca accaggaatg ttcgtgcagg a                                 31

SEQ ID NO: 237         moltype = DNA  length = 35
FEATURE                Location/Qualifiers
source                 1..35
                       mol_type = other DNA
                       organism = synthetic construct
SEQUENCE: 237
cttgctaaga ccacccagcc catctccatg gactc                             35

SEQ ID NO: 238         moltype = DNA  length = 33
FEATURE                Location/Qualifiers
source                 1..33
                       mol_type = other DNA
                       organism = synthetic construct
SEQUENCE: 238
gaaaaccagg tggagcacag ccctcatttt ctg                               33

SEQ ID NO: 239         moltype = DNA  length = 35
FEATURE                Location/Qualifiers
source                 1..35
                       mol_type = other DNA
                       organism = synthetic construct
SEQUENCE: 239
gaagacaagg tggtacaaag ccctctatct ctggt                             35

SEQ ID NO: 240         moltype = DNA  length = 27
FEATURE                Location/Qualifiers
source                 1..27
                       mol_type = other DNA
                       organism = synthetic construct
SEQUENCE: 240
gaagaccagg tgacgcagag tcccgag                                      27

SEQ ID NO: 241         moltype = DNA  length = 31
FEATURE                Location/Qualifiers
source                 1..31
                       mol_type = other DNA
                       organism = synthetic construct
SEQUENCE: 241
gaccagcagc aggtgaaaca aagtcctcaa t                                 31

SEQ ID NO: 242         moltype = DNA  length = 28
FEATURE                Location/Qualifiers
source                 1..28
                       mol_type = other DNA
                       organism = synthetic construct
SEQUENCE: 242
gagcagagtc ctcagaacct gactgccc                                     28

SEQ ID NO: 243         moltype = DNA  length = 35
FEATURE                Location/Qualifiers
source                 1..35
                       mol_type = other DNA
                       organism = synthetic construct
SEQUENCE: 243
gatgaccagc aagttaagca aaattcacca tccct                             35
```

```
SEQ ID NO: 244         moltype = DNA  length = 29
FEATURE                Location/Qualifiers
source                 1..29
                       mol_type = other DNA
                       organism = synthetic construct
SEQUENCE: 244
gccaagaact ggagcagagt cctcagtcc                                  29

SEQ ID NO: 245         moltype = DNA  length = 26
FEATURE                Location/Qualifiers
source                 1..26
                       mol_type = other DNA
                       organism = synthetic construct
SEQUENCE: 245
gcccagtcgg tgacccagct tgacag                                     26

SEQ ID NO: 246         moltype = DNA  length = 30
FEATURE                Location/Qualifiers
source                 1..30
                       mol_type = other DNA
                       organism = synthetic construct
SEQUENCE: 246
gcccagtctg tgagccagca taaccaccac                                 30

SEQ ID NO: 247         moltype = DNA  length = 30
FEATURE                Location/Qualifiers
source                 1..30
                       mol_type = other DNA
                       organism = synthetic construct
SEQUENCE: 247
gcctgttcac ttgccttgta accactccac                                 30

SEQ ID NO: 248         moltype = DNA  length = 31
FEATURE                Location/Qualifiers
source                 1..31
                       mol_type = other DNA
                       organism = synthetic construct
SEQUENCE: 248
gctcagtcag tggctcagcc ggaagatcag g                               31

SEQ ID NO: 249         moltype = DNA  length = 35
FEATURE                Location/Qualifiers
source                 1..35
                       mol_type = other DNA
                       organism = synthetic construct
SEQUENCE: 249
ggacaaaaca ttgaccagcc cactgagatg acagc                           35

SEQ ID NO: 250         moltype = DNA  length = 32
FEATURE                Location/Qualifiers
source                 1..32
                       mol_type = other DNA
                       organism = synthetic construct
SEQUENCE: 250
ggacaaagcc ttgagcagcc ctctgaagtg ac                              32

SEQ ID NO: 251         moltype = DNA  length = 37
FEATURE                Location/Qualifiers
source                 1..37
                       mol_type = other DNA
                       organism = synthetic construct
SEQUENCE: 251
ggacaacagg taatgcaaat tcctcagtac cagcatg                         37

SEQ ID NO: 252         moltype = DNA  length = 33
FEATURE                Location/Qualifiers
source                 1..33
                       mol_type = other DNA
                       organism = synthetic construct
SEQUENCE: 252
ggagagaatg tggagcagca tccttcaacc ctg                             33

SEQ ID NO: 253         moltype = DNA  length = 36
FEATURE                Location/Qualifiers
source                 1..36
                       mol_type = other DNA
                       organism = synthetic construct
SEQUENCE: 253
```

```
ggagaggatg tggagcagag tcttttcctg agtgtc                         36

SEQ ID NO: 254          moltype = DNA  length = 33
FEATURE                 Location/Qualifiers
source                  1..33
                        mol_type = other DNA
                        organism = synthetic construct
SEQUENCE: 254
ggagattcag tggtccagac agaaggccaa gtg                            33

SEQ ID NO: 255          moltype = DNA  length = 29
FEATURE                 Location/Qualifiers
source                  1..29
                        mol_type = other DNA
                        organism = synthetic construct
SEQUENCE: 255
gtctcaacca gagatgtctg tgcaggagg                                 29

SEQ ID NO: 256          moltype = DNA  length = 31
FEATURE                 Location/Qualifiers
source                  1..31
                        mol_type = other DNA
                        organism = synthetic construct
SEQUENCE: 256
gtggaacaaa accctctgtt cctgagcatg c                              31

SEQ ID NO: 257          moltype = DNA  length = 33
FEATURE                 Location/Qualifiers
source                  1..33
                        mol_type = other DNA
                        organism = synthetic construct
SEQUENCE: 257
gtggtcaaca gctgaatcag agtcctcaat cta                            33

SEQ ID NO: 258          moltype = DNA  length = 27
FEATURE                 Location/Qualifiers
source                  1..27
                        mol_type = other DNA
                        organism = synthetic construct
SEQUENCE: 258
gttccggcag gatccgggga gaagact                                   27

SEQ ID NO: 259          moltype = DNA  length = 31
FEATURE                 Location/Qualifiers
source                  1..31
                        mol_type = genomic DNA
                        organism = Homo sapiens
SEQUENCE: 259
gcctcctccc agacatctgt atatttctgc g                              31

SEQ ID NO: 260          moltype = DNA  length = 30
FEATURE                 Location/Qualifiers
source                  1..30
                        mol_type = genomic DNA
                        organism = Homo sapiens
SEQUENCE: 260
aatttccccc tcactctgga gtcagctacc                                30

SEQ ID NO: 261          moltype = DNA  length = 30
FEATURE                 Location/Qualifiers
source                  1..30
                        mol_type = genomic DNA
                        organism = Homo sapiens
SEQUENCE: 261
gatttcctcc tcactctgga gtccgctacc                                30

SEQ ID NO: 262          moltype = DNA  length = 31
FEATURE                 Location/Qualifiers
source                  1..31
                        mol_type = genomic DNA
                        organism = Homo sapiens
SEQUENCE: 262
aggctcaaag gagtagactc cactctcaag a                              31

SEQ ID NO: 263          moltype = DNA  length = 29
FEATURE                 Location/Qualifiers
source                  1..29
                        mol_type = genomic DNA
                        organism = Homo sapiens
```

```
SEQUENCE: 263
caagatccag cctgcaaagc ttgaggact                                29

SEQ ID NO: 264          moltype = DNA  length = 30
FEATURE                 Location/Qualifiers
source                  1..30
                        mol_type = genomic DNA
                        organism = Homo sapiens
SEQUENCE: 264
tagactccac tctcaagatc cagcctgcag                               30

SEQ ID NO: 265          moltype = DNA  length = 30
FEATURE                 Location/Qualifiers
source                  1..30
                        mol_type = genomic DNA
                        organism = Homo sapiens
SEQUENCE: 265
tggaacccag ggacttgggc ctatatttct                               30

SEQ ID NO: 266          moltype = DNA  length = 31
FEATURE                 Location/Qualifiers
source                  1..31
                        mol_type = genomic DNA
                        organism = Homo sapiens
SEQUENCE: 266
tcattctcta ctctgaagat ccagcctgca g                             31

SEQ ID NO: 267          moltype = DNA  length = 30
FEATURE                 Location/Qualifiers
source                  1..30
                        mol_type = genomic DNA
                        organism = Homo sapiens
SEQUENCE: 267
cattctccac tctgaagatc cagccctcag                               30

SEQ ID NO: 268          moltype = DNA  length = 31
FEATURE                 Location/Qualifiers
source                  1..31
                        mol_type = genomic DNA
                        organism = Homo sapiens
SEQUENCE: 268
catcattctc cactctgaag atccagccct c                             31

SEQ ID NO: 269          moltype = DNA  length = 30
FEATURE                 Location/Qualifiers
source                  1..30
                        mol_type = genomic DNA
                        organism = Homo sapiens
SEQUENCE: 269
cagcagagat gcctgatgca actttagcca                               30

SEQ ID NO: 270          moltype = DNA  length = 29
FEATURE                 Location/Qualifiers
source                  1..29
                        mol_type = genomic DNA
                        organism = Homo sapiens
SEQUENCE: 270
gaactgaaca tgagctcctt ggagctggg                                29

SEQ ID NO: 271          moltype = DNA  length = 31
FEATURE                 Location/Qualifiers
source                  1..31
                        mol_type = genomic DNA
                        organism = Homo sapiens
SEQUENCE: 271
ggaggattct ggagtttatt tctgtgccag c                             31

SEQ ID NO: 272          moltype = DNA  length = 30
FEATURE                 Location/Qualifiers
source                  1..30
                        mol_type = genomic DNA
                        organism = Homo sapiens
SEQUENCE: 272
ttctgctttc ttgacatccg ctcaccaggc                               30

SEQ ID NO: 273          moltype = DNA  length = 31
FEATURE                 Location/Qualifiers
source                  1..31
                        mol_type = genomic DNA
```

```
                        organism = Homo sapiens
SEQUENCE: 273
gagatccagg ctacgaagct tgaggattca g                                    31

SEQ ID NO: 274          moltype = DNA  length = 28
FEATURE                 Location/Qualifiers
source                  1..28
                        mol_type = genomic DNA
                        organism = Homo sapiens
SEQUENCE: 274
aacgtcttcc acgctgaaga tccatccc                                        28

SEQ ID NO: 275          moltype = DNA  length = 30
FEATURE                 Location/Qualifiers
source                  1..30
                        mol_type = genomic DNA
                        organism = Homo sapiens
SEQUENCE: 275
aggatccagc aggtagtgcg aggagattcg                                      30

SEQ ID NO: 276          moltype = DNA  length = 30
FEATURE                 Location/Qualifiers
source                  1..30
                        mol_type = genomic DNA
                        organism = Homo sapiens
SEQUENCE: 276
acccgacagc tttctatctc tgtgccagta                                      30

SEQ ID NO: 277          moltype = DNA  length = 30
FEATURE                 Location/Qualifiers
source                  1..30
                        mol_type = genomic DNA
                        organism = Homo sapiens
SEQUENCE: 277
gtgcccatcc tgaagacagc agcttctaca                                      30

SEQ ID NO: 278          moltype = DNA  length = 28
FEATURE                 Location/Qualifiers
source                  1..28
                        mol_type = genomic DNA
                        organism = Homo sapiens
SEQUENCE: 278
cacaaagctg gaggactcag ccatgtac                                        28

SEQ ID NO: 279          moltype = DNA  length = 30
FEATURE                 Location/Qualifiers
source                  1..30
                        mol_type = genomic DNA
                        organism = Homo sapiens
SEQUENCE: 279
tcaggggaca cagcactgta tttctgtgcc                                      30

SEQ ID NO: 280          moltype = DNA  length = 30
FEATURE                 Location/Qualifiers
source                  1..30
                        mol_type = genomic DNA
                        organism = Homo sapiens
SEQUENCE: 280
cacaccagcc aaacagcttt gtacttctgt                                      30

SEQ ID NO: 281          moltype = DNA  length = 28
FEATURE                 Location/Qualifiers
source                  1..28
                        mol_type = genomic DNA
                        organism = Homo sapiens
SEQUENCE: 281
aatcctgtcc tcagaaccgg gagacacg                                        28

SEQ ID NO: 282          moltype = DNA  length = 31
FEATURE                 Location/Qualifiers
source                  1..31
                        mol_type = genomic DNA
                        organism = Homo sapiens
SEQUENCE: 282
ccaaccagac agctctttac ttctgtgcca c                                    31

SEQ ID NO: 283          moltype = DNA  length = 30
FEATURE                 Location/Qualifiers
source                  1..30
```

```
                        mol_type = genomic DNA
                        organism = Homo sapiens
SEQUENCE: 283
cacatacctc tcagtacctc tgtgccagca                                30

SEQ ID NO: 284          moltype = DNA  length = 32
FEATURE                 Location/Qualifiers
source                  1..32
                        mol_type = genomic DNA
                        organism = Homo sapiens
SEQUENCE: 284
ccaaccagac atctgtgtat ctctatgcca gc                             32

SEQ ID NO: 285          moltype = DNA  length = 30
FEATURE                 Location/Qualifiers
source                  1..30
                        mol_type = genomic DNA
                        organism = Homo sapiens
SEQUENCE: 285
accagacctc tctgtacttc tgtgccagca                                30

SEQ ID NO: 286          moltype = DNA  length = 30
FEATURE                 Location/Qualifiers
source                  1..30
                        mol_type = genomic DNA
                        organism = Homo sapiens
SEQUENCE: 286
aaccagacat ctatgtacct ctgtgccagc                                30

SEQ ID NO: 287          moltype = DNA  length = 32
FEATURE                 Location/Qualifiers
source                  1..32
                        mol_type = genomic DNA
                        organism = Homo sapiens
SEQUENCE: 287
acatgagccc tgaagacagc agcatatatc tc                             32

SEQ ID NO: 288          moltype = DNA  length = 30
FEATURE                 Location/Qualifiers
source                  1..30
                        mol_type = genomic DNA
                        organism = Homo sapiens
SEQUENCE: 288
agcttggtga ctctgctgtg tatttctgtg                                30

SEQ ID NO: 289          moltype = DNA  length = 30
FEATURE                 Location/Qualifiers
source                  1..30
                        mol_type = genomic DNA
                        organism = Homo sapiens
SEQUENCE: 289
cttggtgact ctgctgtgta tttctgtgcc                                30

SEQ ID NO: 290          moltype = DNA  length = 29
FEATURE                 Location/Qualifiers
source                  1..29
                        mol_type = genomic DNA
                        organism = Homo sapiens
SEQUENCE: 290
cagccagaag actcagccct gtatctctg                                 29

SEQ ID NO: 291          moltype = DNA  length = 28
FEATURE                 Location/Qualifiers
source                  1..28
                        mol_type = genomic DNA
                        organism = Homo sapiens
SEQUENCE: 291
gccagaagac tcggccctgt atctctgt                                  28

SEQ ID NO: 292          moltype = DNA  length = 30
FEATURE                 Location/Qualifiers
source                  1..30
                        mol_type = genomic DNA
                        organism = Homo sapiens
SEQUENCE: 292
tattccttca cctacacacc ctgcagccag                                30

SEQ ID NO: 293          moltype = DNA  length = 27
FEATURE                 Location/Qualifiers
```

```
source                  1..27
                        mol_type = genomic DNA
                        organism = Homo sapiens
SEQUENCE: 293
agatgaatgt gagcaccttg gagctgg                                       27

SEQ ID NO: 294          moltype = DNA  length = 29
FEATURE                 Location/Qualifiers
source                  1..29
                        mol_type = genomic DNA
                        organism = Homo sapiens
SEQUENCE: 294
tactgagtca aacacggagc taggggact                                    29

SEQ ID NO: 295          moltype = DNA  length = 30
FEATURE                 Location/Qualifiers
source                  1..30
                        mol_type = genomic DNA
                        organism = Homo sapiens
SEQUENCE: 295
gttgctctga gatgaatgtg agtgccttgg                                    30

SEQ ID NO: 296          moltype = DNA  length = 30
FEATURE                 Location/Qualifiers
source                  1..30
                        mol_type = genomic DNA
                        organism = Homo sapiens
SEQUENCE: 296
atagctctga gctgaatgtg aacgccttgg                                    30

SEQ ID NO: 297          moltype = DNA  length = 28
FEATURE                 Location/Qualifiers
source                  1..28
                        mol_type = genomic DNA
                        organism = Homo sapiens
SEQUENCE: 297
gagctgaatg tgaacgcctt gttgctgg                                      28

SEQ ID NO: 298          moltype = DNA  length = 31
FEATURE                 Location/Qualifiers
source                  1..31
                        mol_type = genomic DNA
                        organism = Homo sapiens
SEQUENCE: 298
aactatagct ctgagctgaa tgtgaacgcc t                                  31

SEQ ID NO: 299          moltype = DNA  length = 29
FEATURE                 Location/Qualifiers
source                  1..29
                        mol_type = genomic DNA
                        organism = Homo sapiens
SEQUENCE: 299
agctgaatgt gaacgccttg ttgctaggg                                     29

SEQ ID NO: 300          moltype = DNA  length = 29
FEATURE                 Location/Qualifiers
source                  1..29
                        mol_type = genomic DNA
                        organism = Homo sapiens
SEQUENCE: 300
ctgaatgtga acgccttgga gctggagga                                     29

SEQ ID NO: 301          moltype = DNA  length = 28
FEATURE                 Location/Qualifiers
source                  1..28
                        mol_type = genomic DNA
                        organism = Homo sapiens
SEQUENCE: 301
gctccctccc agacatctgt gtacttct                                      28

SEQ ID NO: 302          moltype = DNA  length = 28
FEATURE                 Location/Qualifiers
source                  1..28
                        mol_type = genomic DNA
                        organism = Homo sapiens
SEQUENCE: 302
gctgctccct cccaaacatc tgtgtact                                      28

SEQ ID NO: 303          moltype = DNA  length = 30
```

```
FEATURE                Location/Qualifiers
source                 1..30
                       mol_type = genomic DNA
                       organism = Homo sapiens
SEQUENCE: 303
gctccctccc aaacatctgt gtacttctgt                                    30

SEQ ID NO: 304         moltype = DNA  length = 29
FEATURE                Location/Qualifiers
source                 1..29
                       mol_type = genomic DNA
                       organism = Homo sapiens
SEQUENCE: 304
aacacagatg atttccccct cacgttggc                                     29

SEQ ID NO: 305         moltype = DNA  length = 29
FEATURE                Location/Qualifiers
source                 1..29
                       mol_type = genomic DNA
                       organism = Homo sapiens
SEQUENCE: 305
gctgctccct cccagacatc tgtgtactt                                     29

SEQ ID NO: 306         moltype = DNA  length = 27
FEATURE                Location/Qualifiers
source                 1..27
                       mol_type = genomic DNA
                       organism = Homo sapiens
SEQUENCE: 306
agttggctgc tccctcccag acatctg                                       27

SEQ ID NO: 307         moltype = DNA  length = 30
FEATURE                Location/Qualifiers
source                 1..30
                       mol_type = genomic DNA
                       organism = Homo sapiens
SEQUENCE: 307
tcagctgctc cctctcagac ttctgtttac                                    30

SEQ ID NO: 308         moltype = DNA  length = 31
FEATURE                Location/Qualifiers
source                 1..31
                       mol_type = genomic DNA
                       organism = Homo sapiens
SEQUENCE: 308
taaacacaga ggatttccca ctcaggctgg t                                  31

SEQ ID NO: 309         moltype = DNA  length = 31
FEATURE                Location/Qualifiers
source                 1..31
                       mol_type = genomic DNA
                       organism = Homo sapiens
SEQUENCE: 309
agtcagctgc tccctcccag acatctgtat a                                  31

SEQ ID NO: 310         moltype = DNA  length = 27
FEATURE                Location/Qualifiers
source                 1..27
                       mol_type = genomic DNA
                       organism = Homo sapiens
SEQUENCE: 310
cagcaggggg acttggctgt gtatctc                                       27

SEQ ID NO: 311         moltype = DNA  length = 25
FEATURE                Location/Qualifiers
source                 1..25
                       mol_type = genomic DNA
                       organism = Homo sapiens
SEQUENCE: 311
gcaggaggac tcggccgtgt atctc                                         25

SEQ ID NO: 312         moltype = DNA  length = 29
FEATURE                Location/Qualifiers
source                 1..29
                       mol_type = genomic DNA
                       organism = Homo sapiens
SEQUENCE: 312
tctactctga agatccagcg cacagagcg                                     29
```

```
SEQ ID NO: 313         moltype = DNA  length = 28
FEATURE                Location/Qualifiers
source                 1..28
                       mol_type = genomic DNA
                       organism = Homo sapiens
SEQUENCE: 313
cacagagcag ggggactcag ctgtgtat                                    28

SEQ ID NO: 314         moltype = DNA  length = 30
FEATURE                Location/Qualifiers
source                 1..30
                       mol_type = genomic DNA
                       organism = Homo sapiens
SEQUENCE: 314
atctttctcc acctgaagat ccagcgcaca                                  30

SEQ ID NO: 315         moltype = DNA  length = 29
FEATURE                Location/Qualifiers
source                 1..29
                       mol_type = genomic DNA
                       organism = Homo sapiens
SEQUENCE: 315
ttctctgcag agaggcctga gggatccat                                   29

SEQ ID NO: 316         moltype = DNA  length = 30
FEATURE                Location/Qualifiers
source                 1..30
                       mol_type = genomic DNA
                       organism = Homo sapiens
SEQUENCE: 316
ctgagggatc cgtctccact ctgaagatcc                                  30

SEQ ID NO: 317         moltype = DNA  length = 30
FEATURE                Location/Qualifiers
source                 1..30
                       mol_type = genomic DNA
                       organism = Homo sapiens
SEQUENCE: 317
ggcctaaggg atctttctcc accttggaga                                  30

SEQ ID NO: 318         moltype = DNA  length = 30
FEATURE                Location/Qualifiers
source                 1..30
                       mol_type = genomic DNA
                       organism = Homo sapiens
SEQUENCE: 318
ttccctcaac cctggagtct actagcacca                                  30

SEQ ID NO: 319         moltype = DNA  length = 29
FEATURE                Location/Qualifiers
source                 1..29
                       mol_type = genomic DNA
                       organism = Homo sapiens
SEQUENCE: 319
ttgagcattt ccccaatcct ggcatccac                                   29

SEQ ID NO: 320         moltype = DNA  length = 30
FEATURE                Location/Qualifiers
source                 1..30
                       mol_type = genomic DNA
                       organism = Homo sapiens
SEQUENCE: 320
gggactcagc tttgtatttc tgtgccagca                                  30

SEQ ID NO: 321         moltype = DNA  length = 65
FEATURE                Location/Qualifiers
source                 1..65
                       mol_type = other DNA
                       organism = synthetic construct
SEQUENCE: 321
gtgactggag ttcagacgtg tgctcttccg atctgcctcc tcccagacat ctgtatattt  60
ctgcg                                                              65

SEQ ID NO: 322         moltype = DNA  length = 64
FEATURE                Location/Qualifiers
source                 1..64
                       mol_type = other DNA
                       organism = synthetic construct
SEQUENCE: 322
```

```
gtgactggag ttcagacgtg tgctcttccg atctaatttc cccctcactc tggagtcagc  60
tacc                                                               64

SEQ ID NO: 323         moltype = DNA  length = 64
FEATURE                Location/Qualifiers
source                 1..64
                       mol_type = other DNA
                       organism = synthetic construct
SEQUENCE: 323
gtgactggag ttcagacgtg tgctcttccg atctgatttc ctcctcactc tggagtccgc  60
tacc                                                               64

SEQ ID NO: 324         moltype = DNA  length = 65
FEATURE                Location/Qualifiers
source                 1..65
                       mol_type = other DNA
                       organism = synthetic construct
SEQUENCE: 324
gtgactggag ttcagacgtg tgctcttccg atctaggctc aaaggagtag actccactct  60
caaga                                                              65

SEQ ID NO: 325         moltype = DNA  length = 63
FEATURE                Location/Qualifiers
source                 1..63
                       mol_type = other DNA
                       organism = synthetic construct
SEQUENCE: 325
gtgactggag ttcagacgtg tgctcttccg atctcaagat ccagcctgca aagcttgagg  60
act                                                                63

SEQ ID NO: 326         moltype = DNA  length = 64
FEATURE                Location/Qualifiers
source                 1..64
                       mol_type = other DNA
                       organism = synthetic construct
SEQUENCE: 326
gtgactggag ttcagacgtg tgctcttccg atcttagact ccactctcaa gatccagcct  60
gcag                                                               64

SEQ ID NO: 327         moltype = DNA  length = 64
FEATURE                Location/Qualifiers
source                 1..64
                       mol_type = other DNA
                       organism = synthetic construct
SEQUENCE: 327
gtgactggag ttcagacgtg tgctcttccg atcttggaac ccagggactt gggcctatat  60
ttct                                                               64

SEQ ID NO: 328         moltype = DNA  length = 65
FEATURE                Location/Qualifiers
source                 1..65
                       mol_type = other DNA
                       organism = synthetic construct
SEQUENCE: 328
gtgactggag ttcagacgtg tgctcttccg atcttcattc tctactctga agatccagcc  60
tgcag                                                              65

SEQ ID NO: 329         moltype = DNA  length = 64
FEATURE                Location/Qualifiers
source                 1..64
                       mol_type = other DNA
                       organism = synthetic construct
SEQUENCE: 329
gtgactggag ttcagacgtg tgctcttccg atctcattct ccactctgaa gatccagccc  60
tcag                                                               64

SEQ ID NO: 330         moltype = DNA  length = 65
FEATURE                Location/Qualifiers
source                 1..65
                       mol_type = other DNA
                       organism = synthetic construct
SEQUENCE: 330
gtgactggag ttcagacgtg tgctcttccg atctcatcat tctccactct gaagatccag  60
ccctc                                                              65

SEQ ID NO: 331         moltype = DNA  length = 64
FEATURE                Location/Qualifiers
source                 1..64
                       mol_type = other DNA
```

```
                        organism = synthetic construct
SEQUENCE: 331
gtgactggag ttcagacgtg tgctcttccg atctcagcag agatgcctga tgcaacttta  60
gcca                                                               64

SEQ ID NO: 332          moltype = DNA  length = 63
FEATURE                 Location/Qualifiers
source                  1..63
                        mol_type = other DNA
                        organism = synthetic construct
SEQUENCE: 332
gtgactggag ttcagacgtg tgctcttccg atctgaactg aacatgagct ccttggagct  60
ggg                                                                63

SEQ ID NO: 333          moltype = DNA  length = 65
FEATURE                 Location/Qualifiers
source                  1..65
                        mol_type = other DNA
                        organism = synthetic construct
SEQUENCE: 333
gtgactggag ttcagacgtg tgctcttccg atctggagga ttctggagtt tatttctgtg  60
ccagc                                                              65

SEQ ID NO: 334          moltype = DNA  length = 64
FEATURE                 Location/Qualifiers
source                  1..64
                        mol_type = other DNA
                        organism = synthetic construct
SEQUENCE: 334
gtgactggag ttcagacgtg tgctcttccg atctttctgc tttcttgaca tccgctcacc  60
aggc                                                               64

SEQ ID NO: 335          moltype = DNA  length = 65
FEATURE                 Location/Qualifiers
source                  1..65
                        mol_type = other DNA
                        organism = synthetic construct
SEQUENCE: 335
gtgactggag ttcagacgtg tgctcttccg atctgagatc caggctacga agcttgagga  60
ttcag                                                              65

SEQ ID NO: 336          moltype = DNA  length = 62
FEATURE                 Location/Qualifiers
source                  1..62
                        mol_type = other DNA
                        organism = synthetic construct
SEQUENCE: 336
gtgactggag ttcagacgtg tgctcttccg atctaacgtc ttccacgctg aagatccatc  60
cc                                                                 62

SEQ ID NO: 337          moltype = DNA  length = 64
FEATURE                 Location/Qualifiers
source                  1..64
                        mol_type = other DNA
                        organism = synthetic construct
SEQUENCE: 337
gtgactggag ttcagacgtg tgctcttccg atctaggatc cagcaggtag tgcgaggaga  60
ttcg                                                               64

SEQ ID NO: 338          moltype = DNA  length = 64
FEATURE                 Location/Qualifiers
source                  1..64
                        mol_type = other DNA
                        organism = synthetic construct
SEQUENCE: 338
gtgactggag ttcagacgtg tgctcttccg atctacccga cagctttcta tctctgtgcc  60
agta                                                               64

SEQ ID NO: 339          moltype = DNA  length = 64
FEATURE                 Location/Qualifiers
source                  1..64
                        mol_type = other DNA
                        organism = synthetic construct
SEQUENCE: 339
gtgactggag ttcagacgtg tgctcttccg atctgtgccc atcctgaaga cagcagcttc  60
taca                                                               64

SEQ ID NO: 340          moltype = DNA  length = 62
FEATURE                 Location/Qualifiers
```

```
source                  1..62
                        mol_type = other DNA
                        organism = synthetic construct
SEQUENCE: 340
gtgactggag ttcagacgtg tgctcttccg atctcacaaa gctggaggac tcagccatgt  60
ac                                                                 62

SEQ ID NO: 341          moltype = DNA  length = 64
FEATURE                 Location/Qualifiers
source                  1..64
                        mol_type = other DNA
                        organism = synthetic construct
SEQUENCE: 341
gtgactggag ttcagacgtg tgctcttccg atcttcaggg gacacagcac tgtatttctg  60
tgcc                                                               64

SEQ ID NO: 342          moltype = DNA  length = 64
FEATURE                 Location/Qualifiers
source                  1..64
                        mol_type = other DNA
                        organism = synthetic construct
SEQUENCE: 342
gtgactggag ttcagacgtg tgctcttccg atctcacacc agccaaacag ctttgtactt  60
ctgt                                                               64

SEQ ID NO: 343          moltype = DNA  length = 62
FEATURE                 Location/Qualifiers
source                  1..62
                        mol_type = other DNA
                        organism = synthetic construct
SEQUENCE: 343
gtgactggag ttcagacgtg tgctcttccg atctaatcct gtcctcagaa ccgggagaca  60
cg                                                                 62

SEQ ID NO: 344          moltype = DNA  length = 65
FEATURE                 Location/Qualifiers
source                  1..65
                        mol_type = other DNA
                        organism = synthetic construct
SEQUENCE: 344
gtgactggag ttcagacgtg tgctcttccg atctccaacc agacagctct ttacttctgt  60
gccac                                                              65

SEQ ID NO: 345          moltype = DNA  length = 64
FEATURE                 Location/Qualifiers
source                  1..64
                        mol_type = other DNA
                        organism = synthetic construct
SEQUENCE: 345
gtgactggag ttcagacgtg tgctcttccg atctcacata cctctcagta cctctgtgcc  60
agca                                                               64

SEQ ID NO: 346          moltype = DNA  length = 66
FEATURE                 Location/Qualifiers
source                  1..66
                        mol_type = other DNA
                        organism = synthetic construct
SEQUENCE: 346
gtgactggag ttcagacgtg tgctcttccg atctccaacc agacatctgt gtatctctat  60
gccagc                                                             66

SEQ ID NO: 347          moltype = DNA  length = 64
FEATURE                 Location/Qualifiers
source                  1..64
                        mol_type = other DNA
                        organism = synthetic construct
SEQUENCE: 347
gtgactggag ttcagacgtg tgctcttccg atctaccaga cctctctgta cttctgtgcc  60
agca                                                               64

SEQ ID NO: 348          moltype = DNA  length = 64
FEATURE                 Location/Qualifiers
source                  1..64
                        mol_type = other DNA
                        organism = synthetic construct
SEQUENCE: 348
gtgactggag ttcagacgtg tgctcttccg atctaaccag acatctatgt acctctgtgc  60
cagc                                                               64
```

```
SEQ ID NO: 349         moltype = DNA  length = 66
FEATURE                Location/Qualifiers
source                 1..66
                       mol_type = other DNA
                       organism = synthetic construct
SEQUENCE: 349
gtgactggag ttcagacgtg tgctcttccg atctacatga gccctgaaga cagcagcata  60
tatctc                                                             66

SEQ ID NO: 350         moltype = DNA  length = 64
FEATURE                Location/Qualifiers
source                 1..64
                       mol_type = other DNA
                       organism = synthetic construct
SEQUENCE: 350
gtgactggag ttcagacgtg tgctcttccg atctagcttg gtgactctgc tgtgtatttc  60
tgtg                                                               64

SEQ ID NO: 351         moltype = DNA  length = 64
FEATURE                Location/Qualifiers
source                 1..64
                       mol_type = other DNA
                       organism = synthetic construct
SEQUENCE: 351
gtgactggag ttcagacgtg tgctcttccg atctcttggt gactctgctg tgtatttctg  60
tgcc                                                               64

SEQ ID NO: 352         moltype = DNA  length = 63
FEATURE                Location/Qualifiers
source                 1..63
                       mol_type = other DNA
                       organism = synthetic construct
SEQUENCE: 352
gtgactggag ttcagacgtg tgctcttccg atctcagcca gaagactcag ccctgtatct  60
ctg                                                                63

SEQ ID NO: 353         moltype = DNA  length = 62
FEATURE                Location/Qualifiers
source                 1..62
                       mol_type = other DNA
                       organism = synthetic construct
SEQUENCE: 353
gtgactggag ttcagacgtg tgctcttccg atctgccaga agactcggcc ctgtatctct  60
gt                                                                 62

SEQ ID NO: 354         moltype = DNA  length = 64
FEATURE                Location/Qualifiers
source                 1..64
                       mol_type = other DNA
                       organism = synthetic construct
SEQUENCE: 354
gtgactggag ttcagacgtg tgctcttccg atcttattcc ttcacctaca caccctgcag  60
ccag                                                               64

SEQ ID NO: 355         moltype = DNA  length = 61
FEATURE                Location/Qualifiers
source                 1..61
                       mol_type = other DNA
                       organism = synthetic construct
SEQUENCE: 355
gtgactggag ttcagacgtg tgctcttccg atctagatga atgtgagcac cttggagctg  60
g                                                                  61

SEQ ID NO: 356         moltype = DNA  length = 63
FEATURE                Location/Qualifiers
source                 1..63
                       mol_type = other DNA
                       organism = synthetic construct
SEQUENCE: 356
gtgactggag ttcagacgtg tgctcttccg atcttactga gtcaaacacg gagctagggg  60
act                                                                63

SEQ ID NO: 357         moltype = DNA  length = 64
FEATURE                Location/Qualifiers
source                 1..64
                       mol_type = other DNA
                       organism = synthetic construct
SEQUENCE: 357
gtgactggag ttcagacgtg tgctcttccg atctgttgct ctgagatgaa tgtgagtgcc  60
```

```
ttgg                                                                64

SEQ ID NO: 358          moltype = DNA  length = 64
FEATURE                 Location/Qualifiers
source                  1..64
                        mol_type = other DNA
                        organism = synthetic construct
SEQUENCE: 358
gtgactggag ttcagacgtg tgctcttccg atctatagct ctgagctgaa tgtgaacgcc  60
ttgg                                                                64

SEQ ID NO: 359          moltype = DNA  length = 62
FEATURE                 Location/Qualifiers
source                  1..62
                        mol_type = other DNA
                        organism = synthetic construct
SEQUENCE: 359
gtgactggag ttcagacgtg tgctcttccg atctgagctg aatgtgaacg ccttgttgct  60
gg                                                                  62

SEQ ID NO: 360          moltype = DNA  length = 65
FEATURE                 Location/Qualifiers
source                  1..65
                        mol_type = other DNA
                        organism = synthetic construct
SEQUENCE: 360
gtgactggag ttcagacgtg tgctcttccg atctaactat agctctgagc tgaatgtgaa  60
cgcct                                                               65

SEQ ID NO: 361          moltype = DNA  length = 63
FEATURE                 Location/Qualifiers
source                  1..63
                        mol_type = other DNA
                        organism = synthetic construct
SEQUENCE: 361
gtgactggag ttcagacgtg tgctcttccg atctagctga atgtgaacgc cttgttgcta  60
ggg                                                                 63

SEQ ID NO: 362          moltype = DNA  length = 63
FEATURE                 Location/Qualifiers
source                  1..63
                        mol_type = other DNA
                        organism = synthetic construct
SEQUENCE: 362
gtgactggag ttcagacgtg tgctcttccg atctctgaat gtgaacgcct tggagctgga  60
gga                                                                 63

SEQ ID NO: 363          moltype = DNA  length = 62
FEATURE                 Location/Qualifiers
source                  1..62
                        mol_type = other DNA
                        organism = synthetic construct
SEQUENCE: 363
gtgactggag ttcagacgtg tgctcttccg atctgctccc tcccagacat ctgtgtactt  60
ct                                                                  62

SEQ ID NO: 364          moltype = DNA  length = 62
FEATURE                 Location/Qualifiers
source                  1..62
                        mol_type = other DNA
                        organism = synthetic construct
SEQUENCE: 364
gtgactggag ttcagacgtg tgctcttccg atctgctgct ccctcccaaa catctgtgta  60
ct                                                                  62

SEQ ID NO: 365          moltype = DNA  length = 64
FEATURE                 Location/Qualifiers
source                  1..64
                        mol_type = other DNA
                        organism = synthetic construct
SEQUENCE: 365
gtgactggag ttcagacgtg tgctcttccg atctgctccc tcccaaacat ctgtgtactt  60
ctgt                                                                64

SEQ ID NO: 366          moltype = DNA  length = 63
FEATURE                 Location/Qualifiers
source                  1..63
                        mol_type = other DNA
                        organism = synthetic construct
```

```
SEQUENCE: 366
gtgactggag ttcagacgtg tgctcttccg atctaacaca gatgatttcc ccctcacgtt  60
ggc                                                                 63

SEQ ID NO: 367         moltype = DNA  length = 63
FEATURE                Location/Qualifiers
source                 1..63
                       mol_type = other DNA
                       organism = synthetic construct
SEQUENCE: 367
gtgactggag ttcagacgtg tgctcttccg atctgctgct ccctcccaga catctgtgta  60
ctt                                                                 63

SEQ ID NO: 368         moltype = DNA  length = 61
FEATURE                Location/Qualifiers
source                 1..61
                       mol_type = other DNA
                       organism = synthetic construct
SEQUENCE: 368
gtgactggag ttcagacgtg tgctcttccg atctagttgg ctgctccctc ccagacatct  60
g                                                                   61

SEQ ID NO: 369         moltype = DNA  length = 64
FEATURE                Location/Qualifiers
source                 1..64
                       mol_type = other DNA
                       organism = synthetic construct
SEQUENCE: 369
gtgactggag ttcagacgtg tgctcttccg atcttcagct gctccctctc agacttctgt  60
ttac                                                                64

SEQ ID NO: 370         moltype = DNA  length = 65
FEATURE                Location/Qualifiers
source                 1..65
                       mol_type = other DNA
                       organism = synthetic construct
SEQUENCE: 370
gtgactggag ttcagacgtg tgctcttccg atcttaaaca cagaggattt cccactcagg  60
ctggt                                                               65

SEQ ID NO: 371         moltype = DNA  length = 65
FEATURE                Location/Qualifiers
source                 1..65
                       mol_type = other DNA
                       organism = synthetic construct
SEQUENCE: 371
gtgactggag ttcagacgtg tgctcttccg atctagtcag ctgctccctc ccagacatct  60
gtata                                                               65

SEQ ID NO: 372         moltype = DNA  length = 61
FEATURE                Location/Qualifiers
source                 1..61
                       mol_type = other DNA
                       organism = synthetic construct
SEQUENCE: 372
gtgactggag ttcagacgtg tgctcttccg atctcagcag ggggacttgg ctgtgtatct  60
c                                                                   61

SEQ ID NO: 373         moltype = DNA  length = 59
FEATURE                Location/Qualifiers
source                 1..59
                       mol_type = other DNA
                       organism = synthetic construct
SEQUENCE: 373
gtgactggag ttcagacgtg tgctcttccg atctgcagga ggactcggcc gtgtatctc   59

SEQ ID NO: 374         moltype = DNA  length = 63
FEATURE                Location/Qualifiers
source                 1..63
                       mol_type = other DNA
                       organism = synthetic construct
SEQUENCE: 374
gtgactggag ttcagacgtg tgctcttccg atcttctact ctgaagatcc agcgcacaga  60
gcg                                                                 63

SEQ ID NO: 375         moltype = DNA  length = 62
FEATURE                Location/Qualifiers
source                 1..62
                       mol_type = other DNA
```

```
                         organism = synthetic construct
SEQUENCE: 375
gtgactggag ttcagacgtg tgctcttccg atctcacaga gcagggggac tcagctgtgt  60
at                                                                 62

SEQ ID NO: 376           moltype = DNA  length = 64
FEATURE                  Location/Qualifiers
source                   1..64
                         mol_type = other DNA
                         organism = synthetic construct
SEQUENCE: 376
gtgactggag ttcagacgtg tgctcttccg atctatcttt ctccacctga agatccagcg  60
caca                                                               64

SEQ ID NO: 377           moltype = DNA  length = 63
FEATURE                  Location/Qualifiers
source                   1..63
                         mol_type = other DNA
                         organism = synthetic construct
SEQUENCE: 377
gtgactggag ttcagacgtg tgctcttccg atctttctct gcagagaggc ctgagggatc  60
cat                                                                63

SEQ ID NO: 378           moltype = DNA  length = 64
FEATURE                  Location/Qualifiers
source                   1..64
                         mol_type = other DNA
                         organism = synthetic construct
SEQUENCE: 378
gtgactggag ttcagacgtg tgctcttccg atctctgagg gatccgtctc cactctgaag  60
atcc                                                               64

SEQ ID NO: 379           moltype = DNA  length = 64
FEATURE                  Location/Qualifiers
source                   1..64
                         mol_type = other DNA
                         organism = synthetic construct
SEQUENCE: 379
gtgactggag ttcagacgtg tgctcttccg atctggccta agggatcttt ctccaccttg  60
gaga                                                               64

SEQ ID NO: 380           moltype = DNA  length = 64
FEATURE                  Location/Qualifiers
source                   1..64
                         mol_type = other DNA
                         organism = synthetic construct
SEQUENCE: 380
gtgactggag ttcagacgtg tgctcttccg atctttccct caaccctgga gtctactagc  60
acca                                                               64

SEQ ID NO: 381           moltype = DNA  length = 63
FEATURE                  Location/Qualifiers
source                   1..63
                         mol_type = other DNA
                         organism = synthetic construct
SEQUENCE: 381
gtgactggag ttcagacgtg tgctcttccg atctttgagc atttccccaa tcctggcatc  60
cac                                                                63

SEQ ID NO: 382           moltype = DNA  length = 64
FEATURE                  Location/Qualifiers
source                   1..64
                         mol_type = other DNA
                         organism = synthetic construct
SEQUENCE: 382
gtgactggag ttcagacgtg tgctcttccg atctgggact cagctttgta tttctgtgcc  60
agca                                                               64

SEQ ID NO: 383           moltype = DNA  length = 30
FEATURE                  Location/Qualifiers
source                   1..30
                         mol_type = other DNA
                         organism = synthetic construct
SEQUENCE: 383
gctgaaatca cccagagccc aagacacaag                                   30

SEQ ID NO: 384           moltype = DNA  length = 29
FEATURE                  Location/Qualifiers
source                   1..29
```

```
                       mol_type = other DNA
                       organism = synthetic construct
SEQUENCE: 384
cacagagaca ggaaggcagg tgaccttga                                29

SEQ ID NO: 385         moltype = DNA  length = 30
FEATURE                Location/Qualifiers
source                 1..30
                       mol_type = other DNA
                       organism = synthetic construct
SEQUENCE: 385
gatgctggaa tcacccagag cccaagacac                               30

SEQ ID NO: 386         moltype = DNA  length = 30
FEATURE                Location/Qualifiers
source                 1..30
                       mol_type = other DNA
                       organism = synthetic construct
SEQUENCE: 386
gccaggctgt ggctttttgg tgtgatccta                               30

SEQ ID NO: 387         moltype = DNA  length = 29
FEATURE                Location/Qualifiers
source                 1..29
                       mol_type = other DNA
                       organism = synthetic construct
SEQUENCE: 387
ggcagagtgt ggctttttgg tgcaatcct                                29

SEQ ID NO: 388         moltype = DNA  length = 31
FEATURE                Location/Qualifiers
source                 1..31
                       mol_type = other DNA
                       organism = synthetic construct
SEQUENCE: 388
ggctttttgg tgcaatccta tttctggcca c                             31

SEQ ID NO: 389         moltype = DNA  length = 30
FEATURE                Location/Qualifiers
source                 1..30
                       mol_type = other DNA
                       organism = synthetic construct
SEQUENCE: 389
gatgctggtg ttatccagtc acccaggcac                               30

SEQ ID NO: 390         moltype = DNA  length = 30
FEATURE                Location/Qualifiers
source                 1..30
                       mol_type = other DNA
                       organism = synthetic construct
SEQUENCE: 390
gtcacccaag catgaggtga cagaaatggg                               30

SEQ ID NO: 391         moltype = DNA  length = 27
FEATURE                Location/Qualifiers
source                 1..27
                       mol_type = other DNA
                       organism = synthetic construct
SEQUENCE: 391
atgctggagt tatccagtca ccccgcc                                  27

SEQ ID NO: 392         moltype = DNA  length = 28
FEATURE                Location/Qualifiers
source                 1..28
                       mol_type = other DNA
                       organism = synthetic construct
SEQUENCE: 392
gagttatcca gtcaccccgg cacgaggt                                 28

SEQ ID NO: 393         moltype = DNA  length = 28
FEATURE                Location/Qualifiers
source                 1..28
                       mol_type = other DNA
                       organism = synthetic construct
SEQUENCE: 393
gctagagtca cccagacacc aaggcaca                                 28

SEQ ID NO: 394         moltype = DNA  length = 27
FEATURE                Location/Qualifiers
```

```
source                  1..27
                        mol_type = other DNA
                        organism = synthetic construct
SEQUENCE: 394
gctgctggag tcatccagtc cccaaga                                       27

SEQ ID NO: 395          moltype = DNA  length = 29
FEATURE                 Location/Qualifiers
source                  1..29
                        mol_type = other DNA
                        organism = synthetic construct
SEQUENCE: 395
gttactcagt tccccagcca cagcgtaat                                     29

SEQ ID NO: 396          moltype = DNA  length = 29
FEATURE                 Location/Qualifiers
source                  1..29
                        mol_type = other DNA
                        organism = synthetic construct
SEQUENCE: 396
gttacccagt ttggaaagcc agtgaccct                                     29

SEQ ID NO: 397          moltype = DNA  length = 30
FEATURE                 Location/Qualifiers
source                  1..30
                        mol_type = other DNA
                        organism = synthetic construct
SEQUENCE: 397
gaagtcgccc agactccaaa acatcttgtc                                    30

SEQ ID NO: 398          moltype = DNA  length = 29
FEATURE                 Location/Qualifiers
source                  1..29
                        mol_type = other DNA
                        organism = synthetic construct
SEQUENCE: 398
cagacacaag gtcaccaaca tgggacagg                                     29

SEQ ID NO: 399          moltype = DNA  length = 29
FEATURE                 Location/Qualifiers
source                  1..29
                        mol_type = other DNA
                        organism = synthetic construct
SEQUENCE: 399
gtcatgttta ctggtatcgg cagctccca                                     29

SEQ ID NO: 400          moltype = DNA  length = 29
FEATURE                 Location/Qualifiers
source                  1..29
                        mol_type = other DNA
                        organism = synthetic construct
SEQUENCE: 400
atgccatgta ctggtaccga caggaccca                                     29

SEQ ID NO: 401          moltype = DNA  length = 29
FEATURE                 Location/Qualifiers
source                  1..29
                        mol_type = other DNA
                        organism = synthetic construct
SEQUENCE: 401
gtcgtctctc aacatccgag ctgggttat                                     29

SEQ ID NO: 402          moltype = DNA  length = 29
FEATURE                 Location/Qualifiers
source                  1..29
                        mol_type = other DNA
                        organism = synthetic construct
SEQUENCE: 402
gaacctgaag tcacccagac tcccagcca                                     29

SEQ ID NO: 403          moltype = DNA  length = 28
FEATURE                 Location/Qualifiers
source                  1..28
                        mol_type = other DNA
                        organism = synthetic construct
SEQUENCE: 403
cacggacacc aaggtcaccc agagacct                                      28

SEQ ID NO: 404          moltype = DNA  length = 28
```

-continued

```
FEATURE                Location/Qualifiers
source                 1..28
                       mol_type = other DNA
                       organism = synthetic construct
SEQUENCE: 404
agctcactgg ggctggatgg gatgtgac                                    28

SEQ ID NO: 405         moltype = DNA  length = 29
FEATURE                Location/Qualifiers
source                 1..29
                       mol_type = other DNA
                       organism = synthetic construct
SEQUENCE: 405
gccaaagtca cacagactcc aggacattt                                   29

SEQ ID NO: 406         moltype = DNA  length = 29
FEATURE                Location/Qualifiers
source                 1..29
                       mol_type = other DNA
                       organism = synthetic construct
SEQUENCE: 406
gtatcgacaa gacccaggac tgggcctac                                   29

SEQ ID NO: 407         moltype = DNA  length = 29
FEATURE                Location/Qualifiers
source                 1..29
                       mol_type = other DNA
                       organism = synthetic construct
SEQUENCE: 407
gctgacatct accagacccc aagatacct                                   29

SEQ ID NO: 408         moltype = DNA  length = 29
FEATURE                Location/Qualifiers
source                 1..29
                       mol_type = other DNA
                       organism = synthetic construct
SEQUENCE: 408
gtatcgacag gacccaggac ttggactga                                   29

SEQ ID NO: 409         moltype = DNA  length = 28
FEATURE                Location/Qualifiers
source                 1..28
                       mol_type = other DNA
                       organism = synthetic construct
SEQUENCE: 409
agcccaagtg acccagaacc caagatac                                    28

SEQ ID NO: 410         moltype = DNA  length = 31
FEATURE                Location/Qualifiers
source                 1..31
                       mol_type = other DNA
                       organism = synthetic construct
SEQUENCE: 410
ctcgtagatg tgaaagtaac ccagagctcg a                                31

SEQ ID NO: 411         moltype = DNA  length = 30
FEATURE                Location/Qualifiers
source                 1..30
                       mol_type = other DNA
                       organism = synthetic construct
SEQUENCE: 411
gatatctgtc aacgtggaac ctccctgacg                                  30

SEQ ID NO: 412         moltype = DNA  length = 29
FEATURE                Location/Qualifiers
source                 1..29
                       mol_type = other DNA
                       organism = synthetic construct
SEQUENCE: 412
ggtcacacag atgggaaacg acaagtcca                                   29

SEQ ID NO: 413         moltype = DNA  length = 29
FEATURE                Location/Qualifiers
source                 1..29
                       mol_type = other DNA
                       organism = synthetic construct
SEQUENCE: 413
ccgtttccca gactccaaaa tacctggtc                                   29
```

```
SEQ ID NO: 414          moltype = DNA  length = 30
FEATURE                 Location/Qualifiers
source                  1..30
                        mol_type = other DNA
                        organism = synthetic construct
SEQUENCE: 414
gaagttaccc agacaccaaa acacctggtc                                     30

SEQ ID NO: 415          moltype = DNA  length = 29
FEATURE                 Location/Qualifiers
source                  1..29
                        mol_type = other DNA
                        organism = synthetic construct
SEQUENCE: 415
gagttacgca gacaccaaga cacctggtc                                      29

SEQ ID NO: 416          moltype = DNA  length = 28
FEATURE                 Location/Qualifiers
source                  1..28
                        mol_type = other DNA
                        organism = synthetic construct
SEQUENCE: 416
ggagttacgc agacaccaag acacctgg                                       28

SEQ ID NO: 417          moltype = DNA  length = 29
FEATURE                 Location/Qualifiers
source                  1..29
                        mol_type = other DNA
                        organism = synthetic construct
SEQUENCE: 417
gtgacactga gctgctcccc tatctctgg                                      29

SEQ ID NO: 418          moltype = DNA  length = 29
FEATURE                 Location/Qualifiers
source                  1..29
                        mol_type = other DNA
                        organism = synthetic construct
SEQUENCE: 418
gaatcaccca agctccaaga cacctgatc                                      29

SEQ ID NO: 419          moltype = DNA  length = 27
FEATURE                 Location/Qualifiers
source                  1..27
                        mol_type = other DNA
                        organism = synthetic construct
SEQUENCE: 419
ctggagtcac ccaaagtccc acacacc                                        27

SEQ ID NO: 420          moltype = DNA  length = 28
FEATURE                 Location/Qualifiers
source                  1..28
                        mol_type = other DNA
                        organism = synthetic construct
SEQUENCE: 420
gactggagtc acccaaagtc ccacacac                                       28

SEQ ID NO: 421          moltype = DNA  length = 29
FEATURE                 Location/Qualifiers
source                  1..29
                        mol_type = other DNA
                        organism = synthetic construct
SEQUENCE: 421
gtcccacaca cctgatcaaa acgagagga                                      29

SEQ ID NO: 422          moltype = DNA  length = 28
FEATURE                 Location/Qualifiers
source                  1..28
                        mol_type = other DNA
                        organism = synthetic construct
SEQUENCE: 422
tagtggacgc tggagtcacc caaagtcc                                       28

SEQ ID NO: 423          moltype = DNA  length = 29
FEATURE                 Location/Qualifiers
source                  1..29
                        mol_type = other DNA
                        organism = synthetic construct
SEQUENCE: 423
ctgatcaaaa cgagaggaca gcacgtgac                                      29
```

```
SEQ ID NO: 424          moltype = DNA  length = 29
FEATURE                 Location/Qualifiers
source                  1..29
                        mol_type = other DNA
                        organism = synthetic construct
SEQUENCE: 424
gagtcacaca aagtcccaca cacctgatc                                    29

SEQ ID NO: 425          moltype = DNA  length = 29
FEATURE                 Location/Qualifiers
source                  1..29
                        mol_type = other DNA
                        organism = synthetic construct
SEQUENCE: 425
gtgaatgctg gtgtcactca gaccccaaa                                    29

SEQ ID NO: 426          moltype = DNA  length = 29
FEATURE                 Location/Qualifiers
source                  1..29
                        mol_type = other DNA
                        organism = synthetic construct
SEQUENCE: 426
gaatgctggt gtcactcaga ccccaaaat                                    29

SEQ ID NO: 427          moltype = DNA  length = 29
FEATURE                 Location/Qualifiers
source                  1..29
                        mol_type = other DNA
                        organism = synthetic construct
SEQUENCE: 427
gctggtgtca ctcagacccc aaaattccg                                    29

SEQ ID NO: 428          moltype = DNA  length = 29
FEATURE                 Location/Qualifiers
source                  1..29
                        mol_type = other DNA
                        organism = synthetic construct
SEQUENCE: 428
gatcacccag gcaccaacat ctcagatcc                                    29

SEQ ID NO: 429          moltype = DNA  length = 29
FEATURE                 Location/Qualifiers
source                  1..29
                        mol_type = other DNA
                        organism = synthetic construct
SEQUENCE: 429
gctggtgtca ctcagacccc aaaattcca                                    29

SEQ ID NO: 430          moltype = DNA  length = 29
FEATURE                 Location/Qualifiers
source                  1..29
                        mol_type = other DNA
                        organism = synthetic construct
SEQUENCE: 430
gctggtgtca ctcagacccc aaaattccg                                    29

SEQ ID NO: 431          moltype = DNA  length = 29
FEATURE                 Location/Qualifiers
source                  1..29
                        mol_type = other DNA
                        organism = synthetic construct
SEQUENCE: 431
gaatgctggt gtcactcaga ccccaaaat                                    29

SEQ ID NO: 432          moltype = DNA  length = 29
FEATURE                 Location/Qualifiers
source                  1..29
                        mol_type = other DNA
                        organism = synthetic construct
SEQUENCE: 432
gctggtgtca ctcagacccc aaaattcca                                    29

SEQ ID NO: 433          moltype = DNA  length = 29
FEATURE                 Location/Qualifiers
source                  1..29
                        mol_type = other DNA
                        organism = synthetic construct
SEQUENCE: 433
```

```
gaatgctggt gtcactcaga ccccaaaat                                       29

SEQ ID NO: 434         moltype = DNA  length = 28
FEATURE                Location/Qualifiers
source                 1..28
                       mol_type = other DNA
                       organism = synthetic construct
SEQUENCE: 434
gtgctggagt ctcccagtcc ctgagaca                                        28

SEQ ID NO: 435         moltype = DNA  length = 29
FEATURE                Location/Qualifiers
source                 1..29
                       mol_type = other DNA
                       organism = synthetic construct
SEQUENCE: 435
gtcccccagt aacaaggtca cagagaagg                                       29

SEQ ID NO: 436         moltype = DNA  length = 29
FEATURE                Location/Qualifiers
source                 1..29
                       mol_type = other DNA
                       organism = synthetic construct
SEQUENCE: 436
gacccccagt aacaaggtca cagagaagg                                       29

SEQ ID NO: 437         moltype = DNA  length = 29
FEATURE                Location/Qualifiers
source                 1..29
                       mol_type = other DNA
                       organism = synthetic construct
SEQUENCE: 437
cagtccccaa ggtacaaagt cgcaaagag                                       29

SEQ ID NO: 438         moltype = DNA  length = 27
FEATURE                Location/Qualifiers
source                 1..27
                       mol_type = other DNA
                       organism = synthetic construct
SEQUENCE: 438
gtctcccagt ccccaaggta cgaagtc                                         27

SEQ ID NO: 439         moltype = DNA  length = 26
FEATURE                Location/Qualifiers
source                 1..26
                       mol_type = other DNA
                       organism = synthetic construct
SEQUENCE: 439
cacaggtgct ggagtctccc agtctc                                          26

SEQ ID NO: 440         moltype = DNA  length = 26
FEATURE                Location/Qualifiers
source                 1..26
                       mol_type = other DNA
                       organism = synthetic construct
SEQUENCE: 440
gtgctggagt ctcccagtcc cctagg                                          26

SEQ ID NO: 441         moltype = DNA  length = 27
FEATURE                Location/Qualifiers
source                 1..27
                       mol_type = other DNA
                       organism = synthetic construct
SEQUENCE: 441
ctggagtctc ccagaacccc agacaca                                         27

SEQ ID NO: 442         moltype = DNA  length = 28
FEATURE                Location/Qualifiers
source                 1..28
                       mol_type = other DNA
                       organism = synthetic construct
SEQUENCE: 442
gaggcaggga tcagccagat accaagat                                        28

SEQ ID NO: 443         moltype = DNA  length = 27
FEATURE                Location/Qualifiers
source                 1..27
                       mol_type = other DNA
                       organism = synthetic construct
```

```
SEQUENCE: 443
gatgctggga tcacccagat gccaaga                                    27

SEQ ID NO: 444         moltype = DNA  length = 28
FEATURE                Location/Qualifiers
source                 1..28
                       mol_type = other DNA
                       organism = synthetic construct
SEQUENCE: 444
tggagtcaca caaaccccaa agcacctg                                   28

SEQ ID NO: 445         moltype = DNA  length = 120
FEATURE                Location/Qualifiers
source                 1..120
                       mol_type = other DNA
                       organism = synthetic construct
SEQUENCE: 445
gaactgtggc tgcaccatct gtcttcatct tcccgccatc tgatgagcag ttgaaatctg  60
gaactgcctc tgttgtgtgc ctgctgaata acttctatcc cagagaggcc aaagtacagt  120

SEQ ID NO: 446         moltype = DNA  length = 120
FEATURE                Location/Qualifiers
source                 1..120
                       mol_type = other DNA
                       organism = synthetic construct
SEQUENCE: 446
ggaaggtgga taacgccctc caatcgggta actcccagga gagtgtcaca gagcaggaca  60
gcaaggacag cacctacagc ctcagcagca ccctgacgct gagcaaagca gactacgaga  120

SEQ ID NO: 447         moltype = DNA  length = 120
FEATURE                Location/Qualifiers
source                 1..120
                       mol_type = other DNA
                       organism = synthetic construct
SEQUENCE: 447
ctcgcccgtc acaaagagct tcaacagggg agagtgttag agggagaagt gcccccacct  60
gctcctcagt tccagcctga ccccctccca tcctttggcc tctgaccctt tttccacagg  120

SEQ ID NO: 448         moltype = DNA  length = 120
FEATURE                Location/Qualifiers
source                 1..120
                       mol_type = other DNA
                       organism = synthetic construct
SEQUENCE: 448
ggacctaccc ctattgcggt cctccagctc atctttcacc tcacccccct cctcctcctt  60
ggctttaatt atgctaatgt tggaggagaa tgaataaata aagtgaatct ttgcacctgt  120

SEQ ID NO: 449         moltype = DNA  length = 120
FEATURE                Location/Qualifiers
source                 1..120
                       mol_type = other DNA
                       organism = synthetic construct
SEQUENCE: 449
gtcagcccaa ggccaacccc actgtcactc tgttcccgcc ctcctctgag gagctccaag  60
ccaacaaggc cacactagtg tgtctgatca gtgacttcta cccgggagct gtgacagtgg  120

SEQ ID NO: 450         moltype = DNA  length = 120
FEATURE                Location/Qualifiers
source                 1..120
                       mol_type = other DNA
                       organism = synthetic construct
SEQUENCE: 450
gacgcccgag cagtggaagt cccacagaag ctacagctgc caggtcacgc atgaagggag  60
caccgtggag aagacagtgg cccctacaga atgttcatag gttcccaact ctaaccccac  120

SEQ ID NO: 451         moltype = DNA  length = 120
FEATURE                Location/Qualifiers
source                 1..120
                       mol_type = other DNA
                       organism = synthetic construct
SEQUENCE: 451
ccacgggagc ctggagctgc aggatcccag gggaggggtc tctctcccca tcccaagtca  60
tccagccctt ctccctgcac tcatgaaacc ccaataaata tcctcattga caaccagaaa  120

SEQ ID NO: 452         moltype = DNA  length = 120
FEATURE                Location/Qualifiers
source                 1..120
                       mol_type = other DNA
                       organism = synthetic construct
```

```
SEQUENCE: 452
gtcagcccaa ggctgccccc tcggtcactc tgttcccgcc ctcctctgag gagcttcaag  60
ccaacaaggc cacactggtg tgtctcataa gtgacttcta cccgggagcc gtgacagtgg  120

SEQ ID NO: 453          moltype = DNA  length = 120
FEATURE                 Location/Qualifiers
source                  1..120
                        mol_type = other DNA
                        organism = synthetic construct
SEQUENCE: 453
cgcctgagca gtggaagtcc cacagaagct acagctgcca ggtcacgcat gaagggagca  60
ccgtggagaa gacagtggcc cctacagaat gttcataggt tctcaaccct caccccccac  120

SEQ ID NO: 454          moltype = DNA  length = 120
FEATURE                 Location/Qualifiers
source                  1..120
                        mol_type = other DNA
                        organism = synthetic construct
SEQUENCE: 454
cacgggagac tagagctgca ggatcccagg ggaggggtct ctcctcccac cccaaggcat  60
caagcccttc tccctgcact caataaaccc tcaataaata ttctcattgt caatcagaaa  120

SEQ ID NO: 455          moltype = DNA  length = 120
FEATURE                 Location/Qualifiers
source                  1..120
                        mol_type = other DNA
                        organism = synthetic construct
SEQUENCE: 455
gtcagcccaa ggctgccccc tcggtcactc tgttcccacc ctcctctgag gagcttcaag  60
ccaacaaggc cacactggtg tgtctcataa gtgacttcta cccgggagcc gtgacagtgg  120

SEQ ID NO: 456          moltype = DNA  length = 120
FEATURE                 Location/Qualifiers
source                  1..120
                        mol_type = other DNA
                        organism = synthetic construct
SEQUENCE: 456
cgcctgagca gtggaagtcc cacaaaagct acagctgcca ggtcacgcat gaagggagca  60
ccgtggagaa gacagtggcc cctacagaat gttcataggt tctcatccct caccccccac  120

SEQ ID NO: 457          moltype = DNA  length = 120
FEATURE                 Location/Qualifiers
source                  1..120
                        mol_type = other DNA
                        organism = synthetic construct
SEQUENCE: 457
cacgggagac tagagctgca ggatcccagg ggaggggtct ctcctcccac cccaaggcat  60
caagcccttc tccctgcact caataaaccc tcaataaata ttctcattgt caatcagaaa  120

SEQ ID NO: 458          moltype = DNA  length = 120
FEATURE                 Location/Qualifiers
source                  1..120
                        mol_type = other DNA
                        organism = synthetic construct
SEQUENCE: 458
gtcagcccaa ggctgccccc tcggtcactc tgttcccacc ctcctctgag gagcttcaag  60
ccaacaaggc cacactggtg tgtctcgtaa gtgacttcaa cccgggagcc gtgacagtgg  120

SEQ ID NO: 459          moltype = DNA  length = 120
FEATURE                 Location/Qualifiers
source                  1..120
                        mol_type = other DNA
                        organism = synthetic construct
SEQUENCE: 459
ccagcagcta cctgagcctg acgcccgagc agtggaagtc ccacagaagc tacagctgcc  60
gggtcacgca tgaagggagc accgtggaga agacagtggc ccctgcagaa tgctcttagg  120

SEQ ID NO: 460          moltype = DNA  length = 120
FEATURE                 Location/Qualifiers
source                  1..120
                        mol_type = other DNA
                        organism = synthetic construct
SEQUENCE: 460
cccccgaccc tcaccccacc cacaggggcc tggagctgca ggttcccagg ggaggggtct  60
ctgcccccat cccaagtcat ccagcccttc tcaataaata tcctcatcgt caacgagaaa  120

SEQ ID NO: 461          moltype = DNA  length = 120
FEATURE                 Location/Qualifiers
source                  1..120
```

```
                         mol_type = other DNA
                         organism = synthetic construct
SEQUENCE: 461
gcatccccga ccagccccaa ggtcttcccg ctgagcctcg acagcacccc ccaagatggg  60
aacgtggtcg tcgcatgcct ggtccagggc ttcttccccc aggagccact cagtgtgacc  120

SEQ ID NO: 462           moltype = DNA  length = 120
FEATURE                  Location/Qualifiers
source                   1..120
                         mol_type = other DNA
                         organism = synthetic construct
SEQUENCE: 462
tggagcgaaa gcggacagaa cgtgaccgcc agaaacttcc cacctagcca ggatgcctcc  60
ggggacctgt acaccacgag cagccagctg accctgccgg ccacacagtg cccagacggc  120

SEQ ID NO: 463           moltype = DNA  length = 120
FEATURE                  Location/Qualifiers
source                   1..120
                         mol_type = other DNA
                         organism = synthetic construct
SEQUENCE: 463
aagtccgtga catgccacgt gaagcactac acgaattcca gccaggatgt gactgtgccc  60
tgccgagttc ccccacctcc cccatgctgc cacccccgac tgtcgctgca ccgaccggcc  120

SEQ ID NO: 464           moltype = DNA  length = 120
FEATURE                  Location/Qualifiers
source                   1..120
                         mol_type = other DNA
                         organism = synthetic construct
SEQUENCE: 464
ctcgaggacc tgctcttagg ttcagaagcg aacctcacgt gcacactgac cggcctgaga  60
gatgcctctg gtgccacctt cacctggacg ccctcaagtg ggaagagcgc tgttcaagga  120

SEQ ID NO: 465           moltype = DNA  length = 120
FEATURE                  Location/Qualifiers
source                   1..120
                         mol_type = other DNA
                         organism = synthetic construct
SEQUENCE: 465
ccacctgagc gtgacctctg tggctgctac agcgtgtcca gtgtcctgcc tggctgtgcc  60
cagccatgga accatgggga gaccttcacc tgcactgctg cccaccccga gttgaagacc  120

SEQ ID NO: 466           moltype = DNA  length = 120
FEATURE                  Location/Qualifiers
source                   1..120
                         mol_type = other DNA
                         organism = synthetic construct
SEQUENCE: 466
ccactaaccg ccaacatcac aaaatccgga aacacattcc ggcccgaggt ccacctgctg  60
ccgccgccgt cggaggagct ggccctgaac gagctggtga cgctgacgtg cctggcacgt  120

SEQ ID NO: 467           moltype = DNA  length = 120
FEATURE                  Location/Qualifiers
source                   1..120
                         mol_type = other DNA
                         organism = synthetic construct
SEQUENCE: 467
ggcttcagcc ccaaggatgt gctggttcgc tggctgcagg ggtcacagga gctgccccgc  60
gagaagtacc tgacttgggc atcccggcag gagcccagcc agggcaccac cacctacgct  120

SEQ ID NO: 468           moltype = DNA  length = 120
FEATURE                  Location/Qualifiers
source                   1..120
                         mol_type = other DNA
                         organism = synthetic construct
SEQUENCE: 468
gtaaccagca tactgcgcgt ggcagctgag gactggaaga agggggagac cttctcctgc  60
atggtgggcc acgaggccct gccgctggcc ttcacacaga agaccatcga ccgcatggcg  120

SEQ ID NO: 469           moltype = DNA  length = 120
FEATURE                  Location/Qualifiers
source                   1..120
                         mol_type = other DNA
                         organism = synthetic construct
SEQUENCE: 469
ggctcttgct gtgttgcaga ttggcagatg ccgcctccct atgtggtgct ggacttgccg  60
caggagaccc tggaggagga gacccccggc gccaacctgt ggcccaccac catcaccttc  120

SEQ ID NO: 470           moltype = DNA  length = 120
```

```
FEATURE                Location/Qualifiers
source                 1..120
                       mol_type = other DNA
                       organism = synthetic construct
SEQUENCE: 470
ctcaccctct tcctgctgag cctgttctat agcacagcac tgaccgtgac cagcgtccgg  60
ggcccatctg gcaagaggga gggcccccag tactgagcgg gagccggcaa ggcacaggga  120

SEQ ID NO: 471         moltype = DNA  length = 120
FEATURE                Location/Qualifiers
source                 1..120
                       mol_type = other DNA
                       organism = synthetic construct
SEQUENCE: 471
ggaagtgtgg aggaacctct tggagaagcc agctatgctt gccagaactc agccctttca  60
gacatcaccg acccgccctt actcacgtgg cttccaggtg caataaagtg gccccaagga  120

SEQ ID NO: 472         moltype = DNA  length = 120
FEATURE                Location/Qualifiers
source                 1..120
                       mol_type = other DNA
                       organism = synthetic construct
SEQUENCE: 472
gcctccacac agagcccatc cgtcttcccc ttgacccgct gctgcaaaaa cattccctcc  60
aatgccacct ccgtgactct gggctgcctg gccacgggct acttcccgga gccggtgatg  120

SEQ ID NO: 473         moltype = DNA  length = 120
FEATURE                Location/Qualifiers
source                 1..120
                       mol_type = other DNA
                       organism = synthetic construct
SEQUENCE: 473
gtgacctggg acacaggctc cctcaacggg acaactatga ccttaccagc caccaccctc  60
acgctctctg gtcactatgc caccatcagc ttgctgaccg tctcgggtgc gtgggccaag  120

SEQ ID NO: 474         moltype = DNA  length = 120
FEATURE                Location/Qualifiers
source                 1..120
                       mol_type = other DNA
                       organism = synthetic construct
SEQUENCE: 474
cagatgttca cctgccgtgt ggcacacact ccatcgtcca cagactgggt cgacaacaaa  60
accttcagcg tctgctccag ggacttcacc ccgcccaccg tgaagatctt acagtcgtcc  120

SEQ ID NO: 475         moltype = DNA  length = 120
FEATURE                Location/Qualifiers
source                 1..120
                       mol_type = other DNA
                       organism = synthetic construct
SEQUENCE: 475
tgcgacggcg gcgggcactt ccccccgacc atccagctcc tgtgcctcgt ctctgggtac  60
accccaggga ctatcaacat cacctggctg gaggacgggc aggtcatgga cgtggacttg  120

SEQ ID NO: 476         moltype = DNA  length = 120
FEATURE                Location/Qualifiers
source                 1..120
                       mol_type = other DNA
                       organism = synthetic construct
SEQUENCE: 476
tccaccgcct ctaccacgca ggagggtgag ctggcctcca cacaaagcga gctcaccctc  60
agccagaagc actggctgtc agaccgcacc tacacctgcc aggtcaccta tcaaggtcac  120

SEQ ID NO: 477         moltype = DNA  length = 120
FEATURE                Location/Qualifiers
source                 1..120
                       mol_type = other DNA
                       organism = synthetic construct
SEQUENCE: 477
acctttgagg acagcaccaa gaagtgtgca gattccaacc cgagaggggt gagcgcctac  60
ctaagccggc ccagcccgtt cgacctgttc atccgcaagt cgcccacgat cacctgtctg  120

SEQ ID NO: 478         moltype = DNA  length = 120
FEATURE                Location/Qualifiers
source                 1..120
                       mol_type = other DNA
                       organism = synthetic construct
SEQUENCE: 478
tcccgggcca gtgggaagcc tgtgaaccac tccaccagaa aggaggagaa gcagcgcaat  60
ggcacgttaa ccgtcacgtc caccctgccg gtgggcaccc gagactggat cgagggggag  120
```

```
SEQ ID NO: 479         moltype = DNA  length = 120
FEATURE                Location/Qualifiers
source                 1..120
                       mol_type = other DNA
                       organism = synthetic construct
SEQUENCE: 479
acctaccagt gcagggtgac ccacccccac ctgcccaggg ccctcatgcg gtccacgacc  60
aagaccagcg gcccgcgtgc tgccccggaa gtctatgcgt ttgcgacgcc ggagtggccg  120

SEQ ID NO: 480         moltype = DNA  length = 120
FEATURE                Location/Qualifiers
source                 1..120
                       mol_type = other DNA
                       organism = synthetic construct
SEQUENCE: 480
gggagccggg acaagcgcac cctcgcctgc ctgatccaga acttcatgcc tgaggacatc  60
tcggtgcagt ggctgcacaa cgaggtgcag ctcccggacg cccggcacag cacgacgcag  120

SEQ ID NO: 481         moltype = DNA  length = 120
FEATURE                Location/Qualifiers
source                 1..120
                       mol_type = other DNA
                       organism = synthetic construct
SEQUENCE: 481
ccccgcaaga ccaagggctc cggcttcttc gtcttcagcc gcctggaggt gaccagggcc  60
gaatgggagc agaaagatga gttcatctgc cgtgcagtcc atgaggcagc aagcccctca  120

SEQ ID NO: 482         moltype = DNA  length = 120
FEATURE                Location/Qualifiers
source                 1..120
                       mol_type = other DNA
                       organism = synthetic construct
SEQUENCE: 482
cagaccgtcc agcgagcggt gtctgtaaat cccgagctgg acgtgtgcgt ggaggaggcc  60
gagggcgagg cgccgtggac gtggaccggc ctctgcatct tcgccgcact cttcctgctc  120

SEQ ID NO: 483         moltype = DNA  length = 120
FEATURE                Location/Qualifiers
source                 1..120
                       mol_type = other DNA
                       organism = synthetic construct
SEQUENCE: 483
agcgtgagct acagcgccgc catcacgctc ctcatggtgc agcggttcct ctcagccacg  60
cggcagggga ggccccagac ctccctcgac tacaccaacg tcctccagcc ccacgcctag  120

SEQ ID NO: 484         moltype = DNA  length = 120
FEATURE                Location/Qualifiers
source                 1..120
                       mol_type = other DNA
                       organism = synthetic construct
SEQUENCE: 484
tcctgcctcc ctccctccca gggctccatc cagctgtgca gtggggagga ctggccagac  60
cttctgtcca ctgttgcaat gaccccagga agctaccccc aataaactgt gcctgctcag  120

SEQ ID NO: 485         moltype = DNA  length = 120
FEATURE                Location/Qualifiers
source                 1..120
                       mol_type = other DNA
                       organism = synthetic construct
SEQUENCE: 485
gcttccacca agggcccatc ggtcttcccc ctggcgccct gctccaggag cacctccgag  60
agcacagccg ccctgggctg cctggtcaag gactacttcc ccgaaccggt gacggtgtcg  120

SEQ ID NO: 486         moltype = DNA  length = 120
FEATURE                Location/Qualifiers
source                 1..120
                       mol_type = other DNA
                       organism = synthetic construct
SEQUENCE: 486
tggaactcag gcgccctgac cagcggcgtg cacaccttcc cggctgtcct acagtcctca  60
ggactctact ccctcagcag cgtggtgacc gtgccctcca gcagcttggg cacgaagacc  120

SEQ ID NO: 487         moltype = DNA  length = 120
FEATURE                Location/Qualifiers
source                 1..120
                       mol_type = other DNA
                       organism = synthetic construct
SEQUENCE: 487
```

```
tacacctgca acgtagatca caagcccagc aacaccaagg tggacaagag agttgagtcc  60
aaatatggtc ccccatgccc atcatgccca gcacctgagt tcctgggggg accatcagtc  120

SEQ ID NO: 488          moltype = DNA  length = 120
FEATURE                 Location/Qualifiers
source                  1..120
                        mol_type = other DNA
                        organism = synthetic construct
SEQUENCE: 488
ttcctgttcc ccccaaaacc caaggacact ctcatgatct cccggacccc tgaggtcacg  60
tgcgtggtgg tggacgtgag ccaggaagac cccgaggtcc agttcaactg gtacgtggat  120

SEQ ID NO: 489          moltype = DNA  length = 120
FEATURE                 Location/Qualifiers
source                  1..120
                        mol_type = other DNA
                        organism = synthetic construct
SEQUENCE: 489
ggcgtggagg tgcataatgc caagacaaag ccgcgggagg agcagttcaa cagcacgtac  60
cgtgtggtca gcgtcctcac cgtcctgcac caggactggc tgaacggcaa ggagtacaag  120

SEQ ID NO: 490          moltype = DNA  length = 120
FEATURE                 Location/Qualifiers
source                  1..120
                        mol_type = other DNA
                        organism = synthetic construct
SEQUENCE: 490
tgcaaggtct ccaacaaagg cctcccgtcc tccatcgaga aaaccatctc caaagccaaa  60
gggcagcccc gagagccaca ggtgtacacc ctgcccccat cccaggagga gatgaccaag  120

SEQ ID NO: 491          moltype = DNA  length = 120
FEATURE                 Location/Qualifiers
source                  1..120
                        mol_type = other DNA
                        organism = synthetic construct
SEQUENCE: 491
aaccaggtca gcctgacctg cctggtcaaa ggcttctacc ccagcgacat cgccgtggag  60
tgggagagca atgggcagcc ggagaacaac tacaagacca cgcctcccgt gctggactcc  120

SEQ ID NO: 492          moltype = DNA  length = 120
FEATURE                 Location/Qualifiers
source                  1..120
                        mol_type = other DNA
                        organism = synthetic construct
SEQUENCE: 492
gacggctcct tcttcctcta cagcaggctc accgtggaca agagcaggtg gcaggagggg  60
aatgtcttct catgctccgt gatgcatgag gctctgcaca accactacac acagaagagc  120

SEQ ID NO: 493          moltype = DNA  length = 120
FEATURE                 Location/Qualifiers
source                  1..120
                        mol_type = other DNA
                        organism = synthetic construct
SEQUENCE: 493
ctctccctgt ctctggagct gcaactggag gagagctgtg cggaggcgca ggacggggag  60
ctggacgggc tgtggacgac catcaccatc ttcatcacac tcttcctgct aagcgtgtgc  120

SEQ ID NO: 494          moltype = DNA  length = 120
FEATURE                 Location/Qualifiers
source                  1..120
                        mol_type = other DNA
                        organism = synthetic construct
SEQUENCE: 494
tacagtgcca ccgtcacctt cttcaaggtg aagtggatct tctcctcagt ggtggacctg  60
aagcagacca tcgtccccga ctacaggaac atgataaggc aggggggccta gggccaccct  120

SEQ ID NO: 495          moltype = DNA  length = 120
FEATURE                 Location/Qualifiers
source                  1..120
                        mol_type = other DNA
                        organism = synthetic construct
SEQUENCE: 495
ccccctgacc tcaccgccct caaccccatg gctctctggc ttcgcagtcg ccctctgagc  60
cctgaaacgc ccccccttcca gaccctgtgc atagcaggtc taccccagac ctccgctgct  120

SEQ ID NO: 496          moltype = DNA  length = 120
FEATURE                 Location/Qualifiers
source                  1..120
                        mol_type = other DNA
```

```
                         organism = synthetic construct
SEQUENCE: 496
tggtgcatgc agggcgctga gggccaggtg tcccctcagc aggacgtccc tgccctctgg  60
accaccaggt gctcacacaa aaggaggtaa ccggcatccc aggcccccac tcaggcagga  120

SEQ ID NO: 497           moltype = DNA  length = 120
FEATURE                  Location/Qualifiers
source                   1..120
                         mol_type = other DNA
                         organism = synthetic construct
SEQUENCE: 497
cctcgccctg gagccaaccc cgtccacgcc agcctcctga acacaggcat ggtttccaga  60
tggtgagtgg gagcatcagt cgccaaggta gggaagccac agcaccatca ggccctgttg  120

SEQ ID NO: 498           moltype = DNA  length = 120
FEATURE                  Location/Qualifiers
source                   1..120
                         mol_type = other DNA
                         organism = synthetic construct
SEQUENCE: 498
gggaggcttc cgagagctgc gaaggctcac tcagacggcc ttcctcccag cccgcagcca  60
gccagcctcc attccgggca ctcccgtgaa ctcctgacat gaggaatgag gttgttctga  120

SEQ ID NO: 499           moltype = DNA  length = 120
FEATURE                  Location/Qualifiers
source                   1..120
                         mol_type = other DNA
                         organism = synthetic construct
SEQUENCE: 499
tttcaagcaa agaacgctgc tctctggctc ctgggaacag tctcggtgcc agcaccaccc  60
cttggctgcc tgcccacact gctggattct cgggtggaac tggacccgca gggacagcca  120

SEQ ID NO: 500           moltype = DNA  length = 120
FEATURE                  Location/Qualifiers
source                   1..120
                         mol_type = other DNA
                         organism = synthetic construct
SEQUENCE: 500
gccccagagt ccgcactggg gagagaaagg gccaggccca ggacactgcc acctaccacc  60
cactccagtc caccgagatc actcggagaa gagcctgggc catgtggccg ctgcaggagc  120

SEQ ID NO: 501           moltype = DNA  length = 120
FEATURE                  Location/Qualifiers
source                   1..120
                         mol_type = other DNA
                         organism = synthetic construct
SEQUENCE: 501
cccacagtgc aagggtgagg atagcccaag gaagggctgg gcatctgccc agacaggcct  60
cccacagaag gctggtgacc aggtcccagg cgggcaagac tcagccttgg tggggcctga  120

SEQ ID NO: 502           moltype = DNA  length = 120
FEATURE                  Location/Qualifiers
source                   1..120
                         mol_type = other DNA
                         organism = synthetic construct
SEQUENCE: 502
ggacagagga ggcccaggag catcggggag agaggtggag ggacaccggg agagccagga  60
gcgtggacac agccagaact catcacagag gctggcgtcc agtcccgggt cacgtgcagc  120

SEQ ID NO: 503           moltype = DNA  length = 120
FEATURE                  Location/Qualifiers
source                   1..120
                         mol_type = other DNA
                         organism = synthetic construct
SEQUENCE: 503
aggaacaagc agccactctg gggcaccag gtggagaggc aagacgacaa agagggtgcc  60
cgtgttcttg cgaaagcggg gctgctggcc acgagtgctg gacagaggcc cccacgctct  120

SEQ ID NO: 504           moltype = DNA  length = 120
FEATURE                  Location/Qualifiers
source                   1..120
                         mol_type = other DNA
                         organism = synthetic construct
SEQUENCE: 504
gctgccccca tcacaccgtt ccgtgactgt cacgcagaat ccacagacag gaagggaggc  60
tcgagcggga ctgcggccag cgcctgcctc ggccgtcagg gaggactccc gggctcactc  120

SEQ ID NO: 505           moltype = DNA  length = 120
FEATURE                  Location/Qualifiers
```

```
source                  1..120
                        mol_type = other DNA
                        organism = synthetic construct
SEQUENCE: 505
gaaggaggtg tcaccatttc agctttggct tttcttcttc ttttaaattt tctaaagctc  60
attaattgtc tttgatgttt cttttgtgat gacaataaaa tatccttttt aagtcttgta  120

SEQ ID NO: 506          moltype = DNA  length = 120
FEATURE                 Location/Qualifiers
source                  1..120
                        mol_type = other DNA
                        organism = synthetic construct
SEQUENCE: 506
agcccccgct ccccgggctc tcggggtcgc gcgaggatgc ttggcacgta ccccgtgtac  60
atacttcccg ggcgcccagc atggaaataa agcacccagc gctgccctgg gcccctgcga  120

SEQ ID NO: 507          moltype = DNA  length = 120
FEATURE                 Location/Qualifiers
source                  1..120
                        mol_type = other DNA
                        organism = synthetic construct
SEQUENCE: 507
gcctccacca agggcccatc ggtcttcccc ctggcgccct gctccaggag cacctccgag  60
agcacagcgg ccctgggctg cctggtcaag gactacttcc ccgaaccggt gacggtgtcg  120

SEQ ID NO: 508          moltype = DNA  length = 120
FEATURE                 Location/Qualifiers
source                  1..120
                        mol_type = other DNA
                        organism = synthetic construct
SEQUENCE: 508
tggaactcag gcgctctgac cagcggcgtg cacaccttcc cggctgtcct acagtcctca  60
ggactctact ccctcagcag cgtggtgacc gtgccctcca gcaacttcgg cacccagacc  120

SEQ ID NO: 509          moltype = DNA  length = 120
FEATURE                 Location/Qualifiers
source                  1..120
                        mol_type = other DNA
                        organism = synthetic construct
SEQUENCE: 509
tacacctgca acgtagatca caagcccagc aacaccaagg tggacaagac agttgagcgc  60
aaatgttgtg tcgagtgccc accgtgccca gcaccacctg tggcaggacc gtcagtcttc  120

SEQ ID NO: 510          moltype = DNA  length = 120
FEATURE                 Location/Qualifiers
source                  1..120
                        mol_type = other DNA
                        organism = synthetic construct
SEQUENCE: 510
ctcttccccc caaaacccaa ggacaccctc atgatctccc ggacccctga ggtcacgtgc  60
gtggtggtgg acgtgagcca cgaagacccc gaggtccagt tcaactggta cgtggacggc  120

SEQ ID NO: 511          moltype = DNA  length = 120
FEATURE                 Location/Qualifiers
source                  1..120
                        mol_type = other DNA
                        organism = synthetic construct
SEQUENCE: 511
gtggaggtgc ataatgccaa gacaaagcca cgggaggagc agttcaacag cacgttccgt  60
gtggtcagcg tcctcaccgt cgtgcaccag gactggctga acggcaagga gtacaagtgc  120

SEQ ID NO: 512          moltype = DNA  length = 120
FEATURE                 Location/Qualifiers
source                  1..120
                        mol_type = other DNA
                        organism = synthetic construct
SEQUENCE: 512
aaggtctcca acaaaggcct cccagccccc atcgagaaaa ccatctccaa aaccaaaggg  60
cagccccgag aaccacaggt gtacaccctg cccccatccc gggaggagat gaccaagaac  120

SEQ ID NO: 513          moltype = DNA  length = 120
FEATURE                 Location/Qualifiers
source                  1..120
                        mol_type = other DNA
                        organism = synthetic construct
SEQUENCE: 513
caggtcagcc tgacctgcct ggtcaaaggc ttctacccca gcgacatctc cgtggagtgg  60
gagagcaatg ggcagccgga gaacaactac aagaccacac ctcccatgct ggactccgac  120
```

```
SEQ ID NO: 514          moltype = DNA  length = 120
FEATURE                 Location/Qualifiers
source                  1..120
                        mol_type = other DNA
                        organism = synthetic construct
SEQUENCE: 514
ggctccttct tcctctacag caagctcacc gtggacaaga gcaggtggca gcaggggaac  60
gtcttctcat gctccgtgat gcatgaggct ctgcacaacc actacacaca gaagagcctc  120

SEQ ID NO: 515          moltype = DNA  length = 120
FEATURE                 Location/Qualifiers
source                  1..120
                        mol_type = other DNA
                        organism = synthetic construct
SEQUENCE: 515
tccctgtctc cggagctgca actggaggag agctgtgcgg aggcgcagga cggggagctg  60
gacgggctgt ggaccaccat caccatcttc atcacactct tcctgctaag cgtgtgctac  120

SEQ ID NO: 516          moltype = DNA  length = 120
FEATURE                 Location/Qualifiers
source                  1..120
                        mol_type = other DNA
                        organism = synthetic construct
SEQUENCE: 516
agtgccacca tcaccttctt caaggtgaag tggatcttct cctcagtggt ggacctgaag  60
cagaccatcg tccccgacta caggaacatg atcaggcagg gggcctaggg ccaccctctg  120

SEQ ID NO: 517          moltype = DNA  length = 120
FEATURE                 Location/Qualifiers
source                  1..120
                        mol_type = other DNA
                        organism = synthetic construct
SEQUENCE: 517
cccccgacct caccgccctc aaccccatgg ctctctggcc tcgcagtcgc cctctgaccc  60
tgacacgccc cccttccaga ccctgtgcat agcaggtcta ccccagacct ccgctgcttg  120

SEQ ID NO: 518          moltype = DNA  length = 120
FEATURE                 Location/Qualifiers
source                  1..120
                        mol_type = other DNA
                        organism = synthetic construct
SEQUENCE: 518
gtgcatgcag ggcgctgggg gccaagtgtc ccctcagcag gacgtccctg ccctccggcc  60
cgccaggtgc tcacacaaaa ggaggtagtg accagcatcc caggccccca ctcaggcagg  120

SEQ ID NO: 519          moltype = DNA  length = 120
FEATURE                 Location/Qualifiers
source                  1..120
                        mol_type = other DNA
                        organism = synthetic construct
SEQUENCE: 519
acctcgccct ggagccaacc ctgtccacgc cagcctcctg aacacaggcg tggtttccag  60
atggtgagtg ggagcatcag tcgccaaggt agggaagtca cagcaccatc aggccctgtt  120

SEQ ID NO: 520          moltype = DNA  length = 120
FEATURE                 Location/Qualifiers
source                  1..120
                        mol_type = other DNA
                        organism = synthetic construct
SEQUENCE: 520
ggggaggctt ccgagagctg cgaaggctca ctcagacggc cttcctccca gcccgcagcc  60
agccagcctc cattccaggc actcccgtga actcctgaca tgaggaatga ggttgttctg  120

SEQ ID NO: 521          moltype = DNA  length = 120
FEATURE                 Location/Qualifiers
source                  1..120
                        mol_type = other DNA
                        organism = synthetic construct
SEQUENCE: 521
atttcaagca aagaacgctg ctctctggct cctgggaaca gtctcagtgc cagcaccacc  60
ccttggctgc ctgcccacac tgctggattc tcgggtggaa ctcgacccgc agggacagcc  120

SEQ ID NO: 522          moltype = DNA  length = 120
FEATURE                 Location/Qualifiers
source                  1..120
                        mol_type = other DNA
                        organism = synthetic construct
SEQUENCE: 522
agccccagag tccgcactgg ggagagaagg ggccaggccc aggacactgc cacctaccac  60
```

```
ccactccagt ccaccgagat cactcggaga agagcctggg ccatgtggcc gctgcaggag  120

SEQ ID NO: 523         moltype = DNA  length = 120
FEATURE                Location/Qualifiers
source                 1..120
                       mol_type = other DNA
                       organism = synthetic construct
SEQUENCE: 523
ccccacggtg caagggtgag gatagcccaa ggaagggctg ggcatctgcc cagacaggcc  60
tcccagagaa ggctggtgac caggtcccag gcgggcaaga ctcagccttg gtggggcctg  120

SEQ ID NO: 524         moltype = DNA  length = 120
FEATURE                Location/Qualifiers
source                 1..120
                       mol_type = other DNA
                       organism = synthetic construct
SEQUENCE: 524
aggacagagg aggcccagga gcatcgggga gagaggtgga gggacaccgg gagagccagg  60
agcgtggaca cagccagaac tcatcacaga ggctggcgtc cagccccggg tcacgtgcag  120

SEQ ID NO: 525         moltype = DNA  length = 120
FEATURE                Location/Qualifiers
source                 1..120
                       mol_type = other DNA
                       organism = synthetic construct
SEQUENCE: 525
caggaacaag cagccactct gggggcacca ggtggagagg caagacgaca aagagggtgc  60
ccgtgttctt gtgaaagcgg ggctgctggc cacgagtgct ggacagaggc ccccacgctc  120

SEQ ID NO: 526         moltype = DNA  length = 120
FEATURE                Location/Qualifiers
source                 1..120
                       mol_type = other DNA
                       organism = synthetic construct
SEQUENCE: 526
tgctgccccc atcacgccgt tccgtgactg tcacgcagaa tccgcagaca gggagactcg  60
agcgggagtg cggccagcgc ctgcctcagc tgtcagggag gactcccggg ctcactcgaa  120

SEQ ID NO: 527         moltype = DNA  length = 120
FEATURE                Location/Qualifiers
source                 1..120
                       mol_type = other DNA
                       organism = synthetic construct
SEQUENCE: 527
ggaggtgcca ccatttcagc tttggtagct tttcttcttc ttttaaattt tctaaagctc  60
attaattgtc tttgatgttt cttttgtgat gacaataaaa tatccttttt aagtcttgta  120

SEQ ID NO: 528         moltype = DNA  length = 120
FEATURE                Location/Qualifiers
source                 1..120
                       mol_type = other DNA
                       organism = synthetic construct
SEQUENCE: 528
agccccccgct ccccaggctc tcggggtcgc gcgaggatgc ttggcacgta ccccgtctac  60
atacttcccg ggcacccagc atggaaataa agcacccagc gctgccctgg gcccctgcga  120

SEQ ID NO: 529         moltype = DNA  length = 120
FEATURE                Location/Qualifiers
source                 1..120
                       mol_type = other DNA
                       organism = synthetic construct
SEQUENCE: 529
gcatccccga ccagccccaa ggtcttcccg ctgagcctct gcagcaccca gccagatggg  60
aacgtggtca tcgcctgcct ggtccagggc ttcttccccc aggagccact cagtgtgacc  120

SEQ ID NO: 530         moltype = DNA  length = 120
FEATURE                Location/Qualifiers
source                 1..120
                       mol_type = other DNA
                       organism = synthetic construct
SEQUENCE: 530
tggagcgaaa gcggacaggg cgtgaccgcc agaaacttcc cacccagcca ggatgcctcc  60
ggggacctgt acaccacgag cagccagctg accctgccgg ccacacagtg cctagccggc  120

SEQ ID NO: 531         moltype = DNA  length = 120
FEATURE                Location/Qualifiers
source                 1..120
                       mol_type = other DNA
                       organism = synthetic construct
```

```
SEQUENCE: 531
aagtccgtga catgccacgt gaagcactac acgaatccca gccaggatgt gactgtgccc  60
tgcccagttc cctcaactcc acctacccca tctccctcaa ctccacctac cccatctccc  120

SEQ ID NO: 532          moltype = DNA  length = 120
FEATURE                 Location/Qualifiers
source                  1..120
                        mol_type = other DNA
                        organism = synthetic construct
SEQUENCE: 532
tcatgctgcc acccccgact gtcactgcac cgaccggccc tcgaggacct gctcttaggt  60
tcagaagcga acctcacgtg cacactgacc ggcctgagag atgcctcagg tgtcaccttc  120

SEQ ID NO: 533          moltype = DNA  length = 120
FEATURE                 Location/Qualifiers
source                  1..120
                        mol_type = other DNA
                        organism = synthetic construct
SEQUENCE: 533
acctggacgc cctcaagtgg gaagagcgct gttcaaggac cacctgagcg tgacctctgt  60
ggctgctaca gcgtgtccag tgtcctgccg ggctgtgccg agccatggaa ccatgggaag  120

SEQ ID NO: 534          moltype = DNA  length = 120
FEATURE                 Location/Qualifiers
source                  1..120
                        mol_type = other DNA
                        organism = synthetic construct
SEQUENCE: 534
ggaggagctg gccctgaacg agctggtgac gctgacgtgc ctggcacgcg gcttcagccc  60
caaggatgtg ctggttcgct ggctgcaggg gtcacaggag ctgccccgcg agaagtacct  120

SEQ ID NO: 535          moltype = DNA  length = 120
FEATURE                 Location/Qualifiers
source                  1..120
                        mol_type = other DNA
                        organism = synthetic construct
SEQUENCE: 535
gacttgggca tcccggcagg agcccagcca gggcaccacc accttcgctg tgaccagcat  60
actgcgcgtg gcagccgagg actggaagaa gggggacacc ttctcctgca tggtgggcca  120

SEQ ID NO: 536          moltype = DNA  length = 120
FEATURE                 Location/Qualifiers
source                  1..120
                        mol_type = other DNA
                        organism = synthetic construct
SEQUENCE: 536
cgaggccctg ccgctggcct tcacacagaa gaccatcgac cgcttggcgg attggcagat  60
gccgcctccc tatgtggtgc tggacttgcc gcaggagacc ctggaggagg agacccccgg  120

SEQ ID NO: 537          moltype = DNA  length = 120
FEATURE                 Location/Qualifiers
source                  1..120
                        mol_type = other DNA
                        organism = synthetic construct
SEQUENCE: 537
cgccaacctg tggcccacca ccatcacctt cctcaccctc ttcctgctga gcctgttcta  60
tagcacagca ctgaccgtga ccagcgtccg gggcccatct ggcaacaggg agggccccca  120

SEQ ID NO: 538          moltype = DNA  length = 120
FEATURE                 Location/Qualifiers
source                  1..120
                        mol_type = other DNA
                        organism = synthetic construct
SEQUENCE: 538
gtactgagca ggagccggca aggcacaggg aggaagtgtg gaggaacctc ttggagaagc  60
cagctatgct tgccagaact cagccctttc agacatcacc gacccgccct tactcacatg  120

SEQ ID NO: 539          moltype = DNA  length = 120
FEATURE                 Location/Qualifiers
source                  1..120
                        mol_type = other DNA
                        organism = synthetic construct
SEQUENCE: 539
cttggcgggt aaacccaccc atgtcaatgt gtctgttgtc atggcggagg tggacggcac  60
ctgctactga gccgcccgcc tgtccccacc cctgaataaa ctccatgctc ccccaagcag  120

SEQ ID NO: 540          moltype = DNA  length = 120
FEATURE                 Location/Qualifiers
source                  1..120
```

```
                         mol_type = other DNA
                         organism = synthetic construct
SEQUENCE: 540
gcctccacca agggcccatc ggtcttcccc ctggcaccct cctccaagag cacctctggg  60
ggcacagcag ccctgggctg cctggtcaag gactacttcc ccgaaccggt gacggtgtcg  120

SEQ ID NO: 541           moltype = DNA  length = 120
FEATURE                  Location/Qualifiers
source                   1..120
                         mol_type = other DNA
                         organism = synthetic construct
SEQUENCE: 541
tggaactcag gcgccctgac cagcggcgtg cacaccttcc cggctgtcct acagtcctca  60
ggactctact ccctcagcag cgtggtgacc gtgccctcca gcagcttggg cacccagacc  120

SEQ ID NO: 542           moltype = DNA  length = 120
FEATURE                  Location/Qualifiers
source                   1..120
                         mol_type = other DNA
                         organism = synthetic construct
SEQUENCE: 542
tacatctgca acgtgaatca caagcccagc aacaccaagg tggacaagaa agttgagccc  60
aaatcttgtg acaaaactca cacatgccca ccgtgcccag cacctgaact cctgggggga  120

SEQ ID NO: 543           moltype = DNA  length = 120
FEATURE                  Location/Qualifiers
source                   1..120
                         mol_type = other DNA
                         organism = synthetic construct
SEQUENCE: 543
ccgtcagtct tcctcttccc cccaaaaccc aaggacaccc tcatgatctc ccggacccct  60
gaggtcacat gcgtggtggt ggacgtgagc cacgaagacc ctgaggtcaa gttcaactgg  120

SEQ ID NO: 544           moltype = DNA  length = 120
FEATURE                  Location/Qualifiers
source                   1..120
                         mol_type = other DNA
                         organism = synthetic construct
SEQUENCE: 544
tacgtggacg gcgtggaggt gcataatgcc aagacaaagc cgcgggagga gcagtacaac  60
agcacgtacc gtgtggtcag cgtcctcacc gtcctgcacc aggactggct gaatggcaag  120

SEQ ID NO: 545           moltype = DNA  length = 120
FEATURE                  Location/Qualifiers
source                   1..120
                         mol_type = other DNA
                         organism = synthetic construct
SEQUENCE: 545
gagtacaagt gcaaggtctc caacaaagcc ctcccagccc ccatcgagaa aaccatctcc  60
aaagccaaag ggcagccccg agaaccacag gtgtacaccc tgcccccatc ccgggatgag  120

SEQ ID NO: 546           moltype = DNA  length = 120
FEATURE                  Location/Qualifiers
source                   1..120
                         mol_type = other DNA
                         organism = synthetic construct
SEQUENCE: 546
ctgaccaaga accaggtcag cctgacctgc ctggtcaaag gcttctatcc cagcgacatc  60
gccgtggagt gggagagcaa tgggcagccg gagaacaact acaagaccac gcctcccgtg  120

SEQ ID NO: 547           moltype = DNA  length = 120
FEATURE                  Location/Qualifiers
source                   1..120
                         mol_type = other DNA
                         organism = synthetic construct
SEQUENCE: 547
ctggactccg acggctcctt cttcctctac agcaagctca ccgtggacaa gagcaggtgg  60
cagcagggga acgtcttctc atgctccgtg atgcatgagg ctctgcacaa ccactacaca  120

SEQ ID NO: 548           moltype = DNA  length = 120
FEATURE                  Location/Qualifiers
source                   1..120
                         mol_type = other DNA
                         organism = synthetic construct
SEQUENCE: 548
cagaagagcc tctccctgtc tccggagctg caactggagg agagctgtgc ggaggcgcag  60
gacggggagc tggacgggct gtggacgacc atcaccatct tcatcacact cttcctgtta  120

SEQ ID NO: 549           moltype = DNA  length = 120
```

-continued

```
FEATURE                Location/Qualifiers
source                 1..120
                       mol_type = other DNA
                       organism = synthetic construct
SEQUENCE: 549
agcgtgtgct acagtgccac cgtcaccttc ttcaaggtga agtggatctt ctcctcggtg  60
gtggacctga agcagaccat catccccgac tacaggaaca tgatcggaca gggggcctag  120

SEQ ID NO: 550         moltype = DNA  length = 120
FEATURE                Location/Qualifiers
source                 1..120
                       mol_type = other DNA
                       organism = synthetic construct
SEQUENCE: 550
cgccctcaac cccatgactc tctggcctcg cagttgccct ctgaccctga cacacctgac  60
acgccccccct tccagaccct gtgcatagca ggtctacccc agacctccgc tgcttggtgc  120

SEQ ID NO: 551         moltype = DNA  length = 120
FEATURE                Location/Qualifiers
source                 1..120
                       mol_type = other DNA
                       organism = synthetic construct
SEQUENCE: 551
atgcagggca ctgggggcca ggtgtcccct cagcaggacg tccttgccct ccggaccaca  60
aggtgctcac acaaaaggag gcagtgaccg gtatcccagg cccccaccca ggcaggacct  120

SEQ ID NO: 552         moltype = DNA  length = 120
FEATURE                Location/Qualifiers
source                 1..120
                       mol_type = other DNA
                       organism = synthetic construct
SEQUENCE: 552
cgccctggag ccaaccccgt ccacgccagc ctcctgaaca caggcgtggt ttccagatgg  60
tgagtgggag cgtcagccgc caaggtaggg aagccacagc accatcaggc cctgttgggg  120

SEQ ID NO: 553         moltype = DNA  length = 120
FEATURE                Location/Qualifiers
source                 1..120
                       mol_type = other DNA
                       organism = synthetic construct
SEQUENCE: 553
aggcttccga gagctgcgaa ggctcactca gacggccttc ctcccagccc gcagccagcc  60
agcctccatt ccgggcactc ccgtgaactc ctgacatgag gaatgaggtt gttctgattt  120

SEQ ID NO: 554         moltype = DNA  length = 120
FEATURE                Location/Qualifiers
source                 1..120
                       mol_type = other DNA
                       organism = synthetic construct
SEQUENCE: 554
caagcaaaga acgctgctct ctggctcctg ggaacagtct cagtgccagc accacccctt  60
ggctgcctgc ccacactgct ggattctcgg gtggaactgg acccgcaggg acagccagcc  120

SEQ ID NO: 555         moltype = DNA  length = 120
FEATURE                Location/Qualifiers
source                 1..120
                       mol_type = other DNA
                       organism = synthetic construct
SEQUENCE: 555
ccagagtccg cactggggag agaaggggcc aggcccagga cactgccacc tcccacccac  60
tccagtccac cgagatcact cagagaagag cctgggccat gtggccgctg caggagcccc  120

SEQ ID NO: 556         moltype = DNA  length = 120
FEATURE                Location/Qualifiers
source                 1..120
                       mol_type = other DNA
                       organism = synthetic construct
SEQUENCE: 556
acagtgcaag ggtgaggata gcccaaggaa gggctgggca tctgcccaga caggcctccc  60
agagaaggct ggtgaccagg tcccaggcgg gcaagactca gccttggtgg ggcctgagga  120

SEQ ID NO: 557         moltype = DNA  length = 120
FEATURE                Location/Qualifiers
source                 1..120
                       mol_type = other DNA
                       organism = synthetic construct
SEQUENCE: 557
cagaggaggc ccaggagcat cggggagaga ggtggaggga caccgggaga gccaggagcg  60
tggacacagc cagaactcat cacagaggct ggcgtccagc cccgggtcac gtgcagcagg  120
```

```
SEQ ID NO: 558         moltype = DNA  length = 120
FEATURE                Location/Qualifiers
source                 1..120
                       mol_type = other DNA
                       organism = synthetic construct
SEQUENCE: 558
aacaagcagc cactctgggg gcaccaggtg gagaggcaag acgacaaaga gggtgcccgt  60
gttcttgcga aagcagggct gctggccacg agtgctggac agaggccccc acgctctgct  120

SEQ ID NO: 559         moltype = DNA  length = 120
FEATURE                Location/Qualifiers
source                 1..120
                       mol_type = other DNA
                       organism = synthetic construct
SEQUENCE: 559
gcccccatca cgccgttccg tgactgtcac gcagaatctg cagacaggaa gggagactcg  60
agcgggagtg cggccagcgc ctgcctcggc cgtcagggag gactcctggg ctcactcgaa  120

SEQ ID NO: 560         moltype = DNA  length = 120
FEATURE                Location/Qualifiers
source                 1..120
                       mol_type = other DNA
                       organism = synthetic construct
SEQUENCE: 560
ggaggtgcca ccatttcagc tttggtagct tttcttcttc ttttaaattt tctaaagctc  60
attaattgtc tttgatgttt cttttgtgat gacaataaaa tatccttttt aagtcttgta  120

SEQ ID NO: 561         moltype = DNA  length = 120
FEATURE                Location/Qualifiers
source                 1..120
                       mol_type = other DNA
                       organism = synthetic construct
SEQUENCE: 561
aagcccccgc tccccaggct ctcggggtcg cgcgaggatg cttggcacgt accccgtgta  60
catacttccc aggcacccag catggaaata aagcacccag cgcttccctg ggcccctgcg  120

SEQ ID NO: 562         moltype = DNA  length = 120
FEATURE                Location/Qualifiers
source                 1..120
                       mol_type = other DNA
                       organism = synthetic construct
SEQUENCE: 562
cttccaccaa gggcccatcg gtcttccccc tggcgccctg ctccaggagc acctctgggg  60
gcacagcggc cctgggctgc ctggtcaagg actacttccc agaaccggtg acggtgtcgt  120

SEQ ID NO: 563         moltype = DNA  length = 120
FEATURE                Location/Qualifiers
source                 1..120
                       mol_type = other DNA
                       organism = synthetic construct
SEQUENCE: 563
ggaactcagg cgccctgacc agcggcgtgc acaccttccc ggctgtccta cagtcctcag  60
gactctactc cctcagcagc gtggtgaccg tgccctccag cagcttgggc acccagacct  120

SEQ ID NO: 564         moltype = DNA  length = 120
FEATURE                Location/Qualifiers
source                 1..120
                       mol_type = other DNA
                       organism = synthetic construct
SEQUENCE: 564
acacctgcaa cgtgaatcac aagcccagca acaccaaggt ggacaagaga gttgagctca  60
aaaccccact tggtgacaca actcacacat gcccacggtg cccagagccc aaatcttgtg  120

SEQ ID NO: 565         moltype = DNA  length = 120
FEATURE                Location/Qualifiers
source                 1..120
                       mol_type = other DNA
                       organism = synthetic construct
SEQUENCE: 565
acacacctcc cccgtgccca cggtgcccag agcccaaatc ttgtgacaca cctcccccat  60
gcccacggtg cccagagccc aaatcttgtg acacacctcc cccgtgccca aggtgcccag  120

SEQ ID NO: 566         moltype = DNA  length = 120
FEATURE                Location/Qualifiers
source                 1..120
                       mol_type = other DNA
                       organism = synthetic construct
SEQUENCE: 566
```

-continued

```
cacctgaact cctgggagga ccgtcagtct tcctcttccc cccaaaaccc aaggataccc  60
ttatgatttc ccggacccct gaggtcacgt gcgtggtggt ggacgtgagc cacgaagacc  120

SEQ ID NO: 567         moltype = DNA  length = 120
FEATURE                Location/Qualifiers
source                 1..120
                       mol_type = other DNA
                       organism = synthetic construct
SEQUENCE: 567
ccgaggtcca gttcaagtgg tacgtggacg gcgtggaggt gcataatgcc aagacaaagc  60
cgcgggagga gcagtacaac agcacgttcc gtgtggtcag cgtcctcacc gtcctgcacc  120

SEQ ID NO: 568         moltype = DNA  length = 120
FEATURE                Location/Qualifiers
source                 1..120
                       mol_type = other DNA
                       organism = synthetic construct
SEQUENCE: 568
aggactggct gaacggcaag gagtacaagt gcaaggtctc caacaaagcc ctcccagccc  60
ccatcgagaa aaccatctcc aaaaccaaag gacagccccg agaaccacag gtgtacaccc  120

SEQ ID NO: 569         moltype = DNA  length = 120
FEATURE                Location/Qualifiers
source                 1..120
                       mol_type = other DNA
                       organism = synthetic construct
SEQUENCE: 569
tgcccccatc ccgggaggag atgaccaaga accaggtcag cctgacctgc ctggtcaaag  60
gcttctaccc cagcgacatc gccgtggagt gggagagcag cgggcagccg gagaacaact  120

SEQ ID NO: 570         moltype = DNA  length = 120
FEATURE                Location/Qualifiers
source                 1..120
                       mol_type = other DNA
                       organism = synthetic construct
SEQUENCE: 570
acaacaccac gcctcccatg ctggactccg acggctcctt cttcctctac agcaagctca  60
ccgtggacaa gagcaggtgg cagcagggga acatcttctc atgctccgtg atgcatgagg  120

SEQ ID NO: 571         moltype = DNA  length = 120
FEATURE                Location/Qualifiers
source                 1..120
                       mol_type = other DNA
                       organism = synthetic construct
SEQUENCE: 571
ctctgcacaa ccgcttcacg cagaagagcc tctccctgtc tccggagctg caactggagg  60
agagctgtgc ggaggcgcag gacggggagc tggacgggct gtggacgacc atcaccatct  120

SEQ ID NO: 572         moltype = DNA  length = 120
FEATURE                Location/Qualifiers
source                 1..120
                       mol_type = other DNA
                       organism = synthetic construct
SEQUENCE: 572
tcatcacact cttcctgtta agcgtgtgct acagtgccac cgtcaccttc ttcaaggtga  60
agtggatctt ctcctcggtg gtggacctga agcagaccat catccccgac tataggaaca  120

SEQ ID NO: 573         moltype = DNA  length = 120
FEATURE                Location/Qualifiers
source                 1..120
                       mol_type = other DNA
                       organism = synthetic construct
SEQUENCE: 573
gacctcaccg ccctcaaccc catggctctc tgtctttgca gtcgccctct gagccctgac  60
acgcccccct tccagaccct gtgcatagca ggtctacccc agacctccgc tgcttggtgc  120

SEQ ID NO: 574         moltype = DNA  length = 120
FEATURE                Location/Qualifiers
source                 1..120
                       mol_type = other DNA
                       organism = synthetic construct
SEQUENCE: 574
atgcagggag ctggggacca ggtgtcccct cagcaggatg tccctgccct ccagaccgcc  60
agatgctcac acaaaaggag gcagtgacca gcatccgagg cccccaccca ggcaggagct  120

SEQ ID NO: 575         moltype = DNA  length = 120
FEATURE                Location/Qualifiers
source                 1..120
                       mol_type = other DNA
```

```
                         organism = synthetic construct
SEQUENCE: 575
ggccctggag ccaaccccgt ccacgccagc ctcctgaaca caggcgtggt ttccagatgg  60
tgagtgggag catcagccgc caaggtaggg aagccacagc accatcaggc cctgttgggg  120

SEQ ID NO: 576           moltype = DNA  length = 120
FEATURE                  Location/Qualifiers
source                   1..120
                         mol_type = other DNA
                         organism = synthetic construct
SEQUENCE: 576
aggcttccga gagctgcgaa ggctcactca gacggccttc ctcccagccc gcagccagcc  60
agcctccatt ccgggcactc ccgtgaactc ctgacatgag gaatgaggtt gttctgattt  120

SEQ ID NO: 577           moltype = DNA  length = 120
FEATURE                  Location/Qualifiers
source                   1..120
                         mol_type = other DNA
                         organism = synthetic construct
SEQUENCE: 577
caagcaaaga acgctgctct ctggctcctg ggaacagtct cggtgccagc accacccctt  60
ggctgcctgc ctacactgct ggattctcgg gtggaactgg acccgcaggg acagccagcc  120

SEQ ID NO: 578           moltype = DNA  length = 120
FEATURE                  Location/Qualifiers
source                   1..120
                         mol_type = other DNA
                         organism = synthetic construct
SEQUENCE: 578
ccagagtccg cactggggag agaaggggcc aggcccagga cactgccacc tcccacccac  60
tccagtccac cgagatcact cagagaagag cctgggccat gtggccactg caggagcccc  120

SEQ ID NO: 579           moltype = DNA  length = 120
FEATURE                  Location/Qualifiers
source                   1..120
                         mol_type = other DNA
                         organism = synthetic construct
SEQUENCE: 579
acagtgcaag agtgaggata gcccaaggaa gggctgggca tctgcccaga caggcctccc  60
agagaaggct ggtgaccagg tcccaggcgg gcaagactca gccttggtgg ggcctgagga  120

SEQ ID NO: 580           moltype = DNA  length = 120
FEATURE                  Location/Qualifiers
source                   1..120
                         mol_type = other DNA
                         organism = synthetic construct
SEQUENCE: 580
cagaggaggc ccaggagcat cggggagaga ggtggaggga caccgggaga gccaggagcg  60
tggacacagc cagaactcat cacagaggct ggcgtccagc cccgggtcac gtgcagcagg  120

SEQ ID NO: 581           moltype = DNA  length = 120
FEATURE                  Location/Qualifiers
source                   1..120
                         mol_type = other DNA
                         organism = synthetic construct
SEQUENCE: 581
aacaagcagc cactctgggg gcaccaggtg gagaggcaag atgccaaaga gggtgcccgt  60
gttcttgcga aagcggggct gctggccacg agtgctggac agaggccccc acgctctgct  120

SEQ ID NO: 582           moltype = DNA  length = 120
FEATURE                  Location/Qualifiers
source                   1..120
                         mol_type = other DNA
                         organism = synthetic construct
SEQUENCE: 582
gcccccatca cgccgttccg tgactgtcac gcagaatccg cagacaggaa gggaggctcg  60
agcgggactg cggccagcgc ctgcctcggc cgtcagggag gactcccggg ctcactcgaa  120

SEQ ID NO: 583           moltype = DNA  length = 120
FEATURE                  Location/Qualifiers
source                   1..120
                         mol_type = other DNA
                         organism = synthetic construct
SEQUENCE: 583
ggaggtgcca ccatttcagc tttggtagct tttcttcttc ttttaaattt tctaaagctc  60
attaattgtc tttgatgttt cttttgtgat gacaataaaa tatccttttt aagtcttgta  120

SEQ ID NO: 584           moltype = DNA  length = 120
FEATURE                  Location/Qualifiers
```

```
source                  1..120
                        mol_type = other DNA
                        organism = synthetic construct
SEQUENCE: 584
agcccccgct ccccgggctc tcggggtcgc gcgaggatgc ttggcacgta ccccgtgtac  60
atacttcccg ggcacccagc atggaaataa agcacccagc gctgccctgg gcccctgcga  120

SEQ ID NO: 585          moltype = DNA  length = 120
FEATURE                 Location/Qualifiers
source                  1..120
                        mol_type = other DNA
                        organism = synthetic construct
SEQUENCE: 585
cacccaccaa ggctccggat gtgttcccca tcatatcagg gtgcagacac ccaaaggata  60
acagccctgt ggtcctggca tgcttgataa ctgggtacca cccaacgtcc gtgactgtca  120

SEQ ID NO: 586          moltype = DNA  length = 120
FEATURE                 Location/Qualifiers
source                  1..120
                        mol_type = other DNA
                        organism = synthetic construct
SEQUENCE: 586
cctggtacat ggggacacag agccagcccc agagaacctt ccctgagata caaagacggg  60
acagctacta catgacaagc agccagctct ccaccccccct ccagcagtgg cgccaaggcg  120

SEQ ID NO: 587          moltype = DNA  length = 120
FEATURE                 Location/Qualifiers
source                  1..120
                        mol_type = other DNA
                        organism = synthetic construct
SEQUENCE: 587
agtacaaatg cgtggtccag cacaccgcca gcaagagtaa gaaggagatc ttccgctggc  60
cagagtctcc aaaggcacag gcctcctcag tgcccactgc acaaccccaa gcagagggca  120

SEQ ID NO: 588          moltype = DNA  length = 120
FEATURE                 Location/Qualifiers
source                  1..120
                        mol_type = other DNA
                        organism = synthetic construct
SEQUENCE: 588
gcctcgccaa ggcaaccaca gccccagcca ccacccgtaa cacaggaaga ggaggagaag  60
agaagaagaa ggagaaggag aaagaggaac aagaagagag agagacaaag acaccagagt  120

SEQ ID NO: 589          moltype = DNA  length = 120
FEATURE                 Location/Qualifiers
source                  1..120
                        mol_type = other DNA
                        organism = synthetic construct
SEQUENCE: 589
gtccgagcca cacccagcct cttggcgtct acctgctaac ccctgcagtg caggacctgt  60
ggctccggga caaagccacc ttcacctgct tcgtggtggg cagtgacctg aaggatgctc  120

SEQ ID NO: 590          moltype = DNA  length = 120
FEATURE                 Location/Qualifiers
source                  1..120
                        mol_type = other DNA
                        organism = synthetic construct
SEQUENCE: 590
acctgacctg ggaggtggct gggaaggtcc ccacaggggg cgtggaggaa gggctgctgg  60
agcggcacag caacggctcc cagagccagc acagccgtct gaccctgccc aggtccttgt  120

SEQ ID NO: 591          moltype = DNA  length = 120
FEATURE                 Location/Qualifiers
source                  1..120
                        mol_type = other DNA
                        organism = synthetic construct
SEQUENCE: 591
ggcctcgtct gaccctcccg aggcggcctc gtggctcctg tgtgaggtgt ctggcttctc  60
gccccccaac atcctcctga tgtggctgga ggaccagcgt gaggtgaaca cttctgggtt  120

SEQ ID NO: 592          moltype = DNA  length = 120
FEATURE                 Location/Qualifiers
source                  1..120
                        mol_type = other DNA
                        organism = synthetic construct
SEQUENCE: 592
tgcccccgca cgcccccctc cacagcccag gagcaccacg ttctgggcct ggagtgtgct  60
gcgtgtccca gccccgccca gccctcagcc agccacctac acgtgtgtgg tcagccacga  120
```

```
SEQ ID NO: 593          moltype = DNA  length = 120
FEATURE                 Location/Qualifiers
source                  1..120
                        mol_type = other DNA
                        organism = synthetic construct
SEQUENCE: 593
ggactcccgg actctgctca acgccagccg gagcctagaa gtcagctacc tggccatgac  60
ccccctgatc cctcagagca aggatgagaa cagcgatgac tacacgacct ttgatgatgt  120

SEQ ID NO: 594          moltype = DNA  length = 120
FEATURE                 Location/Qualifiers
source                  1..120
                        mol_type = other DNA
                        organism = synthetic construct
SEQUENCE: 594
gggcagcctg tggaccaccc tgtccacgtt tgtggccctc ttcatcctca ccctcctcta  60
cagcggcatt gtcactttca tcaaggtgaa gtagccccag aagagcagga cgccctgtac  120

SEQ ID NO: 595          moltype = DNA  length = 120
FEATURE                 Location/Qualifiers
source                  1..120
                        mol_type = other DNA
                        organism = synthetic construct
SEQUENCE: 595
ctgcagagaa gggaagcagc ctctgtacct catctgtggc taccagagag cagaaaggac  60
ccaccctgga ctcttctgtg tgcaggaaga tgcgccagcc cctgcccccg gctcccctct  120

SEQ ID NO: 596          moltype = DNA  length = 120
FEATURE                 Location/Qualifiers
source                  1..120
                        mol_type = other DNA
                        organism = synthetic construct
SEQUENCE: 596
gtccgccaca gaacccagtc ttctagacca gggggacggg cacccatcac tccgcaggcg  60
aatcagagcc cccctgcccc ggccctaacc cctgtgcctc cttcccatgc ttccccgaga  120

SEQ ID NO: 597          moltype = DNA  length = 120
FEATURE                 Location/Qualifiers
source                  1..120
                        mol_type = other DNA
                        organism = synthetic construct
SEQUENCE: 597
gccagctaca cccctgcccc ggccctaacc cccatgcctc cttcctgtgc ttcccccaga  60
gccagctagt cccacctgca gcccgctggc ctccccataa acacactttg gttcatttca  120

SEQ ID NO: 598          moltype = DNA  length = 120
FEATURE                 Location/Qualifiers
source                  1..120
                        mol_type = other DNA
                        organism = synthetic construct
SEQUENCE: 598
gggagtgcat ccgccccaac ccttttcccc ctcgtctcct gtgagaattc cccgtcggat  60
acgagcagcg tggccgttgg ctgcctcgca caggacttcc ttcccgactc catcactttc  120

SEQ ID NO: 599          moltype = DNA  length = 120
FEATURE                 Location/Qualifiers
source                  1..120
                        mol_type = other DNA
                        organism = synthetic construct
SEQUENCE: 599
tcctggaaat acaagaacaa ctctgacatc agcagcaccc ggggcttccc atcagtcctg  60
agagggggca agtacgcagc cacctcacag gtgctgctgc cttccaagga cgtcatgcag  120

SEQ ID NO: 600          moltype = DNA  length = 120
FEATURE                 Location/Qualifiers
source                  1..120
                        mol_type = other DNA
                        organism = synthetic construct
SEQUENCE: 600
ggcacagacg aacacgtggt gtgcaaagtc cagcacccca acggcaacaa agaaaagaac  60
gtgcctcttc cagtgattgc tgagctgcct cccaaagtga gcgtcttcgt cccacccccgc  120

SEQ ID NO: 601          moltype = DNA  length = 120
FEATURE                 Location/Qualifiers
source                  1..120
                        mol_type = other DNA
                        organism = synthetic construct
SEQUENCE: 601
gacggcttct tcggcaaccc ccgcaagtcc aagctcatct gccaggccac gggtttcagt  60
```

```
ccccggcaga ttcaggtgtc ctggctgcgc gaggggaagc aggtggggtc tggcgtcacc  120

SEQ ID NO: 602         moltype = DNA  length = 120
FEATURE                Location/Qualifiers
source                 1..120
                       mol_type = other DNA
                       organism = synthetic construct
SEQUENCE: 602
acggaccagg tgcaggctga ggccaaagag tctgggccca cgacctacaa ggtgaccagc  60
acactgacca tcaaagagag cgactggctc ggccagagca tgttcacctg ccgcgtggat  120

SEQ ID NO: 603         moltype = DNA  length = 120
FEATURE                Location/Qualifiers
source                 1..120
                       mol_type = other DNA
                       organism = synthetic construct
SEQUENCE: 603
cacaggggcc tgaccttcca gcagaatgcg tcctccatgt gtgtccccga tcaagacaca  60
gccatccggg tcttcgccat ccccccatcc tttgccagca tcttcctcac caagtccacc  120

SEQ ID NO: 604         moltype = DNA  length = 120
FEATURE                Location/Qualifiers
source                 1..120
                       mol_type = other DNA
                       organism = synthetic construct
SEQUENCE: 604
aagttgacct gcctggtcac agacctgacc acctatgaca gcgtgaccat ctcctggacc  60
cgccagaatg gcgaagctgt gaaaacccac accaacatct ccgagagcca ccccaatgcc  120

SEQ ID NO: 605         moltype = DNA  length = 120
FEATURE                Location/Qualifiers
source                 1..120
                       mol_type = other DNA
                       organism = synthetic construct
SEQUENCE: 605
agcgccgtgg gtgaggccag catctgcgag gatgactgga attccgggga gaggttcacg  60
tgcaccgtga cccacacaga cctgccctcg ccactgaagc agaccatctc ccggcccaag  120

SEQ ID NO: 606         moltype = DNA  length = 120
FEATURE                Location/Qualifiers
source                 1..120
                       mol_type = other DNA
                       organism = synthetic construct
SEQUENCE: 606
ggggtggccc tgcacaggcc cgatgtctac ttgctgccac cagcccggga gcagctgaac  60
ctgcgggagt cggccaccat cacgtgcctg gtgacgggct tctctcccgc ggacgtcttc  120

SEQ ID NO: 607         moltype = DNA  length = 120
FEATURE                Location/Qualifiers
source                 1..120
                       mol_type = other DNA
                       organism = synthetic construct
SEQUENCE: 607
gtgcagtgga tgcagagggg gcagcccttg tccccggaga agtatgtgac cagcgcccca  60
atgcctgagc cccaggcccc aggccggtac ttcgcccaca gcatcctgac cgtgtccgaa  120

SEQ ID NO: 608         moltype = DNA  length = 120
FEATURE                Location/Qualifiers
source                 1..120
                       mol_type = other DNA
                       organism = synthetic construct
SEQUENCE: 608
gaggaatgga acacggggga gacctacacc tgcgtggtgg cccatgaggc cctgcccaac  60
agggtcaccg agaggaccgt ggacaagtcc accgaggggg aggtgagcgc cgacgaggag  120

SEQ ID NO: 609         moltype = DNA  length = 120
FEATURE                Location/Qualifiers
source                 1..120
                       mol_type = other DNA
                       organism = synthetic construct
SEQUENCE: 609
ggctttgaga acctgtgggc caccgcctcc accttcatcg tcctcttcct cctgagcctc  60
ttctacagta ccaccgtcac cttgttcaag gtgaaatgat cccaacagaa gaacatcgga  120

SEQ ID NO: 610         moltype = DNA  length = 120
FEATURE                Location/Qualifiers
source                 1..120
                       mol_type = other DNA
                       organism = synthetic construct
```

```
SEQUENCE: 610
gaccagagag aggaactcaa aggggcgctg cctccgggtc tggggtcctg gcctgcgtgg  60
cctgttggca cgtgtttctc ttccccgccc ggcctccagt tgtgtgctct cacacaggct  120

SEQ ID NO: 611         moltype = DNA  length = 120
FEATURE                Location/Qualifiers
source                 1..120
                       mol_type = other DNA
                       organism = synthetic construct
SEQUENCE: 611
tccttctcga ccggcagggg ctggctggct tgcaggccac gaggtgggct ctaccccaca  60
ctgctttgct gtgtatacgc ttgttgccct gaaataaata tgcacatttt atccatgaaa  120

SEQ ID NO: 612         moltype = DNA  length = 120
FEATURE                Location/Qualifiers
source                 1..120
                       mol_type = other DNA
                       organism = synthetic construct
SEQUENCE: 612
tgctggcctg cccacaggct cggggcggct ggccgctctg tgtgtgcatg caaactaacc  60
gtgtcaacgg ggtgagatgt tgcatcttat aaaattagaa ataaaaagat ccattcaaaa  120

SEQ ID NO: 613         moltype = DNA  length = 120
FEATURE                Location/Qualifiers
source                 1..120
                       mol_type = other DNA
                       organism = synthetic construct
SEQUENCE: 613
gccacccccct tggtcactct gttcccgccc tcctctgagg agctccaagc caacaaggcc  60
atgctggtgt gtctcataaa tgacttctac ccaggagcca tagaaggaaa atggcaccct  120

SEQ ID NO: 614         moltype = DNA  length = 120
FEATURE                Location/Qualifiers
source                 1..120
                       mol_type = other DNA
                       organism = synthetic construct
SEQUENCE: 614
atgcggccag cagctacctg agcctgacgc ccgagcagtg gaagtcccac agaagctaca  60
gctgccaggt cacgcacaaa gaaagtacca tggagaagac aatggcccat gcagaatgtt  120

SEQ ID NO: 615         moltype = DNA  length = 120
FEATURE                Location/Qualifiers
source                 1..120
                       mol_type = other DNA
                       organism = synthetic construct
SEQUENCE: 615
acaaggccac actggtgtgt ctcatgagtg acttctaccc gagagccatg acagtggcct  60
ggaagataga tggcatcacc atcacccagg gtgtggagac caccacaccc tccaaacaga  120

SEQ ID NO: 616         moltype = DNA  length = 120
FEATURE                Location/Qualifiers
source                 1..120
                       mol_type = other DNA
                       organism = synthetic construct
SEQUENCE: 616
tatgcggcca gcagctacct aagactggca cccgacagtg gaagtcccac aacctctaca  60
gctgccaggt cacgcatgaa aggaacactg tggagaagac agtggcccct gcagaatgtt  120

SEQ ID NO: 617         moltype = DNA  length = 120
FEATURE                Location/Qualifiers
source                 1..120
                       mol_type = other DNA
                       organism = synthetic construct
SEQUENCE: 617
gtcagcccaa ggctgcccca tcggtcactc tgttcccgcc ctcctctgag gagcttcaag  60
ccaacaaggc cacactggtg tgcctgatca gtgacttcta cccgggagct gtgaaagtgg  120

SEQ ID NO: 618         moltype = DNA  length = 120
FEATURE                Location/Qualifiers
source                 1..120
                       mol_type = other DNA
                       organism = synthetic construct
SEQUENCE: 618
gcggccagca gctagctacc tgagcctgac gcctgagcag tggaagtccc acagaagcta  60
cagttgccag gtcacgcatg aagggagcac cgtggagaag acagtggccc ctgcagaatg  120

SEQ ID NO: 619         moltype = DNA  length = 120
FEATURE                Location/Qualifiers
source                 1..120
```

```
                         mol_type = other DNA
                         organism = synthetic construct
SEQUENCE: 619
aggacctgaa caaggtgttc ccacccgagg tcgctgtgtt tgagccatca gaagcagaga  60
tctcccacac ccaaaaggcc acactggtgt gcctggccac aggcttcttc cctgaccacg  120

SEQ ID NO: 620           moltype = DNA  length = 120
FEATURE                  Location/Qualifiers
source                   1..120
                         mol_type = other DNA
                         organism = synthetic construct
SEQUENCE: 620
tggagctgag ctggtgggtg aatgggaagg aggtgcacag tggggtcagc acggacccgc  60
agcccctcaa ggagcagccc gccctcaatg actccagata ctgcctgagc agccgcctga  120

SEQ ID NO: 621           moltype = DNA  length = 120
FEATURE                  Location/Qualifiers
source                   1..120
                         mol_type = other DNA
                         organism = synthetic construct
SEQUENCE: 621
gggtctcggc caccttctgg cagaaccccc gcaaccactt ccgctgtcaa gtccagttct  60
acgggctctc ggagaatgac gagtggaccc aggatagggc caaacccgtc acccagatcg  120

SEQ ID NO: 622           moltype = DNA  length = 120
FEATURE                  Location/Qualifiers
source                   1..120
                         mol_type = other DNA
                         organism = synthetic construct
SEQUENCE: 622
ctcggtgtcc taccagcaag gggtcctgtc tgccaccatc ctctatgaga tcctgctagg  60
gaaggccacc ctgtatgctg tgctggtcag cgcccttgtg ttgatggcca tggtcaagag  120

SEQ ID NO: 623           moltype = DNA  length = 120
FEATURE                  Location/Qualifiers
source                   1..120
                         mol_type = other DNA
                         organism = synthetic construct
SEQUENCE: 623
aaaggatttc tgaaggcagc cctggaagtg gagttaggag cttctaaccc gtcatggttt  60
caatacacat tcttcttttg ccagcgcttc tgaagagctg ctctcacctc tctgcatccc  120

SEQ ID NO: 624           moltype = DNA  length = 120
FEATURE                  Location/Qualifiers
source                   1..120
                         mol_type = other DNA
                         organism = synthetic construct
SEQUENCE: 624
aatagatatc cccctatgtg catgcacacc tgcacactca cggctgaaat ctccctaacc  60
cagggggacc ttagcatgcc taagtgacta aaccaataaa aatgttctgg tctggcctga  120

SEQ ID NO: 625           moltype = DNA  length = 120
FEATURE                  Location/Qualifiers
source                   1..120
                         mol_type = other DNA
                         organism = synthetic construct
SEQUENCE: 625
aggacctgaa aaacgtgttc ccacccaagg tcgctgtgtt tgagccatca gaagcagaga  60
tctcccacac ccaaaaggcc acactggtgt gcctggccac aggcttctac cccgaccacg  120

SEQ ID NO: 626           moltype = DNA  length = 120
FEATURE                  Location/Qualifiers
source                   1..120
                         mol_type = other DNA
                         organism = synthetic construct
SEQUENCE: 626
tggagctgag ctggtgggtg aatgggaagg aggtgcacag tggggtcagc acagacccgc  60
agcccctcaa ggagcagccc gccctcaatg actccagata ctgcctgagc agccgcctga  120

SEQ ID NO: 627           moltype = DNA  length = 120
FEATURE                  Location/Qualifiers
source                   1..120
                         mol_type = other DNA
                         organism = synthetic construct
SEQUENCE: 627
gggtctcggc caccttctgg cagaaccccc gcaaccactt ccgctgtcaa gtccagttct  60
acgggctctc ggagaatgac gagtggaccc aggatagggc caaacctgtc acccagatcg  120

SEQ ID NO: 628           moltype = DNA  length = 120
```

```
FEATURE                 Location/Qualifiers
source                  1..120
                        mol_type = other DNA
                        organism = synthetic construct
SEQUENCE: 628
acctccgagt cttaccagca aggggtcctg tctgccacca tcctctatga gatcttgcta  60
gggaaggcca ccttgtatgc cgtgctggtc agtgccctcg tgctgatggc catggtcaag  120

SEQ ID NO: 629          moltype = DNA  length = 120
FEATURE                 Location/Qualifiers
source                  1..120
                        mol_type = other DNA
                        organism = synthetic construct
SEQUENCE: 629
agaaaggatt ccagaggcta gctccaaaac catcccaggt cattcttcat cctcacccag  60
gattctcctg tacctgctcc caatctgtgt tcctaaaagt gattctcact ctgcttctca  120

SEQ ID NO: 630          moltype = DNA  length = 120
FEATURE                 Location/Qualifiers
source                  1..120
                        mol_type = other DNA
                        organism = synthetic construct
SEQUENCE: 630
tctcctactt acatgaatac ttctctcttt tttctgtttc cctgaagatt gagctcccaa  60
cccccaagta cgaaataggc taaaccaata aaaaattgtg tgttgggcct ggttgcattt  120

SEQ ID NO: 631          moltype = DNA  length = 120
FEATURE                 Location/Qualifiers
source                  1..120
                        mol_type = other DNA
                        organism = synthetic construct
SEQUENCE: 631
atatccagaa ccctgaccct gccgtgtacc agctgagaga ctctaaatcc agtgacaagt  60
ctgtctgcct attcaccgat tttgattctc aaacaaatgt gtcacaaagt aaggattctg  120

SEQ ID NO: 632          moltype = DNA  length = 120
FEATURE                 Location/Qualifiers
source                  1..120
                        mol_type = other DNA
                        organism = synthetic construct
SEQUENCE: 632
atgtgtatat cacagacaaa actgtgctag acatgaggtc tatggacttc aagagcaaca  60
gtgctgtggc ctggagcaac aaatctgact ttgcatgtgc aaacgccttc aacaacagca  120

SEQ ID NO: 633          moltype = DNA  length = 120
FEATURE                 Location/Qualifiers
source                  1..120
                        mol_type = other DNA
                        organism = synthetic construct
SEQUENCE: 633
ttattccaga agacaccttc ttccccagcc cagaaagttc ctgtgatgtc aagctggtcg  60
agaaaagctt tgaaacagat acgaacctaa actttcaaaa cctgtcagtg attgggttcc  120

SEQ ID NO: 634          moltype = DNA  length = 120
FEATURE                 Location/Qualifiers
source                  1..120
                        mol_type = other DNA
                        organism = synthetic construct
SEQUENCE: 634
gaatcctcct cctgaaagtg gccgggttta atctgctcat gacgctgcgg ctgtggtcca  60
gctgagatct gcaagattgt aagacagcct gtgctccctc gctccttcct ctgcattgcc  120

SEQ ID NO: 635          moltype = DNA  length = 120
FEATURE                 Location/Qualifiers
source                  1..120
                        mol_type = other DNA
                        organism = synthetic construct
SEQUENCE: 635
acagagggaa ctctcctacc cccaaggagg tgaaagctgc taccacctct gtgccccccc  60
ggcaatgcca ccaactggat cctacccgaa tttatgatta agattgctga agagctgcca  120

SEQ ID NO: 636          moltype = DNA  length = 120
FEATURE                 Location/Qualifiers
source                  1..120
                        mol_type = other DNA
                        organism = synthetic construct
SEQUENCE: 636
aacactgctg ccaccccctc tgttccctta ttgctgcttg tcactgcctg acattcacgg  60
cagaggcaag gctgctgcag cctcccctgg ctgtgcacat tccctcctgc tccccagaga  120
```

-continued

```
SEQ ID NO: 637          moltype = DNA  length = 120
FEATURE                 Location/Qualifiers
source                  1..120
                        mol_type = other DNA
                        organism = synthetic construct
SEQUENCE: 637
ctgcctccgc catcccacag atgatggatc ttcagtgggt tctcttgggc tctaggtcct  60
gcagaatgtt gtgaggggtt tatttttttt taatagtgtt cataaagaaa tacatagtat  120

SEQ ID NO: 638          moltype = DNA  length = 120
FEATURE                 Location/Qualifiers
source                  1..120
                        mol_type = other DNA
                        organism = synthetic construct
SEQUENCE: 638
tcttcttctc aagacgtggg gggaaattat ctcattatcg aggccctgct atgctgtgta  60
tctgggcgtg ttgtatgtcc tgctgccgat gccttcatta aaatgatttg gaagagcaga  120

SEQ ID NO: 639          moltype = DNA  length = 82
FEATURE                 Location/Qualifiers
source                  1..82
                        mol_type = other DNA
                        organism = synthetic construct
SEQUENCE: 639
ctacacgacg ctcttccgat ctnnnnnnnn nnnnnnnnnn nnnnnnnnnn tttttttttt  60
tttttttttt tttttttttt vn                                            82

SEQ ID NO: 640          moltype = DNA  length = 30
FEATURE                 Location/Qualifiers
source                  1..30
                        mol_type = other DNA
                        organism = synthetic construct
SEQUENCE: 640
cccatgtact ctgcgttgat accactgctt                                    30
```

SPATIAL TRANSCRIPTOMICS FOR ANTIGEN-RECEPTORS

CROSS-REFERENCE TO RELATED APPLICATIONS

This application is a continuation of U.S. Pat. No. 11,692,218, filed Dec. 15, 2021, which is a continuation of International Patent Application No. PCT/US2021/035242 with an international filing date of Jun. 1, 2021, which claims priority to U.S. Provisional Patent Application Ser. No. 63/033,568, filed on Jun. 2, 2020, the contents of each of which are incorporated herein by reference in its entirety.

SEQUENCE LISTING

A computer readable form (CRF) sequence listing text file having the file name 0208001_SequenceListing.txt and file size of 173 KB is being submitted herewith. The sequence information contained in this sequence listing is limited to the sequence information in the application as originally filed, and does not include any new matter

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Understanding spatial heterogeneity in the context of immune cell clonotypes (e.g., T-cell receptor, B-cell receptor) within an intact biological sample, or a portion thereof, can give insight into which cells or cell-types specific T-cell or B-cell clonotypes may be interacting. Single-cell methods can identify clonotype populations, but fail to link the spatial organization of immune cell clonotypes within a biological sample.

SUMMARY

A fundamental understanding of spatial heterogeneity with respect to T-cell receptor (TCR) and B-cell receptor (BCR) clonotypes within a biological sample is needed to understand which cells a TCR or BCR may interacting with, the identity of TCR and/or BCR clonotypes in a given biological sample, or the identity of TCR and/or BCR clonotypes that are autoreactive in different autoimmune disorders. Numerous single-cell sequencing approaches can identify TCR and BCR clonotypes from a biological sample, however, at present methods are needed to link TCR and BCR sequences to spatial locations within a biological sample. Additionally, identifying the clonal regions, that is, regions defined by the places where variable (V), diverse (D), and joining (J) segments join to form the complementarity determining regions, including CDR1, CDR2, and CDR3, which provide specificity to the TCRs and/or BCRs, is important in understanding the TCR and BCR biological interactions. By coupling clonal information to spatial information it is possible to understand which T-cell and B-cell clonotypes may be specifically interacting with given cell types within a biological sample.

Provided herein are methods for determining the presence and/or abundance of an immune cell clonotype at a location in a biological sample. Some embodiments of any of the methods described herein include capturing transcripts to identify an immune cell clonotype. Some embodiments of any of the methods herein include generating a nucleic acid library from captured transcripts. Some embodiments of any of the methods described herein include enriching analytes of interest in the nucleic acid library, including analytes to identify an immune cell clonotype.

Provided herein are methods for determining the presence and/or abundance of an immune cell receptor at a location in a biological sample. Some embodiments of any of the methods described herein include capturing analytes to identify an immune cell receptor. Some embodiments of any of the methods described herein include generating a nucleic acid library from captured analytes. Some embodiments of any of the methods described here include enriching analytes of interest in the nucleic acid library, including analytes to identify an immune cell receptor.

Thus provided herein are methods for determining the presence and/or abundance of an immune cell clonotype at a location in a biological sample, the method including: (a) contacting a biological sample with an array including a plurality of capture probes, where a capture probe of the plurality of capture probes includes (i) a spatial barcode and (ii) a capture domain that binds to a nucleic acid encoding an immune cell receptor of the immune cell clonotype; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

In some embodiments, the immune cell clonotype is a T cell clonotype. In some embodiments, the T cell clonotype is a T cell receptor alpha chain. In some embodiments, the capture domain binds to a nucleic acid sequence encoding a constant region of the T cell receptor alpha chain. In some embodiments, step (b) includes determining a sequence encoding CDR3 of the T cell receptor alpha chain. In some embodiments, step (b) includes determining a sequence encoding one or both of CDR1 and CDR2 of the T cell receptor alpha chain. In some embodiments, step (b) includes determining a sequence encoding a full-length variable domain of the T cell receptor alpha chain.

In some embodiments, the immune cell receptor is a T cell receptor beta chain. In some embodiments, the capture domain binds specifically to a nucleic acid sequence encoding a constant region of the T cell receptor beta chain. In some embodiments, step (b) includes determining a sequence encoding CDR3 of the T cell receptor beta chain. In some embodiments, step (b) includes determining a sequence encoding one or both of CDR1 and CDR2 of the T cell receptor beta chain. In some embodiments, step (b) includes determining a sequence encoding a full-length variable domain of the T cell receptor beta chain.

In some embodiments, the immune cell clonotype is a B cell clonotype. In some embodiments, the B cell clonotype is an immunoglobulin kappa light chain. In some embodiments, the capture domain binds specifically to a nucleic acid sequence encoding a constant region of the immunoglobulin kappa light chain. In some embodiments, step (b) includes determining a sequence encoding CDR3 of the immunoglobulin kappa light chain.

In some embodiments, step (b) includes determining a sequence encoding one or both of CDR1 and CDR2 of the immunoglobulin kappa light chain. In some embodiments, step (b) includes determining a sequence encoding a full-length variable domain of the immunoglobulin kappa light chain. In some embodiments, the B cell clonotype is an immunoglobulin lambda light chain. In some embodiments, the capture domain binds specifically to a nucleic acid sequence encoding a constant region of the immunoglobulin lambda light chain. In some embodiments, step (b) includes determining a sequence encoding CDR3 of the immunoglobulin lambda light chain. In some embodiments, step (b) includes determining a sequence encoding one or both of CDR1 and CDR2 of the immunoglobulin lambda light chain. In some embodiments, step (b) includes determining a sequence encoding a full-length variable domain of the immunoglobulin lambda light chain. In some embodiments, the B cell clonotype is an immunoglobulin heavy chain. In some embodiments, the capture domain binds specifically to a nucleic acid sequence encoding a constant region of the immunoglobulin heavy chain. In some embodiments, step (b) includes determining a sequence encoding CDR3 of the immunoglobulin heavy chain. In some embodiments, step (b) includes determining a sequence encoding one or both of CDR1 and CDR2 of the immunoglobulin heavy chain. In some embodiments, step (b) includes determining a sequence encoding a full-length variable domain of the immunoglobulin heavy chain.

In some embodiments, the capture domain binds a poly (A) sequence of a nucleic acid encoding an immune cell clonotype. In some embodiments, the capture domain binds to a nucleic acid sequence encoding a T cell clonotype. In some embodiments, the T cell clonotype is a T cell receptor alpha chain, a T cell receptor beta chain, and combinations thereof. In some embodiments, step (b) includes determining: a sequence encoding CDR3 of the T cell receptor alpha chain, a sequence encoding CDR3 of the T cell receptor beta chain, and combinations thereof. In some embodiments, step (b) includes determining: a sequence encoding one or both of CDR1 and CDR2 of the T cell receptor alpha chain, a sequence encoding one or both of CDR1 and CDR2 of the T cell receptor beta chain, and combinations thereof. In some embodiments, step (b) includes determining: a sequence encoding a full-length variable domain of the T cell receptor alpha chain, a sequence encoding a full-length variable domain of the T cell receptor beta chain, and combinations thereof.

In some embodiments, the capture domain binds to a nucleic acid encoding a B cell clonotype. In some embodiments, the B cell clonotype is an immunoglobulin kappa light chain, an immunoglobulin lambda light chain, an immunoglobulin heavy chain, and combinations thereof. In some embodiments, step (b) includes determining: a sequence encoding CDR3 of the immunoglobulin kappa light chain, a sequence encoding CDR3 of immunoglobulin lambda light chain, a sequence encoding CDR3 of the immunoglobulin heavy chain, and combinations thereof. In some embodiments, step (b) includes determining: a sequence encoding one or both of CDR1 and CDR2 of the immunoglobulin kappa light chain, a sequence encoding one or both of CDR1 and CDR2 of the immunoglobulin lambda light chain, a sequence encoding one or both of CDR1 and CDR2 of the immunoglobulin heavy chain, and combinations thereof. In some embodiments, step (b) includes determining: a sequence encoding a full-length variable domain of the immunoglobulin kappa light chain, a sequence encoding a full-length variable domain of the immunoglobulin lambda light chain, a sequence encoding a full-length variable domain of the immunoglobulin heavy chain, and combinations thereof.

In some embodiments, step (b) includes the capture probe using the nucleic acid encoding the immune cell receptor as a template, thereby generating an extended capture probe. In some embodiments, step (b) includes extending a 3' end of the capture probe.

In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments, the capture probe includes a cleavage domain, a functional domain, a unique molecular identifier, or any combination thereof. In some embodiments, the capture probe includes a functional domain.

In some embodiments, step (b) includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

In some embodiments, the method includes enriching the nucleic acid encoding the immune cell receptor of the immune cell clonotype.

In some embodiments, enriching includes hybridizing a plurality of hybridization probes to the nucleic acid encoding the immune cell receptor of the immune cell clonotype, where a hybridization probe includes (i) a sequence complementary to a portion of the nucleic acid encoding the immune cell receptor and (ii) a binding moiety that interacts with a capture moiety.

In some embodiments, the binding moiety includes biotin and the capture moiety includes streptavidin.

In some embodiments, enriching the nucleic acid encoding the immune cell receptor of the immune cell clonotype includes one or more blocking probes. In some embodiments, the one or more blocking probes includes a sequence having at least 80% identity to SEQ ID NO: 639. In some embodiments, the one or more blocking probes includes a sequence having at least 80% identity to SEQ ID NO: 640.

In some embodiments, the method includes amplifying the nucleic acid encoding the immune cell receptor of the immune cell clonotype, or a complement thereof, using (i) a first primer including all or a portion of the functional domain, where the functional domain is 5' to the spatial barcode, and (ii) a second primer including a sequence that is substantially complementary to a portion of a sequence encoding a variable region of the immune cell receptor.

In some embodiments, the method includes amplifying the nucleic acid encoding the immune cell receptor of the immune cell clonotype, or a complement thereof, using (i) the first primer including all or a portion of the functional domain, where the functional domain is 5' to the spatial barcode, and (ii) a third primer including a sequence that is substantially complementary to a portion of the nucleic acid sequence encoding a variable region of the immune cell receptor, where the third primer is 5' to the second primer.

In some embodiments, the biological sample includes a tissue sample. In some embodiments, the tissue sample is a tissue section. In some embodiments, the tissue section is a fixed tissue section. In some embodiments, the fixed tissue section is a formalin-fixed paraffin-embedded tissue section. In some embodiments, the tissue section includes a tumor region.

In some embodiments, the nucleic acid encoding the immune cell receptor includes RNA. In some embodiments, the RNA is mRNA. In some embodiments, the nucleic acid encoding the immune cell receptor includes DNA. In some embodiments, the DNA is genomic DNA.

In some embodiments, the method includes imaging the biological sample.

In some embodiments, the determining in step (b) includes sequencing (i) all or a portion of the sequence of the spatial barcode or a complement thereof, and (ii) all or a portion of the sequence of the nucleic acid encoding the immune cell receptor or a complement thereof.

In some embodiments, step (b) includes determining the presence of the immune cell clonotype at a location in the biological sample. In some embodiments, step (b) includes determining the abundance of the immune cell clonotype at a location in the biological sample. In some embodiments, step (b) includes determining the presence and abundance of the immune cell clonotype at a location in the biological sample. In some embodiments, step (b) includes determining the presence of two or more immune cell clonotypes at a location in the biological sample. In some embodiments, step (b) includes determining the abundance of two or more immune cell clonotypes at a location in the biological sample. In some embodiments, step (b) includes determining the presence and abundance of two or more immune cell clonotypes at a location in the biological sample. In some embodiments, the method includes comparing the two or more immune cell clonotypes. In some embodiments, the two or more immune cell clonotypes are each a B cell clonotype.

In some embodiments, the two or more immune cell clonotypes are each a T cell clonotype. In some embodiments, the two or more immune cell clonotypes comprise at least one T cell clonotype and at least one B cell clonotype.

Also provided herein are methods for determining the presence and/or abundance of an immune cell receptor at a location in a biological sample, the method including: (a) contacting a biological sample with an array including a plurality of capture probes, where a capture probe of the plurality of capture probes includes (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

In some embodiments, the immune cell receptor is a T cell receptor alpha chain. In some embodiments, the capture domain binds specifically to a nucleic acid sequence encoding a constant region of the T cell receptor alpha chain. In some embodiments, step (b) includes determining a sequence encoding CDR3 of the T cell receptor alpha chain. In some embodiments, step (b) includes determining a sequence encoding one or both of CDR1 and CDR2 of the T cell receptor alpha chain. In some embodiments, step (b) includes determining a sequence encoding a full-length variable domain of the T cell receptor alpha chain. In some embodiments, the immune cell receptor is a T cell receptor beta chain. In some embodiments, the capture domain binds specifically to a nucleic acid sequence encoding a constant region of the T cell receptor beta chain. In some embodiments, step (b) includes determining a sequence encoding CDR3 of the T cell receptor beta chain. In some embodiments, step (b) includes determining a sequence encoding one or both of CDR1 and CDR2 of the T cell receptor beta chain. In some embodiments, step (b) includes determining a full-length variable domain of the T cell receptor beta chain. In some embodiments, the immune cell receptor is an immunoglobulin kappa light chain. In some embodiments, the capture domain binds specifically to a nucleic acid sequence encoding a constant region of the immunoglobulin kappa light chain. In some embodiments, step (b) includes determining a sequence encoding CDR3 of the immunoglobulin kappa light chain. In some embodiments, step (b) includes determining a sequence encoding one or both of CDR1 and CDR2 of the immunoglobulin kappa light chain. In some embodiments, step (b) includes determining a sequence encoding a full-length variable domain of the immunoglobulin kappa light chain. In some embodiments, the immune cell receptor is an immunoglobulin lambda light chain. In some embodiments, the capture domain binds specifically to a nucleic acid sequence encoding a constant region of the immunoglobulin lambda light chain. In some embodiments, step (b) includes determining a sequence encoding CDR3 of the immunoglobulin lambda light chain. In some embodiments, step (b) includes determining a sequence encoding one or both of CDR1 and CDR2 of the immunoglobulin lambda light chain. In some embodiments, step (b) includes determining a sequence encoding a full-length variable domain of the immunoglobulin lambda light chain. In some embodiments, the immune cell receptor is an immunoglobulin heavy chain. In some embodiments, the capture domain binds specifically to a nucleic acid sequence encoding a constant region of the immunoglobulin heavy chain. In some embodiments, step (b) includes determining a sequence encoding CDR3 of the immunoglobulin heavy chain. In some embodiments, step (b) includes determining a sequence encoding one or both of CDR1 and CDR2 of the immunoglobulin heavy chain. In some embodiments, step (b) includes determining a sequence encoding a full-length variable domain of the immunoglobulin heavy chain.

In some embodiments, the capture domain binds a poly (A) sequence of a nucleic acid encoding an immune cell receptor. In some embodiments, the immune cell receptor is a T cell receptor alpha chain, a T cell receptor beta chain, and combinations thereof. In some embodiments, step (b) includes determining: a sequence encoding CDR3 of the T cell receptor alpha chain, a sequence encoding CDR3 of the T cell receptor beta chain, and combinations thereof. In some embodiments, step (b) includes determining: a sequence encoding one or both of CDR1 and CDR2 of the T cell receptor alpha chain, a sequence encoding one or both of CDR1 and CDR2 of the T cell receptor beta chain, and combinations thereof. In some embodiments, step (b) includes determining: a sequence encoding a full-length variable domain of the T cell receptor alpha chain, a sequence encoding a full-length variable domain of the T cell receptor beta chain, and combinations thereof.

In some embodiments, the immune cell receptor is a B cell receptor an immunoglobulin kappa light chain, an immunoglobulin lambda light chain, an immunoglobulin heavy chain, and combinations thereof. In some embodiments, step (b) includes determining: a sequence encoding CDR3 of the immunoglobulin kappa light chain, a sequence encoding CDR3 of immunoglobulin lambda light chain, a sequence encoding CDR3 of the immunoglobulin heavy chain, and combinations thereof. In some embodiments, step (b) includes determining: a sequence encoding one or both of CDR1 and CDR2 of the immunoglobulin kappa light chain, a sequence encoding one or both of CDR1 and CDR2 of the immunoglobulin lambda light chain, a sequence encoding one or both of CDR1 and CDR2 of the immunoglobulin heavy chain, and combinations thereof. In some embodiments, step (b) includes determining: a sequence encoding a full-length variable domain of the immunoglobulin kappa light chain, a sequence encoding a full-length variable domain of the immunoglobulin lambda light chain, a sequence encoding a full-length variable domain of the immunoglobulin heavy chain, and combinations thereof.

In some embodiments, step (b) includes extending an end of the capture probe using the nucleic acid encoding the immune cell receptor as a template, thereby generating an extended capture probe. In some embodiments, step (b) includes extending a 3' end of the capture probe.

In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments, the capture probe includes a cleavage domain, a functional domain, a unique molecular identifier, or any combination thereof. In some embodiments, the capture probe includes a functional domain.

In some embodiments, step (b) includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

In some embodiments, the method includes enriching the nucleic acid encoding the immune cell receptor. In some embodiments, enriching includes hybridizing a plurality of hybridization probes to the nucleic acid encoding the immune cell receptor, where a hybridization probe includes (i) a sequence complementary to a portion of the nucleic acid encoding the immune cell receptor and (ii) a binding moiety that interacts with a capture moiety. In some embodiments, the binding moiety includes biotin and the capture moiety includes streptavidin. In some embodiments, enriching the nucleic acid encoding the immune cell receptor of the immune cell receptor includes one or more blocking probes. In some embodiments, the one or more blocking probes includes a sequence having at least 80% identity to SEQ ID NO: 639. In some embodiments, the one or more blocking probes includes a sequence having at least 80% identity to SEQ ID NO: 640.

In some embodiments, the method includes amplifying the nucleic acid encoding an immune cell receptor, or a complement thereof, using (i) a first primer including all or a portion of the functional domain, where the functional domain is 5' to the spatial barcode in the second strand of nucleic acid, and (ii) a second primer including a sequence that is substantially complementary to a portion of a sequence encoding a variable region of the immune cell receptor.

In some embodiments, the method includes amplifying the nucleic acid encoding the immune cell receptor, or a complement thereof, using (i) the first primer including all or a portion of the functional domain, where the functional domain is 5' to the spatial barcode, and (ii) a third primer including a sequence that is substantially complementary to a portion of the nucleic acid sequence encoding a variable region of the immune cell receptor, where the third primer is 5' to the second primer.

In some embodiments, the biological sample includes a tissue sample. In some embodiments, the tissue sample is a tissue section. In some embodiments, the tissue section is a fixed tissue section. In some embodiments, the fixed tissue section is a formalin-fixed paraffin-embedded tissue section. In some embodiments, the tissue section includes a tumor region.

In some embodiments, the nucleic acid encoding the immune cell receptor includes RNA. In some embodiments, the RNA is mRNA. In some embodiments, the nucleic acid encoding the immune cell receptor includes DNA. In some embodiments, the DNA is genomic DNA.

In some embodiments, the method includes, prior to step (b), contacting the biological sample with ribosomal RNA depletion probes and mitochondrial RNA depletion probes.

In some embodiments, the method includes imaging the biological sample.

In some embodiments, the determining in step (b) includes sequencing (i) all or a portion of the sequence of the spatial barcode or a complement thereof, and (ii) all or a portion of the sequence of the nucleic acid encoding the immune cell receptor or a complement thereof.

In some embodiments, step (b) includes determining the presence of the immune cell receptor at a location in the biological sample. In some embodiments, step (b) includes determining the abundance of the immune cell receptor at a location in the biological sample. In some embodiments, step (b) includes determining the presence and abundance of the immune cell receptor at a location in the biological sample. In some embodiments, step (b) includes determining the presence of two or more immune cell receptors at a location in the biological sample. In some embodiments, step (b) includes determining the abundance of two or more immune cell receptors at a location in the biological sample. In some embodiments, step (b) includes determining the presence and abundance of two or more immune cell receptors at a location in the biological sample. In some embodiments, the method includes comparing the two or more immune cell receptors. In some embodiments, the two or more immune cell clonotypes are each an immune cell receptor of a B cell. In some embodiments, the two or more immune cell clonotypes are each an immune cell receptor of a T cell. In some embodiments, the two or more immune cell clonotypes comprise at least one immune cell receptor of a T cell and at least one immune cell receptor from a B cell.

Also provided herein are arrays including a plurality of capture probes, where a capture probe of the plurality of capture probes includes (i) a spatial barcode and (ii) a capture domain that binds to a nucleic acid encoding an immune cell receptor of an immune cell clonotype.

In some embodiments, the immune cell clonotype is a T cell clonotype. In some embodiments, the immune cell receptor is a T cell receptor alpha chain. In some embodiments, the capture domain binds specifically to a nucleic acid sequence encoding a constant region of the T cell receptor alpha chain. In some embodiments, the immune cell receptor is a T cell receptor beta chain. In some embodiments, the capture domain binds specifically to a nucleic acid sequence encoding a constant region of the T cell receptor beta chain.

In some embodiments, the immune cell clonotype is a B cell clonotype. In some embodiments, the immune cell receptor is an immunoglobulin kappa light chain. In some embodiments, the capture domain binds specifically to a nucleic acid sequence encoding a constant region of the immunoglobulin kappa light chain. In some embodiments, the immune cell receptor is an immunoglobulin lambda light chain. In some embodiments, the capture domain binds specifically to a nucleic acid sequence encoding a constant region of the immunoglobulin lambda light chain. In some embodiments, the immune cell receptor is an immunoglobulin heavy chain. In some embodiments, the capture domain binds specifically to a nucleic acid sequence encoding a constant region of the immunoglobulin heavy chain.

In some embodiments, the capture probe includes a cleavage domain, a functional domain, a unique molecular identifier, or any combination thereof.

Also provided herein are kits any one of the arrays described herein; one or more hybridization probes, where a hybridization probe includes (i) a sequence substantially complementary to a nucleic acid encoding an immune cell receptor and (ii) a binding moiety that interacts with a capturing moiety; and one or more blocking probes.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
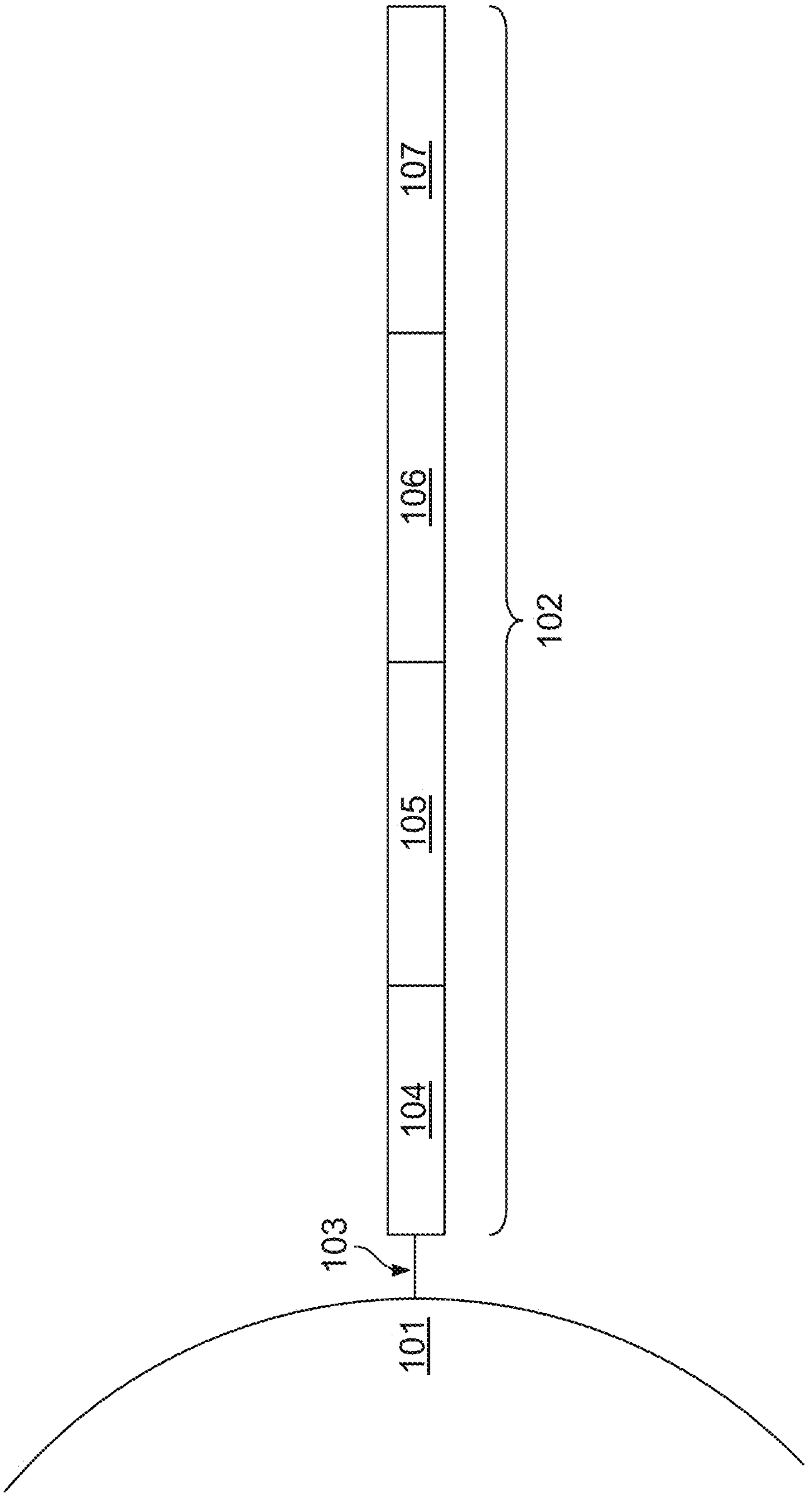
FIG. 1 is a schematic diagram showing an example of a barcoded capture probe, as described herein.

A fundamental understanding of spatial heterogeneity with respect to T-cell receptor (TCR) and B-cell receptor (BCR) clonotypes within a biological sample is needed to understand which cells a TCR or BCR may be interacting with, the identity of TCR and/or BCR clonotypes in a given biological sample, or the identity of TCR and/or BCR clonotypes that are autoreactive in different autoimmune disorders. Numerous single-cell sequencing approaches can identify TCR and BCR clonotypes from a biological sample, however, at present methods are need to link TCR and BCR sequences to spatial locations within a biological sample. Additionally, identifying the clonal regions, that is, regions defined by the places where variable (V), diverse (D), and joining (J) segments join to from the complementarity determining regions, including CDR1, CDR2, and CDR3, which provide specificity to the TCRs and/or BCRs, is needed to help determine biological interactions. By coupling clonal information to spatial information it is possible to understand which T-cell and B-cell clonotypes may be specifically interacting with given cell types within a biological sample.

Provided herein are methods for determining the presence and/or abundance of an immune cell clonotype at a location in a biological sample. Some embodiments of any of the methods described herein include capturing transcripts to identify an immune cell clonotype. Some embodiments of any of the methods herein include generating a nucleic acid library from captured transcripts. Some embodiments of any of the methods described herein include enriching analytes of interest in the nucleic acid library, including analytes to identify an immune cell clonotype.

Provided herein are methods for determining the presence and/or abundance of an immune cell receptor at a location in a biological sample. Some embodiments of any of the methods described herein include capturing analytes to identify an immune cell receptor. Some embodiments of any of the methods described herein include generating a nucleic acid library from captured analytes. Some embodiments of any of the methods described here include enriching analytes of interest in the nucleic acid library, including analytes to identify an immune cell receptor.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3): 442-458, 2015; Trejo et al., PLoS ONE 14(2):e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics® (sequencing technology) Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

In some embodiments, the analyte is an immune cell receptor. In some embodiments, the immune cell receptor is a B cell receptor. In some embodiments, the B cell receptor is an immunoglobulin kappa light chain. In some embodiments, the variable region of the analyte includes a CDR3 region of the immunoglobulin kappa light chain. In some embodiments, the variable region of the analyte includes one or both of CDR1 and CDR2 of the immunoglobulin kappa light chain. In some embodiments, the variable region of the analyte includes a full-length variable domain of the immunoglobulin kappa light chain.

In some embodiments, the B cell receptor is an immunoglobulin lambda light chain. In some embodiments, the variable region of the analyte includes a CDR3 of the immunoglobulin lambda light chain. In some embodiments, the variable region of the analyte includes one or both of CDR1 and CDR2 of the immunoglobulin lambda light chain. In some embodiments, the variable region of the analyte includes a full-length variable domain of the immunoglobulin lambda light chain.

In some embodiments, the B cell receptor is an immunoglobulin heavy chain. In some embodiments, the variable region of the analyte includes a CDR3 of the immunoglobulin heavy chain. In some embodiments, the variable region of the analyte includes one or both of CDR1 and CDR2 of the immunoglobulin heavy chain. In some embodiments, the variable region of the analyte includes a full-length variable domain of the immunoglobulin heavy chain.

In some embodiments, the immune cell receptor is a T cell receptor. In some embodiments, the T cell receptor is a T cell receptor alpha chain. In some embodiments, the variable region of the analyte includes a CDR3 of the T cell receptor alpha chain. In some embodiments, the variable region of the analyte includes one or both of CDR1 and CDR2 of the T cell receptor alpha chain. In some embodiments, the variable region of the analyte includes a full-length variable domain of the T cell receptor alpha chain.

In some embodiments, the T cell receptor is a T cell receptor beta chain. In some embodiments, the variable region of the analyte includes a CDR3 of the T cell receptor beta chain. In some embodiments, the variable region of the analyte includes one or both of CDR1 and CDR2 of the T cell receptor beta chain. In some embodiments, the variable region of the analyte further includes a full-length variable domain of the T cell receptor beta chain.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, ILLUMINA® (sequencing technology) sequencing instruments, PacBio® (sequencing technology), Oxford Nanopore™ (sequencing technology), etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, ILLUMINA® (sequencing technology) sequencing, PacBio SMRT™ sequencing (sequencing technology), and Oxford Nanopore™ sequencing (sequencing technology). Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Spatial Transcriptomics for Antigen Receptors

A fundamental understanding of spatial heterogeneity with respect to T-cell receptor (TCR) and B-cell receptor (BCR) clonotypes within a biological sample is needed to understand multiple facets of their functionality, including, for example, which cells a particular TCR or BCR may be interacting with within the biological sample, the identity of TCR and/or BCR clonotypes in a given biological sample, and/or the identity of TCR and/or BCR clonotypes that are autoreactive in different autoimmune disorders. Numerous single-cell sequencing approaches can identify TCR and BCR clonotypes from a biological sample, however, at present methods are needed to link TCR and BCR sequences to spatial locations within a biological sample. Additionally, identifying the clonal regions, that is, regions defined by the places where variable (V), diverse (D), and joining (J) segments join to form the complementarity determining regions, including CDR1, CDR2, and CDR3, which provide specificity to the TCRs and/or BCRs, would greatly benefit the scientific arts. By coupling clonal information to spatial information it is possible to understand which T-cell and B-cell clonotypes may be specifically interacting with given cell types within a biological sample.

However, capturing analytes encoding immune cell receptors can provide unique challenges. For example, spatially capturing the TCR and BCR gene components with sufficient efficiency to profile the majority of clonotypes in a given tissue is difficult. Capturing analytes encoding immune cell receptors with conventional short-read sequencing methods can result in a loss of sequenced regions that are more than about 1 kb away from the point where sequencing starts. Linking separate TCR or BCR gene components that together form a complete receptor using sequencing data from spots containing multiple different cells are challenges addressed by the methods described herein.

Methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Analytes

The analyte sequences present in the nucleic acid library (e.g., nucleic acid library generated from single-cells or from a biological sample on an array) can be captured from a biological sample (e.g., any of the biological samples described herein). In some embodiments, the biological sample is a tissue sample. In some embodiments, the tissue sample is a tissue section. In some embodiments, the tissue section is a fixed tissue section. In some embodiments, the fixed tissue section is formalin-fixed paraffin-embedded tissue section. In some embodiments, the tissue section is a fresh, frozen tissue section.

The analytes to be detected can be any of the analytes described herein. Analytes can include a nucleic acid molecule with a nucleic acid sequence encoding at least a portion of a V(D)J sequence of an immune cell receptor (e.g., a TCR or BCR). In some embodiments, the analyte is RNA. In some embodiments, the RNA is mRNA. In some embodiments, the analyte is DNA. In some embodiments, the DNA is genomic DNA. In some embodiments, the analytes are analytes encoding immune cell receptors. In some embodiments, analytes encoding immune cell receptors identify clonotype populations from a biological sample.

In some embodiments, analytes include a constant region, such as a constant region present in analytes encoding immune cell receptors. In some embodiments, analytes include a variable region, such as analytes encoding immune cell receptors. In some embodiments, analytes encoding immune cell receptors identify clonotype populations present in a biological sample.

In some embodiments, the analyte is an immune cell receptor. In some embodiments, the immune cell receptor is a B cell receptor. In some embodiments, the B cell receptor is an immunoglobulin kappa light chain. In some embodiments, the variable region of the analyte includes a CDR3 region of the immunoglobulin kappa light chain. In some embodiments, the variable region of the analyte includes one or both of CDR1 and CDR2 of the immunoglobulin kappa light chain. In some embodiments, the variable region of the analyte includes a full-length variable domain of the immunoglobulin kappa light chain.

In some embodiments, the B cell receptor is an immunoglobulin lambda light chain. In some embodiments, the variable region of the analyte includes a CDR3 of the immunoglobulin lambda light chain. In some embodiments, the variable region of the analyte includes one or both of CDR1 and CDR2 of the immunoglobulin lambda light chain. In some embodiments, the variable region of the analyte includes a full-length variable domain of the immunoglobulin lambda light chain.

In some embodiments, the B cell receptor is an immunoglobulin heavy chain. In some embodiments, the variable region of the analyte includes a CDR3 of the immunoglobulin heavy chain. In some embodiments, the variable region of the analyte includes one or both of CDR1 and CDR2 of the immunoglobulin heavy chain. In some embodiments, the variable region of the analyte includes a full-length variable domain of the immunoglobulin heavy chain.

In some embodiments, the immune cell receptor is a T cell receptor. In some embodiments, the T cell receptor is a T cell receptor alpha chain. In some embodiments, the variable region of the analyte includes a CDR3 of the T cell receptor alpha chain. In some embodiments, the variable region of the analyte includes one or both of CDR1 and CDR2 of the T cell receptor alpha chain. In some embodiments, the variable region of the analyte includes a full-length variable domain of the T cell receptor alpha chain.

In some embodiments, the T cell receptor is a T cell receptor beta chain. In some embodiments, the variable region of the analyte includes a CDR3 of the T cell receptor beta chain. In some embodiments, the variable region of the analyte includes one or both of CDR1 and CDR2 of the T cell receptor beta chain. In some embodiments, the variable region of the analyte further includes a full-length variable domain of the T cell receptor beta chain.

Capturing Analytes Encoding Immune Cell Receptors

Provided herein are methods for determining the presence and/or abundance of an immune cell clonotype at a location in a biological sample, the method including (a) contacting a biological sample with an array including a plurality of capture probes, wherein a capture probe of the plurality of capture probes includes (i) a spatial barcode and (ii) a capture domain that specifically binds to a nucleic acid encoding an immune cell receptor of the immune cell clonotype, and, (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Also provided herein are methods for determining the presence and/or abundance of an immune cell receptor at a location in a biological sample, the method including (a)

contacting a biological sample with an array including a plurality of capture probes, wherein a capture probe of the plurality of capture probes includes (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

Also provided herein are methods for determining the presence and/or abundance of an immune cell clonotype at a location in a biological sample, the method including (a) contacting a biological sample with an array including a plurality of capture probes, wherein a capture probe of the plurality of capture probes includes (i) a spatial barcode and (ii) a capture domain that binds to a nucleic acid encoding an immune cell receptor of the immune cell clonotype; (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Also provided herein are methods for determining the presence and/or abundance of an immune cell receptor at a location in a biological sample, the method including (a) contacting a biological sample with an array including a plurality of capture probes, wherein a capture probe of the plurality of capture probes includes (i) a spatial barcode and (ii) a capture domain that binds to a nucleic acid encoding an immune cell receptor and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

In some embodiments of determining the presence and/or abundance of an immune cell clonotype or an immune cell receptor at a location in a biological sample, step (b) includes extending an end of the capture probe using the nucleic acid encoding the immune cell receptor as a template, thereby generating an extended capture probe. In some embodiments, extending an end of the capture probe includes using a reverse transcriptase (e.g., any of the reverse transcriptases described herein). In some embodiments, step (b) includes extending a 3' end of the capture probe. In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments of determining the presence and/or abundance of an immune cell clonotype or an immune cell receptor at a location in a biological sample, the capture probe includes a cleavage domain, a functional domain, a unique molecular identifier, or any combination thereof. In some embodiments, the capture probe includes a functional domain. In some embodiments, the capture domain includes a poly(T) sequence. In some embodiments, the capture domain binds specifically to a nucleic acid sequence encoding a constant region of the T cell receptor alpha chain. In some embodiments, the capture domain binds specifically to a nucleic acid sequence encoding a constant region of the T cell receptor beta chain. In some embodiments, the capture domain binds specifically to a nucleic acid sequence encoding a constant region of the immunoglobulin kappa light chain. In some embodiments, the capture domain binds specifically to a nucleic acid sequence encoding a constant region of the immunoglobulin lambda light chain. In some embodiments, the capture probe binds specifically to a nucleic acid sequence encoding a constant region of the immunoglobulin heavy chain.

Variable Region Primer Enrichment

As demonstrated in the Examples, analytes encoding immune cell receptors were captured and identified with capture domains designed to specifically bind a constant region of a particular immune cell receptor from a biological sample. However, such a strategy does not capture analytes other than analytes encoding immune cell receptors. An additional and alternative approach can include using one or more variable region (V-region) specific primer sets to amplify analytes encoding immune cell receptors (e.g., TCRs and/or BCRs) from nucleic acid libraries generated from poly(T) captured total cDNA libraries, thus allowing sequencing into CDR regions (e.g., CDR3 region) from the 5' end of an amplicon. An advantage of this approach would be the simultaneous detection of lymphocyte clonality alongside global spatial gene expression. An additional consideration is capturing full IGH complexity (e.g., IGH isotypes, e.g., IGHA1-2, IGHG1-4, IGHM, IGHD, and IGHE) without paired end sequencing reads through the CDR3 region. Additional receptor diversity is added to the BCR throughout development and may be difficult to distinguish from sequencing errors with only a single CDR3 read. Additionally, some analytes encoding immune cell receptors are known to be in low abundance (See e.g., Tu, A. A., et al., TCR sequencing paired with massively parallel 3' RNAseq reveals clonotypic T cell signatures, *Nature Immunology,* 20, 1692-1699 (2019); Singh M., et al., High-throughput long-read single cell sequencing reveals the clonal and transcriptional landscape of lymphocytes. *Nature Communications,* 10, 3120 (2019), both of which are incorporated herein by reference in their entireties). Thus, for example, variable region primer enrichment can provide an alternate method to enrich for analytes encoding immune cell receptors from arrays with capture probes including a poly(T) capture domain, followed by one or more amplification reactions (e.g., PCR).

In some embodiments of any of the spatial methods described herein, step (b) further includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor. In some embodiments, step (b) further includes amplifying the second strand of the nucleic acid using (i) a first primer including all or a portion of the functional domain, wherein the functional domain is 5' to the spatial barcode in the second strand of nucleic acid, and (ii) a second primer including a sequence that is substantially complementary to a portion of a sequence encoding a variable region of the immune cell receptor.

In some embodiments, more than one second primer including a sequence substantially complementary to a portion of the sequence encoding the variable region of the immune cell receptor is used. For example, a nested PCR strategy can be used where a first amplification product is generated with a variable region primer and a primer substantially complementary to the functional domain 5' to the spatial barcode, followed by a second, a third, or a fourth round of amplification using a second, a third, or a fourth variable region primer internal to the first region variable region primer (e.g., 5' to the first variable region primer)(for example, see FIG. 22). It will be understood to a person of ordinary skill in the art that additional rounds of amplification require an internal (e.g., 5') located variable region primer in subsequent amplification rounds.

Hybridization Probes and Blocking Probes

In some embodiments, targeted enrichment of cDNAs of interest are enriched from cDNA derived libraries generated from captured analytes (e.g., immune cell analytes). For example, a pool of hybridization probes to an analyte of interest, or a complement thereof, can be designed. In some embodiments, about 10 to about 500 hybridization probes, about 25 to about 450 hybridization probes, about 50 to about 400 hybridization probes, about 75 to about 350 hybridization probes, or about 100 to 300 hybridization probes can be designed for hybridizing to an analyte of interest, or a complement thereof. In some embodiments, the hybridization probes can include an additional moiety, such as a binding moiety, (e.g., biotin) capable of binding another moiety, such as a capture moiety, (e.g., streptavidin). Thus, in some embodiments, one or more hybridization probes (e.g., including an additional moiety, such as biotin) hybridize to the analyte of interest, or complement thereof, in the cDNA library and the total cDNA library is processed on streptavidin beads, for example. The biotin moieties of the hybridization probes specifically bind the streptavidin molecules, thereby enriching for the analytes of interest, or complements thereof. Hybridization probes can be designed to be complementary to any analyte or its complementary sequence, including, for example, analytes encoding immune cell analytes.

In some embodiments, enriching analytes of interest includes the use of blocking probes. Blocking probes can be added to the cDNA library before, after, or concurrently with hybridization probes. In some embodiments, blocking probes reduce background (e.g., non-specific binding events) when enriching for targets within the cDNA library. In some embodiments, blocking probes can be about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, or about 150 nucleotides long. In some embodiments, blocking probes are designed specifically to domains present in one or more members of the cDNA library. In some embodiments, one blocking probe is added to the cDNA library. In some embodiments, two or more blocking probes (e.g., different blocking probes). In some embodiments, 3, 4, 5 or more different blocking probes are added to the cDNA library (e.g., blocking probes having a different sequence). In some embodiments, the blocking probe comprises SEQ ID NO: 639. In some embodiments, the blocking probe comprises SEQ ID NO: 640. In some embodiments, the blocking probe comprises at least 80%, at least 85%, at least 90%, at least 95%, at least 96%, at least 97%, at least 98%, or at least 99% identity to SEQ ID NO: 639. In some embodiments, the blocking probe comprises at least 80%, at least 85%, at least 90%, at least 95%, at least 96%, at least 97%, at least 98%, or at least 99% identity to SEQ ID NO: 640.

Identifying Immune Cell Receptors

In some embodiments of determining the presence and/or abundance of an immune cell clonotype at a location in a biological sample, determining in step (b) includes sequencing (i) all or a portion of the sequence of the spatial barcode or a complement thereof, and (ii) all or a portion of the sequence of the nucleic acid encoding the immune cell receptor or a complement thereof. Any of the sequencing methods described herein can be used. In some embodiments, step (b) includes determining the presence of the immune cell clonotype at a location in the biological sample. In some embodiments, step (b) includes determining the abundance of the immune cell clonotype at a location in the biological sample. In some embodiments, step (b) includes determining the presence and abundance of the immune cell clonotype at a location in the biological sample. In some embodiments, step (b) includes determining the presence of two or more immune cell clonotypes at a location in the biological sample. In some embodiments, step (b) includes determining the abundance of two or more immune cell clonotypes at a location in the biological sample. In some embodiments, step (b) includes determining the presence and abundance of two or more immune cell clonotypes at a location in the biological sample. In some embodiments, the method includes comparing the two or more immune cell clonotypes. In some embodiments, the two or more immune cell clonotypes are each a B cell clonotype. In some embodiments, the two or more immune cell clonotypes are each a T cell clonotype. In some embodiments, the two or more immune cell clonotypes include at least one T cell clonotype and at least one B cell clonotype.

In some embodiments of determining the presence and/or abundance of an immune cell receptor at a location in a biological sample, the determining in step (b) includes sequencing (i) all or a portion of the sequence of the spatial barcode or a complement thereof, and (ii) all or a portion of the sequence of the nucleic acid encoding the immune cell receptor or a complement thereof. In some embodiments, step (b) includes determining the presence of the immune cell receptor at a location in the biological sample. In some embodiments, step (b) includes determining the abundance of the immune cell receptor at a location in the biological sample. In some embodiments, step (b) includes determining the presence and abundance of the immune cell receptor at a location in the biological sample. In some embodiments, step (b) includes determining the presence of two or more immune cell receptors at a location in the biological sample. In some embodiments, step (b) includes determining the abundance of two or more immune cell receptors at a location in the biological sample. In some embodiments, step (b) includes determining the presence and abundance of two or more immune cell receptors at a location in the biological sample. In some embodiments, the method includes comparing the two or more immune cell receptors. In some embodiments, the two or more immune cell clonotypes are each an immune cell receptor of a B cell. In some embodiments, two or more immune cell clonotypes are each an immune cell receptor of a T cell. In some embodiments, two or more immune cell clonotypes include at least one immune cell receptor of a T cell and at least one immune cell receptor from a B cell.

In some embodiments of determining the presence and/or abundance of an immune cell clonotype or an immune cell receptor at a location in a biological sample, includes prior to step (b), contacting the biological sample with ribosomal RNA depletion probes and/or mitochondrial RNA depletion probes. In some embodiments, the biological sample is imaged. In some embodiments, the biological sample is stained.

Arrays and Kits

Provided herein are arrays including a plurality of capture probes, where a capture probe of the plurality of capture probes includes (i) a spatial barcode and (ii) a capture domain that specifically binds to a nucleic acid encoding an immune cell receptor of an immune cell clonotype. In some arrays, the immune cell clonotype is a T cell clonotype. In some arrays, the immune cell receptor is a T cell receptor alpha chain. In some arrays, the capture domain binds specifically to a nucleic acid sequence encoding a constant region of the T cell receptor alpha chain. In some arrays, the immune cell receptor is a T cell receptor beta chain. In some arrays, the capture domain binds specifically to a nucleic acid sequence encoding a constant region of the T cell receptor beta chain. In some arrays, the immune cell clonotype is a B cell clonotype. In some arrays, the immune cell receptor is an immunoglobulin kappa light chain. In some arrays, the capture domain binds specifically to a nucleic acid sequence encoding a constant region of the immunoglobulin kappa light chain. In some arrays, the immune cell receptor is an immunoglobulin lambda light chain. In some arrays, the capture domain binds specifically to a nucleic acid sequence encoding a constant region of the immunoglobulin lambda light chain. In some arrays, the immune cell receptor is an immunoglobulin heavy chain. In some arrays, the capture domain binds specifically to a nucleic acid sequence encoding a constant region of the immunoglobulin heavy chain. In some arrays, the capture probe includes a cleavage domain, a functional domain, a unique molecular identifier, or any combination thereof.

Also provided herein are kits including an array (e.g., any of the arrays described herein) and one or more hybridization probes, wherein a hybridization probe includes (i) a sequence substantially complementary to a nucleic acid encoding an immune cell receptor and (ii) a binding moiety that interacts with a capturing moiety and one or more blocking probes.

Also provided herein are kits, including an array of any of the arrays described herein and one or both of ribosomal RNA depletion probes and mitochondrial RNA depletion probes.

Targeted RNA depletion allows for depletion or removal of one or more species of undesirable RNA molecules (e.g., ribosomal RNA and/or mitochondrial RNA), thereby reducing the pool and concentration of undesirable RNA molecules in the sample which could interfere with desired target detection (e.g., detection of mRNA). To achieve depletion, one or more probes are designed that hybridize to one or more undesirable RNA molecules. For example, in one embodiment, probes can be administered to a biological sample that selectively hybridize to ribosomal RNA (rRNA), thereby reducing the pool and concentration of rRNA in the sample. In one embodiment, probes can be administered to a biological sample that selectively hybridize to mitochondria RNA (mtRNA), thereby reducing the pool and concentration of mtRNA in the sample. Subsequent application of capture probes to the sample can result in improved capture of other types of RNA due to a reduction in undesirable RNA (e.g., down-selected RNA) present in the sample.

Upon depletion of the undesirable RNA, the sample will contain an enriched population of the RNA target of interest (e.g., an mRNA target). In some embodiments, the undesirable RNA comprises less than 20%, 19%, 18%, 17%, 16% 15%, 14%, 13%, 12%, 11% 10%, 9%, 8%, 7%, 6%, 5%, 4%, 3%, 2%, or 1%, or any range therein, of the total RNA in the sample after depletion of the undesirable RNA (i.e., less than 20%, 19%, 18%, 17%, 16% 15%, 14%, 13%, 12%, 11% 10%, 9%, 8%, 7%, 6%, 5%, 4%, 3%, 2%, or 1%, or any range therein compared to a sample that undergoes no depletion step). Consequently, the enriched population of the RNA target of interest may comprise at least 99%, 98%, 97%, 96%, 95%, 94%, 93%, 92%, 91%, 90%, 89%, 88%, 87%, 86%, 85%, 84%, 83%, 82%, 81%, or 80%, or any range therein, of the total RNA in the sample.

As used herein, the term “undesirable RNA molecule”, or “undesirable RNA”, refers to an undesired RNA that is the target for depletion from the biological sample. In some embodiments, examples of the undesirable RNA include, but are not limited to, messenger RNA (mRNA), ribosomal RNA (rRNA), mitochondrial RNA (mtRNA), transfer RNA (tRNA), microRNA (miRNA), and viral RNA. In some embodiments, the undesirable RNA can be a transcript (e.g., present in a tissue section). The undesirable RNA can be small (e.g., less than 200 nucleic acid bases in length) or large (e.g., RNA greater than 200 nucleic acid bases in length).

In some embodiments, the undesirable RNA molecule includes 5.8S ribosomal RNA (rRNA), 5S rRNA, transfer RNA (tRNA), microRNA (miRNA), a small nucleolar RNA (snoRNAs), Piwi-interacting RNA (piRNA), tRNA-derived small RNA (tsRNA), and small rDNA-derived RNA (srRNA), or mitochondrial RNA (mtRNA). In some embodiments, the undesirable RNA molecule includes an RNA molecule that is added (e.g., transfected) into a sample (e.g., a small interfering RNA (siRNA)). The undesirable RNA can be double-stranded RNA or single-stranded RNA. In embodiments where the undesirable RNA is double-stranded it is processed as a single-stranded RNA prior to depletion. In some embodiments, the undesirable RNA can be circular RNA. In some embodiments, the undesirable RNA can be a bacterial rRNA (e.g., 16s rRNA or 23s rRNA). In some embodiments, the undesirable RNA is from *E. coli.*

In some embodiments, the undesirable RNA molecule is rRNA. In some embodiments, the rRNA is eukaryotic rRNA. In some embodiments, the rRNA is cytoplasmic rRNA. In some embodiments, the rRNA is mitochondrial rRNA. Cytoplasmic rRNAs include, for example, 28S, 5.8S, 5S and 18S rRNAs. Mitochondrial rRNAs include, for example, 12S and 16S rRNAs. The rRNA may also be prokaryotic rRNA, which includes, for example, 5S, 16S, and 23S rRNA. The sequences for rRNAs are well known to those skilled in the art and can be readily found in sequence databases such as GenBank or may be found in the literature. For example, the sequence for the human 18S rRNA can be found in GenBank as Accession No. M10098 and the human 28S rRNA as Accession No. M11167.

In some embodiments, the undesirable RNA molecule is mitochondrial RNA. Mitochondrial RNAs include, for example, 12S rRNA (encoded by MT-RNR1), and 16S rRNA (encoded by MT-RNR2), RNAs encoding electron transport chain proteins (e.g., NADH dehydrogenase, coenzyme Q-cytochrome c reductase/cytochrome b, cytochrome c oxidase, ATP synthase, or humanin), and tRNAs (encoded by MT-TA, MT-TR, MT-TN, MT-TD, MT-TC, MT-TE, MT-TQ, MT-TG, MT-TH, MT-TI, MT-TL1, MT-TL2, MT-TK, MT-TM, MT-TF, MT-TP, MT-TS1, MT-TS2, MT-TT, MT-TW, MT-TY, or MT-TV).

In some embodiments, the one or more undesirable RNA depletion probes is a DNA probe. In some embodiments, the DNA probe includes a single-stranded DNA oligonucleotide having a sequence partially or completely complementary to an undesirable RNA and specifically hybridizes to the undesirable RNA. In some embodiments, the one or more undesirable RNA depletion probes are at least 70%, at least 75%, at least 80%, at least 85%, at least 90%, at least 91%, at least 92%, at least 93%, at least 94%, at least 95%, at least 96%, at least 97%, at least 98%, or at least 99% complementary to one or more undesirable RNA molecules. In some embodiments, the one or more undesirable RNA depletion probes is 100% (i.e., completely) complementary to one or more undesirable RNA molecules.

In some embodiments, probes used herein have been described in Morlan et al., PLoS One. 2012; 7(8):e42882, which is incorporated by reference in its entirety. In some embodiments, probes used herein have been described in U.S. Appl. Publ. No. 2011/0111409, which is incorporated by reference in its entirety. In some embodiments, probes used herein have been described in Adiconis et al., Nat Methods. 2013 July; 10(7):623-9, which is incorporated by reference in its entirety.

The DNA probe can be produced by techniques known in the art. For example, in some embodiments, a DNA probe is produced by chemical synthesis, by in vitro expression from recombinant nucleic acid molecules, or by in vivo expression from recombinant nucleic acid molecules. The undesirable RNA depletion probe may also be produced by amplification of the undesirable RNA, e.g., RT-PCR, asymmetric PCR, or rolling circle amplification.

EXAMPLES

Example 1: Analyte Capture and Enrichment Strategies

Figure 3A:
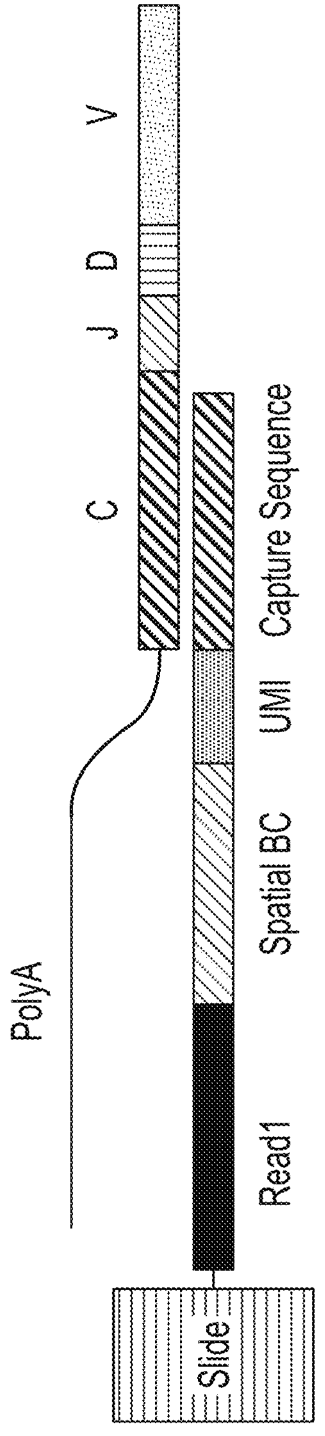
FIG. 3A shows an exemplary capture probe with a capture sequence complementary to a constant region of an analyte.
Figure 3B:
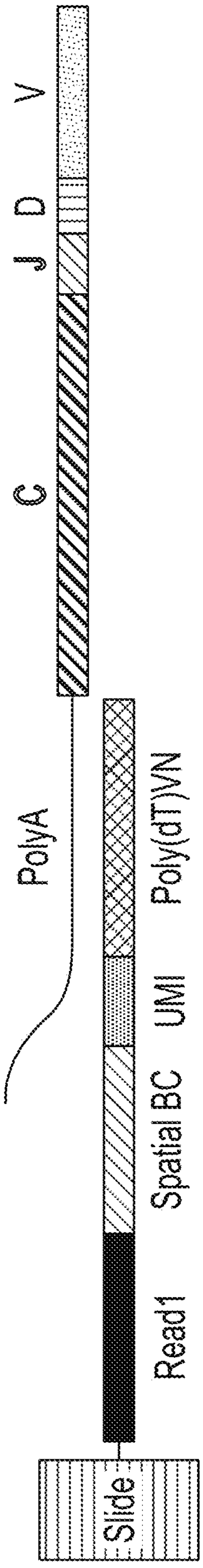
FIG. 3B shows an exemplary capture probe with a poly (dT) capture domain.

FIGS. 3A and 3B show two different capture probes with different exemplary capture strategies to capture analytes encoding immune cell receptors in a biological sample. FIG. 3A shows “targeted” capture where the capture domain is substantially complementary to the constant region of the analyte encoding an immune cell receptor to be detected. Targeted capture increases the likelihood that the portion of interest in the variable domain, CDR3, is retained during library preparation. Alternatively, FIG. 3B shows poly(A) capture with a poly(T) capture domain. A poly(T) capture domain can capture other analytes, including analytes encoding immune cell receptors within the biological sample.

Figure 4:
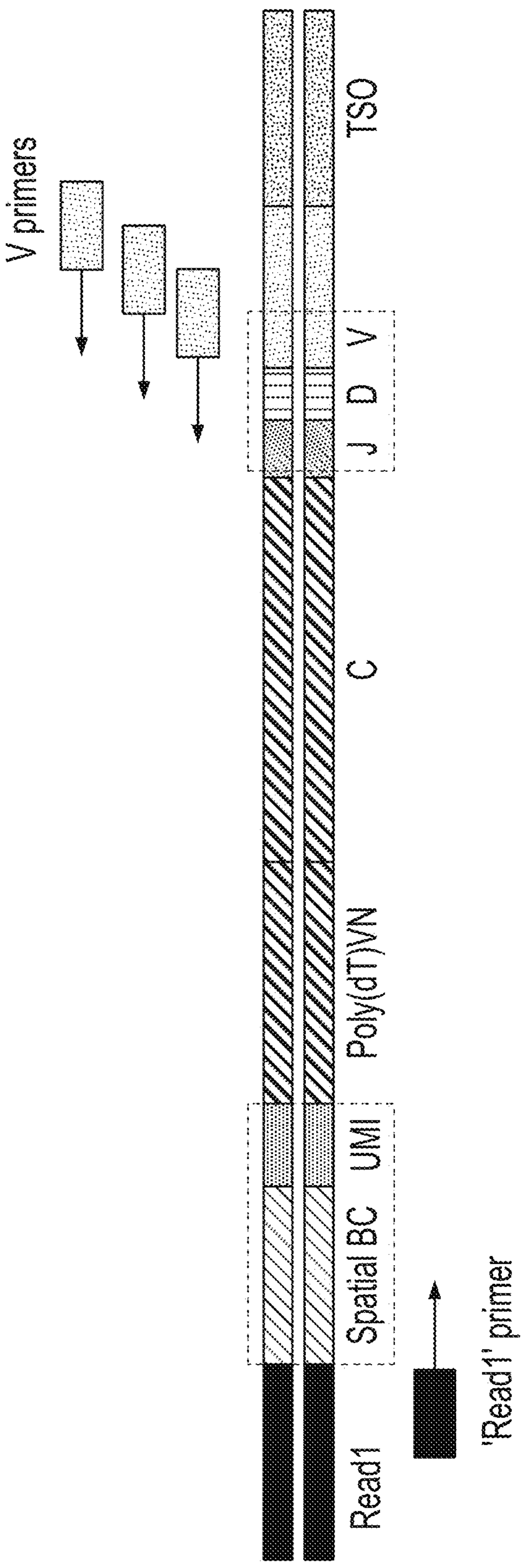
FIG. 4 shows an exemplary enrichment strategy with a Read1 primer and a primer(s) complementary to a variable region of an analyte.

FIG. 4 shows an exemplary analyte enrichment strategy following analyte capture on the array. The portion of the immune cell analyte of interest includes the sequence of the V(D)J region. The CDR sequences are also important because these sequences define the immune cell receptor’s binding specificity. As described herein, a poly(T) capture probe captures an analyte encoding an immune cell receptor, an extended capture probe is generated by a reverse transcription reaction, and a second strand is generated. The resulting nucleic acid library can be enriched by the exemplary scheme shown in FIG. 4, where an amplification reaction including a Read 1 primer complementary to the Read 1 sequence of the capture probe and a primer complementary to a portion of the variable region of the immune cell analyte, can enrich the library via PCR. The enriched library can be further enriched by nested primers complementary to a portion of the variable region internal (e.g., 5') to the initial variable region primer for practicing nested PCR.

Figure 5:
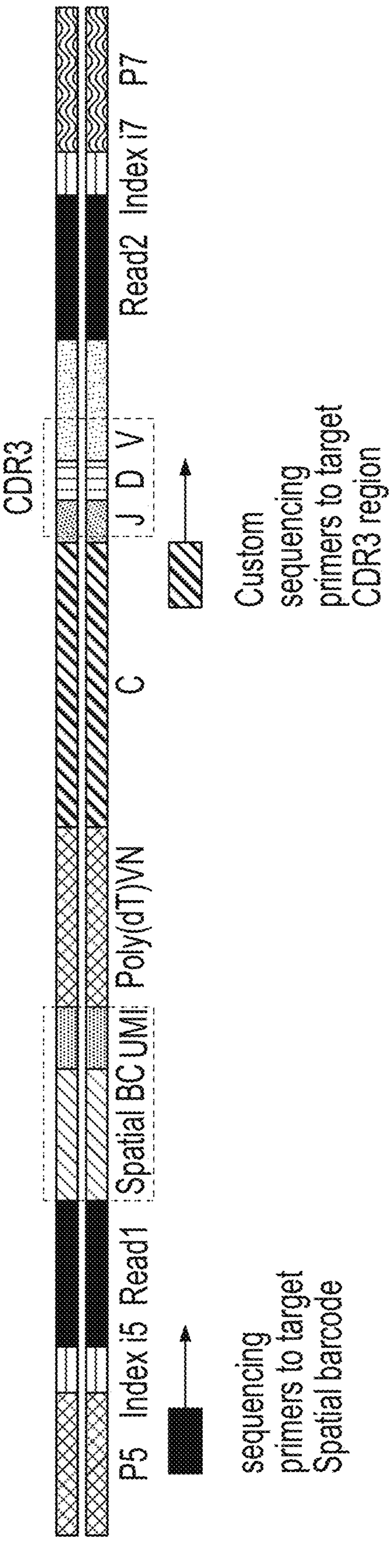
FIG. 5 shows an exemplary sequencing strategy with a ligated sequencing handle (P5) and a custom sequencing primer complementary to a portion of the constant region of an analyte.

FIG. 5 shows a sequencing strategy with a primer specific complementary to the sequencing flow cell attachment sequence (e.g., P5) and a custom sequencing primer complementary to a portion of the constant region of the analyte. This sequencing strategy targets the constant region to obtain the sequence of the CDR regions, including CDR3, while concurrently or sequentially sequencing the spatial barcode (BC) and/or unique molecular identifier (UMI) of the capture probe. By capturing the sequence of a spatial barcode, UMI and a V(D)J region the receptor is not only determined, but its spatial location and abundance within a cell or tissue is also identified.

Example 2—Capture of Analytes Encoding Immune Cell Receptors

Figure 6:
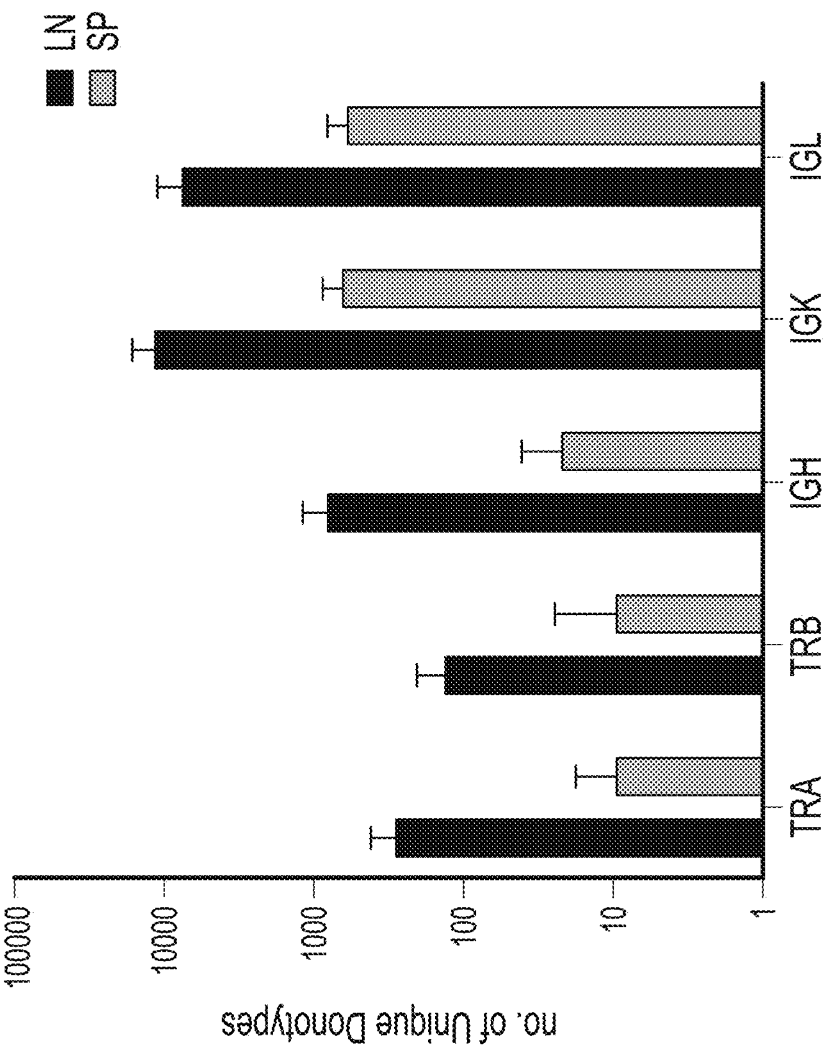
FIG. 6 shows a graph showing the number of unique clonotypes detected from lymph node (LN) and spleen (SP) tissues.

FIG. 6 shows the number of unique clonotypes detected for TRA, TRB, IGH, IGK, and IGL on an array for both lymph node tissue (LN, black) and spleen tissue (SP, gray). It is contemplated that the lack of detected clonotypes found may be the result of inefficient or decreased TRAC/TRBC/IGH transcript capture or decreased sequencing of the variable region (e.g., CDR3 region) due to its distance from the sequencing domain (e.g. Read 1 sequencing domain). A greater abundance of unique clonotypes were detected for IGK and IGL, which may be due in part to the shorter constant regions present in these clonotypes relative to the constant regions present in TRAC, TRAB, and IGH transcripts.

Figure 7A:
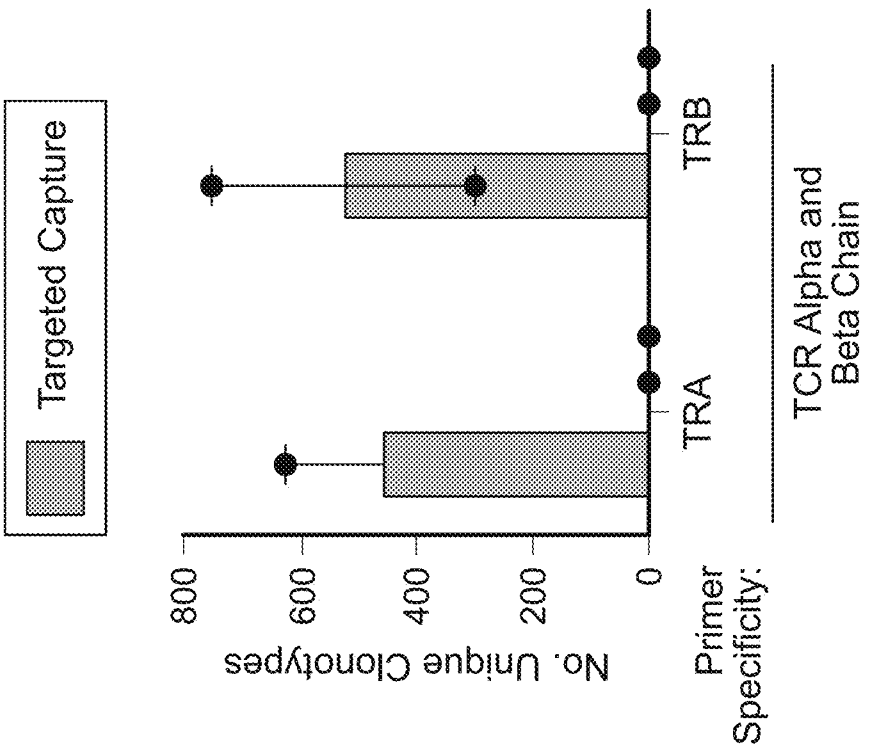
FIG. 7A shows an exemplary graph of the number of unique T-cell receptor A (TRA) and T-cell receptor B (TRB) clonotypes detected with a targeted capture probe compared with a poly(dT) capture probe.
Figure 7B:
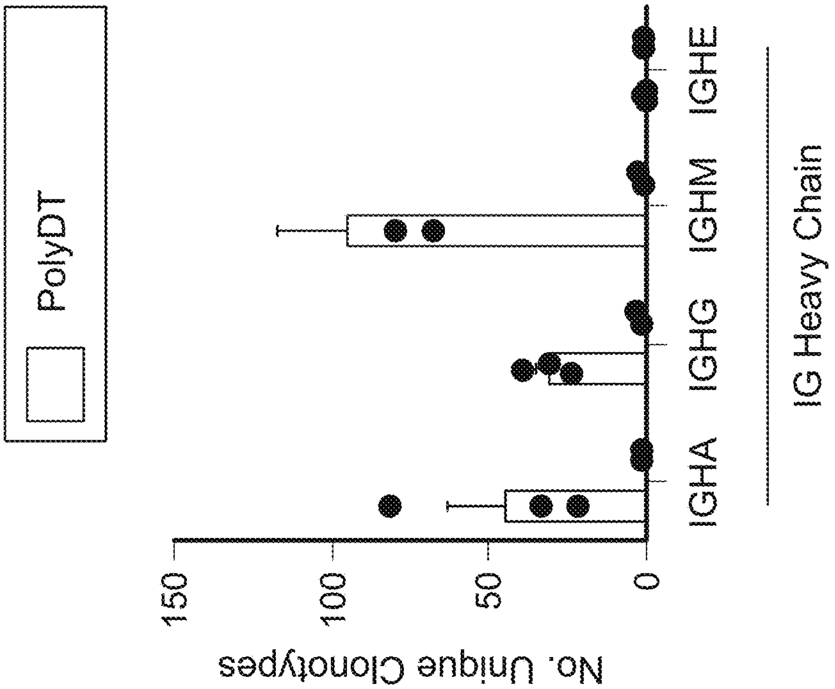
FIG. 7B shows an exemplary graph of the number of unique IG heavy chain clonotypes (e.g., A, G, M and E clonotypes) detected with a targeted capture probe compared with a poly(dT) capture probe.

FIGS. 7A-B show the number of unique clonotypes detected for TRA and TRB (FIG. 7A) and the number of unique clonotypes detected for IGA, IGHG, IGHM, and IGHE (FIG. 7B). The data show that targeted capture (gray bars) yields a higher number of TRA and TRB clonotypes (FIG. 7A) than poly(T) capture as demonstrated by the lack of clonotypes detected. Similarly, targeted capture of IGHA, IGHG, and IGHM yielded a higher number of unique clonotypes detected than poly(T) capture, as demonstrated by the lack of clonotypes detected. Thus the data demonstrate that targeted capture of analytes encoding immune cell receptors is possible for some analytes, but may not be sufficient for other analytes encoding immune cell receptors (e.g., IGHE).

As discussed, undetectable levels of T-cell receptor and B-cell receptor transcripts were captured with poly(T) capture domains as shown in FIGS. 7A-B. Targeted capture, however, requires custom capture domains for each analyte encoding an immune cell receptor and does not allow for the simultaneous capture of analytes other than targeted analytes encoding immune cell receptors.

A strategy to detect whether analytes encoding immune cell receptors were captured was investigated and includes using poly(T) capture sequences in combination with PCR amplification performed on full length cDNA from several different sources, including lymph node tissue and tonsil tissue (Table 1).

TABLE 1

| | |
|---|---|
| Lymph Node (LN) spatial library | n = 6 |
| Tonsil spatial library | n = 2 |
| Tonsil SmartSeq2 (SS2) (single-cell) RNAseq (positive control) | n = 1 |

The tonsil SS2 sample was derived from the same tonsil as the tonsil spatial libraries and adapted from Picelli et al., Full-length RNA-seq from single cells using Smart-seq2, 9, 171-181, *Nature* (2014), and used as a positive control and without PCR enrichment.

To begin, 0.5 ng of each library in Table 1 as input material was run in triplicate for each sample and PCR reaction (TRB, IGHG, and IGHM), except for one LN (#9) and the Tonsil SS2 bulk sample, which were run in duplicate and once, respectively. The PCR primers targeted: a) the constant region of either TRB, IGHG, or IGHM (Table 2), and b) the variable segments for TRB (Balazs, A. B., et al., Isolation of unknown rearranged T-cell receptors from single cells WO 2011/008502, which is incorporated herein by reference in its entirety) and IGH (Vázquez, B., et al., High-Quality Library Preparation for NGS-Based Immunoglobulin Germline Gene Inference and Repertoire Expression Analysis, *Frontiers Immunol,* 10, 660 (2019), which is incorporated herein by reference in its entirety). The constant primers were selected based on their proximity to the CDR3 region and testing of various primers for each target was performed in PCR optimization experiments. Both the forward and reverse primers were tagged with partial P5 and P7 domains that allowed subsequent Truseq indexing for ILLUMINA® (sequencing technology) sequencing. PCR was performed using the KAPA HiFi Hotstart ready mix according to the manufacturer's instructions with 30 amplification cycles.

TABLE 2

| Constant Primer | Sequence |
|---|---|
| TRB | SEQ ID NO: 1 TCTGATGGCTCAAACACAGC |
| IGHG | SEQ ID NO: 2 GCCAGGGGGAAGACCGATGGG |
| IGHM | SEQ ID NO: 3 CACGCTGCTCGTATCCGA |

TABLE 3

| Variable Region Primer | Sequence |
|---|---|
| TCRa V inner pool | |
| TCRaV17 | SEQ ID NO: 4 CAACAGGGAGAAGAGGATCCTCAGGCC |
| TCRaV1-2 | SEQ ID NO: 5 GGACAAAACATTGACCAGCCCACTGAGAT |
| TCRaV10 | SEQ ID NO: 6 AAAAACCAAGTGGAGCAGAGTCCTCAGTCC |
| TCRaV12-1 | SEQ ID NO: 7 CAACGGAAGGAGGTGGAGCAGGATC |
| TCRaV12-2 | SEQ ID NO: 8 CAACAGAAGGAGGTGGAGCAGAATTCTGG |
| TCRaV12-3 | SEQ ID NO: 9 CAACAGAAGGAGGTGGAGCAGGATCCT |
| TCRaV13-1 | SEQ ID NO: 10 GAGAATGTGGAGCAGCATCCTTCAACC |
| TCRaV13-2 | SEQ ID NO: 11 GAGAGTGTGGGGCTGCATCTTCCTACC |
| TCRaV14D4 | SEQ ID NO: 12 CAGAAGATAACTCAAACCCAACCAGGAATGTTC |
| TCRav16 | SEQ ID NO: 13 CAGAGAGTGACTCAGCCCGAGAAGCTC |
| TCRaV18 | SEQ ID NO: 14 GACTCGGTTACCCAGACAGAAGGCCC |
| TCRaV19 | SEQ ID NO: 15 CAGAAGGTAACTCAAGCGCAGACTGAAATTTCT |
| TCRaV2 | SEQ ID NO: 16 AAGGACCAAGTGTTTCAGCCTTCCACAGTG |
| TCRaV20 | SEQ ID NO: 17 GAAGACCAGGTGACGCAGAGTCCCG |
| TCRaV21 | SEQ ID NO: 18 AAACAGGAGGTGACGCAGATTCCTGC |
| TCRaV22 | SEQ ID NO: 19 ATACAAGTGGAGCAGAGTCCTCCAGACCTGA |
| TCRaV23DV6 | SEQ ID NO: 20 CAACAGAAGGAGAAAAGTGACCAGCAGCA |
| TCRaV24 | SEQ ID NO: 21 ATACTGAACGTGGAACAAAGTCCTCAGTCACTG |
| TCRaV25 | SEQ ID NO: 22 CAACAGGTAATGCAAATTCCTCAGTACCAGC |
| TCRaV26-1 | SEQ ID NO: 23 AAGACCACCCAGCCCCCCTCC |
| TCRaV26-2 | SEQ ID NO: 24 AAGACCACACAGCCAAATTCAATGGAGAGTAAC |
| TCRaV27 | SEQ ID NO: 25 CAGCTGCTGGAGCAGAGCCCTCAGT |
| TCRaV29DV5 | SEQ ID NO: 26 CAACAGAAGAATGATGACCAGCAAGTTAAGCAA |
| TCRaV3 | SEQ ID NO: 27 CAGTCAGTGGCTCAGCCGGAAGATC |
| TCRaV30 | SEQ ID NO: 28 CAACAACCAGTGCAGAGTCCTCAAGCC |
| TCRaV34 | SEQ ID NO: 29 CAAGAACTGGAGCAGAGTCCTCAGTCCTTG |
| TCRaV35 | SEQ ID NO: 30 CAACAGCTGAATCAGAGTCCTCAATCTATGTTTATC |

TABLE 3-continued

| Variable Region Primer | Sequence |
|---|---|
| TCRaV36DV7 | SEQ ID NO: 31 GAAGACAAGGTGGTACAAAGCCCTCTATCTCTG |
| TCRaV38-2DV8 | SEQ ID NO: 32 CAGACAGTCACTCAGTCTCAACCAGAGATGTCT |
| TCRaV39 | SEQ ID NO: 33 GAGCTGAAAGTGGAACAAAACCCTCTGTTC |
| TCRaV4 | SEQ ID NO: 34 AAGACCACCCAGCCCATCTCCATG |
| TCRaV40 | SEQ ID NO: 35 AATTCAGTCAAGCAGACGGGCCAAATAAC |
| TCRaV41 | SEQ ID NO: 36 GCCAAAAATGAAGTGGAGCAGAGTCCTC |
| TCRaV5 | SEQ ID NO: 37 GAGGATGTGGAGCAGAGTCTTTTCCTGAGTG |
| TCRaV6 | SEQ ID NO: 38 CAAAAGATAGAACAGAATTCCGAGGCCCTG |
| TCRaV7 | SEQ ID NO: 39 GAAAACCAGGTGGAGCACAGCCCTC |
| TCRaV8-1 | SEQ ID NO: 40 CAGTCTGTGAGCCAGCATAACCACCAC |
| TCRaV8-2 | SEQ ID NO: 41 CAGTCGGTGACCCAGCTTGACAGC |
| TCRaV8-3 | SEQ ID NO: 42 CAGTCAGTGACCCAGCCTGACATCCAC |
| TCRaV8-4 | SEQ ID NO: 43 CAGTCGGTGACCCAGCTTGGCAG |
| TCRaV8-6 | SEQ ID NO: 44 CAGTCTGTGACCCAGCTTGACAGCCA |
| TCRaV8-7 | SEQ ID NO: 45 CAGTCGGTGACCCAGCTTGATGGC |
| TCRaV9-1 | SEQ ID NO: 46 GATTCAGTGGTCCAGACAGAAGGCCAAGT |
| TCRaV9-2 | SEQ ID NO: 47 AATTCAGTGACCCAGATGGAAGGGCC |
| TCRb V Inner Pool | |
| TCRb_JM_V2 | SEQ ID NO: 48 GAACCTGAAGTCACCCAGACTCCCAGC |
| TCRb_JM_V3-1 | SEQ ID NO: 49 GCTGTTTCCCAGACTCCAAAATACCTGGTC |
| TCRb_JM_V4-1 | SEQ ID NO: 50 GAAGTTACCCAGACACCAAAACACCTGGTC |
| TCRb_JM_V5-1 | SEQ ID NO: 51 GGAGTCACTCAAACTCCAAGATATCTGATCAAAAC |
| TCRb_JM_V6-1 | SEQ ID NO: 52 GGTGTCACTCAGACCCCAAAATTCCAG |
| TCRb_JM_V7-1 | SEQ ID NO: 53 GGAGTCTCCCAGTCCCTGAGACACAAGG |
| TCRb_JM_V4-2 | SEQ ID NO: 54 GGAGTTACGCAGACACCAAGACACCTGG |
| TCRb_JM_V6-2 | SEQ ID NO: 55 GGTGTCACTCAGACCCCAAAATTCCG |
| TCRb_JM_V7-2 | SEQ ID NO: 56 GGAGTCTCCCAGTCCCCCAGTAACAAG |
| TCRb_JM_V6-4 | SEQ ID NO: 57 GGGATCACCCAGGCACCAACATCTC |
| TCRb_JM_V7-3 | SEQ ID NO: 58 GGAGTCTCCCAGACCCCCAGTAACAAG |
| TCRb_JM_V5-3 | SEQ ID NO: 59 GGAGTCACCCAAAGTCCCACACACCT |
| TCRb_JM_V9 | SEQ ID NO: 60 GGAGTCACACAAACCCCAAAGCACCT |
| TCRb_JM_V10-1 | SEQ ID NO: 61 GAAATCACCCAGAGCCCAAGACACAAGA |
| TCRb_JM_V11-1 | SEQ ID NO: 62 GAAGTTGCCCAGTCCCCCAGATATAAGATTA |
| TCRb_JM_V10-2 | SEQ ID NO: 63 GGAATCACCCAGAGCCCAAGATACAAGAT |
| TCRb_JM_V11-2 | SEQ ID NO: 64 GGAGTTGCCCAGTCTCCCAGATATAAGATTATAGAG |
| TCRb_JM_V7-4 | SEQ ID NO: 65 GGAGTCTCCCAGTCCCCAAGGTACAAAG |
| TCRb_JM_V7-5 | SEQ ID NO: 66 GGAGTCTCCCAGTCCCCAAGGTACGA |
| TCRb_JM_V6-7 | SEQ ID NO: 67 GGTGTCACTCAGACCCCAAAATTCCAC |

TABLE 3-continued

| Variable Region Primer | Sequence |
|---|---|
| TCRb_JM_V7-6 | SEQ ID NO: 68 GGAGTCTCCCAGTCTCCCAGGTACAAAGTC |
| TCRb_JM_V6-8 | SEQ ID NO: 69 GGTGTCACTCAGACCCCAAAATTCCACAT |
| TCRb_JM_V7-8 | SEQ ID NO: 70 GGAGTCTCCCAGTCCCCTAGGTACAAAGTC |
| TCRb_JM_V5-8 | SEQ ID NO: 71 GGAGTCACACAAAGTCCCACACACCTGA |
| TCRb_JM_V7-9 | SEQ ID NO: 72 GGAGTCTCCCAGAACCCCAGACACAAG |
| TCRb_JM_V13 | SEQ ID NO: 73 GGAGTCATCCAGTCCCCAAGACATCTGAT |
| TCRb_JM_V12-3 | SEQ ID NO: 74 GGAGTTATCCAGTCACCCCGCCATG |
| TCRb_JM_V12-4 | SEQ ID NO: 75 GGAGTTATCCAGTCACCCCGGCAC |
| TCRb_JM_V12-5 | SEQ ID NO: 76 AGAGTCACCCAGACACCAAGGCACAAG |
| TCRb_JM_V14 | SEQ ID NO: 77 GGAGTTACTCAGTTCCCCAGCCACAGC |
| TCRb_JM_V15 | SEQ ID NO: 78 ATGGTCATCCAGAACCCAAGATACCAGGTT |
| TCRb_JM_V17 | SEQ ID NO: 79 GAGCCTGGAGTCAGCCAGACCCC |
| TCRb_JM_V18 | SEQ ID NO: 80 GGCGTCATGCAGAACCCAAGACAC |
| TCRb_JM_V19 | SEQ ID NO: 81 GGAATCACTCAGTCCCCAAAGTACCTGTTCA |
| TCRb_JM_V20-1 | SEQ ID NO: 82 GCTGTCGTCTCTCAACATCCGAGCTG |
| TCRb_JM_V22 | SEQ ID NO: 83 ATTCCAGCTCACTGGGGCTGGATG |
| TCRb_JM_V23-1 | SEQ ID NO: 84 AAAGTCACACAGACTCCAGGACATTTGGTCA |
| TCRb_JM_V24-1 | SEQ ID NO: 85 GATGTTACCCAGACCCCAAGGAATAGGATC |
| TCRb_JM_V25-1 | SEQ ID NO: 86 GACATCTACCAGACCCCAAGATACCTTGTTATAGG |
| TCRb_JM_V26 | SEQ ID NO: 87 GTAGTTACACAATTCCCAAGACACAGAATCATTGG |
| TCRb_JM_V27 | SEQ ID NO: 88 CAAGTGACCCAGAACCCAAGATACCTCATC |
| IGH V pool | |
| IGH_MTPX_1 | SEQ ID NO: 89 GGTGGCAGCAGTCACAGATGCCTACTC |
| IGH_MTPX_2 | SEQ ID NO: 90 GGTGGCAGCAGCCACAGGTGCCCACTC |
| IGH_MTPX_3 | SEQ ID NO: 91 GGTGGCAGCAGCTACAGGTGTCCAGTC |
| IGH_MTPX_4 | SEQ ID NO: 92 GGTGGSAGCAGCAACARGWGCCCACTC |
| IGH_MTPX_5 | SEQ ID NO: 93 GCTGGCTGTAGCTCCAGGTGCTCACTC |
| IGH_MTPX_6 | SEQ ID NO: 94 CCTGCTGCTGACCAYCCCTTCMTGGGTCTTGTC |
| IGH_MTPX_7 | SEQ ID NO: 95 CCTGCTACTGACTGTCCCGTCCTGGGTCTTATC |
| IGH_MTPX_8 | SEQ ID NO: 96 GGGTTTTCCTCGTTGCTCTTTTAAGAGGTGTCCAGTG |
| IGH_MTPX_9 | SEQ ID NO: 97 GGGTTTTCCTTGTTGCTATTTTAAAAGGTGTCCARTG |
| IGH_MTPX_10 | SEQ ID NO: 98 GGATTTTCCTTGCTGCTATTTTAAAAGGTGTCCAGTG |
| IGH_MTPX_11 | SEQ ID NO: 99 GGGTTTTCCTTKTKGCTATWTTAGAAGGTGTCCAGTG |
| IGH_MTPX_12 | SEQ ID NO: 100 GGTGGCRGCTCCCAGATGGGTCCTGTC |
| IGH_MTPX_13 | SEQ ID NO: 101 CTGGCTGTTCTCCAAGGAGTCTGTG |
| IGH_MTPX_14 | SEQ ID NO: 102 GGCCTCCCATGGGGTGTCCTGTC |
| IGH_MTPX_15 | SEQ ID NO: 103 GGTGGCAGCAGCAACAGGTGCCCACT |
| IGH_MTPX_16 | SEQ ID NO: 104 ATGGAACTGGGGCTCCGCTGGGTTTTCC |
| IGH_MTPX 17 | SEQ ID NO: 105 ATGGACTGCACCTGGAGGATCCTCCTC |

TABLE 3-continued

| Variable Region Primer | Sequence |
|---|---|
| IGH_MTPX_18 | SEQ ID NO: 106 TGGCTGAGCTGGGTTTYCCTTGTTGC |
| IGH_MTPX_19 | SEQ ID NO: 107 GGAGTTKGGGCTGMGCTGGGTTTTCC |
| IGH_MTPX 20 | SEQ ID NO: 108 GCACCTGTGGTTTTTCCTCCTGCTGGTG |
| IGH_MTPX_21 | SEQ ID NO: 109 CACCTGTGGTTCTTCCTCCTSCTGG |
| IGH_MTPX 22 | SEQ ID NO: 110 CCAGGATGGGGTCAACCGCCATCCTC |
| IGH_MTPX_23 | SEQ ID NO: 111 CAGAGGACTCACCATGGAGTTTGGGCTGAG |
| IGH_MTPX 24 | SEQ ID NO: 112 GGACTCACCATGGAGTTGGGACTGAGC |
| IGH_MTPX_25 | SEQ ID NO: 113 GGGCTGAGCTGGCTTTTTCTTGTGGC |
| TSO Sequence | SEQ ID NO: 114 AAGCAGTGGTATCAACGCAGAGTACATGGG |
| TSO Sequence Portion | SEQ ID NO: 115 TCTGCGTTGATACCACT |
| CDR3 | |
| TRAV1-2 | SEQ ID NO: 116 gaaggagctccagatgaaagactctgcctc |
| TRAV2 | SEQ ID NO: 117 gttctcttcatcgctgctcatcctccaggt |
| TRAV3 | SEQ ID NO: 118 cttgtgagcgactccgctttgtacttctgt |
| TRAV4 | SEQ ID NO: 119 ttatccctgccgacagaaagtccagcactc |
| TRAV5 | SEQ ID NO: 120 aaggataaacatctgtctctgcgcattgcag |
| TRAV6 | SEQ ID NO: 121 ttgtttcatatcacagcctcccagcctgca |
| TRAV7 | SEQ ID NO: 122 tacattacagccgtgcagcctgaagattcag |
| TRAV8-1 | SEQ ID NO: 123 aatctgaggaaaccctctgtgcagtggagt |
| TRAV8-2 | SEQ ID NO: 124 gaaacctccttccacctgacgaaaccctca |
| TRAV8-3 | SEQ ID NO: 125 caatctgaggaaaccctctgtgcattggag |
| TRAV8-4 | SEQ ID NO: 126 cacctgacgaaaccctcagcccatatgagc |
| TRAV8-6 | SEQ ID NO: 127 ggaaaccctcagtccatataagcgacacgg |
| TRAV8-7 | SEQ ID NO: 128 gaggaaaccatcaacccatgtgagtgatgc |
| TRAV9-1 | SEQ ID NO: 129 ggaaggaacaaaggttttgaagccatgtaccg |
| TRAV9-2 | SEQ ID NO: 130 tccacttggagaaaggctcagttcaagtgt |
| TRAV10 | SEQ ID NO: 131 gcagacacaaagcaaagctctctgcacatc |
| TRAV12-1 | SEQ ID NO: 132 gccagccagtatatttccctgctcatcaga |
| TRAV12-2 | SEQ ID NO: 133 gccagccagtatgtttctctgctcatcaga |
| TRAV12-3 | SEQ ID NO: 134 ggtttacagcacaggtcgataaatccagca |
| TRAV13-1 | SEQ ID NO: 135 gccaaacatttctccctgcacatcacagag |
| TRAV13-2 | SEQ ID NO: 136 tctgcaaattgcagctactcaacctggaga |
| TRAV14D4 | SEQ ID NO: 137 gccaaccttgtcatctccgcttcacaactg |
| TRAV16 | SEQ ID NO: 138 gaccttaacaaaggcgagacatctttccacc |
| TRAV17 | SEQ ID NO: 139 gtcacgcttgacacttccaagaaaagcagt |
| TRAV18 | SEQ ID NO: 140 cctatcaagagtgacagttccttccacctg |
| TRAV19 | SEQ ID NO: 141 ggaacttccagaaatccaccagttccttca |
| TRAV20 | SEQ ID NO: 142 agaaggaaagctttctgcacatcacagcc |

TABLE 3-continued

| Variable Region Primer | Sequence |
|---|---|
| TRAV21 | SEQ ID NO: 143 caagtggaagacttaatgcctcgctggata |
| TRAV22 | SEQ ID NO: 144 gactgtcgctacggaacgctacagcttatt |
| TRAV23DV6 | SEQ ID NO: 145 tgccaagcagttctcatcgcatatcatgga |
| TRAV24 | SEQ ID NO: 146 gccactcttaataccaaggagggttacagc |
| TRAV25 | SEQ ID NO: 147 cacatcacagccacccagactacagatgta |
| TRAV26-1 | SEQ ID NO: 148 tcatcacagaagacagaaagtccagcacct |
| TRAV26-2 | SEQ ID NO: 149 agaaagtccagtaccttgatcctgcaccgt |
| TRAV27 | SEQ ID NO: 150 gttctctccacatcactgcagcccagactg |
| TRAV29DV5 | SEQ ID NO: 151 aaagtgccaagcacctctctctgcacattg |
| TRAV30 | SEQ ID NO: 152 ctgtaccttacggcctcccagctcagttac |
| TRAV34 | SEQ ID NO: 153 gccaagttggatgagaaaaagcagcaaagt |
| TRAV35 | SEQ ID NO: 154 gacctcaaatggaagactgactgctcagtt |
| TRAV36DV7 | SEQ ID NO: 155 tttcagcatcctgaacatcacagccaccca |
| TRAV38-2DV8 | SEQ ID NO: 156 ccttcagtctcaagatctcagactcacagc |
| TRAV39 | SEQ ID NO: 157 aatggcctcacttgataccaaagcccgtc |
| TRAV40 | SEQ ID NO: 158 ctcccccattgtgaaatattcagtccaggt |
| TRAV41 | SEQ ID NO: 159 catacaggaaaagcacagctccctgcacat |
| TRAV11 | SEQ ID NO: 160 atatcgcagcctctcatctgggagattcagc |
| TRAV1-1 | SEQ ID NO: 161 caggagctccagatgaaagactctgcctctt |
| TRAV8-5 | SEQ ID NO: 162 acttccttccacttgaggaaaccctcagtcca |
| Inner TRAV Primers | |
| TRAV-Handle 1 | SEQ ID NO: 163 gtgactggagttcagacgtgtgctcttccgatctgaaggagctccagatgaaagactctgcctc |
| TRAV-Handle 2 | SEQ ID NO: 164 gtgactggagttcagacgtgtgctcttccgatctgttctcttcatcgctgctcatcctccaggt |
| TRAV-Handle 3 | SEQ ID NO: 165 gtgactggagttcagacgtgtgctcttccgatctcttgtgagcgactccgctttgtacttctgt |
| TRAV-Handle 4 | SEQ ID NO: 166 gtgactggagttcagacgtgtgctcttccgatctttatccctgccgacagaaagtccagcactc |
| TRAV-Handle 5 | SEQ ID NO: 167 gtgactggagttcagacgtgtgctcttccgatctaaggataaacatctgtctctgcgcattgcag |
| TRAV-Handle 6 | SEQ ID NO: 168 gtgactggagttcagacgtgtgctcttccgatctttgtttcatatcacagcctcccagcctgca |
| TRAV-Handle 7 | SEQ ID NO: 169 gtgactggagttcagacgtgtgctcttccgatcttacattacagccgtgcagcctgaagattcag |
| TRAV-Handle 8 | SEQ ID NO: 170 gtgactggagttcagacgtgtgctcttccgatctaatctgaggaaaccctctgtgcagtggagt |
| TRAV-Handle 9 | SEQ ID NO: 171 gtgactggagttcagacgtgtgctcttccgatctgaaacctccttccacctgacgaaaccctca |
| TRAV-Handle 10 | SEQ ID NO: 172 gtgactggagttcagacgtgtgctcttccgatctcaatctgaggaaaccctctgtgcattggag |
| TRAV-Handle 11 | SEQ ID NO: 173 gtgactggagttcagacgtgtgctcttccgatctcacctgacgaaaccctcagcccatatgagc |

TABLE 3-continued

| Variable Region Primer | Sequence |
|---|---|
| TRAV-Handle 12 | SEQ ID NO: 174<br>gtgactggagttcagacgtgtgctcttccgatctggaaaccctcagtccatataagcgacacgg |
| TRAV-Handle 13 | SEQ ID NO: 175<br>gtgactggagttcagacgtgtgctcttccgatctgaggaaaccatcaacccatgtgagtgatgc |
| TRAV-Handle 14 | SEQ ID NO: 176<br>gtgactggagttcagacgtgtgctcttccgatctggaaggaacaaaggttttgaagccatgtaccg |
| TRAV-Handle 15 | SEQ ID NO: 177<br>gtgactggagttcagacgtgtgctcttccgatcttccacttggagaaaggctcagttcaagtgt |
| TRAV-Handle 16 | SEQ ID NO: 178<br>gtgactggagttcagacgtgtgctcttccgatctgcagacacaaagcaaagctctctgcacatc |
| TRAV-Handle 17 | SEQ ID NO: 179<br>gtgactggagttcagacgtgtgctcttccgatctgccagccagtatatttccctgctcatcaga |
| TRAV-Handle 18 | SEQ ID NO: 180<br>gtgactggagttcagacgtgtgctcttccgatctgccagccagtatgtttctctgctcatcaga |
| TRAV-Handle 19 | SEQ ID NO: 181<br>gtgactggagttcagacgtgtgctcttccgatctggtttacagcacaggtcgataaatccagca |
| TRAV-Handle 20 | SEQ ID NO: 182<br>gtgactggagttcagacgtgtgctcttccgatctgccaaacatttctccctgcacatcacagag |
| TRAV-Handle 21 | SEQ ID NO: 183<br>gtgactggagttcagacgtgtgctcttccgatcttctgcaaattgcagctactcaacctggaga |
| TRAV-Handle 22 | SEQ ID NO: 184<br>gtgactggagttcagacgtgtgctcttccgatctgccaaccttgtcatctccgcttcacaactg |
| TRAV-Handle 23 | SEQ ID NO: 185<br>gtgactggagttcagacgtgtgctcttccgatctgaccttaacaaaggcgagacatctttccacc |
| TRAV-Handle 24 | SEQ ID NO: 186<br>gtgactggagttcagacgtgtgctcttccgatctgtcacgcttgacacttccaagaaaagcagt |
| TRAV-Handle 25 | SEQ ID NO: 187<br>gtgactggagttcagacgtgtgctcttccgatctcctatcaagagtgacagttccttccacctg |
| TRAV-Handle 26 | SEQ ID NO: 188<br>gtgactggagttcagacgtgtgctcttccgatctggaacttccagaaatccaccagttccttca |
| TRAV-Handle 27 | SEQ ID NO: 189<br>gtgactggagttcagacgtgtgctcttccgatctagaaggaaagctttctgcacatcacagcc |
| TRAV-Handle 28 | SEQ ID NO: 190<br>gtgactggagttcagacgtgtgctcttccgatctcaagtggaagacttaatgcctcgctggata |
| TRAV-Handle 29 | SEQ ID NO: 191<br>gtgactggagttcagacgtgtgctcttccgatctgactgtcgctacggaacgctacagcttatt |
| TRAV-Handle 30 | SEQ ID NO: 192<br>gtgactggagttcagacgtgtgctcttccgatcttgccaagcagttctcatcgcatatcatgga |
| TRAV-Handle 31 | SEQ ID NO: 193<br>gtgactggagttcagacgtgtgctcttccgatctgccactcttaataccaaggagggttacagc |
| TRAV-Handle 32 | SEQ ID NO: 194<br>gtgactggagttcagacgtgtgctcttccgatctcacatcacagccacccagactacagatgta |
| TRAV-Handle 33 | SEQ ID NO: 195<br>gtgactggagttcagacgtgtgctcttccgatcttcatcacagaagacagaaagtccagcacct |
| TRAV-Handle 34 | SEQ ID NO: 196<br>gtgactggagttcagactgtggctcttccgatctagaaagtccagtaccttgatcctgcaccgt |
| TRAV-Handle 35 | SEQ ID NO: 197<br>gtgactggagttcagacgtgtgctcttccgatctgttctctccacatcactgcagcccagactg |
| TRAV-Handle 36 | SEQ ID NO: 198<br>gtgactggagttcagacgtgtgctcttccgatctaaagtgccaagcacctctctctgcacattg |

TABLE 3-continued

| Variable Region Primer | Sequence |
|---|---|
| TRAV-Handle 37 | SEQ ID NO: 199 gtgactggagttcagacgtgtgctcttccgatctctgtaccttacggcctcccagctcagttac |
| TRAV-Handle 38 | SEQ ID NO: 200 gtgactggagttcagacgtgtgctcttccgatctgccaagttggatgagaaaaagcagcaaagt |
| TRAV-Handle 39 | SEQ ID NO: 201 gtgactggagttcagacgtgtgctcttccgatctgacctcaaatggaagactgactgctcagtt |
| TRAV-Handle 40 | SEQ ID NO: 202 gtgactggagttcagacgtgtgctcttccgatcttttcagcatcctgaacatcacagccaccca |
| TRAV-Handle 41 | SEQ ID NO: 203 gtgactggagttcagacgtgtgctcttccgatctccttcagtctcaagatctcagactcacagc |
| TRAV-Handle 42 | SEQ ID NO: 204 gtgactggagttcagacgtgtgctcttccgatctaatggcctcacttgataccaaagcccgtc |
| TRAV-Handle 43 | SEQ ID NO: 205 gtgactggagttcagacgtgtgctcttccgatctctcccccattgtgaaatattcagtccaggt |
| TRAV-Handle 44 | SEQ ID NO: 206 gtgactggagttcagacgtgtgctcttccgatctcatacaggaaaagcacagctccctgcacat |
| TRAV-Handle 45 | SEQ ID NO: 207 gtgactggagttcagacgtgtgctcttccgatctcaggagctccagatgaaagactctgcctctt |
| TRAV-Handle 46 | SEQ ID NO: 208 gtgactggagttcagacgtgtgctcttccgatctcaggagctccagatgaaagactctgcctctt |
| TRAV-Handle 47 | SEQ ID NO: 209 gtgactggagttcagacgtgtgctcttccgatctacttccttccacttgaggaaaccctcagtcca |
| 5' Sequence Handle LN2 | SEQ ID NO: 210 gtgactggagttcagacgtgtgctcttccgatct |
| Outer TRAV Primers | |
| TRAV10*01_outer | SEQ ID NO: 211 aaaaaccaagtggagcagagtcctcagtccctg |
| TRAV21*01_outer | SEQ ID NO: 212 aaacaggaggtgacgcagattcctgcagctc |
| TRAV2*01_outer | SEQ ID NO: 213 aaggaccaagtgtttcagccttccacagtggc |
| TRAV8-6*02_outer | SEQ ID NO: 214 acccagcttgacagccaagtccctgtct |
| TRAV8-7*02_outer | SEQ ID NO: 215 acccagcttgatggccacatcactgtctct |
| TRAV8-4*01_outer | SEQ ID NO: 216 acccagcttggcagccacgtctctg |
| TRAV19*01_outer | SEQ ID NO: 217 actcaagcgcagactgaaatttctgtggtgg |
| TRAV12-3*01_outer | SEQ ID NO: 218 agaaggaggtggagcaggatcctggacca |
| TRAV6*01_outer | SEQ ID NO: 219 agaattccgaggctctgaacattcaggagggtaa |
| TRAV16*01_outer | SEQ ID NO: 220 agagagtgactcagcccgagaagctcctct |
| TRAV8-3*01_outer | SEQ ID NO: 221 agagcccagtcagtgacccagcctgac |
| TRAV8-5*01_outer | SEQ ID NO: 222 agagcccagtcagtgacccagcctgac |
| TRAV27*01_outer | SEQ ID NO: 223 agctgctggagcagagccctcagtttc |
| TRAV17*01_outer | SEQ ID NO: 224 agtcaacagggagaagaggatcctcaggccttg |
| TRAV18*01_outer | SEQ ID NO: 225 agtggagactcggttacccagacagaaggcc |
| TRAV22*01_outer | SEQ ID NO: 226 agtggagcagagtcctccagacctgattctc |
| TRAV13-2*01_outer | SEQ ID NO: 227 agtgtggggctgcatcttcctaccctga |
| TRAV24*01_outer | SEQ ID NO: 228 atactgaacgtggaacaaagtcctcagtcactgcatg |
| TRAV9-2*01_outer | SEQ ID NO: 229 attcagtgacccagatggaagggccagtga |

TABLE 3-continued

| Variable Region Primer | Sequence |
|---|---|
| TRAV26-1*01_outer | SEQ ID NO: 230 attgatgctaagaccacccagcccacctc |
| TRAV12-2*01_outer | SEQ ID NO: 231 cagaaggaggtggagcagaattctggacccc |
| TRAV40*01_outer | SEQ ID NO: 232 cagcaattcagtcaagcagacgggccaa |
| TRAV30*01_outer | SEQ ID NO: 233 ccaacaaccagtgcagagtcctcaagccg |
| TRAV12-1*01_outer | SEQ ID NO: 234 cggaaggaggtggagcaggatcctgga |
| TRAV11-1*01_outer | SEQ ID NO: 235 ctacatacgccggagcagagtccttcattcctgag |
| TRAV14/DV4*02_ outer | SEQ ID NO: 236 ctcaaacccaaccaggaatgttcgtgcagga |
| TRAV4*01_outer | SEQ ID NO: 237 cttgctaagaccacccagcccatctccatggactc |
| TRAV7*01_outer | SEQ ID NO: 238 gaaaaccaggtggagcacagccctcattttctg |
| TRAV36/DV7*01_outer | SEQ ID NO: 239 gaagacaaggtggtacaaagccctctatctctggt |
| TRAV20*01_outer | SEQ ID NO: 240 gaagaccaggtgacgcagagtcccgag |
| TRAV23/DV6*01_outer | SEQ ID NO: 241 gaccagcagcaggtgaaacaaagtcctcaat |
| TRAV41*01_outer | SEQ ID NO: 242 gagcagagtcctcagaacctgactgccc |
| TRAV29/DV5*01_outer | SEQ ID NO: 243 gatgaccagcaagttaagcaaaattcaccatccct |
| TRAV34*01_outer | SEQ ID NO: 244 gccaagaactggagcagagtcctcagtcc |
| TRAV8-2*01_outer | SEQ ID NO: 245 gcccagtcggtgacccagcttgacag |
| TRAV8-1*01_outer | SEQ ID NO: 246 gcccagtctgtgagccagcataaccaccac |
| TRAV26-2*01_outer | SEQ ID NO: 247 gcctgttcacttgccttgtaaccactccac |
| TRAV3*01_outer | SEQ ID NO: 248 gctcagtcagtggctcagccggaagatcagg |
| TRAV1-2*01_outer | SEQ ID NO: 249 ggacaaaacattgaccagcccactgagatgacagc |
| TRAV1-1*01_outer | SEQ ID NO: 250 ggacaaagccttgagcagccctctgaagtgac |
| TRAV25*01_outer | SEQ ID NO: 251 ggacaacaggtaatgcaaattcctcagtaccagcatg |
| TRAV13-1*01_outer | SEQ ID NO: 252 ggagagaatgtggagcagcatccttcaaccctg |
| TRAV5*01_outer | SEQ ID NO: 253 ggagaggatgtggagcagagtcttttcctgagtgtc |
| TRAV9-1*01_outer | SEQ ID NO: 254 ggagattcagtggtccagacagaaggccaagtg |
| TRAV38-2/ DV8*01_outer | SEQ ID NO: 255 gtctcaaccagagatgtctgtgcaggagg |
| TRAV39*01_outer | SEQ ID NO: 256 gtggaacaaaaccctctgttcctgagcatgc |
| TRAV35*01_outer | SEQ ID NO: 257 gtggtcaacagctgaatcagagtcctcaatcta |
| TRAV11*01_outer | SEQ ID NO: 258 gttccggcaggatccggggagaagact |
| CDR3 | |
| TRBV10-1 | SEQ ID NO: 259 gcctcctcccagacatctgtatatttctgcg |
| TRBV10-2 | SEQ ID NO: 261 gatttcctcctcactctggagtccgctacc |
| TRBV10-3 | SEQ ID NO: 262 aggctcaaaggagtagactccactctcaaga |
| TRBV11-1 | SEQ ID NO: 263 caagatccagcctgcaaagcttgaggact |
| TRBV11-2 | SEQ ID NO: 264 tagactccactctcaagatccagcctgcag |
| TRBV11-3 | SEQ ID NO: 260 aatttccccctcactctggagtcagctacc |
| TRBV12-1 | SEQ ID NO: 265 tggaacccagggacttgggcctatatttct |
| TRBV12-2 | SEQ ID NO: 266 tcattctctactctgaagatccagcctgcag |

TABLE 3-continued

| Variable Region Primer | Sequence |
|---|---|
| TRBV12-3 | SEQ ID NO: 267 cattctccactctgaagatccagccctcag |
| TRBV12-4 | SEQ ID NO: 268 catcattctccactctgaagatccagccctc |
| TRBV12-5 | SEQ ID NO: 269 cagcagagatgcctgatgcaactttagcca |
| TRBV13 | SEQ ID NO: 270 gaactgaacatgagctccttggagctggg |
| TRBV14 | SEQ ID NO: 271 ggaggattctggagtttatttctgtgccagc |
| TRBV15 | SEQ ID NO: 272 ttctgctttcttgacatccgctcaccaggc |
| TRBV16 | SEQ ID NO: 273 gagatccaggctacgaagcttgaggattcag |
| TRBV17 | SEQ ID NO: 274 aacgtcttccacgctgaagatccatccc |
| TRBV18 | SEQ ID NO: 275 aggatccagcaggtagtgcgaggagattcg |
| TRBV19 | SEQ ID NO: 276 acccgacagctttctatctctgtgccagta |
| TRBV20-1 | SEQ ID NO: 277 gtgcccatcctgaagacagcagcttctaca |
| TRBV2 | SEQ ID NO: 278 cacaaagctggaggactcagccatgtac |
| TRBV21-1 | SEQ ID NO: 279 tcaggggacacagcactgtatttctgtgcc |
| TRBV22-1 | SEQ ID NO: 280 cacaccagccaaacagctttgtacttctgt |
| TRBV23-1 | SEQ ID NO: 281 aatcctgtcctcagaaccgggagacacg |
| TRBV24-1 | SEQ ID NO: 282 ccaaccagacagctctttacttctgtgccac |
| TRBV25-1 | SEQ ID NO: 283 cacatacctctcagtacctctgtgccagca |
| TRBV26 | SEQ ID NO: 284 ccaaccagacatctgtgtatctctatgccagc |
| TRBV27 | SEQ ID NO: 285 accagacctctctgtacttctgtgccagca |
| TRBV28 | SEQ ID NO: 286 aaccagacatctatgtacctctgtgccagc |
| TRBV29-1 | SEQ ID NO: 287 acatgagccctgaagacagcagcatatatctc |
| TRBV3-1 | SEQ ID NO: 288 agcttggtgactctgctgtgtatttctgtg |
| TRBV3-2 | SEQ ID NO: 289 cttggtgactctgctgtgtatttctgtgcc |
| TRBV4-1 | SEQ ID NO: 290 cagccagaagactcagccctgtatctctg |
| TRBV4-2 | SEQ ID NO: 291 gccagaagactcggccctgtatctctgt |
| TRBV4-3 | SEQ ID NO: 292 tattccttcacctacacaccctgcagccag |
| TRBV5-1 | SEQ ID NO: 293 agatgaatgtgagcaccttggagctgg |
| TRBV5-2 | SEQ ID NO: 294 tactgagtcaaacacggagctaggggact |
| TRBV5-3 | SEQ ID NO: 295 gttgctctgagatgaatgtgagtgccttgg |
| TRBV5-4 | SEQ ID NO: 296 atagctctgagctgaatgtgaacgccttgg |
| TRBV5-5 | SEQ ID NO: 297 gagctgaatgtgaacgccttgttgctgg |
| TRBV5-6 | SEQ ID NO: 298 aactatagctctgagctgaatgtgaacgcct |
| TRBV5-7 | SEQ ID NO: 299 agctgaatgtgaacgccttgttgctaggg |
| TRBV5-8 | SEQ ID NO: 300 ctgaatgtgaacgccttggagctggagga |
| TRBV6-1 | SEQ ID NO: 301 gctccctcccagacatctgtgtacttct |
| TRBV6-2 | SEQ ID NO: 302 gctgctccctcccaaacatctgtgtact |
| TRBV6-3 | SEQ ID NO: 303 gctccctcccaaacatctgtgtacttctgt |
| TRBV6-4 | SEQ ID NO: 304 aacacagatgatttccccctcacgttggc |

TABLE 3-continued

| Variable Region Primer | Sequence |
|---|---|
| TRBV6-5 | SEQ ID NO: 305 gctgctccctcccagacatctgtgtactt |
| TRBV6-6 | SEQ ID NO: 306 agttggctgctccctcccagacatctg |
| TRBV6-7 | SEQ ID NO: 307 tcagctgctccctctcagacttctgtttac |
| TRBV6-8 | SEQ ID NO: 308 taaacacagaggatttcccactcaggctggt |
| TRBV6-9 | SEQ ID NO: 309 agtcagctgctccctcccagacatctgtata |
| TRBV7-1 | SEQ ID NO: 310 cagcaggggggacttggctgtgtatctc |
| TRBV7-2 | SEQ ID NO: 311 gcaggaggactcggccgtgtatctc |
| TRBV7-3 | SEQ ID NO: 312 tctactctgaagatccagcgcacagagcg |
| TRBV7-4 | SEQ ID NO: 313 cacagagcagggggactcagctgtgtat |
| TRBV7-5 | SEQ ID NO: 314 atctttctccacctgaagatccagcgcaca |
| TRBV7-6 | SEQ ID NO: 315 ttctctgcagagaggcctgagggatccat |
| TRBV7-8 | SEQ ID NO: 316 ctgagggatccgtctccactctgaagatcc |
| TRBV7-9 | SEQ ID NO: 317 ggcctaagggatctttctccaccttggaga |
| TRBV8-1 | SEQ ID NO: 318 ttccctcaaccctggagtctactagcacca |
| TRBV8-2 | SEQ ID NO: 319 ttgagcatttccccaatcctggcatccac |
| TRBV9 | SEQ ID NO: 320 gggactcagctttgtatttctgtgccagca |
| Inner TRBV Primers | |
| TRBV-Handle 1 | SEQ ID NO: 321 gtgactggagttcagacgtgtgctcttccgatctgcctcctcccagacatctgtatatttctgcg |
| TRBV-Handle 2 | SEQ ID NO: 322 gtgactggagttcagacgtgtgctcttccgatctaatttccccctcactctggagtcagctacc |
| TRBV-Handle 3 | SEQ ID NO: 323 gtgactggagttcagacgtgtgctcttccgatctgatttcctcctcactctggagtccgctacc |
| TRBV-Handle 4 | SEQ ID NO: 324 gtgactggagttcagacgtgtgctcttccgatctaggctcaaaggagtagactccactctcaaga |
| TRBV-Handle 5 | SEQ ID NO: 325 gtgactggagttcagacgtgtgctcttccgatctcaagatccagcctgcaaagcttgaggact |
| TRBV-Handle 6 | SEQ ID NO: 326 gtgactggagttcagacgtgtgctcttccgatcttagactccactctcaagatccagcctgcag |
| TRBV-Handle 7 | SEQ ID NO: 327 gtgactggagttcagacgtgtgctcttccgatcttggaacccagggacttgggcctatatttct |
| TRBV-Handle 8 | SEQ ID NO: 328 gtgactggagttcagacgtgtgctcttccgatcttcattctctactctgaagatccagcctgcag |
| TRBV-Handle 9 | SEQ ID NO: 329 gtgactggagttcagacgtgtgctcttccgatctcattctccactctgaagatccagccctcag |
| TRBV-Handle 10 | SEQ ID NO: 330 gtgactggagttcagacgtgtgctcttccgatctcatcattctccactctgaagatccagccctc |
| TRBV-Handle 11 | SEQ ID NO: 331 gtgactggagttcagacgtgtgctcttccgatctcagcagagatgcctgatgcaactttagcca |
| TRBV-Handle 12 | SEQ ID NO: 332 gtgactggagttcagacgtgtgctcttccgatctgaactgaacatgagctccttggagctggg |
| TRBV-Handle 13 | SEQ ID NO: 333 gtgactggagttcagacgtgtgctcttccgatctggaggattctggagtttatttctgtgccagc |
| TRBV-Handle 14 | SEQ ID NO: 334 gtgactggagttcagacgtgtgctcttccgatctttctgctttcttgacatccgctcaccaggc |

TABLE 3-continued

| Variable Region Primer | Sequence |
|---|---|
| TRBV-Handle 15 | SEQ ID NO: 335 gtgactggagttcagacgtgtgctcttccgatctgagatccaggctacgaagcttgaggattcag |
| TRBV-Handle 16 | SEQ ID NO: 336 gtgactggagttcagacgtgtgctcttccgatctaacgtcttccacgctgaagatccatccc |
| TRBV-Handle 17 | SEQ ID NO: 337 gtgactggagttcagacgtgtgctcttccgatctaggatccagcaggtagtgcgaggagattcg |
| TRBV-Handle 18 | SEQ ID NO: 338 gtgactggagttcagacgtgtgctcttccgatctacccgacagctttctatctctgtgccagta |
| TRBV-Handle 19 | SEQ ID NO: 339 gtgactggagttcagacgtgtgctcttccgatctgtgcccatcctgaagacagcagcttctaca |
| TRBV-Handle 20 | SEQ ID NO: 340 gtgactggagttcagacgtgtgctcttccgatctcacaaagctggaggactcagccatgtac |
| TRBV-Handle 21 | SEQ ID NO: 341 gtgactggagttcagacgtgtgctcttccgatcttcaggggacacagcactgtatttctgtgcc |
| TRBV-Handle 22 | SEQ ID NO: 342 gtgactggagttcagacgtgtgctcttccgatctcacaccagccaaacagctttgtacttctgt |
| TRBV-Handle 23 | SEQ ID NO: 343 gtgactggagttcagacgtgtgctcttccgatctaatcctgtcctcagaaccgggagacacg |
| TRBV-Handle 24 | SEQ ID NO: 344 gtgactggagttcagacgtgtgctcttccgatctccaaccagacagctctttacttctgtgccac |
| TRBV-Handle 25 | SEQ ID NO: 345 gtgactggagttcagacgtgtgctcttccgatctcacatacctctcagtacctctgtgccagca |
| TRBV-Handle 26 | SEQ ID NO: 346 gtgactggagttcagacgtgtgctcttccgatctccaaccagacatctgtgtatctctatgccagc |
| TRBV-Handle 27 | SEQ ID NO: 347 gtgactggagttcagacgtgtgctcttccgatctaccagacctctctgtacttctgtgccagca |
| TRBV-Handle 28 | SEQ ID NO: 348 gtgactggagttcagacgtgtgctcttccgatctaaccagacatctatgtacctctgtgccagc |
| TRBV-Handle 29 | SEQ ID NO: 349 gtgactggagttcagacgtgtgctcttccgatctacatgagccctgaagacagcagcatatatctc |
| TRBV-Handle 30 | SEQ ID NO: 350 gtgactggagttcagacgtgtgctcttccgatctagcttggtgactctgctgtgtatttctgtg |
| TRBV-Handle 31 | SEQ ID NO: 351 gtgactggagttcagacgtgtgctcttccgatctcttggtgactctgctgtgtatttctgtgcc |
| TRBV-Handle 32 | SEQ ID NO: 352 gtgactggagttcagacgtgtgctcttccgatctcagccagaagactcagccctgtatctctg |
| TRBV-Handle 33 | SEQ ID NO: 353 gtgactggagttcagacgtgtgctcttccgatctgccagaagactcggccctgtatctctgt |
| TRBV-Handle 34 | SEQ ID NO: 354 gtgactggagttcagacgtgtgctcttccgatcttattccttcacctacacaccctgcagccag |
| TRBV-Handle 35 | SEQ ID NO: 355 gtgactggagttcagacgtgtgctcttccgatctagatgaatgtgagcaccttggagctgg |
| TRBV-Handle 36 | SEQ ID NO: 356 gtgactggagttcagacgtgtgctcttccgatcttactgagtcaaacacggagctaggggact |
| TRBV-Handle 37 | SEQ ID NO: 357 gtgactggagttcagacgtgtgctcttccgatctgttgctctgagatgaatgtgagtgccttgg |
| TRBV-Handle 38 | SEQ ID NO: 358 gtgactggagttcagacgtgtgctcttccgatctatagctctgagctgaatgtgaacgccttgg |
| TRBV-Handle 39 | SEQ ID NO: 359 gtgactggagttcagacgtgtgctcttccgatctgagctgaatgtgaacgccttgttgctgg |

TABLE 3-continued

| Variable Region Primer | Sequence |
| --- | --- |
| TRBV-Handle 40 | SEQ ID NO: 360 gtgactggagttcagacgtgtgctcttccgatctaactatagctctgagctgaatgtgaacgcct |
| TRBV-Handle 41 | SEQ ID NO: 361 gtgactggagttcagacgtgtgctcttccgatctagctgaatgtgaacgccttgttgctaggg |
| TRBV-Handle 42 | SEQ ID NO: 362 gtgactggagttcagacgtgtgctcttccgatctctgaatgtgaacgcctggagctggagga |
| TRBV-Handle 43 | SEQ ID NO: 363 gtgactggagttcagacgtgtgctcttccgatctgctccctcccagacatctgtgtacttct |
| TRBV-Handle 44 | SEQ ID NO: 364 gtgactggagttcagacgtgtgctcttccgatctgctgctccctcccaaacatctgtgtact |
| TRBV-Handle 45 | SEQ ID NO: 365 gtgactggagttcagacgtgtgctcttccgatctgctccctcccaaacatctgtgtacttctgt |
| TRBV-Handle 46 | SEQ ID NO: 366 gtgactggagttcagacgtgtgctcttccgatctaacacagatgatttccccctcacgttggc |
| TRBV-Handle 47 | SEQ ID NO: 367 gtgactggagttcagacgtgtgctcttccgatctgctgctccctcccagacatctgtgtactt |
| TRBV-Handle 48 | SEQ ID NO: 368 gtgactggagttcagacgtgtgctcttccgatctagttggctgctccctcccagacatctg |
| TRBV-Handle 49 | SEQ ID NO: 369 gtgactggagttcagacgtgtgctcttccgatcttcagctgctccctctcagacttctgtttac |
| TRBV-Handle 50 | SEQ ID NO: 370 gtgactggagttcagacgtgtgctcttccgatcttaaacacagaggatttcccactcaggctggt |
| TRBV-Handle 51 | SEQ ID NO: 371 gtgactggagttcagacgtgtgctcttccgatctagtcagctgctccctcccagacatctgtata |
| TRBV-Handle 52 | SEQ ID NO: 372 gtgactggagttcagacgtgtgctcttccgatctcagcagggggacttggctgtgtatctc |
| TRBV-Handle 53 | SEQ ID NO: 373 gtgactggagttcagacgtgtgctcttccgatctgcaggaggactcggccgtgtatctc |
| TRBV-Handle 54 | SEQ ID NO: 374 gtgactggagttcagacgtgtgctcttccgatcttctactctgaagatccagcgcacagagcg |
| TRBV-Handle 55 | SEQ ID NO: 375 gtgactggagttcagacgtgtgctcttccgatctcacagagcagggggactcagctgtgtat |
| TRBV-Handle 56 | SEQ ID NO: 376 gtgactggagttcagacgtgtgctcttccgatctatctttctccacctgaagatccagcgcaca |
| TRBV-Handle 57 | SEQ ID NO: 377 gtgactggagttcagacgtgtgctcttccgatctttctctgcagagaggcctgagggatccat |
| TRBV-Handle 58 | SEQ ID NO: 378 gtgactggagttcagacgtgtgctcttccgatctctgagggatccgtctccactctgaagatcc |
| TRBV-Handle 59 | SEQ ID NO: 379 gtgactggagttcagacgtgtgctcttccgatctggcctaagggatctttctccaccttggaga |
| TRBV-Handle 60 | SEQ ID NO: 380 gtgactggagttcagacgtgtgctcttccgatctttccctcaaccctggagtctactagcacca |
| TRBV-Handle 61 | SEQ ID NO: 381 gtgactggagttcagacgtgtgctcttccgatctttgagcatttccccaatcctggcatccac |
| TRBV-Handle 62 | SEQ ID NO: 382 gtgactggagttcagacgtgtgctcttccgatctgggactcagctttgtatttctgtgccagca |
| Outer TRBV Primers | |
| TRBV10-1_outer | SEQ ID NO: 383 gctgaaatcacccagagcccaagacacaag |
| TRBV10-2_outer | SEQ ID NO: 384 cacagagacaggaaggcaggtgaccttga |
| TRBV10-3_outer | SEQ ID NO: 385 gatgctggaatcacccagagcccaagacac |

TABLE 3-continued

| Variable Region Primer | Sequence |
|---|---|
| TRBV11-1_outer | SEQ ID NO: 386 gccaggctgtggctttttggtgtgatccta |
| TRBV11-2_outer | SEQ ID NO: 387 ggcagagtgtggctttttggtgcaatcct |
| TRBV11-3_outer | SEQ ID NO: 388 ggctttttggtgcaatcctatttctggccac |
| TRBV12-1_outer | SEQ ID NO: 389 gatgctggtgttatccagtcacccaggcac |
| TRBV12-2_outer | SEQ ID NO: 390 gtcacccaagcatgaggtgacagaaatggg |
| TRBV12-3_outer | SEQ ID NO: 391 atgctggagttatccagtcaccccgcc |
| TRBV12-4_outer | SEQ ID NO: 392 gagttatccagtcaccccggcacgaggt |
| TRBV12-5_outer | SEQ ID NO: 393 gctagagtcacccagacaccaaggcaca |
| TRBV13_outer | SEQ ID NO: 394 gctgctggagtcatccagtccccaaga |
| TRBV14_outer | SEQ ID NO: 395 gttactcagttccccagccacagcgtaat |
| TRBV15_outer | SEQ ID NO: 396 gttacccagtttggaaagccagtgaccct |
| TRBV16_outer | SEQ ID NO: 397 gaagtcgcccagactccaaaacatcttgtc |
| TRBV17_outer | SEQ ID NO: 398 cagacacaaggtcaccaacatgggacagg |
| TRBV18_outer | SEQ ID NO: 399 gtcatgtttactggtatcggcagctccca |
| TRBV19_outer | SEQ ID NO: 400 atgccatgtactggtaccgacaggaccca |
| TRBV20-1_outer | SEQ ID NO: 401 gtcgtctctcaacatccgagctgggttat |
| TRBV2_outer | SEQ ID NO: 402 gaacctgaagtcacccagactcccagcca |
| TRBV21-1_outer | SEQ ID NO: 403 cacggacaccaaggtcacccagagacct |
| TRBV22-1_outer | SEQ ID NO: 404 agctcactggggctggatgggatgtgac |
| TRBV23-1_outer | SEQ ID NO: 405 gccaaagtcacacagactccaggacattt |
| TRBV24-1_outer | SEQ ID NO: 406 gtatcgacaagacccaggactgggcctac |
| TRBV25-1_outer | SEQ ID NO: 407 gctgacatctaccagaccccaagatacct |
| TRBV26_outer | SEQ ID NO: 408 gtatcgacaggacccaggacttggactga |
| TRBV27_outer | SEQ ID NO: 409 agcccaagtgacccagaacccaagatac |
| TRBV28_outer | SEQ ID NO: 410 ctcgtagatgtgaaagtaacccagagctcga |
| TRBV29-1_outer | SEQ ID NO: 411 gatatctgtcaacgtggaacctccctgacg |
| TRBV3-1_outer | SEQ ID NO: 412 ggtcacacagatgggaaacgacaagtcca |
| TRBV3-2_outer | SEQ ID NO: 413 ccgtttcccagactccaaaatacctggtc |
| TRBV4-1_outer | SEQ ID NO: 414 gaagttacccagacaccaaaacacctggtc |
| TRBV4-2_outer | SEQ ID NO: 415 gagttacgcagacaccaagacacctggtc |
| TRBV4-3_outer | SEQ ID NO: 416 ggagttacgcagacaccaagacacctgg |
| TRBV5-1_outer | SEQ ID NO: 417 gtgacactgagctgctcccctatctctgg |
| TRBV5-2_outer | SEQ ID NO: 418 gaatcacccaagctccaagacacctgatc |
| TRBV5-3_outer | SEQ ID NO: 419 ctggagtcacccaaagtcccacacacc |
| TRBV5-4_outer | SEQ ID NO: 420 gactggagtcacccaaagtcccacacac |
| TRBV5-5_outer | SEQ ID NO: 421 gtcccacacacctgatcaaaacgagagga |
| TRBV5-6_outer | SEQ ID NO: 422 tagtggacgctggagtcacccaaagtcc |
| TRBV5-7_outer | SEQ ID NO: 423 ctgatcaaaacgagaggacagcacgtgac |

TABLE 3-continued

| Variable Region Primer | Sequence |
|---|---|
| TRBV5-8_outer | SEQ ID NO: 424 gagtcacacaaagtcccacacacctgatc |
| TRBV6-1_outer | SEQ ID NO: 425 gtgaatgctggtgtcactcagaccccaaa |
| TRBV6-2_outer | SEQ ID NO: 426 gaatgctggtgtcactcagaccccaaaat |
| TRBV6-3_outer | SEQ ID NO: 427 gctggtgtcactcagaccccaaaattccg |
| TRBV6-4_outer | SEQ ID NO: 428 gatcacccaggcaccaacatctcagatcc |
| TRBV6-5_outer | SEQ ID NO: 429 gctggtgtcactcagaccccaaaattcca |
| TRBV6-6_outer | SEQ ID NO: 430 gctggtgtcactcagaccccaaaattccg |
| TRBV6-7_outer | SEQ ID NO: 431 gaatgctggtgtcactcagaccccaaaat |
| TRBV6-8_outer | SEQ ID NO: 432 gctggtgtcactcagaccccaaaattcca |
| TRBV6-9_outer | SEQ ID NO: 433 gaatgctggtgtcactcagaccccaaaat |
| TRBV7-1_outer | SEQ ID NO: 434 gtgctggagtctcccagtccctgagaca |
| TRBV7-2_outer | SEQ ID NO: 435 gtcccccagtaacaaggtcacagagaagg |
| TRBV7-3_outer | SEQ ID NO: 436 gacccccagtaacaaggtcacagagaagg |
| TRBV7-4_outer | SEQ ID NO: 437 cagtccccaaggtacaaagtcgcaaagag |
| TRBV7-5_outer | SEQ ID NO: 438 gtctcccagtccccaaggtacgaagtc |
| TRBV7-6_outer | SEQ ID NO: 439 cacaggtgctggagtctcccagtctc |
| TRBV7-8_outer | SEQ ID NO: 440 gtgctggagtctcccagtcccctagg |
| TRBV7-9_outer | SEQ ID NO: 441 ctggagtctcccagaaccccagacaca |
| TRBV8-1_outer | SEQ ID NO: 442 gaggcagggatcagccagataccaagat |
| TRBV8-2_outer | SEQ ID NO: 443 gatgctgggatcacccagatgccaaga |
| TRBV9_outer | SEQ ID NO: 444 tggagtcacacaaaccccaaagcacctg |

Hybridization Probe Pool

Ig1 SEQ ID NO: 445
GAACTGTGGCTGCACCATCTGTCTTCATCTTCCCGCCATCTGATGAGCAGTTGAAATCTGGAACTG
CCTCTGTTGTGTGCCTGCTGAATAACTTCTATCCCAGAGAGGCCAAAGTACAGT

Ig2 SEQ ID NO: 446
GGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGA

Ig3 SEQ ID NO: 447
CTCGCCCGTCACAAAGAGCTTCAACAGGGGAGAGTGTTAGAGGGAGAAGTGCCCCCACCTGCTCC
TCAGTTCCAGCCTGACCCCCTCCCATCCTTTGGCCTCTGACCCTTTTTCCACAGG

Ig4 SEQ ID NO: 448
GGACCTACCCCTATTGCGGTCCTCCAGCTCATCTTTCACCTCACCCCCCTCCTCCTCCTTGGCTTTA
ATTATGCTAATGTTGGAGGAGAATGAATAAATAAAGTGAATCTTTGCACCTGT

Ig5 SEQ ID NO: 449
GTCAGCCCAAGGCCAACCCCACTGTCACTCTGTTCCCGCCCTCCTCTGAGGAGCTCCAAGCCAACA
AGGCCACACTAGTGTGTCTGATCAGTGACTTCTACCCGGGAGCTGTGACAGTGG

Ig6 SEQ ID NO: 450
GACGCCCGAGCAGTGGAAGTCCCACAGAAGCTACAGCTGCCAGGTCACGCATGAAGGGAGCACC
GTGGAGAAGACAGTGGCCCCTACAGAATGTTCATAGGTTCCCAACTCTAACCCCAC

Ig7 SEQ ID NO: 451
CCACGGGAGCCTGGAGCTGCAGGATCCCAGGGGAGGGGTCTCTCTCCCCATCCCAAGTCATCCAG
CCCTTCTCCCTGCACTCATGAAACCCCAATAAATATCCTCATTGACAACCAGAAA

Ig8 SEQ ID NO: 452
GTCAGCCCAAGGCTGCCCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACAGTGG

TABLE 3-continued

| Variable Region Primer | Sequence |
|---|---|
| Ig9 SEQ ID NO: 453 | |
| CGCCTGAGCAGTGGAAGTCCCACAGAAGCTACAGCTGCCAGGTCACGCATGAAGGGAGCACCGTG GAGAAGACAGTGGCCCCTACAGAATGTTCATAGGTTCTCAACCCTCACCCCCCAC | |
| Ig10 SEQ ID NO: 454 | |
| CACGGGAGACTAGAGCTGCAGGATCCCAGGGGAGGGGTCTCTCCTCCCACCCCAAGGCATCAAGC CCTTCTCCCTGCACTCAATAAACCCTCAATAAATATTCTCATTGTCAATCAGAAA | |
| Ig11 SEQ ID NO: 455 | |
| GTCAGCCCAAGGCTGCCCCCTCGGTCACTCTGTTCCCACCCTCCTCTGAGGAGCTTCAAGCCAACA AGGCCACACTGGTGTGTCTCATAAGTGACTTCTACCCGGGAGCCGTGACAGTGG | |
| Ig12 SEQ ID NO: 456 | |
| CGCCTGAGCAGTGGAAGTCCCACAAAAGCTACAGCTGCCAGGTCACGCATGAAGGGAGCACCGTG GAGAAGACAGTGGCCCCTACAGAATGTTCATAGGTTCTCATCCCTCACCCCCCAC | |
| Ig13 SEQ ID NO: 457 | |
| CACGGGAGACTAGAGCTGCAGGATCCCAGGGGAGGGGTCTCTCCTCCCACCCCAAGGCATCAAGC CCTTCTCCCTGCACTCAATAAACCCTCAATAAATATTCTCATTGTCAATCAGAAA | |
| Ig14 SEQ ID NO: 458 | |
| GTCAGCCCAAGGCTGCCCCCTCGGTCACTCTGTTCCCACCCTCCTCTGAGGAGCTTCAAGCCAACA AGGCCACACTGGTGTGTCTCGTAAGTGACTTCAACCCGGGAGCCGTGACAGTGG | |
| Ig15 SEQ ID NO: 459 | |
| CCAGCAGCTACCTGAGCCTGACGCCCGAGCAGTGGAAGTCCCACAGAAGCTACAGCTGCCGGGTC ACGCATGAAGGGAGCACCGTGGAGAAGACAGTGGCCCCTGCAGAATGCTCTTAGG | |
| Ig16 SEQ ID NO: 460 | |
| CCCCCGACCCTCACCCCACCCACAGGGGCCTGGAGCTGCAGGTTCCCAGGGGAGGGGTCTCTGCC CCCATCCCAAGTCATCCAGCCCTTCTCAATAAATATCCTCATCGTCAACGAGAAA | |
| Ig17 SEQ ID NO: 461 | |
| GCATCCCCGACCAGCCCCAAGGTCTTCCCGCTGAGCCTCGACAGCACCCCCCAAGATGGGAACGT GGTCGTCGCATGCCTGGTCCAGGGCTTCTTCCCCCAGGAGCCACTCAGTGTGACC | |
| Ig18 SEQ ID NO: 462 | |
| TGGAGCGAAAGCGGACAGAACGTGACCGCCAGAAACTTCCCACCTAGCCAGGATGCCTCCGGGGA CCTGTACACCACGAGCAGCCAGCTGACCCTGCCGGCCACACAGTGCCCAGACGGC | |
| Ig19 SEQ ID NO: 463 | |
| AAGTCCGTGACATGCCACGTGAAGCACTACACGAATTCCAGCCAGGATGTGACTGTGCCCTGCCG AGTTCCCCCACCTCCCCCATGCTGCCACCCCCGACTGTCGCTGCACCGACCGGCC | |
| Ig20 SEQ ID NO: 464 | |
| CTCGAGGACCTGCTCTTAGGTTCAGAAGCGAACCTCACGTGCACACTGACCGGCCTGAGAGATGC CTCTGGTGCCACCTTCACCTGGACGCCCTCAAGTGGGAAGAGCGCTGTTCAAGGA | |
| Ig21 SEQ ID NO: 465 | |
| CCACCTGAGCGTGACCTCTGTGGCTGCTACAGCGTGTCCAGTGTCCTGCCTGGCTGTGCCCAGCCA TGGAACCATGGGGAGACCTTCACCTGCACTGCTGCCCACCCCGAGTTGAAGACC | |
| Ig22 SEQ ID NO: 466 | |
| CCACTAACCGCCAACATCACAAAATCCGGAAACACATTCCGGCCCGAGGTCCACCTGCTGCCGCC GCCGTCGGAGGAGCTGGCCCTGAACGAGCTGGTGACGCTGACGTGCCTGGCACGT | |
| Ig23 SEQ ID NO: 467 | |
| GGCTTCAGCCCCAAGGATGTGCTGGTTCGCTGGCTGCAGGGGTCACAGGAGCTGCCCCGCGAGAA GTACCTGACTTGGGCATCCCGGCAGGAGCCCAGCCAGGGCACCACCACCTACGCT | |
| Ig24 SEQ ID NO: 468 | |
| GTAACCAGCATACTGCGCGTGGCAGCTGAGGACTGGAAGAAGGGGGAGACCTTCTCCTGCATGGT GGGCCACGAGGCCCTGCCGCTGGCCTTCACACAGAAGACCATCGACCGCATGGCG | |
| Ig25 SEQ ID NO: 469 | |
| GGCTCTTGCTGTGTTGCAGATTGGCAGATGCCGCCTCCCTATGTGGTGCTGGACTTGCCGCAGGAG ACCCTGGAGGAGGAGACCCCCGGCGCCAACCTGTGGCCCACCACCATCACCTTC | |
| Ig26 SEQ ID NO: 470 | |
| CTCACCCTCTTCCTGCTGAGCCTGTTCTATAGCACAGCACTGACCGTGACCAGCGTCCGGGGCCCA TCTGGCAAGAGGGAGGGCCCCCAGTACTGAGCGGGAGCCGGCAAGGCACAGGGA | |
| Ig27 SEQ ID NO: 471 | |
| GGAAGTGTGGAGGAACCTCTTGGAGAAGCCAGCTATGCTTGCCAGAACTCAGCCCTTTCAGACAT CACCGACCCGCCCTTACTCACGTGGCTTCCAGGTGCAATAAAGTGGCCCCAAGGA | |

TABLE 3-continued

| Variable Region Primer | Sequence |
|---|---|
| Ig28 SEQ ID NO: 472 | GCCTCCACACAGAGCCCATCCGTCTTCCCCTTGACCCGCTGCTGCAAAAACATTCCCTCCAATGCC ACCTCCGTGACTCTGGGCTGCCTGGCCACGGGCTACTTCCCGGAGCCGGTGATG |
| Ig29 SEQ ID NO: 473 | GTGACCTGGGACACAGGCTCCCTCAACGGGACAACTATGACCTTACCAGCCACCACCCTCACGCTC TCTGGTCACTATGCCACCATCAGCTTGCTGACCGTCTCGGGTGCGTGGGCCAAG |
| Ig30 SEQ ID NO: 474 | CAGATGTTCACCTGCCGTGTGGCACACACTCCATCGTCCACAGACTGGGTCGACAACAAAACCTTC AGCGTCTGCTCCAGGGACTTCACCCCGCCCACCGTGAAGATCTTACAGTCGTCC |
| Ig31 SEQ ID NO: 475 | TGCGACGGCGGCGGGCACTTCCCCCCGACCATCCAGCTCCTGTGCCTCGTCTCTGGGTACACCCCA GGGACTATCAACATCACCTGGCTGGAGGACGGGCAGGTCATGGACGTGGACTTG |
| Ig32 SEQ ID NO: 476 | TCCACCGCCTCTACCACGCAGGAGGGTGAGCTGGCCTCCACACAAAGCGAGCTCACCCTCAGCCA GAAGCACTGGCTGTCAGACCGCACCTACACCTGCCAGGTCACCTATCAAGGTCAC |
| Ig33 SEQ ID NO: 477 | ACCTTTGAGGACAGCACCAAGAAGTGTGCAGATTCCAACCCGAGAGGGGTGAGCGCCTACCTAAG CCGGCCCAGCCCGTTCGACCTGTTCATCCGCAAGTCGCCCACGATCACCTGTCTG |
| Ig34 SEQ ID NO: 478 | TCCCGGGCCAGTGGGAAGCCTGTGAACCACTCCACCAGAAAGGAGGAGAAGCAGCGCAATGGCA CGTTAACCGTCACGTCCACCCTGCCGGTGGGCACCCGAGACTGGATCGAGGGGGAG |
| Ig35 SEQ ID NO: 479 | ACCTACCAGTGCAGGGTGACCCACCCCCACCTGCCCAGGGCCCTCATGCGGTCCACGACCAAGAC CAGCGGCCCGCGTGCTGCCCCGGAAGTCTATGCGTTTGCGACGCCGGAGTGGCCG |
| Ig36 SEQ ID NO: 480 | GGGAGCCGGGACAAGCGCACCCTCGCCTGCCTGATCCAGAACTTCATGCCTGAGGACATCTCGGT GCAGTGGCTGCACAACGAGGTGCAGCTCCCGGACGCCCGGCACAGCACGACGCAG |
| Ig37 SEQ ID NO: 481 | CCCCGCAAGACCAAGGGCTCCGGCTTCTTCGTCTTCAGCCGCCTGGAGGTGACCAGGGCCGAATG GGAGCAGAAAGATGAGTTCATCTGCCGTGCAGTCCATGAGGCAGCAAGCCCCTCA |
| Ig38 SEQ ID NO: 482 | CAGACCGTCCAGCGAGCGGTGTCTGTAAATCCCGAGCTGGACGTGTGCGTGGAGGAGGCCGAGGG CGAGGCGCCGTGGACGTGGACCGGCCTCTGCATCTTCGCCGCACTCTTCCTGCTC |
| Ig39 SEQ ID NO: 483 | AGCGTGAGCTACAGCGCCGCCATCACGCTCCTCATGGTGCAGCGGTTCCTCTCAGCCACGCGGCAG GGGAGGCCCCAGACCTCCCTCGACTACACCAACGTCCTCCAGCCCCACGCCTAG |
| Ig40 SEQ ID NO: 484 | TCCTGCCTCCCTCCCTCCCAGGGCTCCATCCAGCTGTGCAGTGGGGAGGACTGGCCAGACCTTCTG TCCACTGTTGCAATGACCCCAGGAAGCTACCCCCAATAAACTGTGCCTGCTCAG |
| Ig41 SEQ ID NO: 485 | GCTTCCACCAAGGGCCCATCGGTCTTCCCCCTGGCGCCCTGCTCCAGGAGCACCTCCGAGAGCACA GCCGCCCTGGGCTGCCTGGTCAAGGACTACTTCCCCGAACCGGTGACGGTGTCG |
| Ig42 SEQ ID NO: 486 | TGGAACTCAGGCGCCCTGACCAGCGGCGTGCACACCTTCCCGGCTGTCCTACAGTCCTCAGGACTC TACTCCCTCAGCAGCGTGGTGACCGTGCCCTCCAGCAGCTTGGGCACGAAGACC |
| Ig43 SEQ ID NO: 487 | TACACCTGCAACGTAGATCACAAGCCCAGCAACACCAAGGTGGACAAGAGAGTTGAGTCCAAATA TGGTCCCCCATGCCCATCATGCCCAGCACCTGAGTTCCTGGGGGGACCATCAGTC |
| Ig44 SEQ ID NO: 488 | TTCCTGTTCCCCCCAAAACCCAAGGACACTCTCATGATCTCCCGGACCCCTGAGGTCACGTGCGTG GTGGTGGACGTGAGCCAGGAAGACCCCGAGGTCCAGTTCAACTGGTACGTGGAT |
| Ig45 SEQ ID NO: 489 | GGCGTGGAGGTGCATAATGCCAAGACAAAGCCGCGGGAGGAGCAGTTCAACAGCACGTACCGTGT GGTCAGCGTCCTCACCGTCCTGCACCAGGACTGGCTGAACGGCAAGGAGTACAAG |
| Ig46 SEQ ID NO: 490 | TGCAAGGTCTCCAACAAAGGCCTCCCGTCCTCCATCGAGAAAACCATCTCCAAAGCCAAAGGGCA GCCCCGAGAGCCACAGGTGTACACCCTGCCCCCATCCCAGGAGGAGATGACCAAG |

TABLE 3-continued

| Variable Region Primer | Sequence |
|---|---|
| Ig47 SEQ ID NO: 491 | AACCAGGTCAGCCTGACCTGCCTGGTCAAAGGCTTCTACCCCAGCGACATCGCCGTGGAGTGGGAGAGCAATGGGCAGCCGGAGAACAACTACAAGACCACGCCTCCCGTGCTGGACTCC |
| Ig48 SEQ ID NO: 492 | GACGGCTCCTTCTTCCTCTACAGCAGGCTCACCGTGGACAAGAGCAGGTGGCAGGAGGGGAATGTCTTCTCATGCTCCGTGATGCATGAGGCTCTGCACAACCACTACACACAGAAGAGC |
| Ig49 SEQ ID NO: 493 | CTCTCCCTGTCTCTGGAGCTGCAACTGGAGGAGAGCTGTGCGGAGGCGCAGGACGGGGAGCTGGACGGGCTGTGGACGACCATCACCATCTTCATCACACTCTTCCTGCTAAGCGTGTGC |
| Ig50 SEQ ID NO: 494 | TACAGTGCCACCGTCACCTTCTTCAAGGTGAAGTGGATCTTCTCCTCAGTGGTGGACCTGAAGCAGACCATCGTCCCCGACTACAGGAACATGATAAGGCAGGGGGCCTAGGGCCACCCT |
| Ig51 SEQ ID NO: 495 | CCCCCTGACCTCACCGCCCTCAACCCCATGGCTCTCTGGCTTCGCAGTCGCCCTCTGAGCCCTGAAACGCCCCCCTTCCAGACCCTGTGCATAGCAGGTCTACCCCAGACCTCCGCTGCT |
| Ig52 SEQ ID NO: 496 | TGGTGCATGCAGGGCGCTGAGGGCCAGGTGTCCCCTCAGCAGGACGTCCCTGCCCTCTGGACCACCAGGTGCTCACACAAAAGGAGGTAACCGGCATCCCAGGCCCCCACTCAGGCAGGA |
| Ig53 SEQ ID NO: 497 | CCTCGCCCTGGAGCCAACCCCGTCCACGCCAGCCTCCTGAACACAGGCATGGTTTCCAGATGGTGAGTGGGAGCATCAGTCGCCAAGGTAGGGAAGCCACAGCACCATCAGGCCCTGTTG |
| Ig54 SEQ ID NO: 498 | GGGAGGCTTCCGAGAGCTGCGAAGGCTCACTCAGACGGCCTTCCTCCCAGCCCGCAGCCAGCCAGCCTCCATTCCGGGCACTCCCGTGAACTCCTGACATGAGGAATGAGGTTGTTCTGA |
| Ig55 SEQ ID NO: 499 | TTTCAAGCAAAGAACGCTGCTCTCTGGCTCCTGGGAACAGTCTCGGTGCCAGCACCACCCCTTGGCTGCCTGCCCACACTGCTGGATTCTCGGGTGGAACTGGACCCGCAGGGACAGCCA |
| Ig56 SEQ ID NO: 500 | GCCCCAGAGTCCGCACTGGGGAGAGAAAGGGCCAGGCCCAGGACACTGCCACCTACCACCCACTCCAGTCCACCGAGATCACTCGGAGAAGAGCCTGGGCCATGTGGCCGCTGCAGGAGC |
| Ig57 SEQ ID NO: 501 | CCCACAGTGCAAGGGTGAGGATAGCCCAAGGAAGGGCTGGGCATCTGCCCAGACAGGCCTCCCACAGAAGGCTGGTGACCAGGTCCCAGGCGGGCAAGACTCAGCCTTGGTGGGGCCTGA |
| Ig58 SEQ ID NO: 502 | GGACAGAGGAGGCCCAGGAGCATCGGGGAGAGAGGTGGAGGGACACCGGGAGAGCCAGGAGCGTGGACACAGCCAGAACTCATCACAGAGGCTGGCGTCCAGTCCCGGGTCACGTGCAGC |
| Ig59 SEQ ID NO: 503 | AGGAACAAGCAGCCACTCTGGGGGCACCAGGTGGAGAGGCAAGACGACAAAGAGGGTGCCCGTGTTCTTGCGAAAGCGGGGCTGCTGGCCACGAGTGCTGGACAGAGGCCCCCACGCTCT |
| Ig60 SEQ ID NO: 504 | GCTGCCCCCATCACACCGTTCCGTGACTGTCACGCAGAATCCACAGACAGGAAGGGAGGCTCGAGCGGGACTGCGGCCAGCGCCTGCCTCGGCCGTCAGGGAGGACTCCCGGGCTCACTC |
| Ig61 SEQ ID NO: 505 | GAAGGAGGTGTCACCATTTCAGCTTTGGCTTTTCTTCTTCTTTTAAATTTTCTAAAGCTCATTAATTGTCTTTGATGTTTCTTTTGTGATGACAATAAAATATCCTTTTTAAGTCTTGTA |
| Ig62 SEQ ID NO: 506 | AGCCCCCGCTCCCCGGGCTCTCGGGGTCGCGCGAGGATGCTTGGCACGTACCCCGTGTACATACTTCCCGGGCGCCCAGCATGGAAATAAAGCACCCAGCGCTGCCCTGGGCCCCTGCGA |
| Ig63 SEQ ID NO: 507 | GCCTCCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCG |
| Ig64 SEQ ID NO: 508 | TGGAACTCAGGCGCTCTGACCAGCGGCGTGCACACCTTCCCGGCTGTCCTACAGTCCTCAGGACTCTACTCCCTCAGCAGCGTGGTGACCGTGCCCTCCAGCAACTTCGGCACCCAGACC |
| Ig65 SEQ ID NO: 509 | TACACCTGCAACGTAGATCACAAGCCCAGCAACACCAAGGTGGACAAGACAGTTGAGCGCAAATGTTGTGTCGAGTGCCCACCGTGCCCAGCACCACCTGTGGCAGGACCGTCAGTCTTC |

TABLE 3-continued

| Variable Region Primer | Sequence |
|---|---|
| Ig66 SEQ ID NO: 510 | |
| CTCTTCCCCCCAAAACCCAAGGACACCCTCATGATCTCCCGGACCCCTGAGGTCACGTGCGTGGTG GTGGACGTGAGCCACGAAGACCCCGAGGTCCAGTTCAACTGGTACGTGGACGGC | |
| Ig67 SEQ ID NO: 511 | |
| GTGGAGGTGCATAATGCCAAGACAAAGCCACGGGAGGAGCAGTTCAACAGCACGTTCCGTGTGGT CAGCGTCCTCACCGTCGTGCACCAGGACTGGCTGAACGGCAAGGAGTACAAGTGC | |
| Ig68 SEQ ID NO: 512 | |
| AAGGTCTCCAACAAAGGCCTCCCAGCCCCCATCGAGAAAACCATCTCCAAAACCAAAGGGCAGCC CCGAGAACCACAGGTGTACACCCTGCCCCCATCCCGGGAGGAGATGACCAAGAAC | |
| Ig69 SEQ ID NO: 513 | |
| CAGGTCAGCCTGACCTGCCTGGTCAAAGGCTTCTACCCCAGCGACATCTCCGTGGAGTGGGAGAG CAATGGGCAGCCGGAGAACAACTACAAGACCACACCTCCCATGCTGGACTCCGAC | |
| Ig70 SEQ ID NO: 514 | |
| GGCTCCTTCTTCCTCTACAGCAAGCTCACCGTGGACAAGAGCAGGTGGCAGCAGGGGAACGTCTTC TCATGCTCCGTGATGCATGAGGCTCTGCACAACCACTACACACAGAAGAGCCTC | |
| Ig71 SEQ ID NO: 515 | |
| TCCCTGTCTCCGGAGCTGCAACTGGAGGAGAGCTGTGCGGAGGCGCAGGACGGGGAGCTGGACGG GCTGTGGACCACCATCACCATCTTCATCACACTCTTCCTGCTAAGCGTGTGCTAC | |
| Ig72 SEQ ID NO: 516 | |
| AGTGCCACCATCACCTTCTTCAAGGTGAAGTGGATCTTCTCCTCAGTGGTGGACCTGAAGCAGACC ATCGTCCCCGACTACAGGAACATGATCAGGCAGGGGGCCTAGGGCCACCCTCTG | |
| Ig73 SEQ ID NO: 517 | |
| CCCCCGACCTCACCGCCCTCAACCCCATGGCTCTCTGGCCTCGCAGTCGCCCTCTGACCCTGACAC GCCCCCCTTCCAGACCCTGTGCATAGCAGGTCTACCCCAGACCTCCGCTGCTTG | |
| Ig74 SEQ ID NO: 518 | |
| GTGCATGCAGGGCGCTGGGGGCCAAGTGTCCCCTCAGCAGGACGTCCCTGCCCTCCGGCCCGCCA GGTGCTCACACAAAAGGAGGTAGTGACCAGCATCCCAGGCCCCCACTCAGGCAGG | |
| Ig75 SEQ ID NO: 519 | |
| ACCTCGCCCTGGAGCCAACCCTGTCCACGCCAGCCTCCTGAACACAGGCGTGGTTTCCAGATGGTG AGTGGGAGCATCAGTCGCCAAGGTAGGGAAGTCACAGCACCATCAGGCCCTGTT | |
| Ig76 SEQ ID NO: 520 | |
| GGGGAGGCTTCCGAGAGCTGCGAAGGCTCACTCAGACGGCCTTCCTCCCAGCCCGCAGCCAGCCA GCCTCCATTCCAGGCACTCCCGTGAACTCCTGACATGAGGAATGAGGTTGTTCTG | |
| Ig77 SEQ ID NO: 521 | |
| ATTTCAAGCAAAGAACGCTGCTCTCTGGCTCCTGGGAACAGTCTCAGTGCCAGCACCACCCCTTGG CTGCCTGCCCACACTGCTGGATTCTCGGGTGGAACTCGACCCGCAGGGACAGCC | |
| Ig78 SEQ ID NO: 522 | |
| AGCCCCAGAGTCCGCACTGGGGAGAGAAGGGGCCAGGCCCAGGACACTGCCACCTACCACCCACT CCAGTCCACCGAGATCACTCGGAGAAGAGCCTGGGCCATGTGGCCGCTGCAGGAG | |
| Ig79 SEQ ID NO: 523 | |
| CCCCACGGTGCAAGGGTGAGGATAGCCCAAGGAAGGGCTGGGCATCTGCCCAGACAGGCCTCCCA GAGAAGGCTGGTGACCAGGTCCCAGGCGGGCAAGACTCAGCCTTGGTGGGGCCTG | |
| Ig80 SEQ ID NO: 524 | |
| AGGACAGAGGAGGCCCAGGAGCATCGGGGAGAGAGGTGGAGGGACACCGGGAGAGCCAGGAGC GTGGACACAGCCAGAACTCATCACAGAGGCTGGCGTCCAGCCCCGGGTCACGTGCAG | |
| Ig81 SEQ ID NO: 525 | |
| CAGGAACAAGCAGCCACTCTGGGGGCACCAGGTGGAGAGGCAAGACGACAAAGAGGGTGCCCGT GTTCTTGTGAAAGCGGGGCTGCTGGCCACGAGTGCTGGACAGAGGCCCCCACGCTC | |
| Ig82 SEQ ID NO: 526 | |
| TGCTGCCCCCATCACGCCGTTCCGTGACTGTCACGCAGAATCCGCAGACAGGGAGACTCGAGCGG GAGTGCGGCCAGCGCCTGCCTCAGCTGTCAGGGAGGACTCCCGGGCTCACTCGAA | |
| Ig83 SEQ ID NO: 527 | |
| GGAGGTGCCACCATTTCAGCTTTGGTAGCTTTTCTTCTTCTTTTAAATTTTCTAAAGCTCATTAATTG TCTTTGATGTTTCTTTTGTGATGACAATAAAATATCCTTTTTAAGTCTTGTA | |
| Ig84 SEQ ID NO: 528 | |
| AGCCCCCGCTCCCCAGGCTCTCGGGGTCGCGCGAGGATGCTTGGCACGTACCCCGTCTACATACTT CCCGGGCACCCAGCATGGAAATAAAGCACCCAGCGCTGCCCTGGGCCCCTGCGA | |

TABLE 3-continued

| Variable Region Primer | Sequence |
|---|---|
| Ig85 SEQ ID NO: 529 GCATCCCCGACCAGCCCCAAGGTCTTCCCGCTGAGCCTCTGCAGCACCCAGCCAGATGGGAACGT GGTCATCGCCTGCCTGGTCCAGGGCTTCTTCCCCCAGGAGCCACTCAGTGTGACC | |
| Ig86 SEQ ID NO: 530 TGGAGCGAAAGCGGACAGGGCGTGACCGCCAGAAACTTCCCACCCAGCCAGGATGCCTCCGGGGA CCTGTACACCACGAGCAGCCAGCTGACCCTGCCGGCCACACAGTGCCTAGCCGGC | |
| Ig87 SEQ ID NO: 531 AAGTCCGTGACATGCCACGTGAAGCACTACACGAATCCCAGCCAGGATGTGACTGTGCCCTGCCC AGTTCCCTCAACTCCACCTACCCCATCTCCCTCAACTCCACCTACCCCATCTCCC | |
| Ig88 SEQ ID NO: 532 TCATGCTGCCACCCCCGACTGTCACTGCACCGACCGGCCCTCGAGGACCTGCTCTTAGGTTCAGAA GCGAACCTCACGTGCACACTGACCGGCCTGAGAGATGCCTCAGGTGTCACCTTC | |
| Ig89 SEQ ID NO: 533 ACCTGGACGCCCTCAAGTGGGAAGAGCGCTGTTCAAGGACCACCTGAGCGTGACCTCTGTGGCTG CTACAGCGTGTCCAGTGTCCTGCCGGGCTGTGCCGAGCCATGGAACCATGGGAAG | |
| Ig90 SEQ ID NO: 534 GGAGGAGCTGGCCCTGAACGAGCTGGTGACGCTGACGTGCCTGGCACGCGGCTTCAGCCCCAAGG ATGTGCTGGTTCGCTGGCTGCAGGGGTCACAGGAGCTGCCCCGCGAGAAGTACCT | |
| Ig91 SEQ ID NO: 535 GACTTGGGCATCCCGGCAGGAGCCCAGCCAGGGCACCACCACCTTCGCTGTGACCAGCATACTGC GCGTGGCAGCCGAGGACTGGAAGAAGGGGGACACCTTCTCCTGCATGGTGGGCCA | |
| Ig92 SEQ ID NO: 536 CGAGGCCCTGCCGCTGGCCTTCACACAGAAGACCATCGACCGCTTGGCGGATTGGCAGATGCCGC CTCCCTATGTGGTGCTGGACTTGCCGCAGGAGACCCTGGAGGAGGAGACCCCCGG | |
| Ig93 SEQ ID NO: 537 CGCCAACCTGTGGCCCACCACCATCACCTTCCTCACCCTCTTCCTGCTGAGCCTGTTCTATAGCACA GCACTGACCGTGACCAGCGTCCGGGGCCCATCTGGCAACAGGGAGGGCCCCCA | |
| Ig94 SEQ ID NO: 538 GTACTGAGCAGGAGCCGGCAAGGCACAGGGAGGAAGTGTGGAGGAACCTCTTGGAGAAGCCAGC TATGCTTGCCAGAACTCAGCCCTTTCAGACATCACCGACCCGCCCTTACTCACATG | |
| Ig95 SEQ ID NO: 539 CTTGGCGGGTAAACCCACCCATGTCAATGTGTCTGTTGTCATGGCGGAGGTGGACGGCACCTGCTA CTGAGCCGCCCGCCTGTCCCCACCCCTGAATAAACTCCATGCTCCCCCAAGCAG | |
| Ig96 SEQ ID NO: 540 GCCTCCACCAAGGGCCCATCGGTCTTCCCCCTGGCACCCTCCTCCAAGAGCACCTCTGGGGGCACA GCAGCCCTGGGCTGCCTGGTCAAGGACTACTTCCCCGAACCGGTGACGGTGTCG | |
| Ig97 SEQ ID NO: 541 TGGAACTCAGGCGCCCTGACCAGCGGCGTGCACACCTTCCCGGCTGTCCTACAGTCCTCAGGACTC TACTCCCTCAGCAGCGTGGTGACCGTGCCCTCCAGCAGCTTGGGCACCCAGACC | |
| Ig98 SEQ ID NO: 542 TACATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGA | |
| Ig99 SEQ ID NO: 543 CCGTCAGTCTTCCTCTTCCCCCCAAAACCCAAGGACACCCTCATGATCTCCCGGACCCCTGAGGTC ACATGCGTGGTGGTGGACGTGAGCCACGAAGACCCTGAGGTCAAGTTCAACTGG | |
| Ig100 SEQ ID NO: 544 TACGTGGACGGCGTGGAGGTGCATAATGCCAAGACAAAGCCGCGGGAGGAGCAGTACAACAGCA CGTACCGTGTGGTCAGCGTCCTCACCGTCCTGCACCAGGACTGGCTGAATGGCAAG | |
| Ig101 SEQ ID NO: 545 GAGTACAAGTGCAAGGTCTCCAACAAAGCCCTCCCAGCCCCCATCGAGAAAACCATCTCCAAAGC CAAAGGGCAGCCCCGAGAACCACAGGTGTACACCCTGCCCCCATCCCGGGATGAG | |
| Ig102 SEQ ID NO: 546 CTGACCAAGAACCAGGTCAGCCTGACCTGCCTGGTCAAAGGCTTCTATCCCAGCGACATCGCCGTG GAGTGGGAGAGCAATGGGCAGCCGGAGAACAACTACAAGACCACGCCTCCCGTG | |
| Ig103 SEQ ID NO: 547 CTGGACTCCGACGGCTCCTTCTTCCTCTACAGCAAGCTCACCGTGGACAAGAGCAGGTGGCAGCAG GGGAACGTCTTCTCATGCTCCGTGATGCATGAGGCTCTGCACAACCACTACACA | |

TABLE 3-continued

| Variable Region Primer | Sequence |
|---|---|
| Ig104 SEQ ID NO: 548 CAGAAGAGCCTCTCCCTGTCTCCGGAGCTGCAACTGGAGGAGAGCTGTGCGGAGGCGCAGGACGG GGAGCTGGACGGGCTGTGGACGACCATCACCATCTTCATCACACTCTTCCTGTTA | |
| Ig105 SEQ ID NO: 549 AGCGTGTGCTACAGTGCCACCGTCACCTTCTTCAAGGTGAAGTGGATCTTCTCCTCGGTGGTGGAC CTGAAGCAGACCATCATCCCCGACTACAGGAACATGATCGGACAGGGGGCCTAG | |
| Ig106 SEQ ID NO: 550 CGCCCTCAACCCCATGACTCTCTGGCCTCGCAGTTGCCCTCTGACCCTGACACACCTGACACGCCC CCCTTCCAGACCCTGTGCATAGCAGGTCTACCCCAGACCTCCGCTGCTTGGTGC | |
| Ig107 SEQ ID NO: 551 ATGCAGGGCACTGGGGGCCAGGTGTCCCCTCAGCAGGACGTCCTTGCCCTCCGGACCACAAGGTG CTCACACAAAAGGAGGCAGTGACCGGTATCCCAGGCCCCCACCCAGGCAGGACCT | |
| Ig108 SEQ ID NO: 552 CGCCCTGGAGCCAACCCCGTCCACGCCAGCCTCCTGAACACAGGCGTGGTTTCCAGATGGTGAGTG GGAGCGTCAGCCGCCAAGGTAGGGAAGCCACAGCACCATCAGGCCCTGTTGGGG | |
| Ig109 SEQ ID NO: 553 AGGCTTCCGAGAGCTGCGAAGGCTCACTCAGACGGCCTTCCTCCCAGCCCGCAGCCAGCCAGCCTC CATTCCGGGCACTCCCGTGAACTCCTGACATGAGGAATGAGGTTGTTCTGATTT | |
| Ig110 SEQ ID NO: 554 CAAGCAAAGAACGCTGCTCTCTGGCTCCTGGGAACAGTCTCAGTGCCAGCACCACCCCTTGGCTGC CTGCCCACACTGCTGGATTCTCGGGTGGAACTGGACCCGCAGGGACAGCCAGCC | |
| Ig111 SEQ ID NO: 555 CCAGAGTCCGCACTGGGGAGAGAAGGGGCCAGGCCCAGGACACTGCCACCTCCCACCCACTCCAG TCCACCGAGATCACTCAGAGAAGAGCCTGGGCCATGTGGCCGCTGCAGGAGCCCC | |
| Ig112 SEQ ID NO: 556 ACAGTGCAAGGGTGAGGATAGCCCAAGGAAGGGCTGGGCATCTGCCCAGACAGGCCTCCCAGAG AAGGCTGGTGACCAGGTCCCAGGCGGGCAAGACTCAGCCTTGGTGGGGCCTGAGGA | |
| Ig113 SEQ ID NO: 557 CAGAGGAGGCCCAGGAGCATCGGGGAGAGAGGTGGAGGGACACCGGGAGAGCCAGGAGCGTGG ACACAGCCAGAACTCATCACAGAGGCTGGCGTCCAGCCCCGGGTCACGTGCAGCAGG | |
| Ig114 SEQ ID NO: 558 AACAAGCAGCCACTCTGGGGGCACCAGGTGGAGAGGCAAGACGACAAAGAGGGTGCCCGTGTTC TTGCGAAAGCAGGGCTGCTGGCCACGAGTGCTGGACAGAGGCCCCCACGCTCTGCT | |
| Ig115 SEQ ID NO: 559 GCCCCCATCACGCCGTTCCGTGACTGTCACGCAGAATCTGCAGACAGGAAGGGAGACTCGAGCGG GAGTGCGGCCAGCGCCTGCCTCGGCCGTCAGGGAGGACTCCTGGGCTCACTCGAA | |
| Ig116 SEQ ID NO: 560 GGAGGTGCCACCATTTCAGCTTTGGTAGCTTTTCTTCTTCTTTTAAATTTTCTAAAGCTCATTAATTG TCTTTGATGTTTCTTTTGTGATGACAATAAAATATCCTTTTTAAGTCTTGTA | |
| Ig117 SEQ ID NO: 561 AAGCCCCCGCTCCCCAGGCTCTCGGGGTCGCGCGAGGATGCTTGGCACGTACCCCGTGTACATACT TCCCAGGCACCCAGCATGGAAATAAAGCACCCAGCGCTTCCCTGGGCCCCTGCG | |
| Ig118 SEQ ID NO: 562 CTTCCACCAAGGGCCCATCGGTCTTCCCCCTGGCGCCCTGCTCCAGGAGCACCTCTGGGGGCACAG CGGCCCTGGGCTGCCTGGTCAAGGACTACTTCCCAGAACCGGTGACGGTGTCGT | |
| Ig119 SEQ ID NO: 563 GGAACTCAGGCGCCCTGACCAGCGGCGTGCACACCTTCCCGGCTGTCCTACAGTCCTCAGGACTCT ACTCCCTCAGCAGCGTGGTGACCGTGCCCTCCAGCAGCTTGGGCACCCAGACCT | |
| Ig120 SEQ ID NO: 564 ACACCTGCAACGTGAATCACAAGCCCAGCAACACCAAGGTGGACAAGAGAGTTGAGCTCAAAACC CCACTTGGTGACACAACTCACACATGCCCACGGTGCCCAGAGCCCAAATCTTGTG | |
| Ig121 SEQ ID NO: 565 ACACACCTCCCCCGTGCCCACGGTGCCCAGAGCCCAAATCTTGTGACACACCTCCCCCATGCCCAC GGTGCCCAGAGCCCAAATCTTGTGACACACCTCCCCCGTGCCCAAGGTGCCCAG | |
| Ig122 SEQ ID NO: 566 CACCTGAACTCCTGGGAGGACCGTCAGTCTTCCTCTTCCCCCCAAAACCCAAGGATACCCTTATGA TTTCCCGGACCCCTGAGGTCACGTGCGTGGTGGTGGACGTGAGCCACGAAGACC | |

TABLE 3-continued

| Variable Region Primer | Sequence |
|---|---|
| Ig123 SEQ ID NO: 567 | CCGAGGTCCAGTTCAAGTGGTACGTGGACGGCGTGGAGGTGCATAATGCCAAGACAAAGCCGCGG GAGGAGCAGTACAACAGCACGTTCCGTGTGGTCAGCGTCCTCACCGTCCTGCACC |
| Ig124 SEQ ID NO: 568 | AGGACTGGCTGAACGGCAAGGAGTACAAGTGCAAGGTCTCCAACAAAGCCCTCCCAGCCCCCATC GAGAAAACCATCTCCAAAACCAAAGGACAGCCCCGAGAACCACAGGTGTACACCC |
| Ig125 SEQ ID NO: 569 | TGCCCCCATCCCGGGAGGAGATGACCAAGAACCAGGTCAGCCTGACCTGCCTGGTCAAAGGCTTC TACCCCAGCGACATCGCCGTGGAGTGGGAGAGCAGCGGGCAGCCGGAGAACAACT |
| Ig126 SEQ ID NO: 570 | ACAACACCACGCCTCCCATGCTGGACTCCGACGGCTCCTTCTTCCTCTACAGCAAGCTCACCGTGG ACAAGAGCAGGTGGCAGCAGGGGAACATCTTCTCATGCTCCGTGATGCATGAGG |
| Ig127 SEQ ID NO: 571 | CTCTGCACAACCGCTTCACGCAGAAGAGCCTCTCCCTGTCTCCGGAGCTGCAACTGGAGGAGAGCT GTGCGGAGGCGCAGGACGGGGAGCTGGACGGGCTGTGGACGACCATCACCATCT |
| Ig128 SEQ ID NO: 572 | TCATCACACTCTTCCTGTTAAGCGTGTGCTACAGTGCCACCGTCACCTTCTTCAAGGTGAAGTGGAT CTTCTCCTCGGTGGTGGACCTGAAGCAGACCATCATCCCCGACTATAGGAACA |
| Ig129 SEQ ID NO: 573 | GACCTCACCGCCCTCAACCCCATGGCTCTCTGTCTTTGCAGTCGCCCTCTGAGCCCTGACACGCCCC CCTTCCAGACCCTGTGCATAGCAGGTCTACCCCAGACCTCCGCTGCTTGGTGC |
| Ig130 SEQ ID NO: 574 | ATGCAGGGAGCTGGGGACCAGGTGTCCCCTCAGCAGGATGTCCCTGCCCTCCAGACCGCCAGATG CTCACACAAAAGGAGGCAGTGACCAGCATCCGAGGCCCCCACCCAGGCAGGAGCT |
| Ig131 SEQ ID NO: 575 | GGCCCTGGAGCCAACCCCGTCCACGCCAGCCTCCTGAACACAGGCGTGGTTTCCAGATGGTGAGT GGGAGCATCAGCCGCCAAGGTAGGGAAGCCACAGCACCATCAGGCCCTGTTGGGG |
| Ig132 SEQ ID NO: 576 | AGGCTTCCGAGAGCTGCGAAGGCTCACTCAGACGGCCTTCCTCCCAGCCCGCAGCCAGCCAGCCTC CATTCCGGGCACTCCCGTGAACTCCTGACATGAGGAATGAGGTTGTTCTGATTT |
| Ig133 SEQ ID NO: 577 | CAAGCAAAGAACGCTGCTCTCTGGCTCCTGGGAACAGTCTCGGTGCCAGCACCACCCCTTGGCTGC CTGCCTACACTGCTGGATTCTCGGGTGGAACTGGACCCGCAGGGACAGCCAGCC |
| Ig134 SEQ ID NO: 578 | CCAGAGTCCGCACTGGGGAGAGAAGGGGCCAGGCCCAGGACACTGCCACCTCCCACCCACTCCAG TCCACCGAGATCACTCAGAGAAGAGCCTGGGCCATGTGGCCACTGCAGGAGCCCC |
| Ig135 SEQ ID NO: 579 | ACAGTGCAAGAGTGAGGATAGCCCAAGGAAGGGCTGGGCATCTGCCCAGACAGGCCTCCCAGAG AAGGCTGGTGACCAGGTCCCAGGCGGGCAAGACTCAGCCTTGGTGGGGCCTGAGGA |
| Ig136 SEQ ID NO: 580 | CAGAGGAGGCCCAGGAGCATCGGGGAGAGAGGTGGAGGGACACCGGGAGAGCCAGGAGCGTGG ACACAGCCAGAACTCATCACAGAGGCTGGCGTCCAGCCCCGGGTCACGTGCAGCAGG |
| Ig137 SEQ ID NO: 581 | AACAAGCAGCCACTCTGGGGGCACCAGGTGGAGAGGCAAGATGCCAAAGAGGGTGCCCGTGTTCT TGCGAAAGCGGGGCTGCTGGCCACGAGTGCTGGACAGAGGCCCCCACGCTCTGCT |
| Ig138 SEQ ID NO: 582 | GCCCCCATCACGCCGTTCCGTGACTGTCACGCAGAATCCGCAGACAGGAAGGGAGGCTCGAGCGG GACTGCGGCCAGCGCCTGCCTCGGCCGTCAGGGAGGACTCCCGGGCTCACTCGAA |
| Ig139 SEQ ID NO: 583 | GGAGGTGCCACCATTTCAGCTTTGGTAGCTTTTCTTCTTCTTTTAAATTTTCTAAAGCTCATTAATTG TCTTTGATGTTTCTTTTGTGATGACAATAAAATATCCTTTTTAAGTCTTGTA |
| Ig140 SEQ ID NO: 584 | AGCCCCCGCTCCCCGGGCTCTCGGGGTCGCGCGAGGATGCTTGGCACGTACCCCGTGTACATACTT CCCGGGCACCCAGCATGGAAATAAAGCACCCAGCGCTGCCCTGGGCCCCTGCGA |
| Ig141 SEQ ID NO: 585 | CACCCACCAAGGCTCCGGATGTGTTCCCCATCATATCAGGGTGCAGACACCCAAAGGATAACAGC CCTGTGGTCCTGGCATGCTTGATAACTGGGTACCACCCAACGTCCGTGACTGTCA |

TABLE 3-continued

| Variable Region Primer | Sequence |
|---|---|
| Ig142 SEQ ID NO: 586 | CCTGGTACATGGGGACACAGAGCCAGCCCCAGAGAACCTTCCCTGAGATACAAAGACGGGACAGC TACTACATGACAAGCAGCCAGCTCTCCACCCCCCTCCAGCAGTGGCGCCAAGGCG |
| Ig143 SEQ ID NO: 587 | AGTACAAATGCGTGGTCCAGCACACCGCCAGCAAGAGTAAGAAGGAGATCTTCCGCTGGCCAGAG TCTCCAAAGGCACAGGCCTCCTCAGTGCCCACTGCACAACCCCAAGCAGAGGGCA |
| Ig144 SEQ ID NO: 588 | GCCTCGCCAAGGCAACCACAGCCCCAGCCACCACCCGTAACACAGGAAGAGGAGGAGAAGAGAA GAAGAAGGAGAAGGAGAAAGAGGAACAAGAAGAGAGAGAGACAAAGACACCAGAGT |
| Ig145 SEQ ID NO: 589 | GTCCGAGCCACACCCAGCCTCTTGGCGTCTACCTGCTAACCCCTGCAGTGCAGGACCTGTGGCTCC GGGACAAAGCCACCTTCACCTGCTTCGTGGTGGGCAGTGACCTGAAGGATGCTC |
| Ig146 SEQ ID NO: 590 | ACCTGACCTGGGAGGTGGCTGGGAAGGTCCCCACAGGGGGCGTGGAGGAAGGGCTGCTGGAGCG GCACAGCAACGGCTCCCAGAGCCAGCACAGCCGTCTGACCCTGCCCAGGTCCTTGT |
| Ig147 SEQ ID NO: 591 | GGCCTCGTCTGACCCTCCCGAGGCGGCCTCGTGGCTCCTGTGTGAGGTGTCTGGCTTCTCGCCCCCC AACATCCTCCTGATGTGGCTGGAGGACCAGCGTGAGGTGAACACTTCTGGGTT |
| Ig148 SEQ ID NO: 592 | TGCCCCCGCACGCCCCCCTCCACAGCCCAGGAGCACCACGTTCTGGGCCTGGAGTGTGCTGCGTGT CCCAGCCCCGCCCAGCCCTCAGCCAGCCACCTACACGTGTGTGGTCAGCCACGA |
| Ig149 SEQ ID NO: 593 | GGACTCCCGGACTCTGCTCAACGCCAGCCGGAGCCTAGAAGTCAGCTACCTGGCCATGACCCCCCT GATCCCTCAGAGCAAGGATGAGAACAGCGATGACTACACGACCTTTGATGATGT |
| Ig150 SEQ ID NO: 594 | GGGCAGCCTGTGGACCACCCTGTCCACGTTTGTGGCCCTCTTCATCCTCACCCTCCTCTACAGCGGC ATTGTCACTTTCATCAAGGTGAAGTAGCCCCAGAAGAGCAGGACGCCCTGTAC |
| Ig151 SEQ ID NO: 595 | CTGCAGAGAAGGGAAGCAGCCTCTGTACCTCATCTGTGGCTACCAGAGAGCAGAAAGGACCCACC CTGGACTCTTCTGTGTGCAGGAAGATGCGCCAGCCCCTGCCCCCGGCTCCCCTCT |
| Ig152 SEQ ID NO: 596 | GTCCGCCACAGAACCCAGTCTTCTAGACCAGGGGGACGGGCACCCATCACTCCGCAGGCGAATCA GAGCCCCCCTGCCCCGGCCCTAACCCCTGTGCCTCCTTCCCATGCTTCCCCGAGA |
| Ig153 SEQ ID NO: 597 | GCCAGCTACACCCCTGCCCCGGCCCTAACCCCCATGCCTCCTTCCTGTGCTTCCCCCAGAGCCAGCT AGTCCCACCTGCAGCCCGCTGGCCTCCCCATAAACACACTTTGGTTCATTTCA |
| Ig154 SEQ ID NO: 598 | GGGAGTGCATCCGCCCCAACCCTTTTCCCCCTCGTCTCCTGTGAGAATTCCCCGTCGGATACGAGC AGCGTGGCCGTTGGCTGCCTCGCACAGGACTTCCTTCCCGACTCCATCACTTTC |
| Ig155 SEQ ID NO: 599 | TCCTGGAAATACAAGAACAACTCTGACATCAGCAGCACCCGGGGCTTCCCATCAGTCCTGAGAGG GGGCAAGTACGCAGCCACCTCACAGGTGCTGCTGCCTTCCAAGGACGTCATGCAG |
| Ig156 SEQ ID NO: 600 | GGCACAGACGAACACGTGGTGTGCAAAGTCCAGCACCCCAACGGCAACAAAGAAAAGAACGTGC CTCTTCCAGTGATTGCTGAGCTGCCTCCCAAAGTGAGCGTCTTCGTCCCACCCCGC |
| Ig157 SEQ ID NO: 601 | GACGGCTTCTTCGGCAACCCCCGCAAGTCCAAGCTCATCTGCCAGGCCACGGGTTTCAGTCCCCGG CAGATTCAGGTGTCCTGGCTGCGCGAGGGGAAGCAGGTGGGGTCTGGCGTCACC |
| Ig158 SEQ ID NO: 602 | ACGGACCAGGTGCAGGCTGAGGCCAAAGAGTCTGGGCCCACGACCTACAAGGTGACCAGCACACT GACCATCAAAGAGAGCGACTGGCTCGGCCAGAGCATGTTCACCTGCCGCGTGGAT |
| Ig159 SEQ ID NO: 603 | CACAGGGGCCTGACCTTCCAGCAGAATGCGTCCTCCATGTGTGTCCCCGATCAAGACACAGCCATC CGGGTCTTCGCCATCCCCCCATCCTTTGCCAGCATCTTCCTCACCAAGTCCACC |
| Ig160 SEQ ID NO: 604 | AAGTTGACCTGCCTGGTCACAGACCTGACCACCTATGACAGCGTGACCATCTCCTGGACCCGCCAG AATGGCGAAGCTGTGAAAACCCACACCAACATCTCCGAGAGCCACCCCAATGCC |

TABLE 3-continued

| Variable Region Primer | Sequence |
|---|---|
| Ig161 SEQ ID NO: 605 | AGCGCCGTGGGTGAGGCCAGCATCTGCGAGGATGACTGGAATTCCGGGGAGAGGTTCACGTGCACCGTGACCCACACAGACCTGCCCTCGCCACTGAAGCAGACCATCTCCCGGCCCAAG |
| Ig162 SEQ ID NO: 606 | GGGGTGGCCCTGCACAGGCCCGATGTCTACTTGCTGCCACCAGCCCGGGAGCAGCTGAACCTGCGGGAGTCGGCCACCATCACGTGCCTGGTGACGGGCTTCTCTCCCGCGGACGTCTTC |
| Ig163 SEQ ID NO: 607 | GTGCAGTGGATGCAGAGGGGGCAGCCCTTGTCCCCGGAGAAGTATGTGACCAGCGCCCCAATGCCTGAGCCCCAGGCCCCAGGCCGGTACTTCGCCCACAGCATCCTGACCGTGTCCGAA |
| Ig164 SEQ ID NO: 608 | GAGGAATGGAACACGGGGGAGACCTACACCTGCGTGGTGGCCCATGAGGCCCTGCCCAACAGGGTCACCGAGAGGACCGTGGACAAGTCCACCGAGGGGGAGGTGAGCGCCGACGAGGAG |
| Ig165 SEQ ID NO: 609 | GGCTTTGAGAACCTGTGGGCCACCGCCTCCACCTTCATCGTCCTCTTCCTCCTGAGCCTCTTCTACAGTACCACCGTCACCTTGTTCAAGGTGAAATGATCCCAACAGAAGAACATCGGA |
| Ig166 SEQ ID NO: 610 | GACCAGAGAGAGGAACTCAAAGGGGCGCTGCCTCCGGGTCTGGGGTCCTGGCCTGCGTGGCCTGTTGGCACGTGTTTCTCTTCCCCGCCCGGCCTCCAGTTGTGTGCTCTCACACAGGCT |
| Ig167 SEQ ID NO: 611 | TCCTTCTCGACCGGCAGGGGCTGGCTGGCTTGCAGGCCACGAGGTGGGCTCTACCCCACACTGCTTTGCTGTGTATACGCTTGTTGCCCTGAAATAAATATGCACATTTTATCCATGAAA |
| Ig168 SEQ ID NO: 612 | TGCTGGCCTGCCCACAGGCTCGGGGCGGCTGGCCGCTCTGTGTGTGCATGCAAACTAACCGTGTCAACGGGGTGAGATGTTGCATCTTATAAAATTAGAAATAAAAAGATCCATTCAAAA |
| Ig169 SEQ ID NO: 613 | GCCACCCCCTTGGTCACTCTGTTCCCGCCCTCCTCTGAGGAGCTCCAAGCCAACAAGGCCATGCTGGTGTGTCTCATAAATGACTTCTACCCAGGAGCCATAGAAGGAAAATGGCACCCT |
| Ig170 SEQ ID NO: 614 | ATGCGGCCAGCAGCTACCTGAGCCTGACGCCCGAGCAGTGGAAGTCCCACAGAAGCTACAGCTGCCAGGTCACGCACAAAGAAAGTACCATGGAGAAGACAATGGCCCATGCAGAATGTT |
| Ig171 SEQ ID NO: 615 | ACAAGGCCACACTGGTGTGTCTCATGAGTGACTTCTACCCGAGAGCCATGACAGTGGCCTGGAAGATAGATGGCATCACCATCACCCAGGGTGTGGAGACCACCACACCCTCCAAACAGA |
| Ig172 SEQ ID NO: 616 | TATGCGGCCAGCAGCTACCTAAGACTGGCACCCGACAGTGGAAGTCCCACAACCTCTACAGCTGCCAGGTCACGCATGAAAGGAACACTGTGGAGAAGACAGTGGCCCCTGCAGAATGTT |
| Ig173 SEQ ID NO: 617 | GTCAGCCCAAGGCTGCCCCATCGGTCACTCTGTTCCCGCCCTCCTCTGAGGAGCTTCAAGCCAACAAGGCCACACTGGTGTGCCTGATCAGTGACTTCTACCCGGGAGCTGTGAAAGTGG |
| Ig174 SEQ ID NO: 618 | GCGGCCAGCAGCTAGCTACCTGAGCCTGACGCCTGAGCAGTGGAAGTCCCACAGAAGCTACAGTTGCCAGGTCACGCATGAAGGGAGCACCGTGGAGAAGACAGTGGCCCCTGCAGAATG |
| TCR1 SEQ ID NO: 619 | AGGACCTGAACAAGGTGTTCCCACCCGAGGTCGCTGTGTTTGAGCCATCAGAAGCAGAGATCTCCCACACCCAAAAGGCCACACTGGTGTGCCTGGCCACAGGCTTCTTCCCTGACCACG |
| TCR2 SEQ ID NO: 620 | TGGAGCTGAGCTGGTGGGTGAATGGGAAGGAGGTGCACAGTGGGGTCAGCACGGACCCGCAGCCCCTCAAGGAGCAGCCCGCCCTCAATGACTCCAGATACTGCCTGAGCAGCCGCCTGA |
| TCR3 SEQ ID NO: 621 | GGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCG |
| TCR4 SEQ ID NO: 622 | CTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAG |
| TCR5 SEQ ID NO: 623 | AAAGGATTTCTGAAGGCAGCCCTGGAAGTGGAGTTAGGAGCTTCTAACCCGTCATGGTTTCAATACACATTCTTCTTTTGCCAGCGCTTCTGAAGAGCTGCTCTCACCTCTCTGCATCCC |

TABLE 3-continued

| Variable Region Primer | Sequence |
|---|---|
| TCR6 SEQ ID NO: 624 | AATAGATATCCCCCTATGTGCATGCACACCTGCACACTCACGGCTGAAATCTCCCTAACCCAGGGGGACCTTAGCATGCCTAAGTGACTAAACCAATAAAAATGTTCTGGTCTGGCCTGA |
| TCR7 SEQ ID NO: 625 | AGGACCTGAAAAACGTGTTCCCACCCAAGGTCGCTGTGTTTGAGCCATCAGAAGCAGAGATCTCCCACACCCAAAAGGCCACACTGGTGTGCCTGGCCACAGGCTTCTACCCCGACCACG |
| TCR8 SEQ ID NO: 626 | TGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGA |
| TCR9 SEQ ID NO: 627 | GGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCTGTCACCCAGATCG |
| TCR10 SEQ ID NO: 628 | ACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAG |
| TCR11 SEQ ID NO: 629 | AGAAAGGATTCCAGAGGCTAGCTCCAAAACCATCCCAGGTCATTCTTCATCCTCACCCAGGATTCTCCTGTACCTGCTCCCAATCTGTGTTCCTAAAAGTGATTCTCACTCTGCTTCTCA |
| TCR12 SEQ ID NO: 630 | TCTCCTACTTACATGAATACTTCTCTCTTTTTTCTGTTTCCCTGAAGATTGAGCTCCCAACCCCCAAGTACGAAATAGGCTAAACCAATAAAAAATTGTGTGTTGGGCCTGGTTGCATTT |
| TCR13 SEQ ID NO: 631 | ATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTG |
| TCR14 SEQ ID NO: 632 | ATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCA |
| TCR15 SEQ ID NO: 633 | TTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCC |
| TCR16 SEQ ID NO: 634 | GAATCCTCCTCCTGAAAGTGGCCGGGTTTAATCTGCTCATGACGCTGCGGCTGTGGTCCAGCTGAGATCTGCAAGATTGTAAGACAGCCTGTGCTCCCTCGCTCCTTCCTCTGCATTGCC |
| TCR17 SEQ ID NO: 635 | ACAGAGGGAACTCTCCTACCCCCAAGGAGGTGAAAGCTGCTACCACCTCTGTGCCCCCCCGGCAATGCCACCAACTGGATCCTACCCGAATTTATGATTAAGATTGCTGAAGAGCTGCCA |
| TCR18 SEQ ID NO: 636 | AACACTGCTGCCACCCCCTCTGTTCCCTTATTGCTGCTTGTCACTGCCTGACATTCACGGCAGAGGCAAGGCTGCTGCAGCCTCCCCTGGCTGTGCACATTCCCTCCTGCTCCCCAGAGA |
| TCR19 SEQ ID NO: 637 | CTGCCTCCGCCATCCCACAGATGATGGATCTTCAGTGGGTTCTCTTGGGCTCTAGGTCCTGCAGAATGTTGTGAGGGGTTTATTTTTTTTTAATAGTGTTCATAAAGAAATACATAGTAT |
| TCR20 SEQ ID NO: 638 | TCTTCTTCTCAAGACGTGGGGGGAAATTATCTCATTATCGAGGCCCTGCTATGCTGTGTATCTGGGCGTGTTGTATGTCCTGCTGCCGATGCCTTCATTAAAATGATTTGGAAGAGCAGA |
| Blocking Oligonucleotides | |
| Read1 and poly(T) SEQ ID NO: 639 | CTACACGACGCTCTTCCGATCTNNNNNNNNNNNNNNNNNNNNNNNNNNNNTTTTTTTTTTTTTTTTTTTTTTTTTTTTTTVN |
| Blocking Template Switching Oligonucleotide SEQ ID NO: 640 | CCCATGTACTCTGCGTTGATACCACTGCTT |

Variable Region Primer

After PCR enrichment, the PCR product was purified before the PCR indexing reaction. Quant-iT (ThermoFisher Scientific) analysis measured the DNA concentration of each sample, which was also normalized to the input material in the PCR indexing reaction (1.25 ng/reaction). Indexing PCR was performed as previously described (Ståhl, P. L., et al., Visualization and analysis of gene expression in tissue sections by spatial transcriptomics, *Science,* 353(6294), 78-82, (2016)). In total, 24 unique indexes were used, with each cDNA library receiving a unique index (TRB, IGHG, and IGHM products from the same cDNA library received the same indexing since the TCR and BCR clonotypes can be distinguished from each other bioinformatically using the constant primer sequence). After purification, PCR reactions were pooled. The pooled PCR library was run on a gel and a large band at around 500 bp excised was gel-purified and sequenced (NovaSeq, 2×150 bp). The resulting data were de-multiplexed and the FastQ files were analyzed using MiXCR (Bolotin, D. A., et al., MiXCR: software for comprehensive adaptive immune profiling, *Nature Methods,* 12, 380-381 (2015), which is incorporated herein by reference in its entirety).

After PCR variable region primer enrichment, a number of TRB and IGH clonotypes in all prepared libraries were detected. For TRB, about 10,000 unique clonotypes were detected in spatial libraries prepared from tonsil tissue (data not shown) and between about 12,000 and about 25,000 unique clonotypes were detected in spatial libraries prepared from lymph node (data not shown). The positive control (SmartSeq2 RNAseq after PCR enrichment) yielded about 35,000 unique clonotypes. Variable region primer enrichment of the Smartseq2 library increased the TRB unique clonotype count over 35-fold, however, the SmartSeq2 library contained RNA extracted from two tonsil sections, whereas only a single tissue section was used for the spatial samples.

Figure 8:
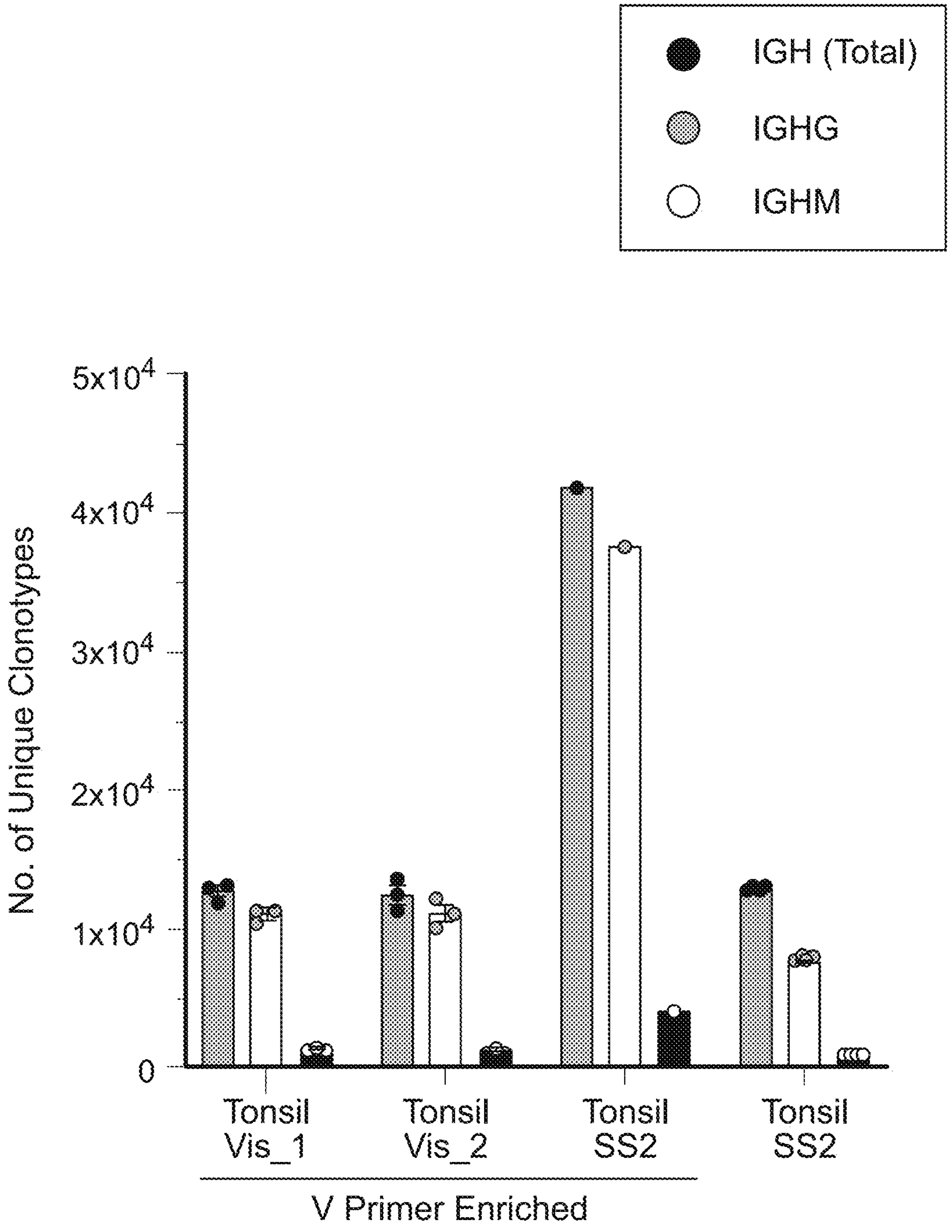
FIG. 8 shows an exemplary graph of the number of unique IG clonotypes detected in tonsil tissue on a spatial array (Vis) compared with single cell (SS2) analysis, with or without an enrichment strategy.
Figure 9:
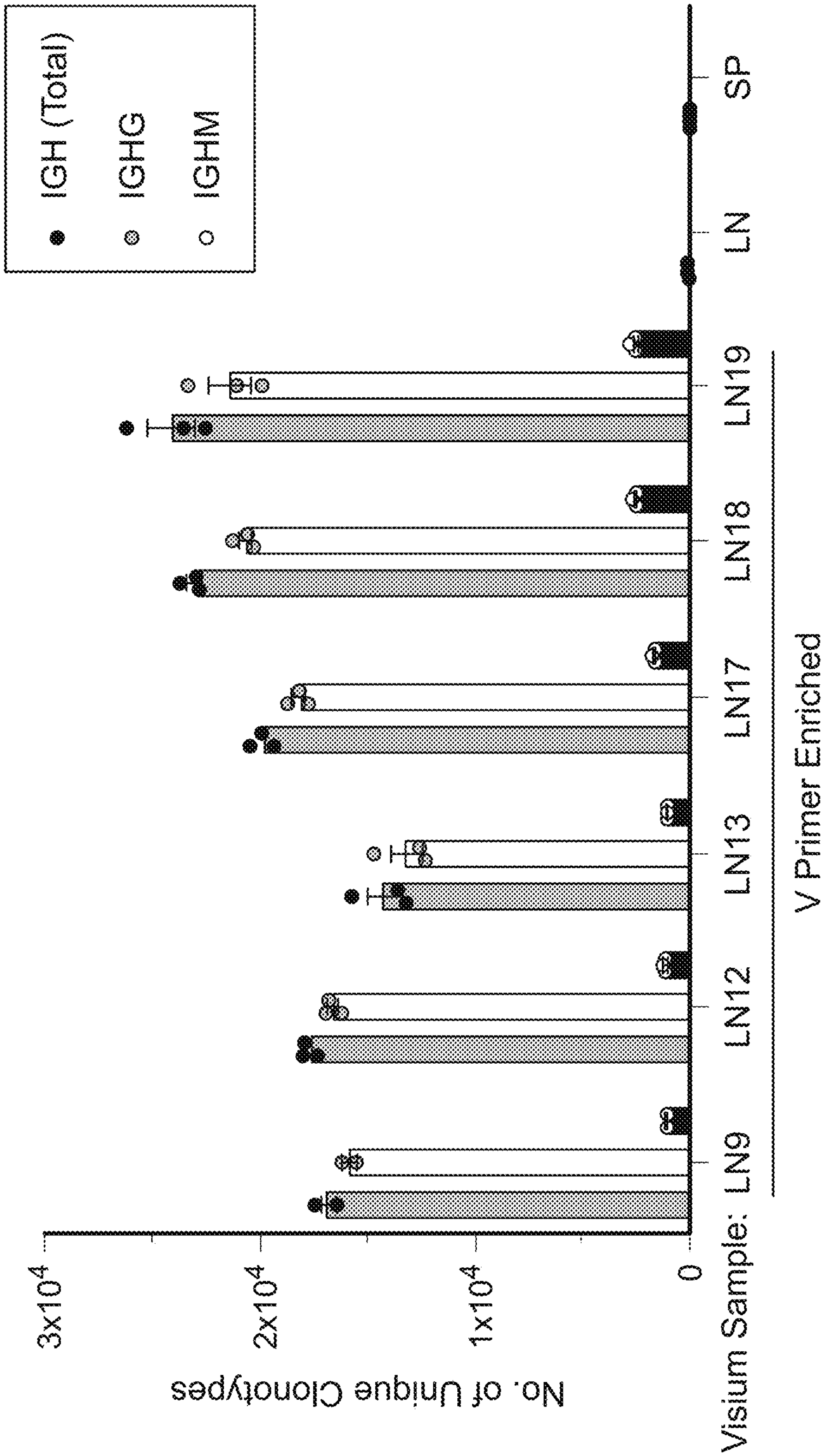
FIG. 9 shows an exemplary graph of the number of unique IG clonotypes detected in lymph node (LN) tissue on a spatial array with and without an enrichment strategy. Lymph node and spleen (SP) non-enrichment samples serve as controls.

Similar results were observed for IGH detection with about 10,000 unique clonotypes detected from spatial libraries prepared from tonsil (FIG. 8) and between about 12,000 and about 25,000 unique clonotypes detected from spatial libraries prepared from the lymph node (FIG. 9). FIGS. 8 and 9 also shows the number of unique clonotypes found in non-enriched samples (far right) and the data show the number of unique clonotypes found is less than the V primer enriched samples. Approximately 10-fold higher IGHG clonotypes were detected relative to IGHM clonotypes similar to previous results for the SmartSeq2 RNAseq libraries (data not shown).

Variable region primer enrichment also resulted in a 4-fold increase in detected clonotypes for single-cell SmartSeq2 libraries. The clonotype increase observed after PCR variable primer enrichment of TRB relative to IGH is consistent with a known lower abundance of TRB transcripts in the cDNA library. For example, it is known that TRA/TRB transcript expression per T-cell is less relative to IGH/IGK/IGL expression per B-cell, and in particular, for plasma cells. Substantial, but not complete overlap, of IGH clonotypes between technical replicates detected in spatial libraries from tonsil tissue was observed. Similarly, substantial, but not complete, overlap of TRB clonotypes between technical replicates detected in spatial libraries from tonsil tissue was also observed. The data show that approximately half the clonotypes from a given technical replicate were detected in at least one or more of the other two technical replicates, which suggests many clonotypes were detected in a given technical replicate, but not all clonotypes were detected in each sample (data not shown). Approximately 10-20 fold increase in clonotype counts were detected with a poly(T) capture domain combined with PCR variable region primer enrichment relative to targeted capture, without variable region primer enrichment.

Collectively, these data show that PCR primer enrichment of analytes encoding immune cell receptors captured by poly(A) capture domains is possible. The use of a poly(A) capture domain allows for the simultaneous capture of analytes that do not encode for immune cell receptors and also does not require a custom array with targeted capture domains.

Figure 10B:
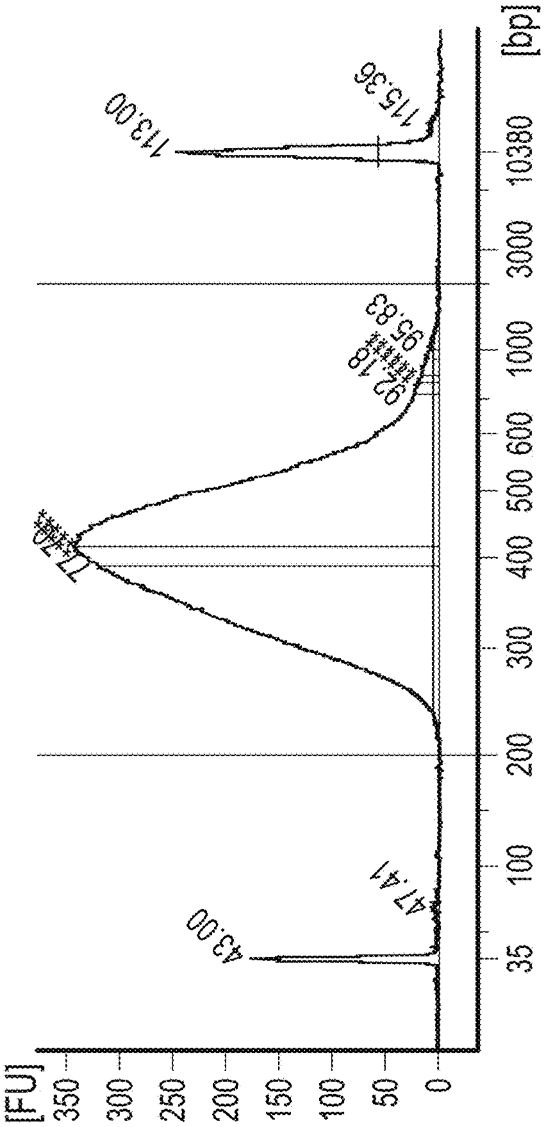
FIG. 10B shows a gene expression library generated from the tonsil tissue in FIG. 10A.
Figure 10A:
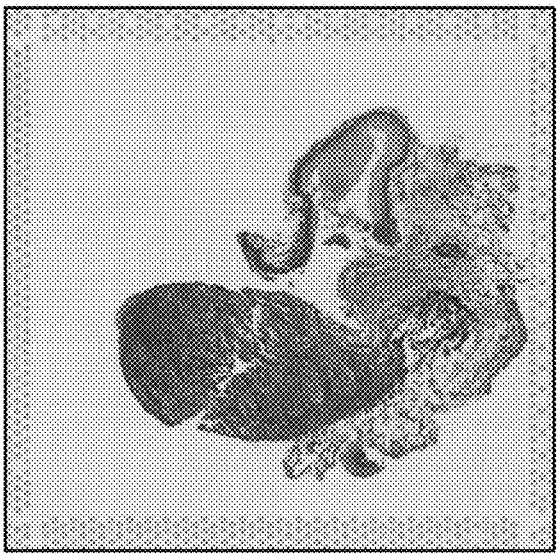
FIG. 10A shows H&E stained tonsil tissue.
Figure 11:
FIG. 11 shows single-cell clustering analysis of the T-cell receptor and B-cell receptor clonotypes present in a breast tumor sample.

FIG. 10A shows H&E stained tonsil tissue on a spatial array and FIG. 10B shows the size distribution of spatial libraries prepared from tonsil tissue. The data shown in FIGS. 10A-B show the stained tonsil tissue and size distribution of the spatial libraries of the data included in this Example. Similar H&E staining was performed on breast tumor tissue on a spatial array and size distribution of spatial libraries were also prepared from breast tumor tissue (data not shown). FIG. 11 shows clustering of B-cells and T-cells from the single-cell analysis performed in this Example. FIG. 11 shows that while identifying populations of cells that include immune cell receptors, there is no connection to the spatial location of those cells within a biological sample. FIG. 11 shows a single-cell analysis which is not designed to be a spatial representation of immune cells within a biological sample.

Example 3—Enrichment of Analytes Encoding Immune Cell Receptors

Figure 2:
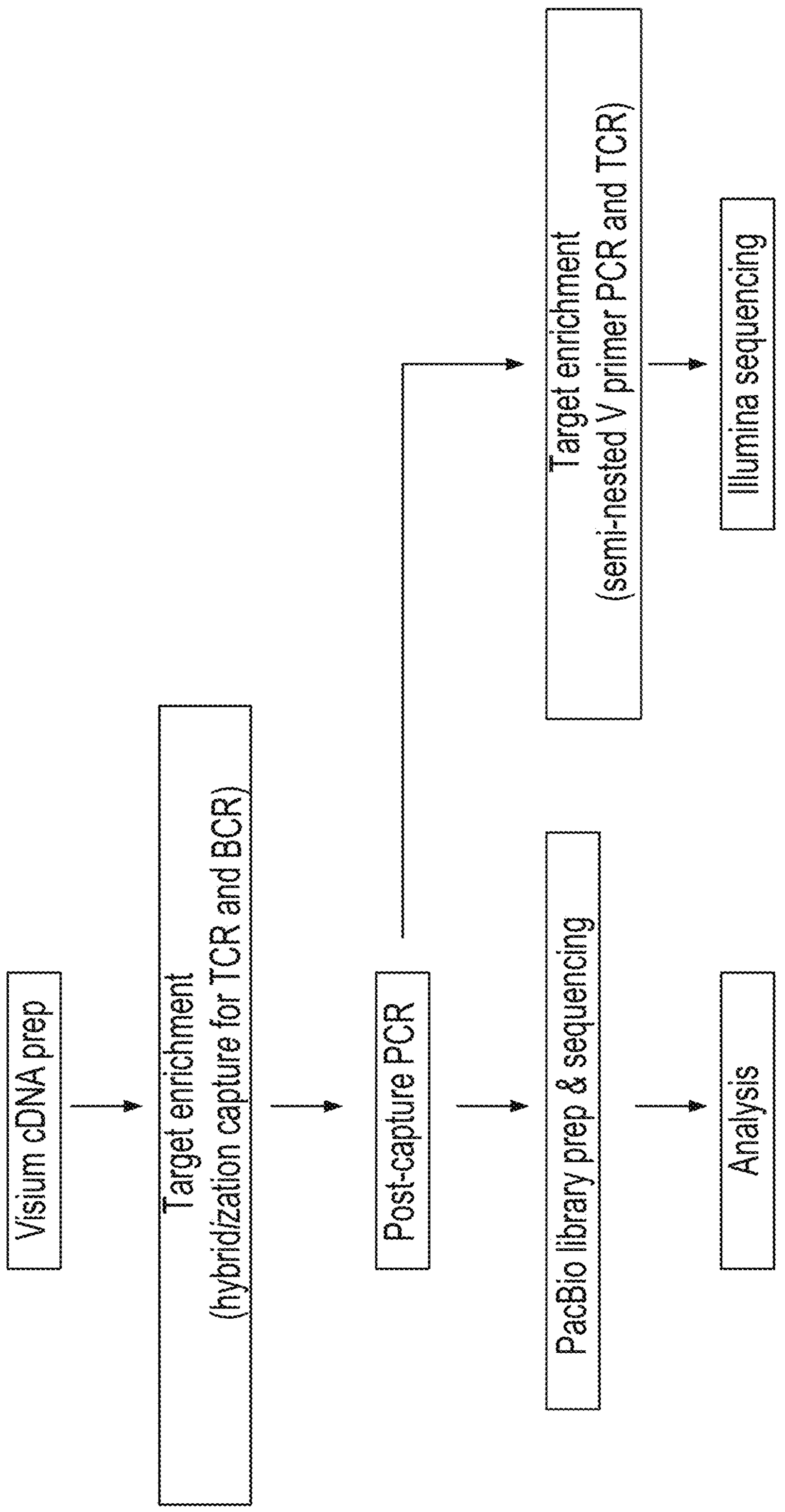
FIG. 2 shows an exemplary workflow for spatial transcriptomics for antigen-receptors.

FIG. 2 shows an exemplary workflow for the enrichment of T-cell receptor (TCR) analytes and B-cell receptor (BCR) analytes after capture on a spatial array. After capture of analytes (e.g., TCR and BCR analytes) cDNA is synthesized, followed by target enrichment and either library preparation and sequencing or further target enrichment via a semi-nested PCR for TCR analytes followed by ILLUMINA® (sequencing technology) sequencing and finally analysis.

Preparation of Visium Spatial Gene Expression Libraries

Sections of fresh-frozen breast tumor and tonsil tissue were sliced to 10 μm thickness and mounted onto slides from the Visium Spatial Gene Expression Slide & Reagent kit (10× Genomics® (sequencing technology)). Sequencing libraries were prepared following the manufacturer's protocol (Document number CG000239 Rev A, 10× Genomics® (sequencing technology)). Prior to imaging, coverslips were mounted on the slides according to the protocol's optional step “Coverslip Application & Removal”. Tissue images were taken at magnification using a Metafer Slide Scanning platform (MetaSystems) and raw images were stitched with VSlide software (MetaSystems). Adaptions of the protocol were made in that the Hematoxylin and Eosin (H&E) staining time was reduced to 4 minutes and tissue permeabilization was performed for 12 minutes.

Sequencing and Data Processing of Visium Spatial Gene Expression Libraries

Final sequencing libraries were sequenced on NextSeq™ 2000 (sequencer) (ILLUMINA® (sequencing technology)) with a 28-10-10-150 setup (tonsil), or NovaSeq6000 (ILLUMINA® (sequencing technology)) with a 28-10-10-120 setup (breast tumor). 172M and 93M raw read pairs were obtained from tonsil-1 and tonsil-2, respectively, and 215M and 244M from breast tumor 1 and breast tumor 2, respectively.

Following demultiplexing of the bcl files, read 2 fastq files were trimmed using Cutadapt (Martin, M., Cutadapt removes adapter sequences from high-throughput sequencing reads, *EMBnet Journal,* 17(1) (2011)) to remove full-length or truncated template switch oligo (TSO) sequences from the 5' end (e.g., beginning of Read 2) and poly(A) homopolymers from the 3' end (e.g., end of read 2). The TSO sequence (SEQ ID NO: 114) (AAGCAGTGGTATCAACGCAGAGTACATGGG) was used as a non-internal 5' adapter with a minimum overlap of 5, meaning that partial matches (up to 5 base pairs) or intact TSO sequences were removed from the 5' end. The error tolerance was set to 0.1 for the TSO trimming to allow for a maximum of 3 errors. For the 3' end homopolymer trimming, a sequence of 10 As was used as a regular 3' adapter to remove potential polyA tail products regardless of its position in the read, also with a minimum overlap of 5 base pairs. The trimmed data was processed with the SpaceRanger pipeline (10× Genomics® (sequencing technology)), version 1.2.1 (tonsil) and version 1.0.0 (BC) and mapped to the GRCH38 v93 genome assembly.

Target Enrichment with Hybridization Capture

TCR and BCR target enrichment was performed using IDT xGen Hybridization and Wash Kit (#1080584) with one enrichment probe pool (IDT) each for BCR and TCR transcripts (IG and TCR pool, Table 3). Custom blocking oligos (IDT, Table 3) were designed to hybridize to adaptor sequences of the cDNA library and to prevent off-target fragments from binding to BCR/TCR transcripts and contaminating the enriched library. The IG and TCR enrichment probe pools were mixed at ratio 1:3 and 1:12, respectively and each sample was enriched using both settings.

The "xGen hybridization capture of DNA libraries", version 4 (IDT) protocol was followed with an input of 10 μl Visium cDNA per reaction, corresponding to between about 45-130 ng and the hybridization enrichment reaction was performed overnight.

The enriched and purified libraries were amplified twice with an AMPure bead wash after each PCR reaction, using 25 μl 2×KAPA mix, 7.5 μl cDNA primers (10× Genomics® (sequencing technology)) and 17.5 μl sample in MQ water. The following settings were used for the PCRs: 1. 98° C. 3 min; 2. 98° C. 15 sec; 3. 63° C. 30 sec; 4. 72° C. 2 min; 5. Repeat steps 2-5 6× for a total of 7 cycles (1st PCR) and 4× for a total of 5 cycles (2nd PCR); 6. 72° C. 1 min Library Preparation and Sequencing The resulting product from the hybridization enrichment capture method was used as input into the SMRTbell™ library preparation protocol (PacBio®; sequencing technology). The DNA was concentrated by AMPure Bead Purification (0.8×), eluting in 6 μl of Elution Buffer, using 1 μl for Qubit measurements. At least 1 μg of input was used for each library and multiplexed 8 samples in total per sequencing run. PacBio® Barcoded overhang adapter kit (sequencing technology) was used for multiplexing and followed the manufacturer's instructions for the library preparations. The pooled library had a concentration of 11.4 ng/μl (50 μl total eluted volume). A SMRT Enzyme™ clean up kit was used to remove linear and single stranded DNA. The final libraries were sequenced at 2.7 million long read sequences (168-422 K reads/sample) on a Sequel II at the National Genomics Infrastructure (NGI)/Uppsala Genome Center.

Sequencing Data Analysis

The input for the analysis was de-multiplexed consensus reads obtained from PacBio® sequencing (sequencing technology) and performed with Python programming language. The fastq files were parsed into a dataframe with readID, sequence and quality columns. Data was searched for the Truseq adapter sequence and the TSO sequence to anchor the ends of each of the reads, and reads that lacked these sequences were discarded. A portion of the Truseq adapter starting in the first seven bases of either the read or its reverse complement was identified. If any of the positions matched the sequence with hamming distance 1 or less they were tagged. The same was performed for a portion of the TSO sequence. The sequences were reverse complemented as needed so that all the reads had the Truseq adapter (SEQ ID NO: 115) at the beginning and the TSO (SEQ ID NO: 114) at the end. The spatial barcode and the UMI were identified. The first 16 bases were obtained following the TruSeq adapter to determine the spatial barcode and subsequent bases determined the unique molecular identifier (UMI). Additionally, following the sequence of the UMI at least 4 bases were identified as all thymines (e.g., the poly(dT) capture domain) and filtered out of the reads that had any other bases within that interval. Any read with a UMI identified as a poly(dT) sequence was removed. The end of poly(dT) region is defined as the first matching position for the pattern '[^1]T{0,2}[^1]T{0,2}[^T]'.

Clonality Analysis and Visualization

To run MIXCR (version 3.0.3), poly(dT) and TSO sequences were trimmed and the reads were written to a new fastq file. The reads were analyzed with MIXCR and the following command:

'mixer analyze shotgun -s hsa -align -OsaveOriginalReads=true -starting-material ma<TrimmedFastq><SampleName>'

The following MIXCR command was performed to report alignments for each read:

'mixer exportAlignments -f -cloneIdWithMappingType -cloneId -readIds -descrsR1 <SampleName>.clna <ReportFile>'

The resulting tabular file was used to assign reads to the clonotypes in MIXCR output. Any reads that did not map to any clone were filtered out (cloneID==−1), then the reads were grouped in a table by the spatial barcode and UMI and counted how many reads were present and how many clones were associated with each UMI. UMIs that were assigned to more than one clonotype were filtered out, since they are likely due to PCR or sequencing errors.

The resulting clonotype count matrices were subsequently loaded into R (R Core Team, A language and environment for statistical computing, *R Foundation for Statistical Computing*, (2017)). Tissue images, spatial coordinates and total gene expression counts obtained through the Visium platform and SpaceRanger pipeline were also loaded, and one Seurat object (Stuart et al. Comprehensive Integration of Single-Cell Data, *Cell*, 177(7) (2019)) per sample type (tonsil and breast tumor tumor) was created using the STutility package (Bergenstrahle et al., Seamless integration of image and molecular analysis for spatial transcriptomics workflows, *BMC Genomics*, 21(1), (2020)). The clonotype count matrix was extended by adding any missing spatial barcodes that were present in the total gene expression count matrix, and filled with zero counts for all added barcodes. The new, extended matrix was loaded as a new assay into the Seurat object, where genes and clonotypes were visualized on the tissue images using built-in functions of the STUtility package.

Cell Processing for Single-Cell RNA Sequencing

Single cell suspensions from five breast tumor regions (Tumor A-E) were prepared by enzymatic tissue dissociation using the human Tumor Dissociation Kit (Miltenyi Biotec, 130-095-929) and gentleMACS dissociator (Miltenyi Biotec). Cell suspensions were stained with the Zombie Aqua Fixable viability dye (Biolegend, 423101) at room temperature for 20 minutes, then washed with Phosphate Buffered Saline (PBS). The cells were incubated with Human TruStain Fc block (Biolegend, 422302) for 10 minutes to limit non-specific antibody binding, then stained for 20 minutes with anti-EPCAM (1:40, Biolegend, 324206) and anti-CD45 (1:40, Biolegend, 304021) in FACS buffer (PBS+0.5% Bovine Serum Albumin). The cells were subsequently washed and resuspended in FACS buffer. Fluorescence-activated cell sorting (FACS) using an influx flow cytometer (BD Biosciences) was performed to sort live EPCAM+

CD45+ single cells an Eppendorf tube for 10× Genomics® (sequencing technology) Chromium Single Cell gene expression analysis. Single stain controls (e.g., cells and beads) and fluorescence minus one controls (FMO), containing all the fluorochromes in the panel except the one being measured, were used to set voltages and to define the proper gating strategy.

10× Genomics® (Sequencing Technology) Chromium Single-Cell Library Preparation and Sequencing Single-cell gene expression and VDJ clonotype libraries were generated from EPCAM-CD45+ cells using the 10× Genomics® (sequencing technology) Chromium Single Cell 5' assay following the manufacturer's instructions. Libraries were profiled and quantified using a Bioanalyzer High Sensitivity DNA kit (Agilent Technologies) and Qubit High sensitivity kit (Thermo Fischer Scientific). Final single-cell gene expression libraries were sequenced (aiming for at least 30,000 reads per cell) on a NovaSeq 6000 SP flowcell (ILLUMINA® (sequencing technology) 150-8-8-150 read set-up) by the National Genomics Infrastructure, SciLifeLab.

Single-Cell Gene Expression and VDJ Data Processing

Sequencing outputs were processed by Cell Ranger (version 5.0, 10× Genomics® (sequencing technology)). Gene-barcode count matrices were analyzed with the Seurat package (version 4.0, Satija Lab). Two steps of filtering were introduced here. First, raw gene expression matrices were subset by the barcode list in VDJ output, including T cell subsets and B cell subsets. Based on the UMI count, gene count, and mitochondrial percentage of raw gene expression matrices and their subsets, each threshold was selected to keep the maximum count of high-quality cells and avoid losing T and B cells which have VDJ sequencing outputs. Second, doublets in each sample were detected and filtered out by HTODemux( ) function in Seurat. All samples were integrated and scaled into one count matrix by Seurat. Dimension reduction, UMAP generation, and clustering, were performed on the merged dataset by Seurat. The merged dataset was clustered by a gradient of the resolution, from 0.2 to 2. The final resolution was determined by the significance of top-listed differentially expressed genes in each cluster. Cell types were annotated by differentially expressed genes and their marker genes expression level. All dimension reduction and annotation results, along with the VDJ output files were imported into Loupe Browser (version 5.0, 10× Genomics® (sequencing technology)) and Loupe VDJ Browser (version 4.0, 10× Genomics® (sequencing technology)) for interactive analysis.

Semi-Nested PCR

After hybridization capture and post-capture PCR amplification (14 cycles), semi-nested PCR reactions were performed with the following primers: V primers targeting either the TRAV or TRBV genes, 5' of the CDR3 region (i.e. 'Outer' TRAV or TRBV primers, see Table 3 for sequences) and a primer ('partRead1', see Table 3) targeting the universal partial read 1 sequence present on the transcripts in Visium cDNA libraries. PartRead1 is also compatible with TruSeq indexes to allow multiplexing of samples for sequencing. For the semi-nested PCR experiments, the Visium cDNA was further pre-amplified prior to hybridization capture to generate more input needed for testing. The Outer V primer PCR input was 1-5 ng of hybridization captured cDNA from two breast tumor tissue Visium libraries (replicate, adjacent sections) and the reaction was run with KAPA HiFi HotStart ReadyMix (2λ) (KAPA Biosystems). All primers were diluted 40× for a final concentration of 2.5 μM (Integrated DNA Technologies). The PCR was run for 15 cycles under the following conditions: 1. 98° C. 5 min; 2. 98° C. 20 sec; 3. 65° C. 30 sec; 4. 72° C. 1:30 min; 5. Repeat steps 2-5 14× for a total of 15 cycles; and 6. 72° C. 7 min.

Quantitative real-time PCR (qPCR) was performed to determine the appropriate number of cycles (to avoid exponential amplification). The Outer V primer PCR product was purified using AMPure beads (0.6×), followed by two 80% EtOH washes. The Outer V primer PCR product was eluted in EB buffer after incubation at 15 min at 37° C. The cleaned up PCR product was quantified using Qubit and BioAnalyzer (Agilent). 3-5 ng of each PCR product was used as input to the subsequent Inner V primer PCR.

The Inner V primer PCR was performed with the following primers: V primers targeting either the TRAV or the TRBV gene, close/adjacent to the CDR3 region (e.g., 'Inner' V primers) and the same universal partial read 1 primer as described for the Outer V primer PCR ('partRead1'). These Inner V primers have a handle compatible with TruSeq indexing. The primer concentrations and reagents were as described for the OUTER V primer PCR. qPCR was used to determine the optimal number of cycles (7). The following conditions were used for the PCR reaction: 7. 98° C. 5 min; 8. 98° C. 20 sec; 9. 72° C. 30 sec; 10. 72° C. 1:30 min; 11. Repeat steps 2-5 14× for a total of 15 cycles; 12. 72° C. 7 min.

The same AMPure bead-clean up and ethanol washes were performed as described above. The final eluted PCR product was quantified using Qubit and BioAnalyzer (Agilent). The samples were PCR indexed using TruSeq Indexes (5 cycles) and sequenced on a Novaseq sequencing instrument using a short read 1 and a longer read 2 to capture the entire CDR3 region and part of the constant region from the 5' end.

Target Enrichment with Hybridization Capture for TCR and BCR Sequences

Figure 12:
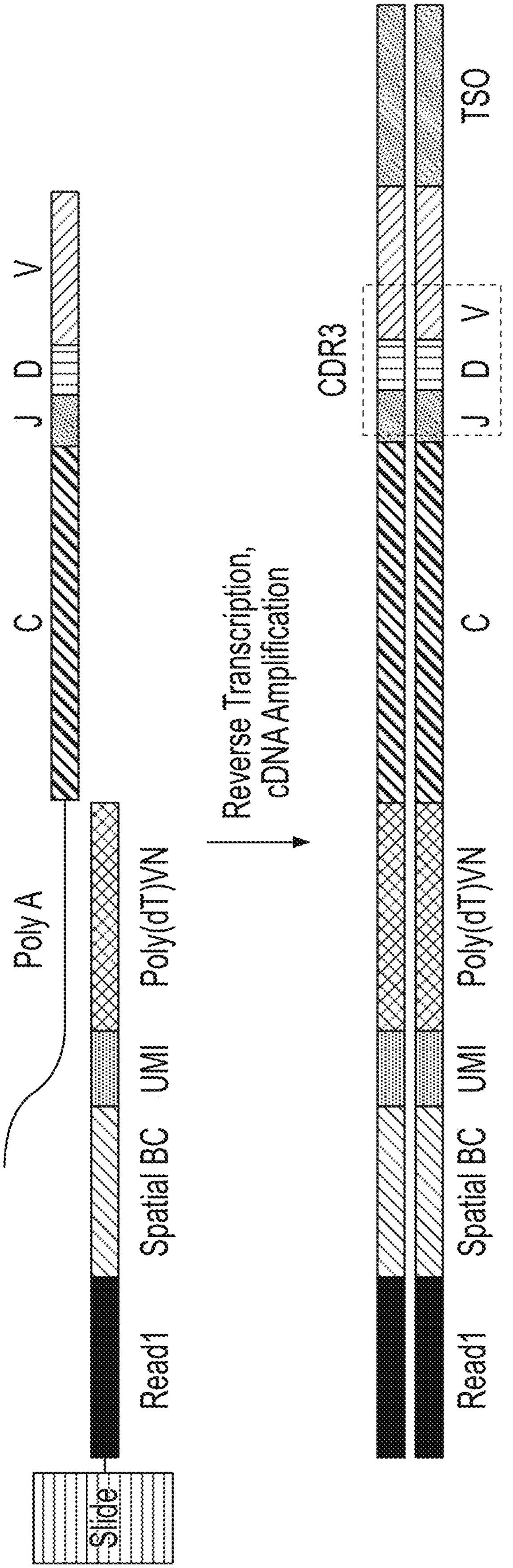
FIG. 12 shows an exemplary capture probe with a poly (dT) capture domain (top) followed by reverse transcription to generate cDNA of an analyte.
Figure 13:
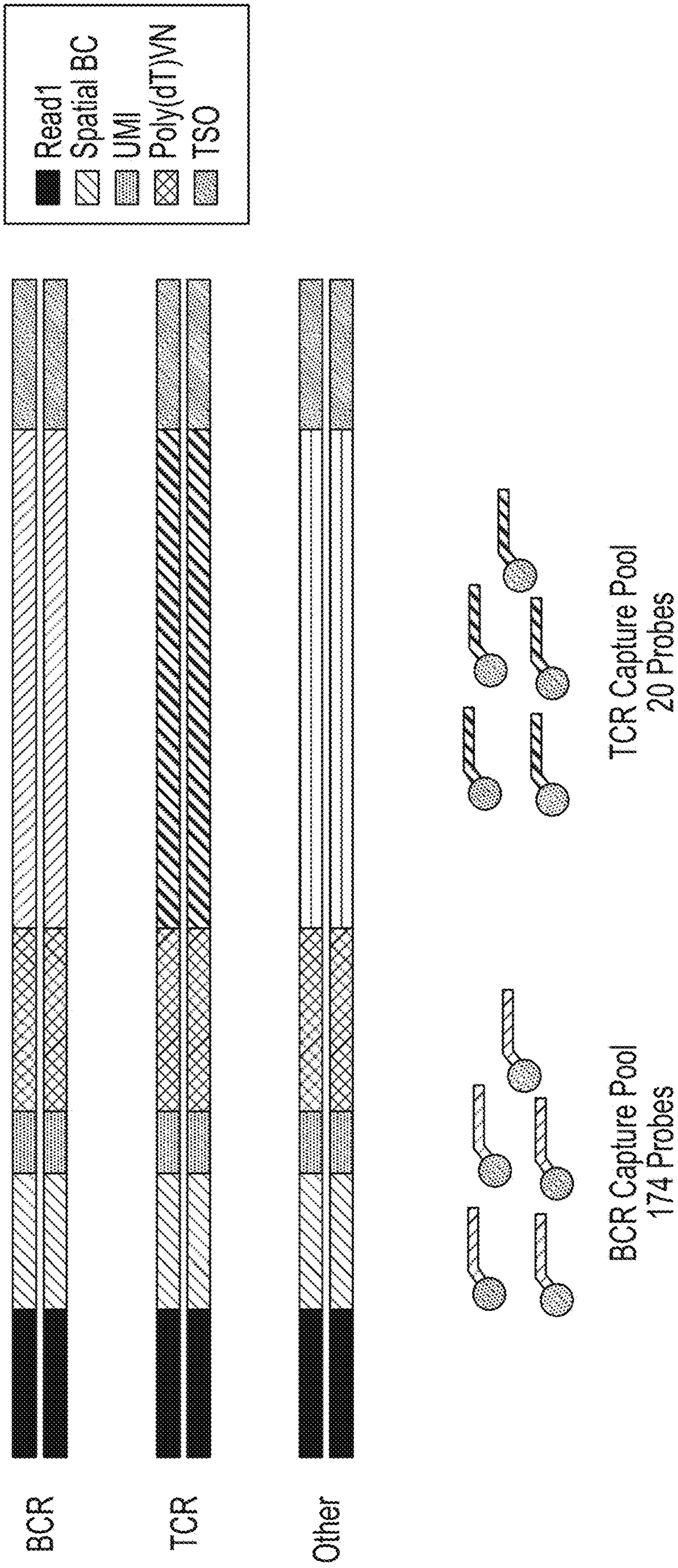
FIG. 13 shows cDNA libraries for either B-cell receptors (BCR), T-cell receptors (TCR), or other analytes and pools of BCR and TCR with enrichment hybridization probes.
Figure 14:
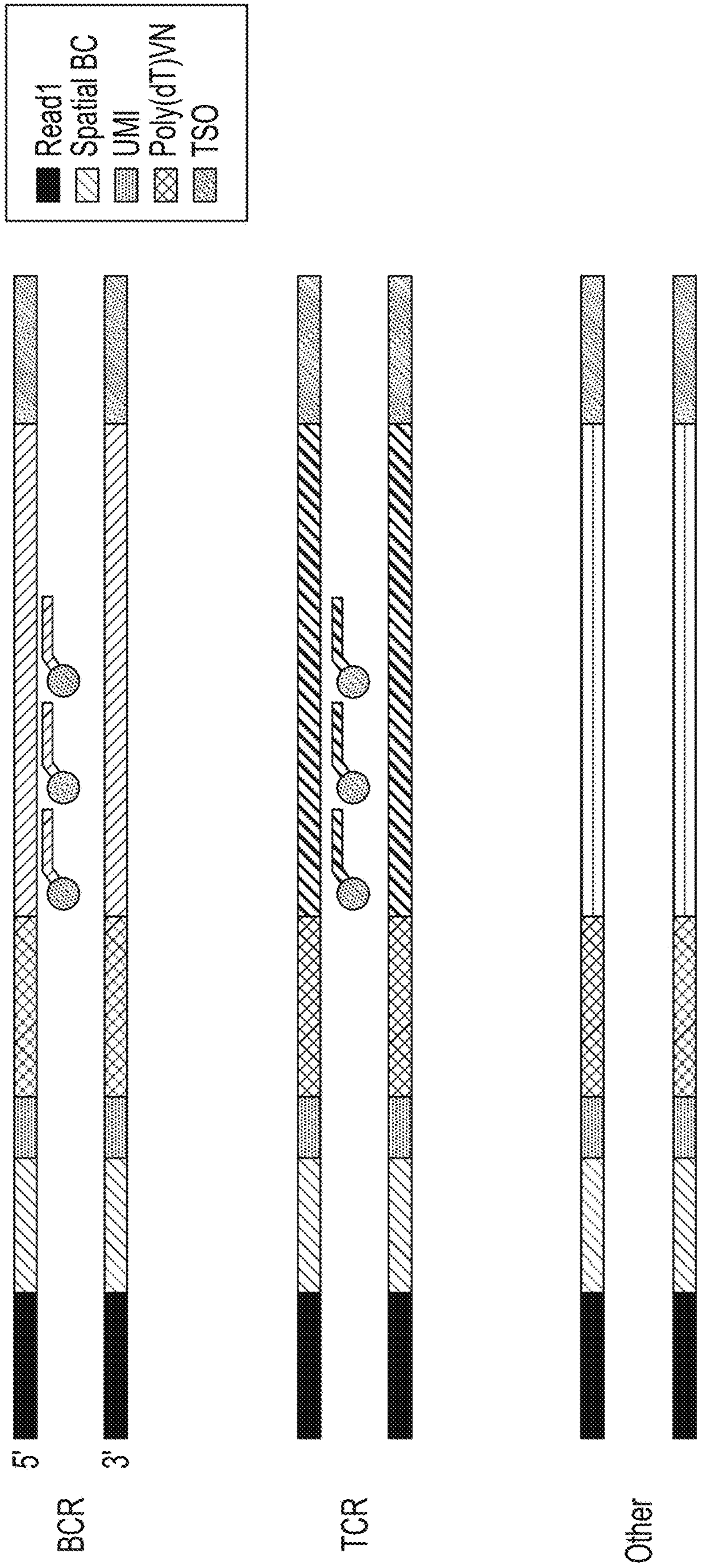
FIG. 14 shows hybridization of the BCR and TCR specific enrichment hybridization probes to their respective targets in the cDNA library.
Figure 15:
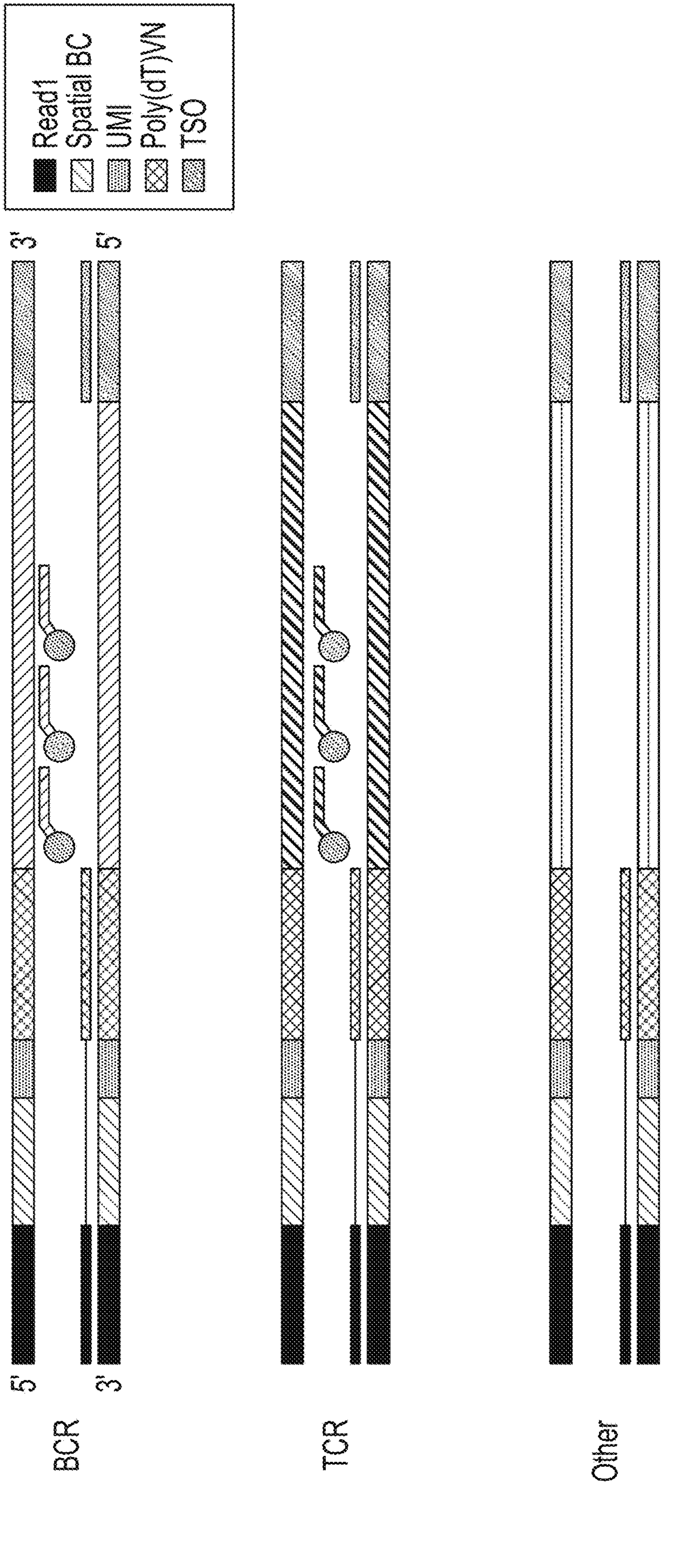
FIG. 15 shows hybridization of blocking oligonucleotides targeting various domains present in the cDNA library.

As discussed above BCR (IGH, IGK, IGL) and TCR (TRA, TRB) clones can be amplified using PCR from poly(dT) captured cDNA libraries, e.g., Visium (10× Genomics® (sequencing technology)). In some instances, the obtained amplicons lacked the spatial barcode. Therefore, to enrich for TCR and BCR sequences while preserving the spatial barcode and the CDR3 clonal information, a target enrichment strategy with hybridization probes (IDT technologies) was tested. Manufacturer's instructions were followed with some minor adaptations according to the methods described above. Visium cDNA from two tonsil sections (e.g., from the same tonsil, spaced 150 μM apart) were used as input material. FIG. 12 shows poly(A) capture with a poly(T) capture domain. A poly(T) capture domain can capture other mRNA analytes from a tissue, including mRNA analytes encoding immune cell receptors, however, immune cell analytes were enriched using a hybridization enrichment probe strategy. BCR hybridization probes (n=174) were designed to span all BCR constant genes (e.g., IGH, IGL, IGK), see Table 3. Similarly, TCR hybridization probes (n=20) were designed to target the TCR constant genes (e.g., TRA, TRB), see Table 3. FIG. 13 shows an exemplary cDNA library that would include BCR, TCR, other analytes and a pool of hybridization probes specific for BCR and TCR analytes. The Visium cDNA samples were hybridized with the hybridization enrichment capture probes and the hybridization reaction was performed overnight (FIG. 14), in the presence of blocking oligos as shown in FIG. 15 targeting Read 1, Poly(dT)VN, and TSO sequences present on the transcripts in the cDNA library. After a series of washes, a post-capture PCR reaction was performed, which amplifies all, or a portion of, the captured analyte pool. Indexed PacBio® (sequencing technology) libraries were prepared for long read sequencing from the eluted PCR products. To avoid unnecessary PCR cycles, which can introduce artifacts, errors, and chimeric fragments, barcoded overhang adapter ligation was performed to add unique sample indexes to each sample. The enriched libraries were then sequenced, de-multiplexed, and analyzed.

Figure 16A:
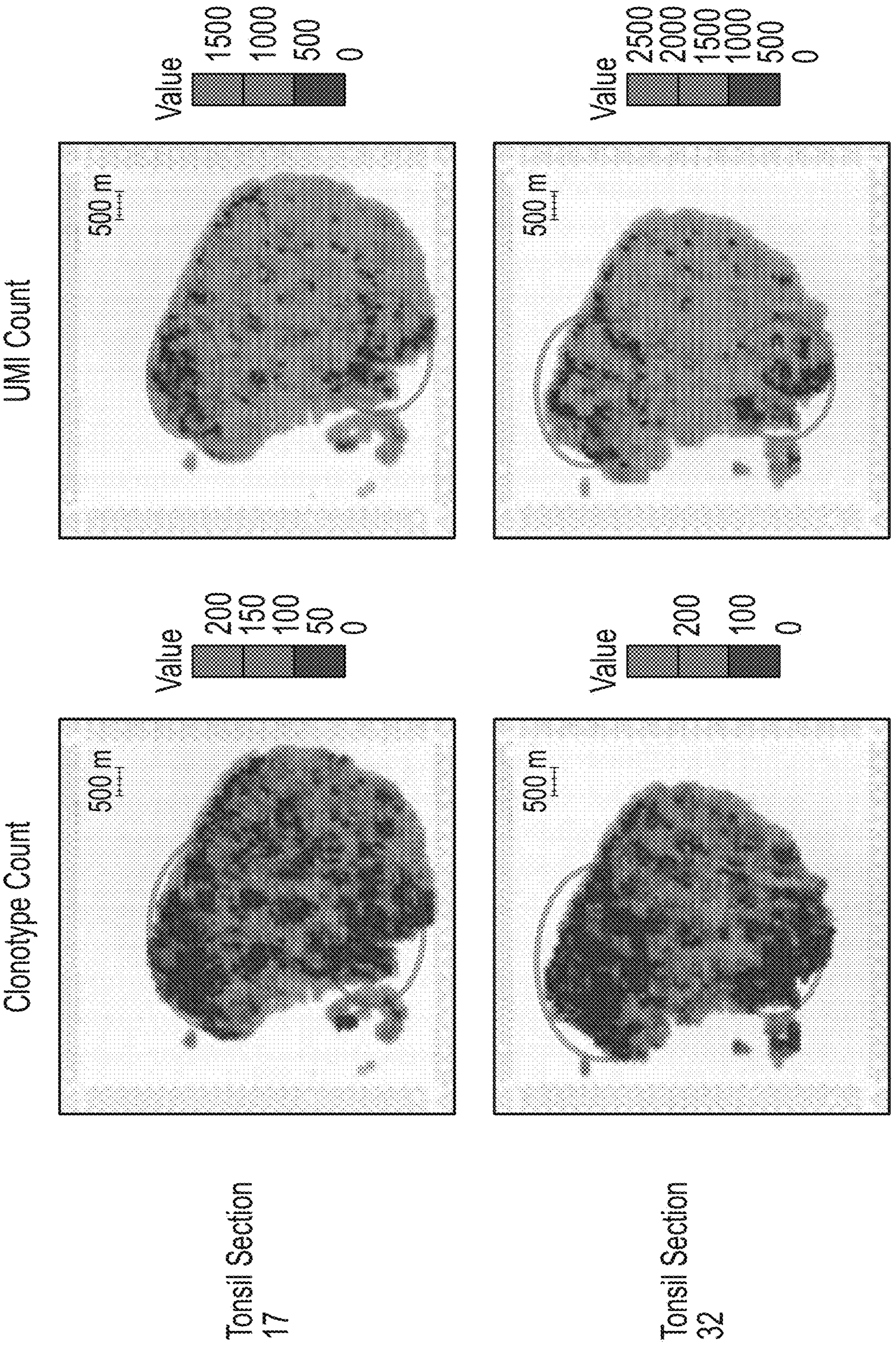
FIG. 16A shows replicate tonsil sections (top and bottom) and detection of BCR and TCR clonotype count (left) and BCR and TCR unique molecular identifier count (right).
Figure 16B:
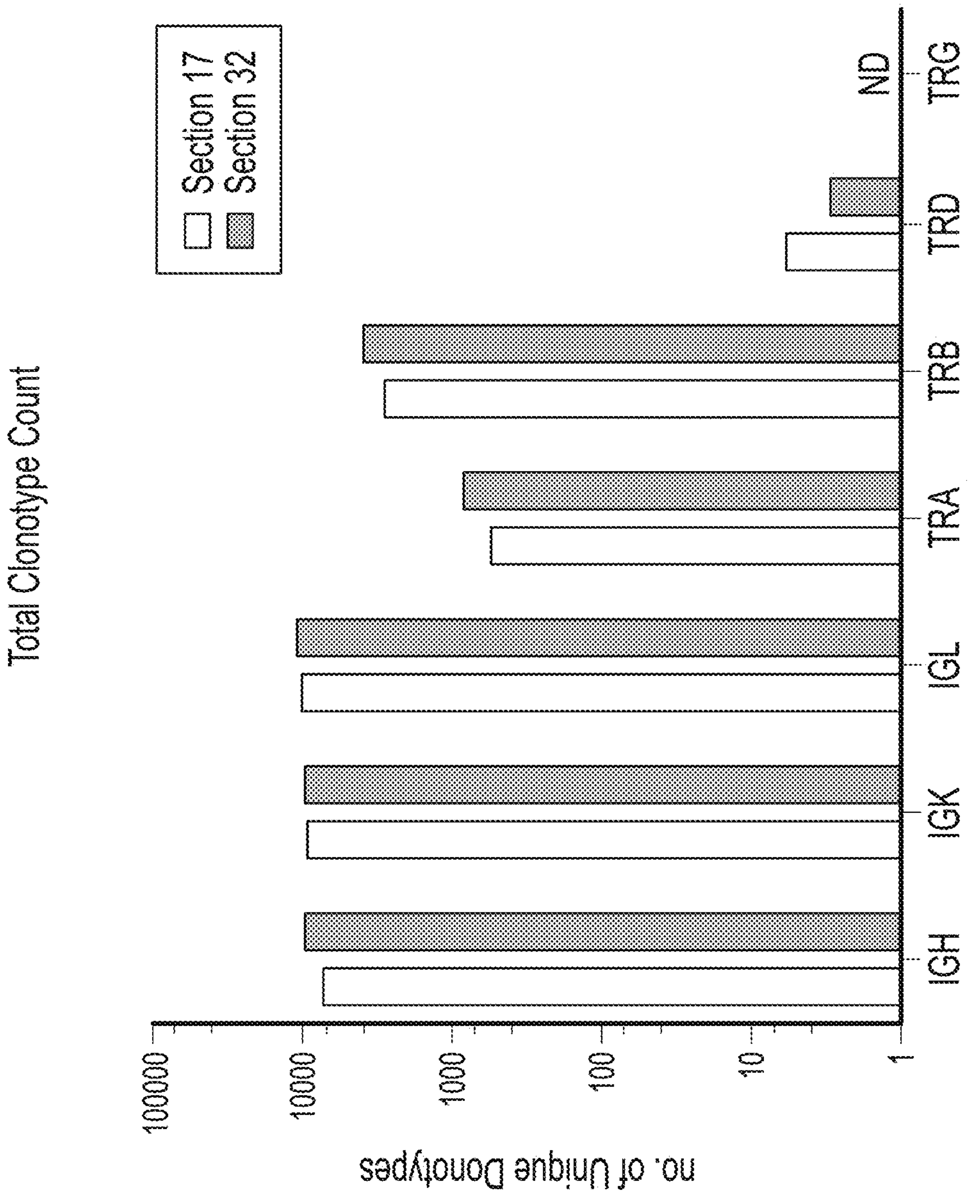
FIG. 16B shows a graph showing the total number of unique clonotypes found in the replicate tonsil sections from FIG. 16A.
Figure 16C:
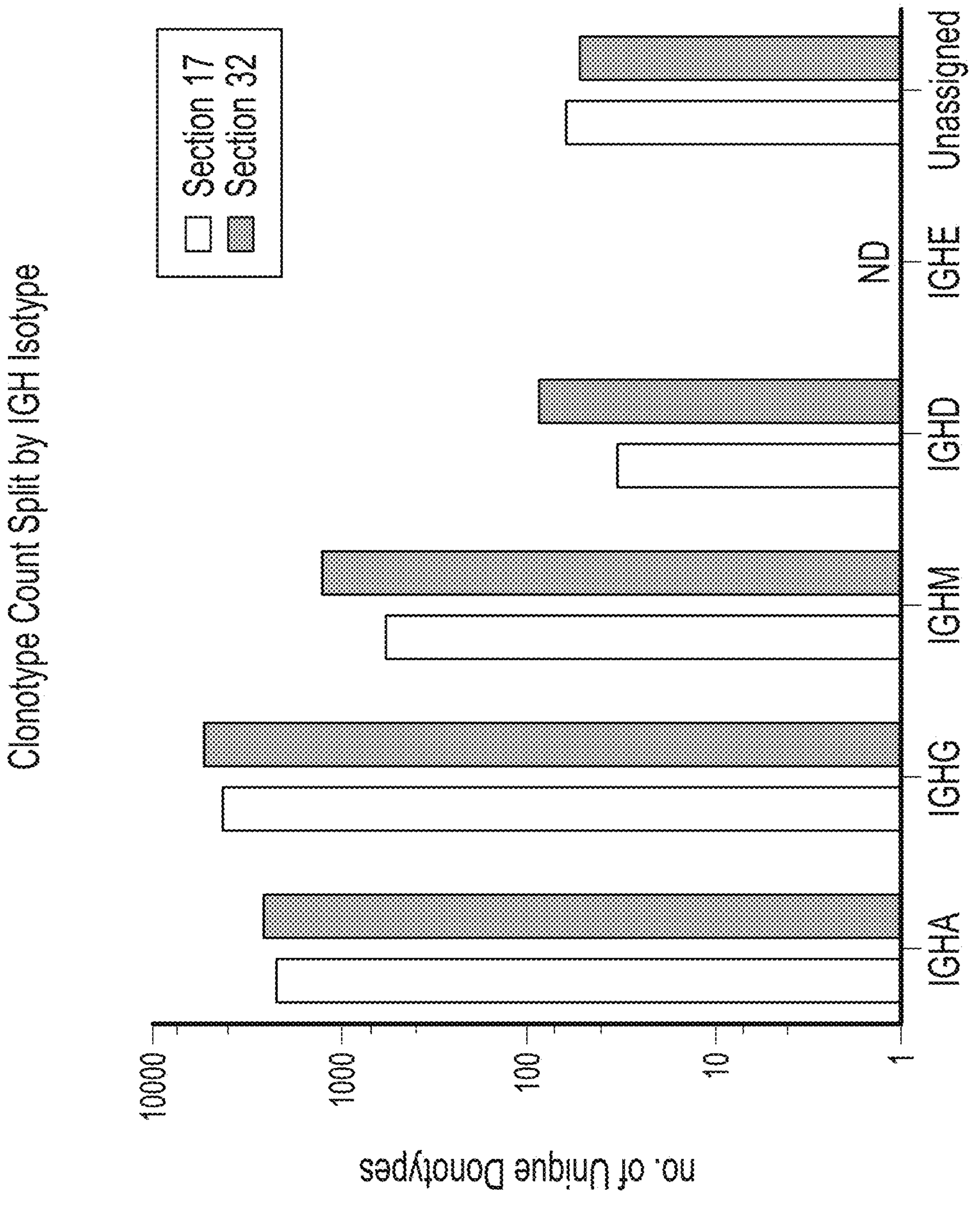
FIG. 16C shows a graph showing the clonotype count split by IGH isotype found in the replicate tonsil sections from FIG. 16A.

Clonotype Numbers cDNA prepared from captured immune cell mRNA analytes were enriched via a hybridization capture approach as described above and combined with PacBio® (sequencing technology) long read sequencing. The resulting data successfully identified spatially barcoded BCR and TCR clones from tonsil Visium libraries (FIGS. 16A-C). A clone was defined as a single-chain with a unique combination of VDJ gene segments and a CDR3 region, based on MIXCR analysis (previously described) (Bolotin et al., (2015)). FIG. 16A shows the distribution of the clonotype (left) and UMI (right) count for two tonsil sections, spaced 150 μm apart, from the same tonsil. The number of clonotypes per spot ranged between 0 and 300. For each tonsil sample, approximately 10,000 IGH, IGK and IGL clones (BCR) were identified (FIG. 16B). For TCRs, 3,437 TRB clonotypes and 687 TRA clonotypes were captured on average. The approximately five-fold lower capture of TRA clones was likely due to the lower expression of TRAC on a per cell basis consistent with previous results. The date demonstrate more successful capture of BCR clones (relative to TCR clones), which, without wishing to be bound by theory may be due to several reasons, including a higher receptor expression by B cell lineage cells (particularly plasma cells) and a higher number of cells per B cell clone. Furthermore, all IGH isotypes were found, except for IGHE, which is expressed by very rare IgE positive B cell lineage cells (FIG. 16C). A small number of IGH clones were not assigned a constant gene. As expected, IGHG and IGHA-expressing cells dominate, followed by IGHM. The BCR light chains (IGK and IGL) were expressed at comparable numbers.

Collectively, the data demonstrate that target enrichment with hybridization probes from Visium cDNA mRNA libraries successfully enrich BCR and TCR clones from lymphocyte rich tissue.

B and T Cell Spatial Segregation in the Tonsil

Figure 17A:
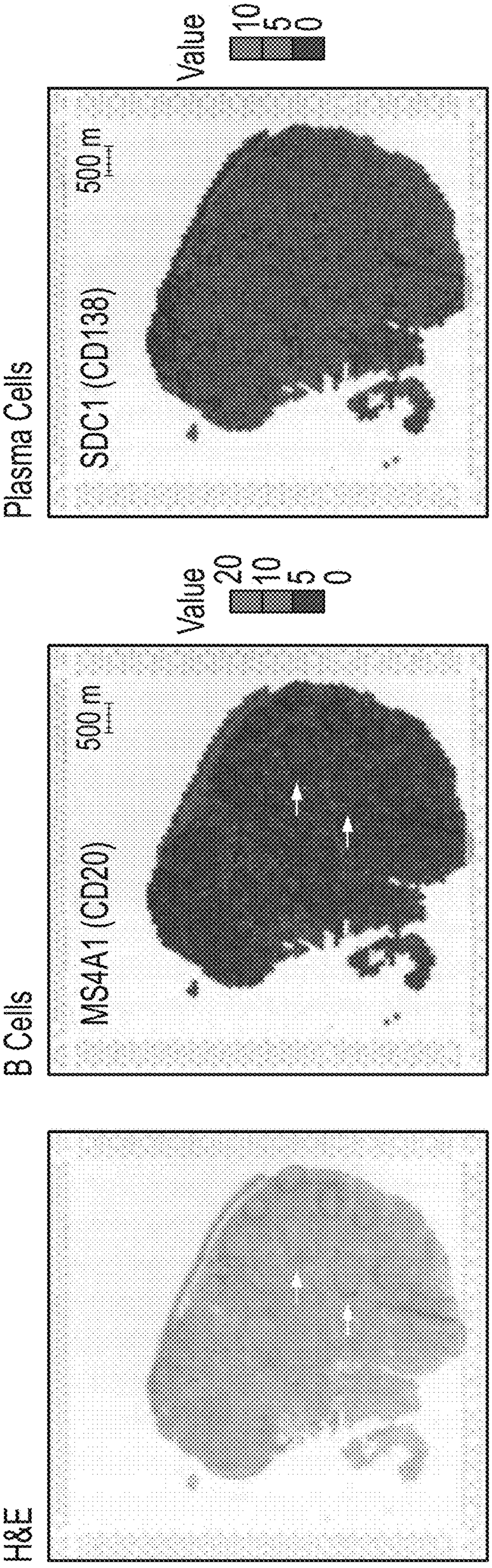
FIG. 17A shows H&E stained tonsil tissue (left), CD20 spatial expression (middle), and CD138 expression (control).
Figure 17B:
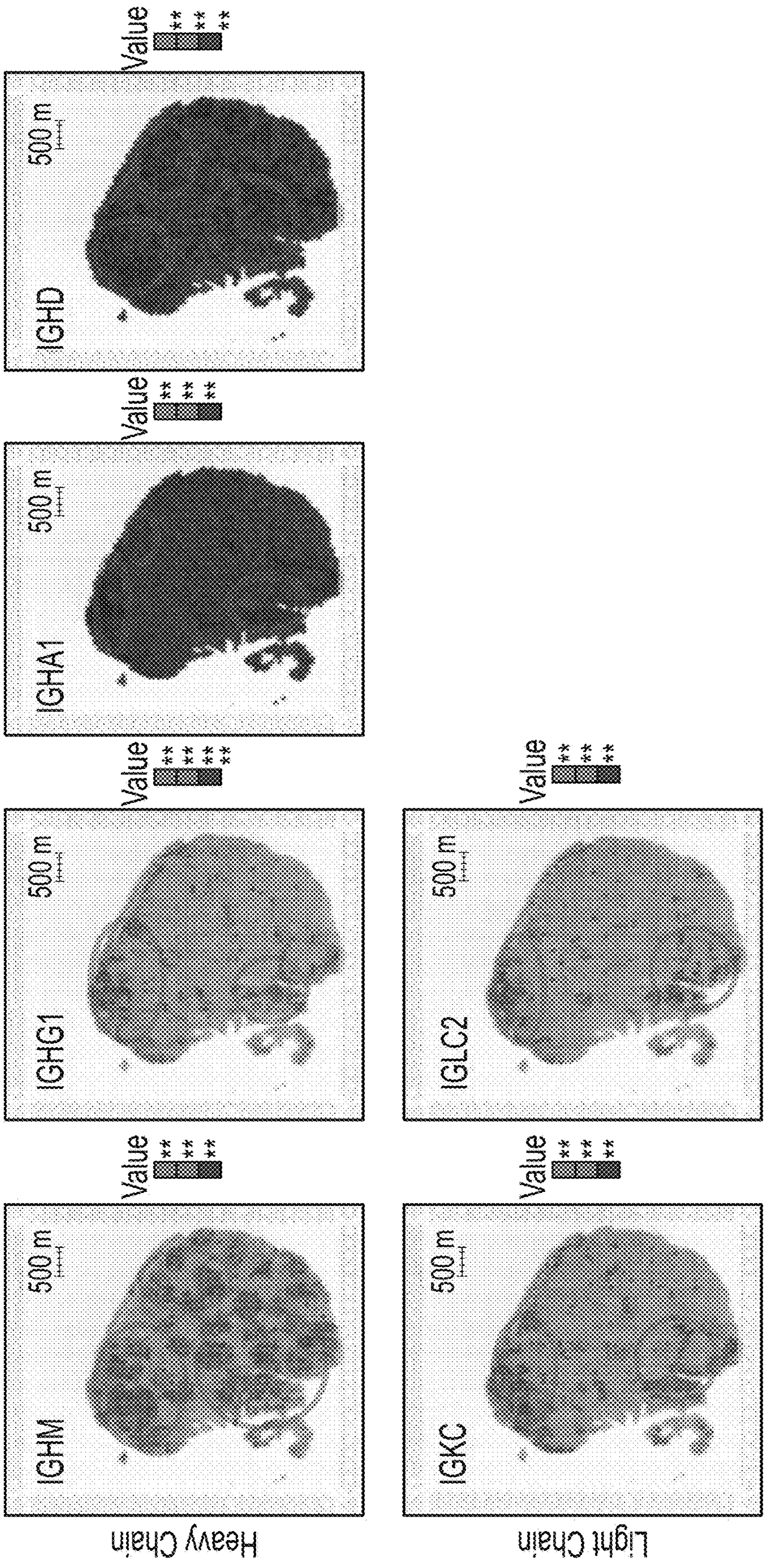
FIG. 17B shows spatial expression in tonsil tissue of the heavy chain IGH constant gene (top) including IGHM, IGHG1, IGHA1, and IGHD and the light chain (bottom) including IGKC and IGLC2.
Figure 17C:
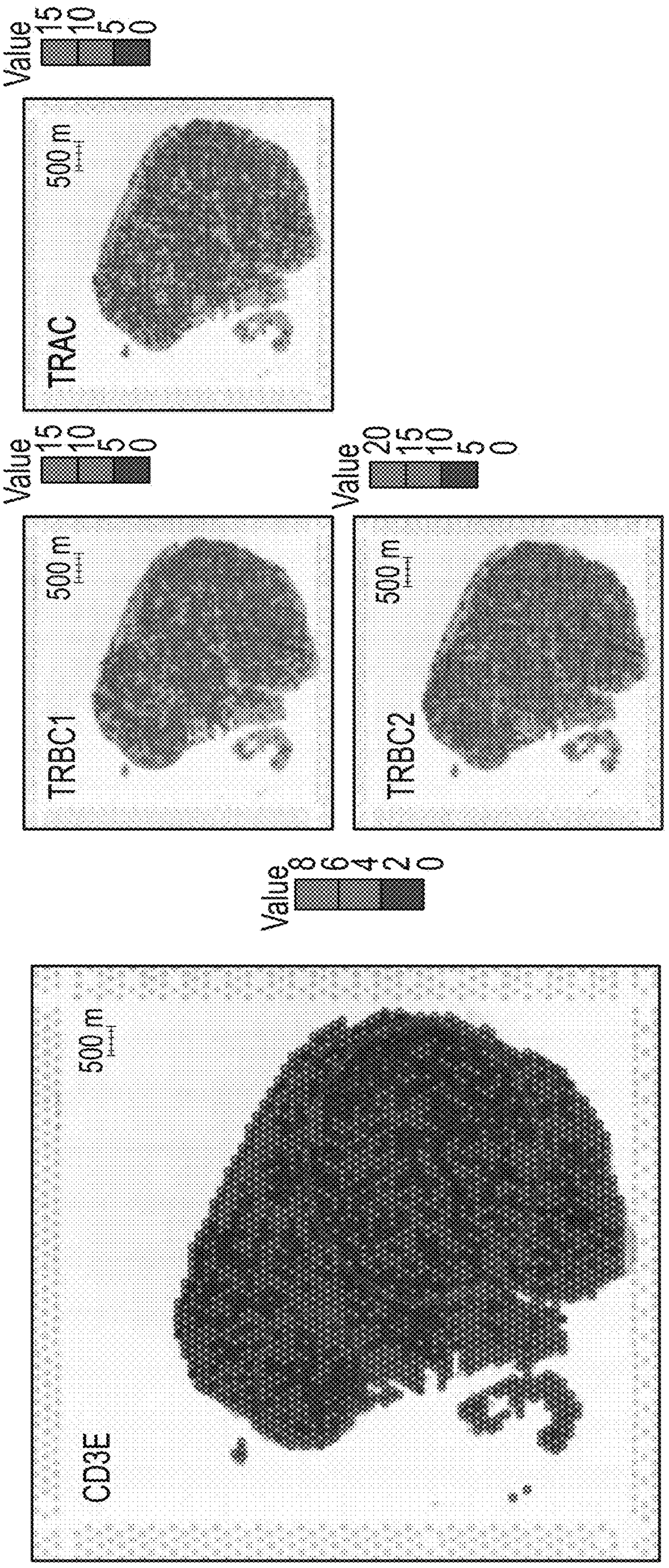
FIG. 17C shows T-cell specific spatial expression for CD3E, TRBC1, TRABC2, and TRAC in tonsil tissue.

It was expected that with tonsil and similar tissues, e.g., lymph node, B cell clones would segregate mainly in follicles or germinal centers, in which B cell clonal selection and expansion occurs. In the Visium gene expression data, MS4A1, which encodes CD20 a B cell specific gene, was expressed in a cluster-like pattern that corresponded with increased cell density as visualized by the H&E staining, suggestive of B cell follicles ("B cell follicles") (FIG. 17A, arrows). In contrast, SDC1, which encodes CD138 and is considered a reliable plasma cell enriched gene, was expressed mainly at the borders of the tissue and around B cell follicles, as expected from plasma cells (FIG. 17A). This cell type distribution was also supported by the spatial expression of the IGH constant gene (FIG. 17B, top), IGHM, which is expressed by B cells prior to class switching into other isotypes and was mostly enriched in the same B cell follicle-like areas as MS4A1. Similarly, IGHD, though more sparsely expressed, was also enriched in the B cell follicular areas. For other IGH isotypes (FIG. 17A, top) and the light chain (FIG. 17B, bottom), the highest gene expression was mainly outside B cell follicles, suggestive of increased expression by plasma cells. Based on CD3E and TCR constant gene (e.g., TRAC, TRBC1, TRBC2) expression, T cells were likely situated outside or around B cell follicles, which corresponds well with the presence of known, so-called "T cell zones" in lymphoid tissues (FIG. 17C).

Clonotype Distribution in the Tonsil

Figure 18A:
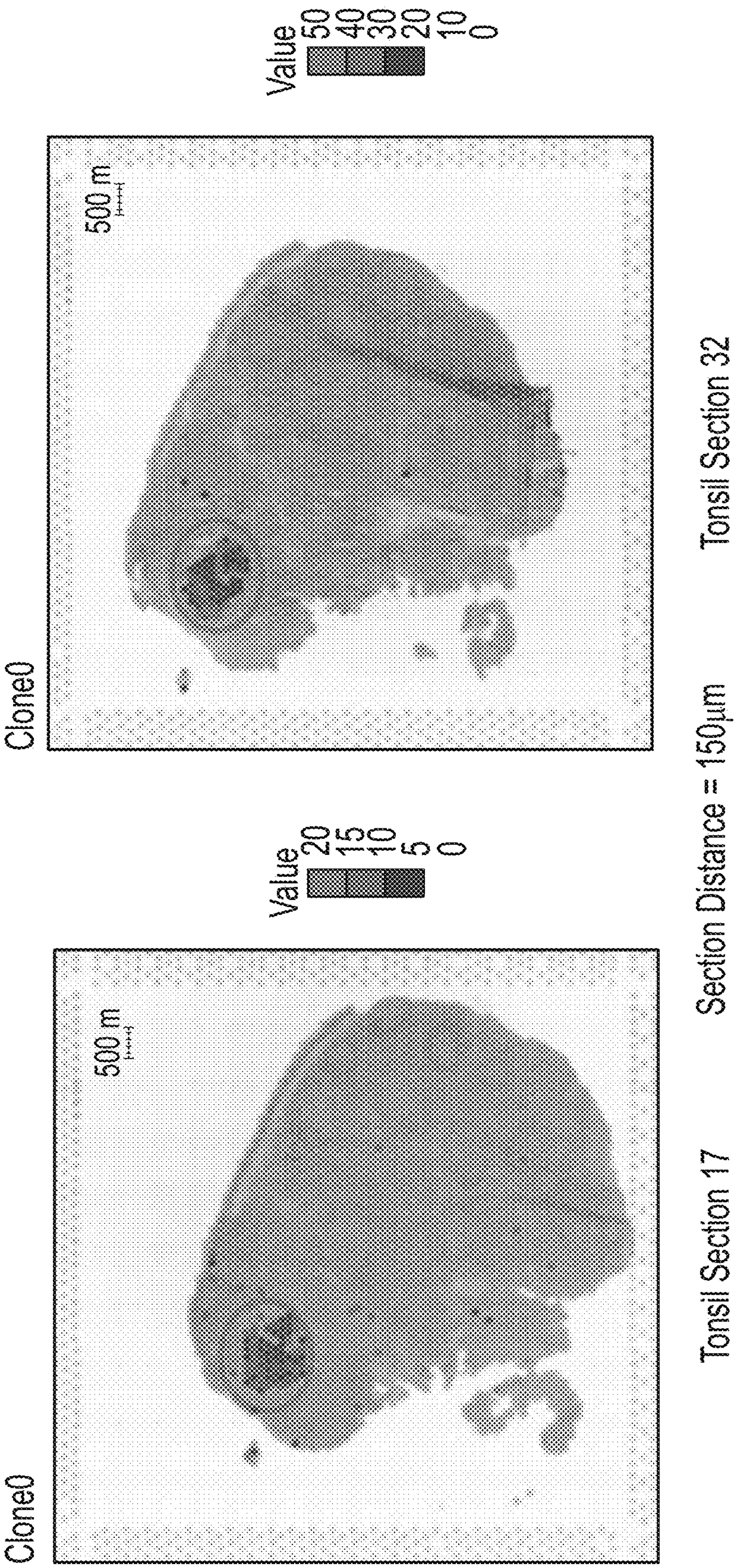
FIG. 18A shows a detected IG clone expression (IGKC) restricted to about one B-cell follicle of in tonsil tissue in replicate experiments.
Figure 18B:
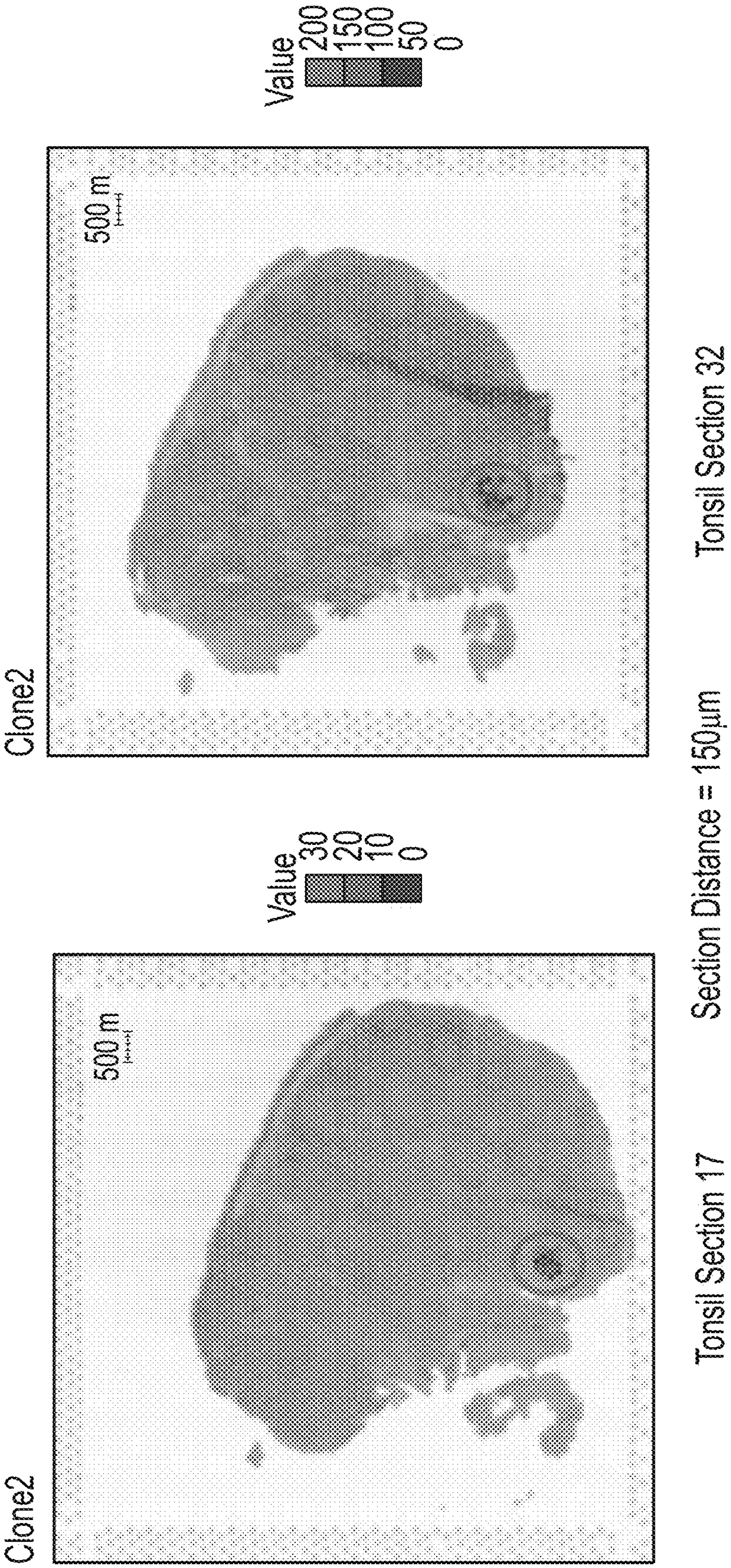
FIG. 18B shows a detected IG clone expression (IGLC) restricted to a B-cell follicle in tonsil tissue in replicate experiments.
Figure 18C:
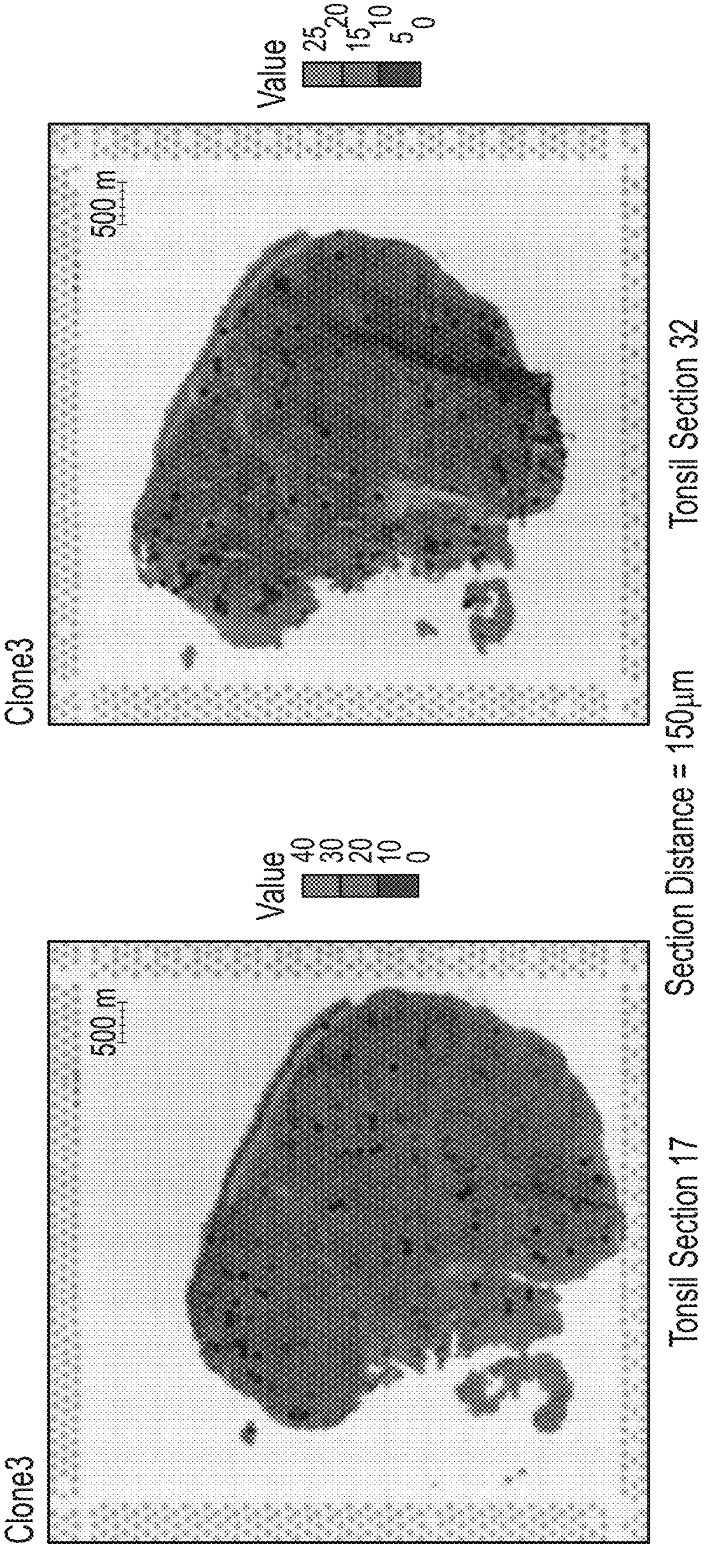
FIG. 18C shows detected IG clone expression (IGLV3-1, IGLJ2, IGLC2/IGLC3) with expression not restricted to B-cell follicles in tonsil tissue in replicate experiments.
Figure 18D:
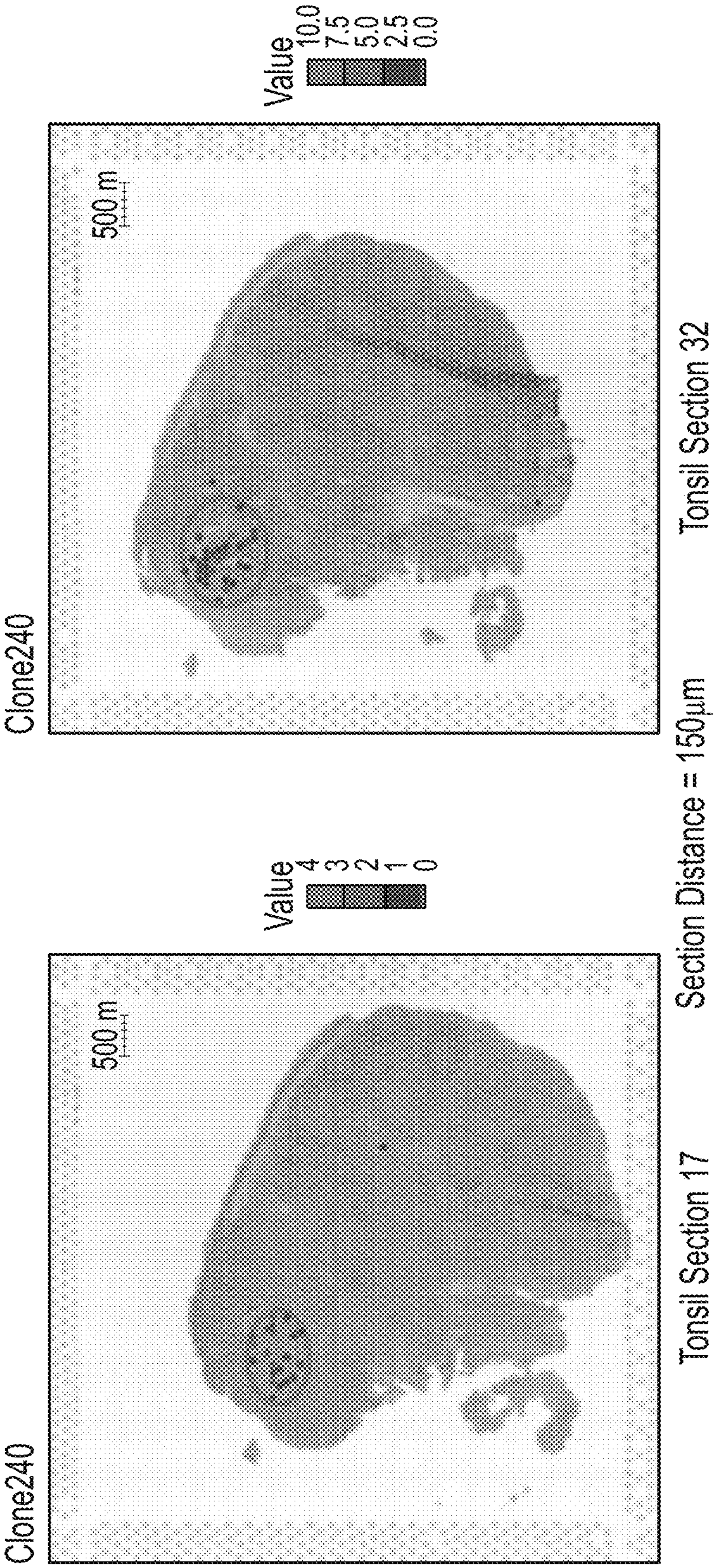
FIG. 18D shows detected IG clone expression (IGHM) in single B-cell follicles in tonsil tissue in replicate experiments.
Figure 18E:
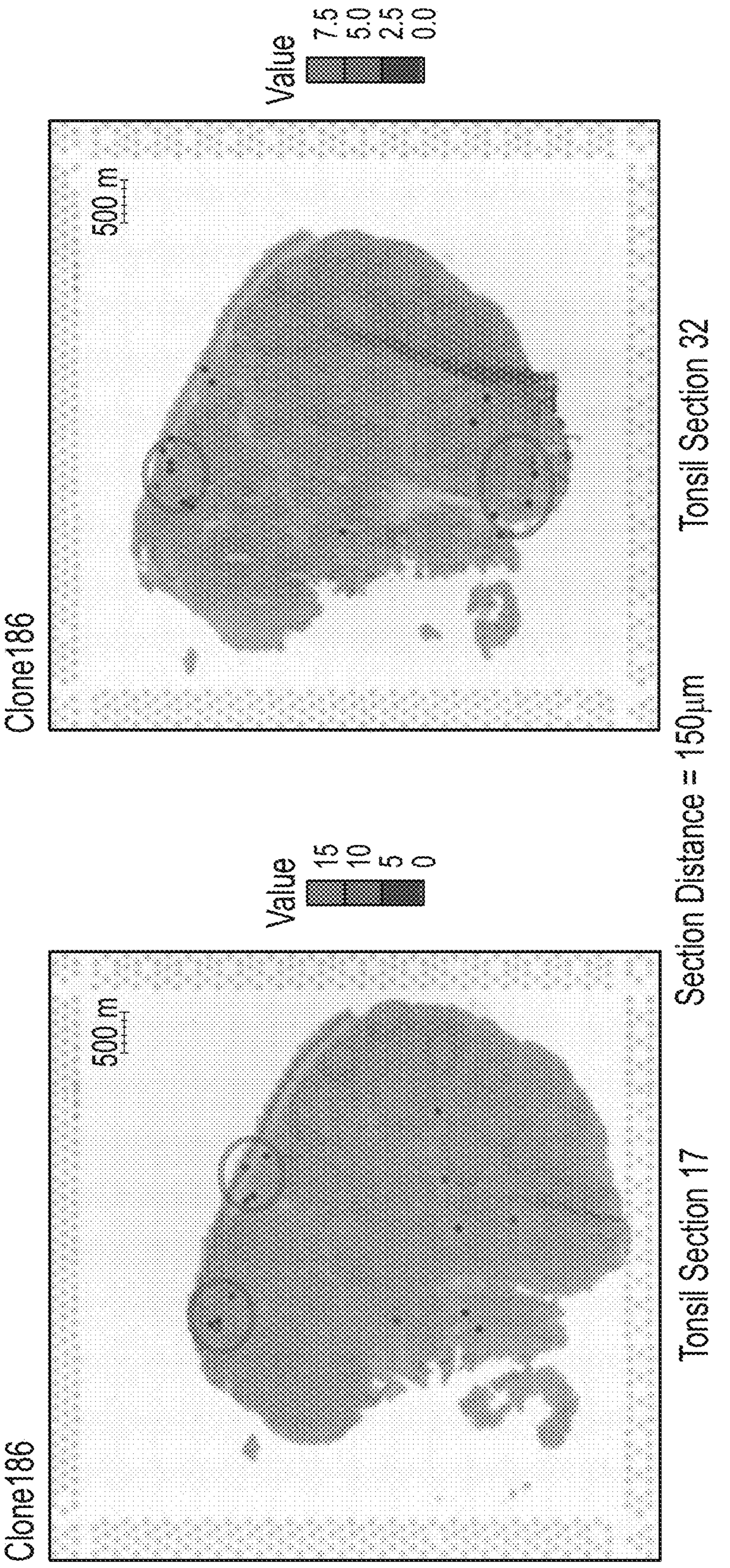
FIG. 18E shows detected IG clone expression (IGHA) expression outside B-cell follicles in tonsil tissue in replicate experiments.
Figure 18F:
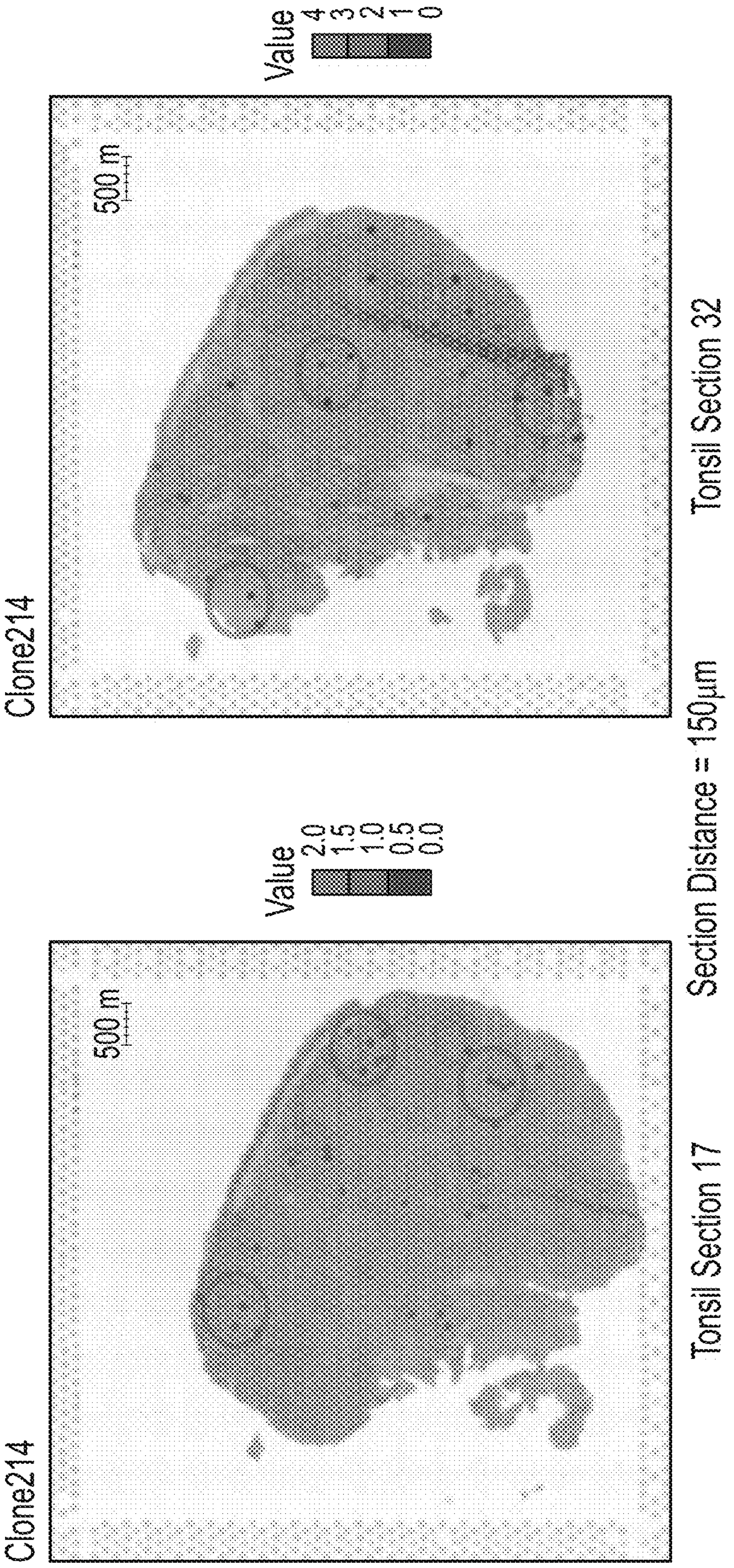
FIG. 18F shows a representative T-cell clone expression (TRB) distributed outside of B-cell follicles in tonsil tissue in replicate experiments.
Figure 18G:
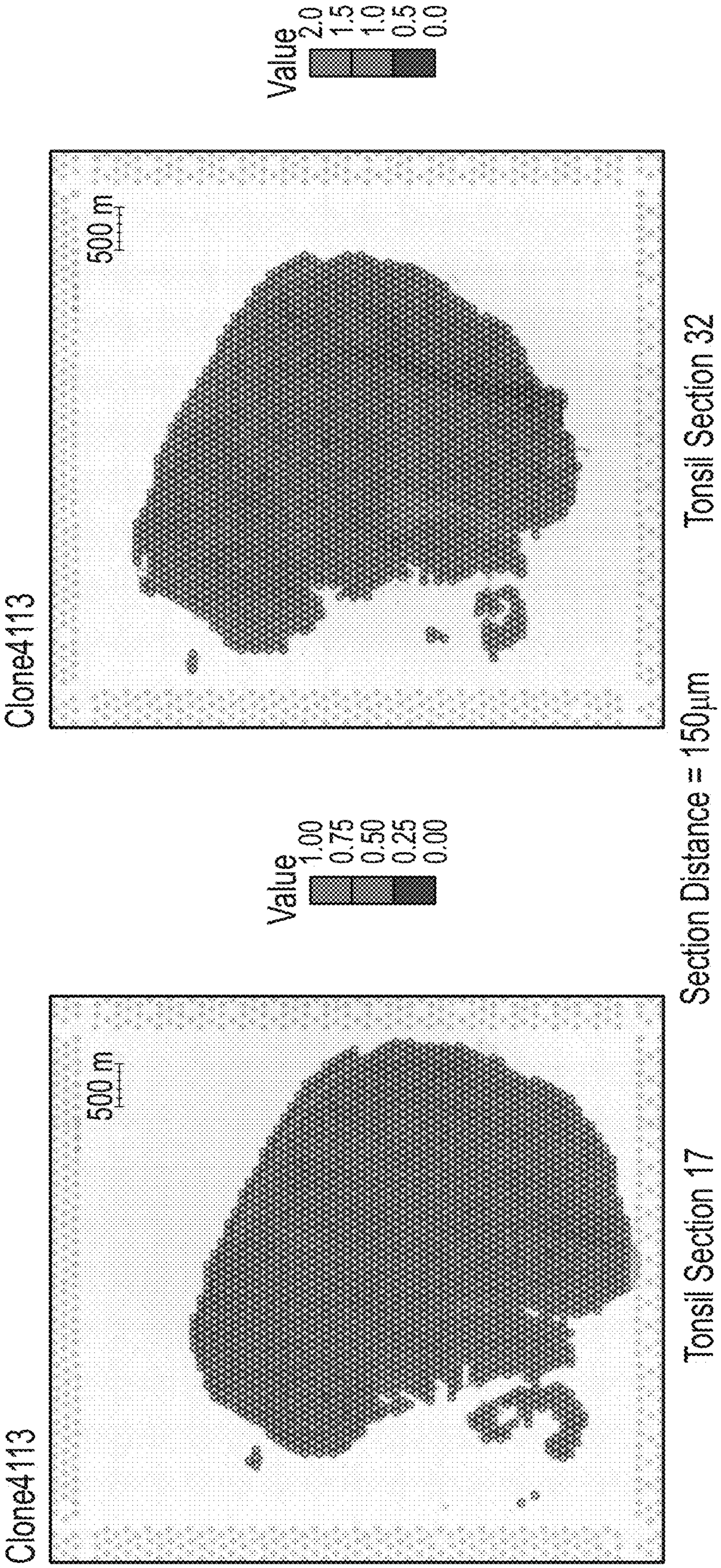
FIG. 18G shows a representative T-cell clone expression (TRA) distributed outside of B-cell follicles in tonsil tissue in replicate experiments.

The data determined whether captured clones spatially segregate in tonsil tissue relative to the observed B and T cell segregation (FIGS. 17A-C and FIGS. 18A-G). The most abundant clone, IGKC, was highly expressed almost exclusively in a single B cell follicle, as captured by the two tonsil sections spaced 150 μM apart (FIG. 18A). Similar expression patterns were also observed for many clones; e.g., in FIG. 18B, a second representative clone, IGLC, was restricted to another B cell follicle. Without wishing to be bound by theory, these light chains may be expressed by B cells under-going selection and therefore are present in higher concentrations. Large clones, whose expression was not restricted to B cell follicles, were also found (see, e.g., FIG. 18C). These results indicate that clones can be captured with distinct spatial segregation within a tissue section. In accordance with IGHM gene expression, IGHM clones were also found in single follicles (see, e.g., FIG. 18D for a representative example). In contrast, IGHA-expressing clones, tended to be expressed along the border of the tonsil tissue (FIG. 18E), consistent with the spatial IGHA gene expression (FIG. 18B). TCR clones tended to locate at the border of B cell follicles (see, e.g., FIG. 18F and FIG. 18G for representative examples of TRB and TRA clones, respectively). TCR clones also tended to have lower UMI counts per clone on average compared to the BCR clones, again, confirming that TCR transcripts are less abundant in tonsil Visium cDNA libraries and subsequently in the enriched libraries.

Target Enrichment of Lymphocyte Receptors in Breast Tumor Tissue

Figure 19A:
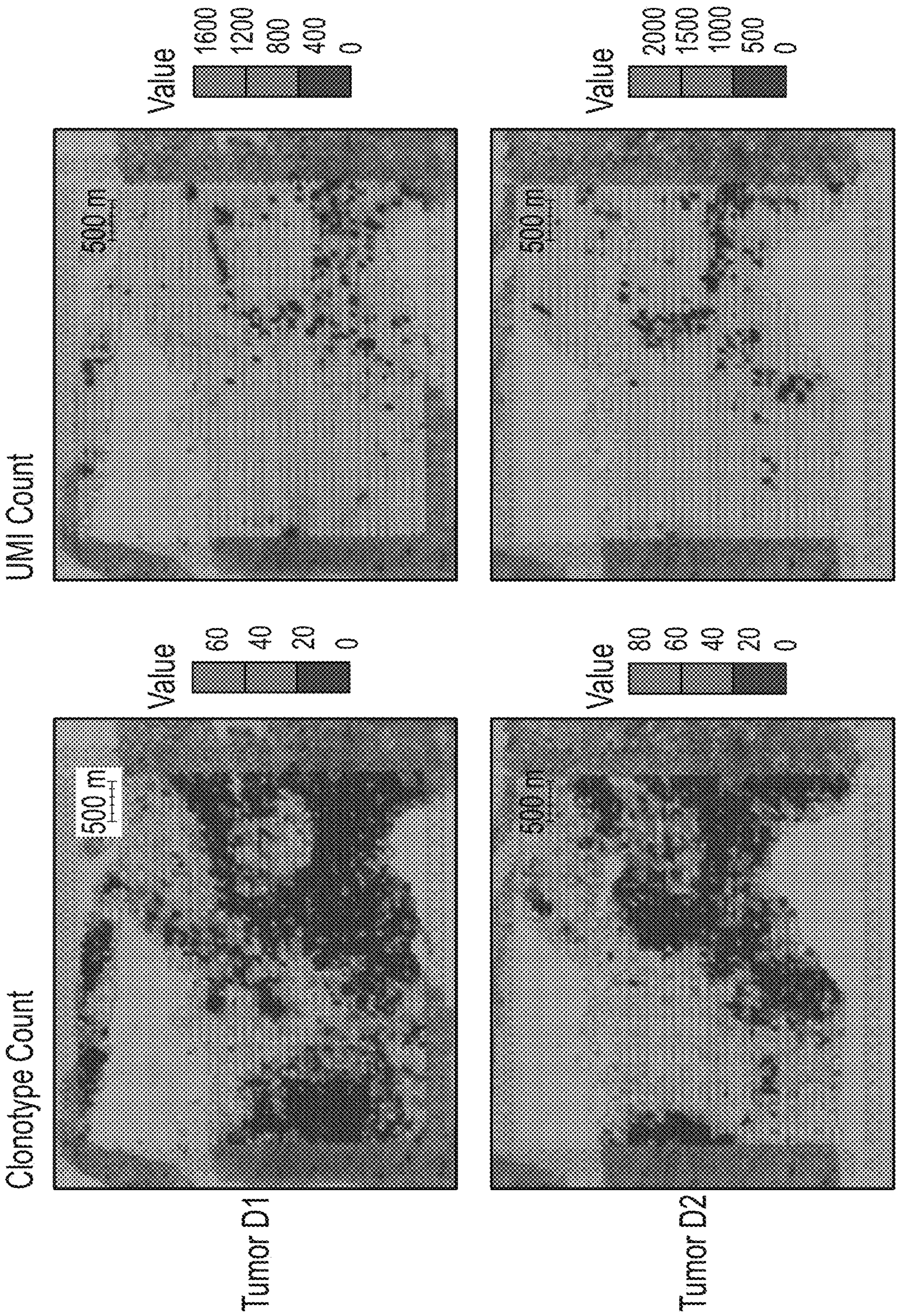
FIG. 19A shows clonotype distribution in replicate breast tumor samples (Tumor D1, Tumor D2) and clonotype count (left) and UMI count (right).
Figure 19B:
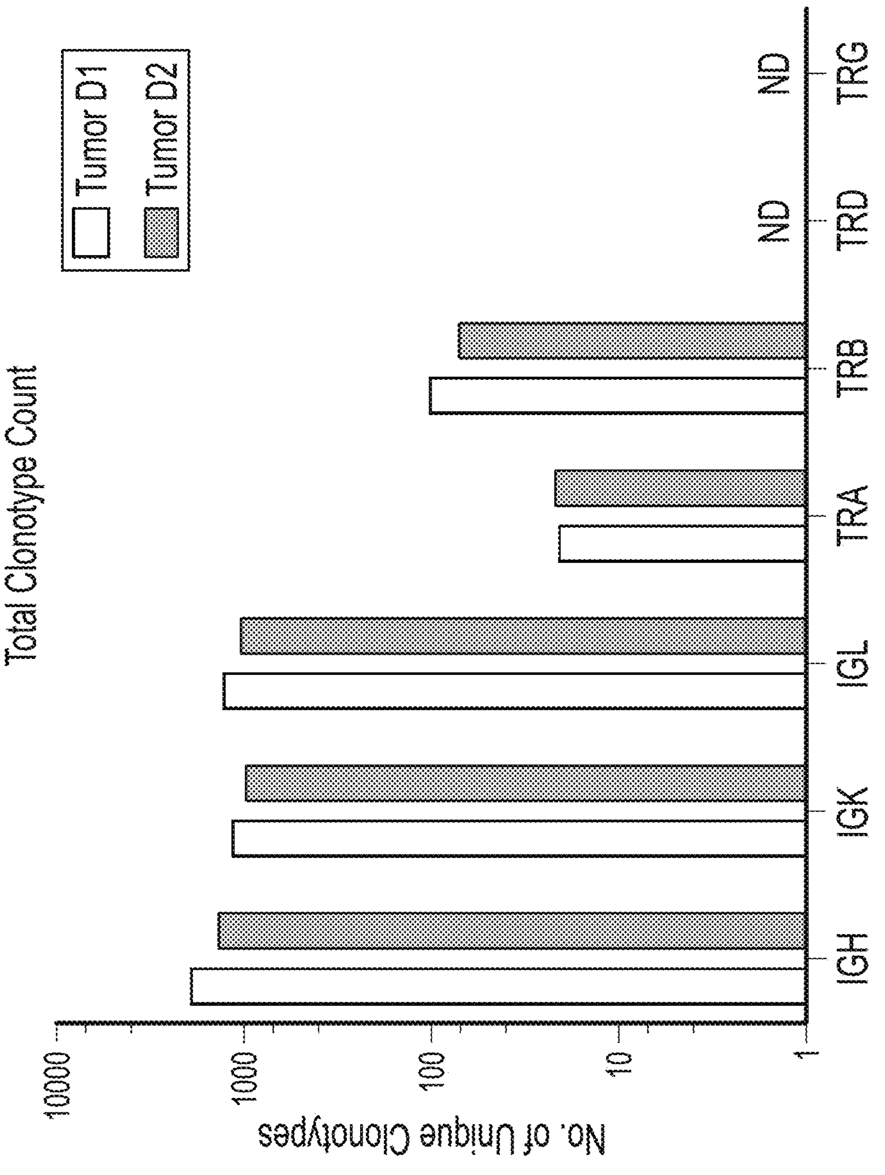
FIG. 19B is a graph showing total clonotype count of the replicate breast tumor samples shown in FIG. 19A.
Figure 19C:
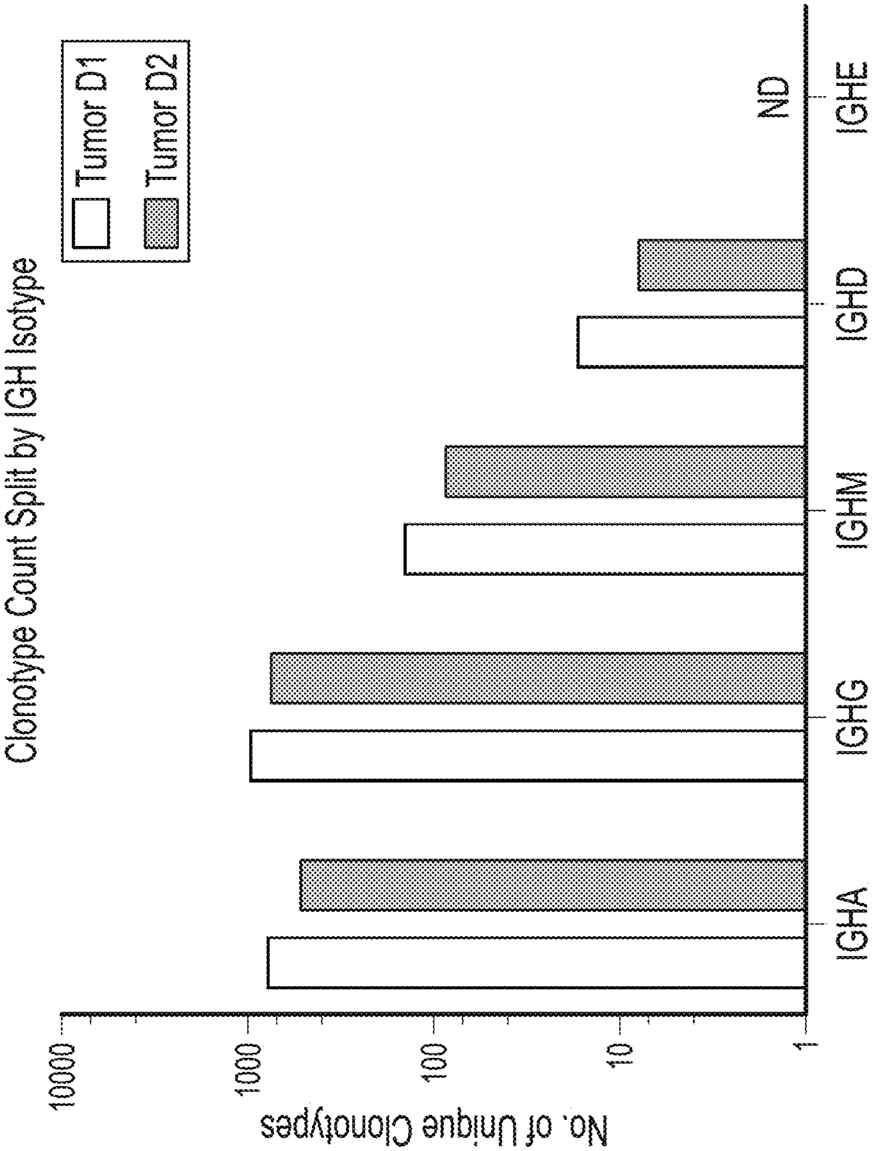
FIG. 19C is a graph showing clonotype count split by IGH isotype of the replicate breast tumor samples shown in FIG. 19A.

Target enrichment strategies as described herein were also tested on breast tumor tissue. Due to the high frequency of tumor cells and stromal cells in breast tumor tissue, it was expected that lymphocyte-associated transcripts would be less abundant, relative to tonsil tissue. Visium libraries were generated from two consecutive sections from breast tumor tissue, isolated from a HER2+ breast tumor patient. FIG. 19A shows the distribution of the clonotype (left) and UMI (right) count for two breast tumor sections. The number of clonotypes per spot ranged between 0 and 300. For each tonsil sample, we identified approximately 10,000 IGH, IGK and IGL clones (BCR) (FIG. 19B). Using the same approach, approximately 1000 IGH, IGK, and IGL clones and between 20-100 TCR clones from each breast tumor section were captured (FIGS. 19B and 19C). Fewer B and T cell clones were expected in the breast tumor samples relative to tonsil tissue, however, there were far fewer T cell clones relative to the B cell clones. Without wishing to be bound by theory, single-cell gene expression and VDJ libraries from the same tumor were prepared and 10-fold more T cells compared to B cell lineage cells (data not shown) were obtained from the single-cell data. Thus, the spatial methods described herein may be more efficient than single-cell approaches in capturing B cell expression and gene expression indicative of plasma, whereas single-cell techniques may be superior in capturing T cells, relative to spatial transcriptomics for antigen receptors.

Figure 20:
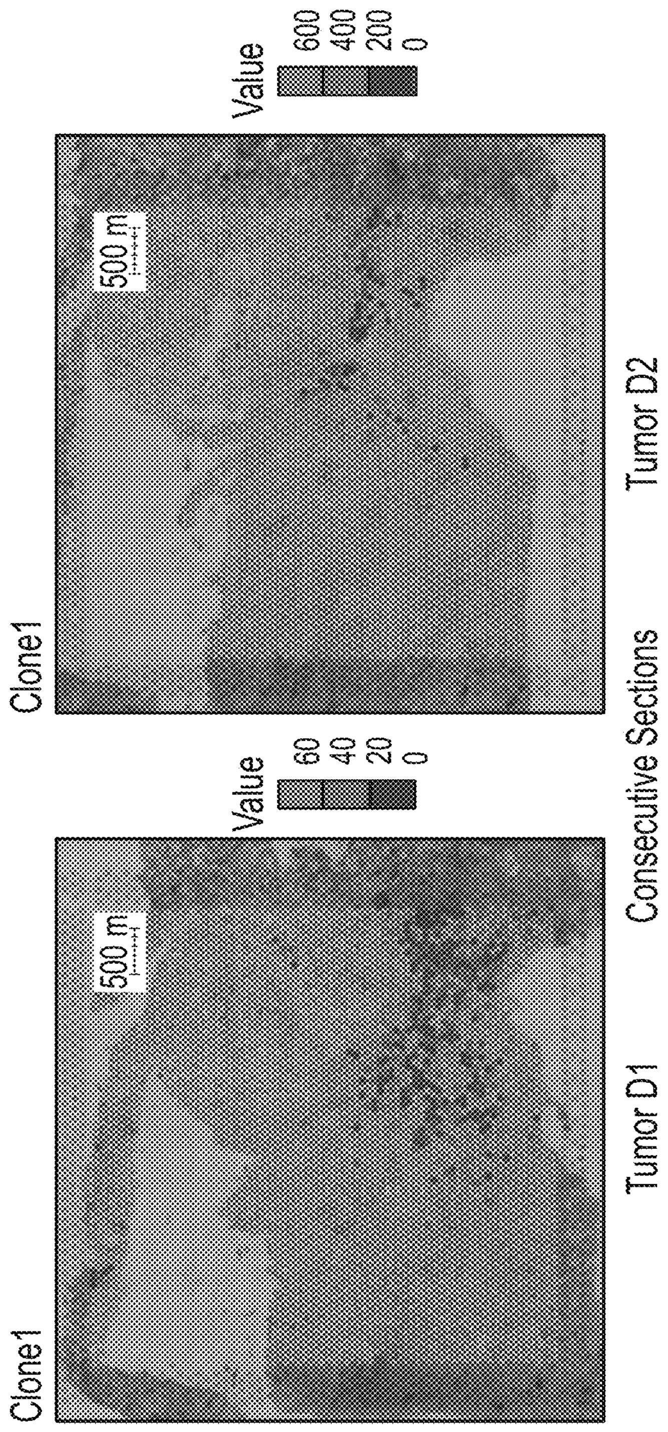
FIG. 20 shows the distribution of a representative IGH clonotypes of the replicate breast tumor samples shown in FIG. 19A.
Figure 21A:
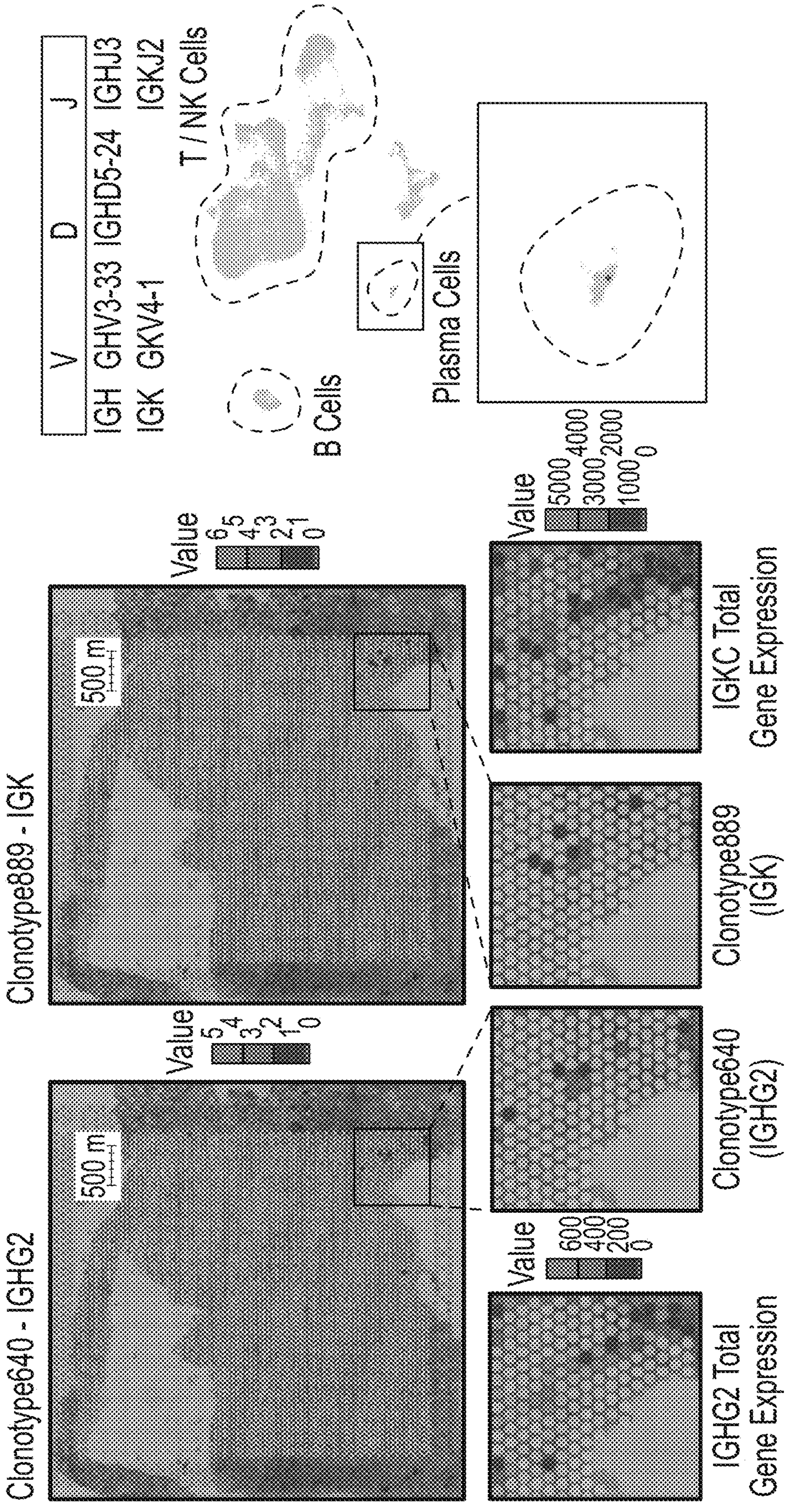
FIG. 21A shows spatial patterning of paired IG receptors (IGHG2 and IGK) (left) in breast tumor tissue and single-cell RNA-seq (right).
Figure 21B:
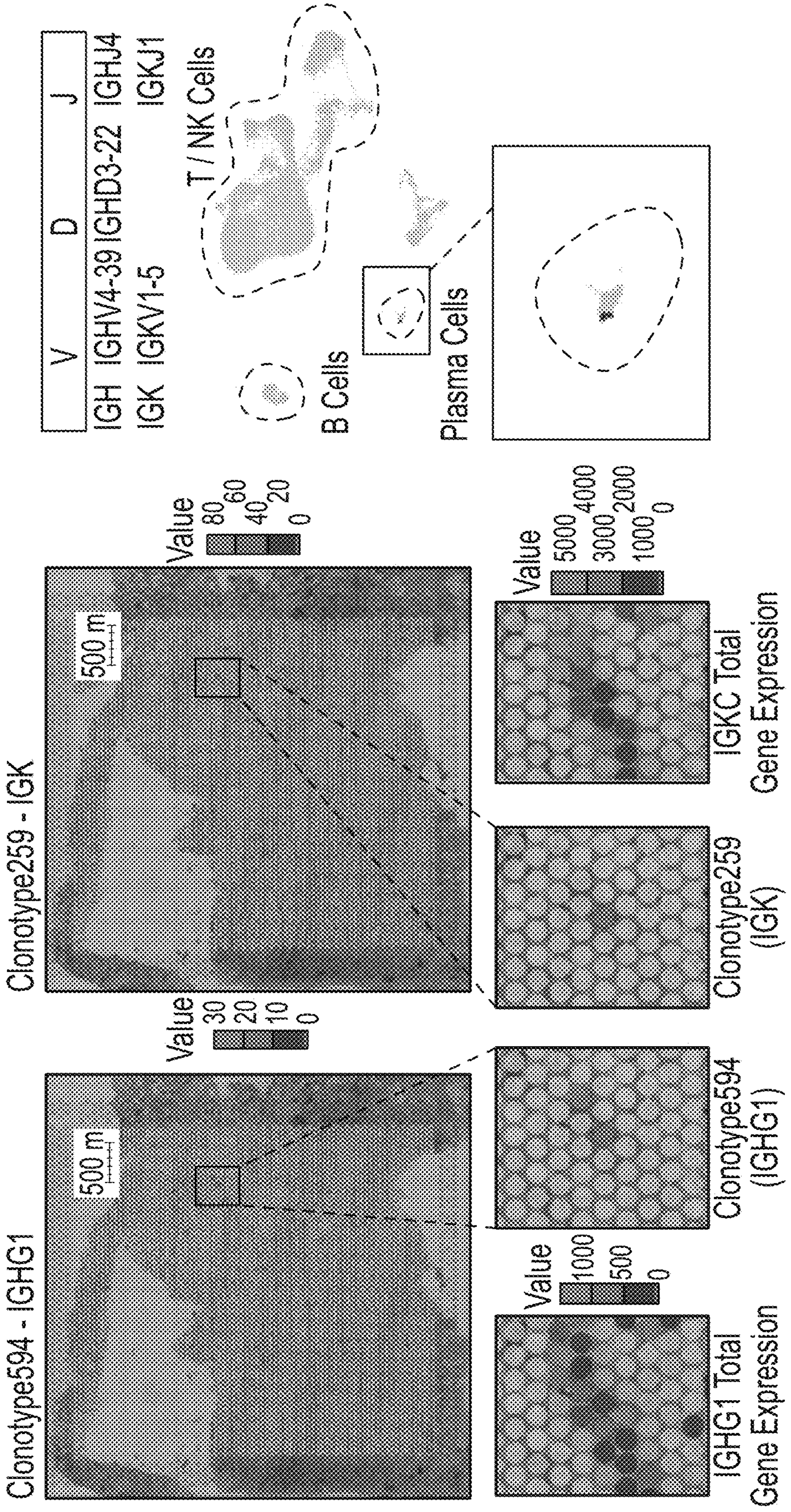
FIG. 21B shows spatial patterning of paired IG receptors (IGHG1 and IGK) (left) in breast tumor tissue and single-cell RNA-seq (right).
Figure 21C:
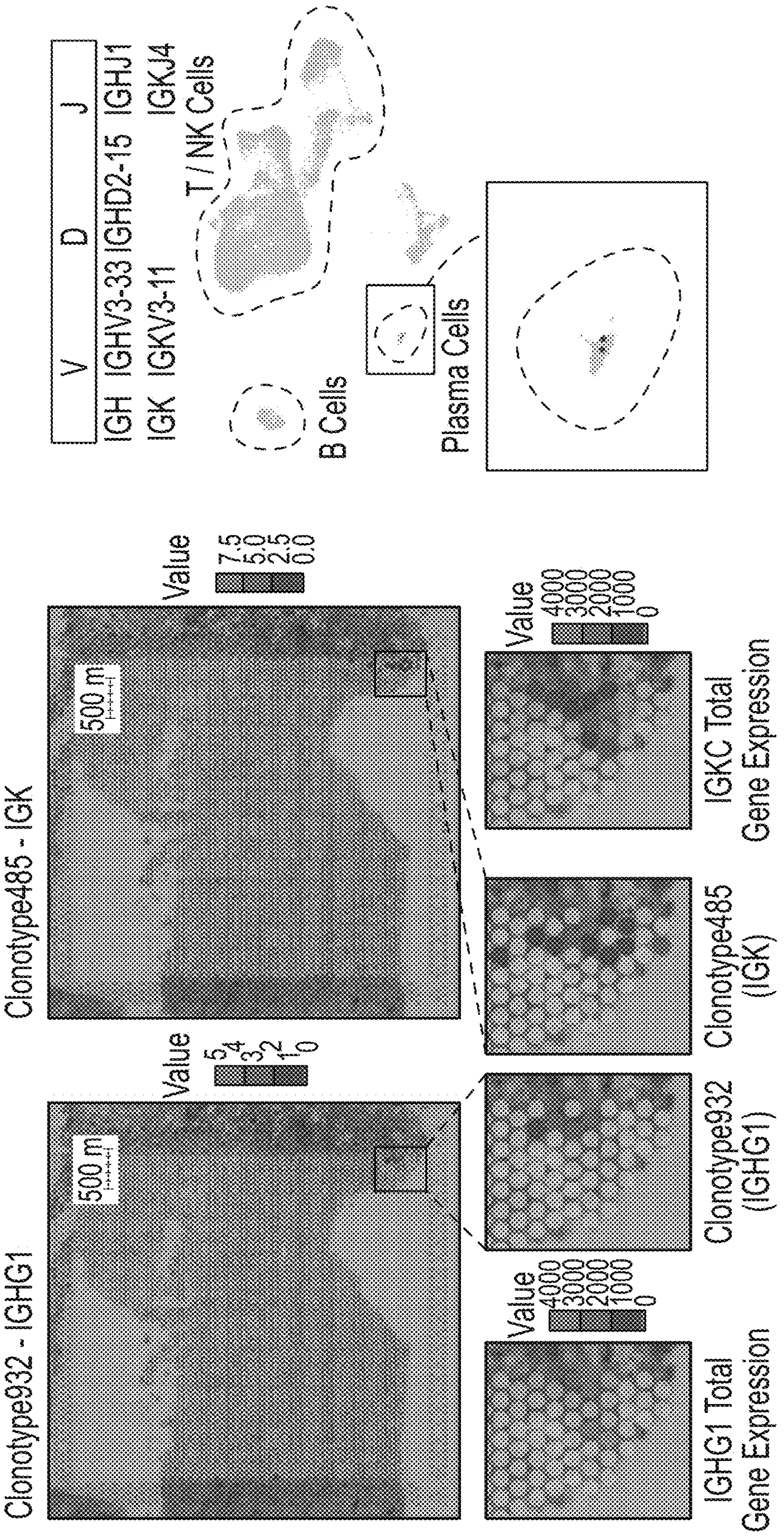
FIG. 21C shows spatial patterning of paired IG receptors (IGHG2 and IGK) (left) in breast tumor tissue and single-cell RNA-seq (right).

Spatial segregation of IGH clones (e.g., IGHV4-28, IGHD3-3, IGHD3-9, IGHJ4, IGHG1/IGHG3) within the breast tumor tissue was found consistent between two adjacent sections (See FIG. 20 for a representative example). Furthermore, since the linked single-cell VDJ data from the same tumor sample was available, detection of paired clones in the spatial clonotype data was also performed. While the single-cell data was processed from a much larger tissue section relative to the 10 μM tissue section used for spatial transcriptomic analysis, it was expected that large clones would be represented in both samples. By comparing the spatial transcriptomics for antigen receptor clonotype lists with the single-cell VDJ data, a total of 6 sets of paired BCR receptors were found in both datasets. The spatial gene expression of three such pairs are shown in FIGS. 21A-C. The similar spatial distribution for both chains for each clone and the concordance with the total respective IGH constant gene expression is demonstrated. For TCR clones, only two sets of paired receptors were found, with sparse UMI count (data not shown). The data show detection of paired receptors using spatial transcriptomics for antigen receptors and that these paired receptors are expressed in a spatially concordant manner.

Target Enrichment for TCR Using Semi-Nested PCR

Figure 22:
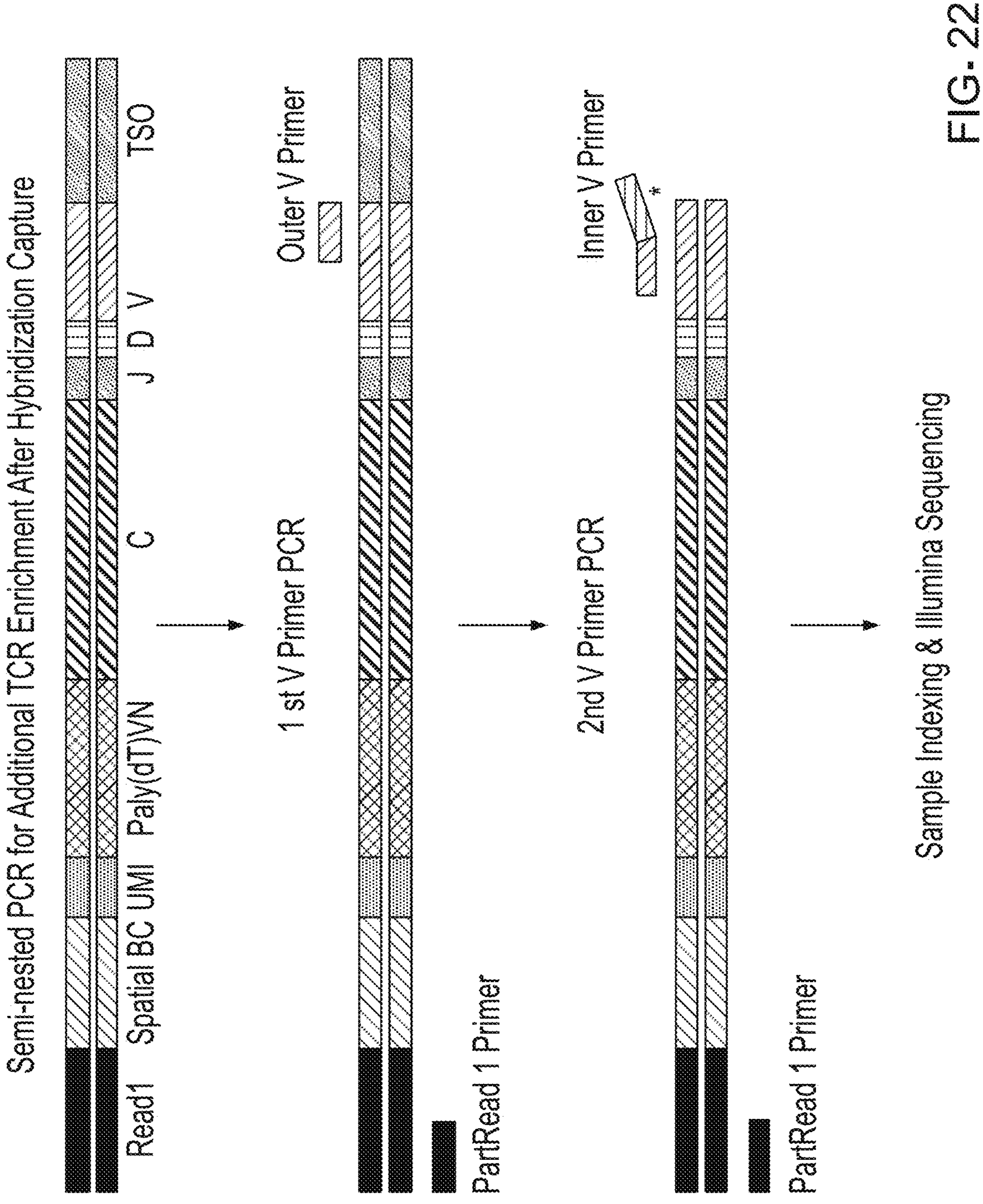
FIG. 22 shows an exemplary nested PCR strategy for additional TCR enrichment.

As described above, the hybridization probe approach was more efficient at capturing BCR clonotypes, most probably due to higher expression on a per cell basis than TCR clonotypes. In order to improve TCR capture, a second target enrichment step was introduced to increase the T cell clonotype yield and to prepare libraries compatible with ILLUMINA® (sequencing technology) sequencing. After hybridization probe capture and subsequent PCR amplification, TCR analytes were enriched using a semi-nested PCR approach as shown in FIG. 22. The PCR is a two-step PCR in which two sets of V (e.g., primer to the variable domain region "V") primers (e.g., "Outer" and "Inner") targeting the TRAV and TRBV genes, respectively, were combined with a universal primer targeting the partial Read1 present on transcripts in the Visium cDNA library. The "Outer" primer can be referred to as a second primer and the "Inner" primer can be referred to as a third primer. The outer primers target gene regions further away from the start of the CDR3 (e.g., between about 200-270 bp from the end of the coding V segment), whereas the inner primers target gene segments closer to the CDR3 (between about 20-25 bp from the end of the coding V segment).

The results show amplification of both TRA and TRB transcripts using the semi-nested PCR approach from breast tumor Visium libraries and that these libraries had the expected sizes (data not shown).

Collectively, the data demonstrate that spatial transcriptomics for antigen receptors can isolate high numbers of BCR and TCR clonotypes from tonsil and breast tumor tissue.

These clones segregate in the tissue in characteristic ways concordant with their biology and cell type gene expression patterns.

Embodiments

Embodiment 1 is a method for determining the presence and/or abundance of an immune cell clonotype at a location in a biological sample, the method comprising: (a) contacting a biological sample with an array comprising a plurality of capture probes, wherein a capture probe of the plurality of capture probes comprises (i) a spatial barcode and (ii) a capture domain that specifically binds to a nucleic acid encoding an immune cell receptor of the immune cell clonotype; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Embodiment 2 is the method of embodiment 1, wherein the immune cell clonotype is a T cell clonotype.

Embodiment 3. The method of embodiment 2, wherein the immune cell receptor is a T cell receptor alpha chain.

Embodiment 4 is the method of embodiment 3, wherein the capture domain binds specifically to a nucleic acid sequence encoding a constant region of the T cell receptor alpha chain.

Embodiment 5 is the method of embodiment 3 or 4, wherein step (b) comprises determining a sequence encoding CDR3 of the T cell receptor alpha chain.

Embodiment 6 is the method of embodiment 5, wherein step (b) further comprises determining a sequence encoding one or both of CDR1 and CDR2 of the T cell receptor alpha chain.

Embodiment 7 is the method of embodiment 5, wherein step (b) further comprises determining a sequence encoding a full-length variable domain of the T cell receptor alpha chain.

Embodiment 8 is the method of embodiment 2, wherein the immune cell receptor is a T cell receptor beta chain.

Embodiment 9 is the method of embodiment 8, wherein the capture domain binds specifically to a nucleic acid sequence encoding a constant region of the T cell receptor beta chain.

Embodiment 10 is the method of embodiment 8 or 9, wherein step (b) comprises determining a sequence encoding CDR3 of the T cell receptor beta chain.

Embodiment 11 is the method of embodiment 10, wherein step (b) further comprises determining a sequence encoding one or both of CDR1 and CDR2 of the T cell receptor beta chain.

Embodiment 12 is the method of embodiment 10, wherein step (b) further comprises determining a full-length variable domain of the T cell receptor beta chain.

Embodiment 13 is the method of embodiment 1, wherein the immune cell clonotype is a B cell clonotype.

Embodiment 14 is the method of embodiment 13, wherein the immune cell receptor is an immunoglobulin kappa light chain.

Embodiment 15 is the method of embodiment 14, wherein the capture domain binds specifically to a nucleic acid sequence encoding a constant region of the immunoglobulin kappa light chain.

Embodiment 16 is the method of embodiment 14 or 15, wherein step (b) comprises determining a sequence encoding CDR3 of the immunoglobulin kappa light chain.

Embodiment 17 is the method of embodiment 16, wherein step (b) further comprises determining a sequence encoding one or both of CDR1 and CDR2 of the immunoglobulin kappa light chain.

Embodiment 18 is the method of embodiment 16, wherein step (b) further comprises determining a sequence encoding a full-length variable domain of the immunoglobulin kappa light chain.

Embodiment 19 is the method of embodiment 13, wherein the immune cell receptor is an immunoglobulin lambda light chain.

Embodiment 20 is the method of embodiment 19, wherein the capture domain binds specifically to a nucleic acid sequence encoding a constant region of the immunoglobulin lambda light chain.

Embodiment 21 is the method of embodiment 19 or 20, wherein step (b) comprises determining a sequence encoding CDR3 of the immunoglobulin lambda light chain.

Embodiment 22 is the method of embodiment 21, wherein step (b) further comprises determining a sequence encoding one or both of CDR1 and CDR2 of the immunoglobulin lambda light chain.

Embodiment 23 is the method of embodiment 21, wherein step (b) further comprises determining a sequence encoding a full-length variable domain of the immunoglobulin lambda light chain.

Embodiment 24 is the method of embodiment 13, wherein the immune cell receptor is an immunoglobulin heavy chain.

Embodiment 25 is the method of embodiment 24, wherein the capture domain binds specifically to a nucleic acid sequence encoding a constant region of the immunoglobulin heavy chain.

Embodiment 26 is the method of embodiment 24 or 25, wherein step (b) comprises determining a sequence encoding CDR3 of the immunoglobulin heavy chain.

Embodiment 27 is the method of embodiment 26, wherein step (b) further comprises determining a sequence encoding one or both of CDR1 and CDR2 of the immunoglobulin heavy chain.

Embodiment 28 is the method of embodiment 26, wherein step (b) further comprises determining a sequence encoding a full-length variable domain of the immunoglobulin heavy chain.

Embodiment 29 is the method of any one of embodiments 1-28, wherein step (b) comprises the capture probe using the nucleic acid encoding the immune cell receptor as a template, thereby generating an extended capture probe.

Embodiment 30 is the method of embodiment 29, wherein step (b) comprises extending a 3' end of the capture probe.

Embodiment 31 is the method of embodiment 29 or 30, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 32 is the method of any one of embodiments 1-31, wherein the capture probe further comprises a cleavage domain, a functional domain, a unique molecular identifier, or any combination thereof.

Embodiment 33 is the method of any one of embodiments 1-30, wherein the capture probe further comprises a functional domain.

Embodiment 34 is the method of embodiment 33, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 35 is the method of embodiment 34, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 36 is the method of any one of embodiments 1-35, wherein the biological sample comprises a tissue sample.

Embodiment 37 is the method of embodiment 36, wherein the tissue sample is a tissue section.

Embodiment 38 is the method of embodiment 37, wherein the tissue section is a fixed tissue section.

Embodiment 39 is the method of embodiment 38, wherein the fixed tissue section is a formalin-fixed paraffin-embedded tissue section.

Embodiment 40 is the method of any one of embodiments 37-39, wherein the tissue section comprises a tumor region.

Embodiment 41 is the method of any one of embodiments 1-40, wherein the nucleic acid encoding the immune cell receptor comprises RNA.

Embodiment 42 is the method of embodiment 41, wherein the RNA is mRNA.

Embodiment 43 is the method of any one of embodiments 1-40, wherein the nucleic acid encoding the immune cell receptor comprises DNA.

Embodiment 44 is the method of embodiment 43, wherein the DNA is genomic DNA.

Embodiment 45 is the method of any one of embodiments 1-44, wherein the method further comprises, prior to step (b), contacting the biological sample with ribosomal RNA depletion probes and mitochondrial RNA depletion probes.

Embodiment 46 is the method of any one of embodiments 1-45, wherein the method further comprises imaging the biological sample.

Embodiment 47 is the method of any one of embodiments 1-46, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 48 is the method of any one of embodiments 1-47, wherein step (b) comprises determining the presence of the immune cell clonotype at a location in the biological sample.

Embodiment 49 is the method of any one of embodiments 1-47, wherein step (b) comprises determining the abundance of the immune cell clonotype at a location in the biological sample.

Embodiment 50 is the method of any one of embodiments 1-47, wherein step (b) comprises determining the presence and abundance of the immune cell clonotype at a location in the biological sample.

Embodiment 51 is the method of any one of embodiments 1-47, wherein step (b) comprises determining the presence of two or more immune cell clonotypes at a location in the biological sample.

Embodiment 52 is the method of any one of embodiments 1-47, wherein step (b) comprises determining the abundance of two or more immune cell clonotypes at a location in the biological sample.

Embodiment 53 is the method of any one of embodiments 1-47, wherein step (b) comprises determining the presence and abundance of two or more immune cell clonotypes at a location in the biological sample.

Embodiment 54 is the method of any one of embodiments 51-53, wherein the method further comprises comparing the two or more immune cell clonotypes.

Embodiment 55 is the method of any one of embodiments 51-54, wherein the two or more immune cell clonotypes are each a B cell clonotype.

Embodiment 56 is the method of any one of embodiments 51-54, wherein the two or more immune cell clonotypes are each a T cell clonotype.

Embodiment 57 is the method of any one of embodiments 51-54, wherein the two or more immune cell clonotypes comprise at least one T cell clonotype and at least one B cell clonotype.

Embodiment 58 is a method for determining the presence and/or abundance of an immune cell receptor at a location in a biological sample, the method comprising: (a) contacting a biological sample with an array comprising a plurality of capture probes, wherein a capture probe of the plurality of capture probes comprises (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

Embodiment 59 is the method of embodiment 58, wherein the immune cell receptor is a T cell receptor alpha chain.

Embodiment 60 is the method of embodiment 59, wherein the capture domain binds specifically to a nucleic acid sequence encoding a constant region of the T cell receptor alpha chain.

Embodiment 61 is the method of embodiment 59 or 60, wherein step (b) comprises determining a sequence encoding CDR3 of the T cell receptor alpha chain.

Embodiment 62 is the method of embodiment 61, wherein step (b) further comprises determining a sequence encoding one or both of CDR1 and CDR2 of the T cell receptor alpha chain.

Embodiment 63 is the method of embodiment 61, wherein step (b) further comprises determining a sequence encoding a full-length variable domain of the T cell receptor alpha chain.

Embodiment 64 is the method of embodiment 58, wherein the immune cell receptor is a T cell receptor beta chain.

Embodiment 65 is the method of embodiment 64, wherein the capture domain binds specifically to a nucleic acid sequence encoding a constant region of the T cell receptor beta chain.

Embodiment 66 is the method of embodiment 64 or 65, wherein step (b) comprises determining a sequence encoding CDR3 of the T cell receptor beta chain.

Embodiment 67 is the method of embodiment 66, wherein step (b) further comprises determining a sequence encoding one or both of CDR1 and CDR2 of the T cell receptor beta chain.

Embodiment 68 is the method of embodiment 66, wherein step (b) further comprises determining a full-length variable domain of the T cell receptor beta chain.

Embodiment 69 is the method of embodiment 58, wherein the immune cell receptor is an immunoglobulin kappa light chain.

Embodiment 70 is the method of embodiment 69, wherein the capture domain binds specifically to a nucleic acid sequence encoding a constant region of the immunoglobulin kappa light chain.

Embodiment 71 is the method of embodiment 69 or 70, wherein step (b) comprises determining a sequence encoding CDR3 of the immunoglobulin kappa light chain.

Embodiment 72 is the method of embodiment 71, wherein step (b) further comprises determining a sequence encoding one or both of CDR1 and CDR2 of the immunoglobulin kappa light chain.

Embodiment 73 is the method of embodiment 71, wherein step (b) further comprises determining a sequence encoding a full-length variable domain of the immunoglobulin kappa light chain.

Embodiment 74 is the method of embodiment 58, wherein the immune cell receptor is an immunoglobulin lambda light chain.

Embodiment 75 is the method of embodiment 74, wherein the capture domain binds specifically to a nucleic acid sequence encoding a constant region of the immunoglobulin lambda light chain.

Embodiment 76 is the method of embodiment 74 or 75, wherein step (b) comprises determining a sequence encoding CDR3 of the immunoglobulin lambda light chain.

Embodiment 77 is the method of embodiment 76, wherein step (b) further comprises determining a sequence encoding one or both of CDR1 and CDR2 of the immunoglobulin lambda light chain.

Embodiment 78 is the method of embodiment 76, wherein step (b) further comprises determining a sequence encoding a full-length variable domain of the immunoglobulin lambda light chain.

Embodiment 79 is the method of embodiment 58, wherein the immune cell receptor is an immunoglobulin heavy chain.

Embodiment 80 is the method of embodiment 79, wherein the capture domain binds specifically to a nucleic acid sequence encoding a constant region of the immunoglobulin heavy chain.

Embodiment 81 is the method of embodiment 79 or 80, wherein step (b) comprises determining a sequence encoding CDR3 of the immunoglobulin heavy chain.

Embodiment 82 is the method of embodiment 81, wherein step (b) further comprises determining a sequence encoding one or both of CDR1 and CDR2 of the immunoglobulin heavy chain.

Embodiment 83 is the method of embodiment 81, wherein step (b) further comprises determining a sequence encoding a full-length variable domain of the immunoglobulin heavy chain.

Embodiment 84 is the method of any one of embodiments 58-83, wherein step (b) comprises extending an end of the capture probe using the nucleic acid encoding the immune cell receptor as a template, thereby generating an extended capture probe.

Embodiment 85 is the method of embodiment 84, wherein step (b) comprises extending a 3' end of the capture probe.

Embodiment 86 is the method of embodiment 84 or 85, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 87 is the method of any one of embodiments 58-86, where the capture probe further comprises a cleavage domain, a functional domain, a unique molecular identifier, or any combination thereof.

Embodiment 88 is the method of any one of embodiments 58-85, wherein the capture probe further comprises a functional domain.

Embodiment 89 is the method of embodiment 88, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 90 is the method of embodiment 89, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 91 is the method of any one of embodiments 58-90, wherein the biological sample comprises a tissue sample.

Embodiment 92 is the method of embodiment 91, wherein the tissue sample is a tissue section.

Embodiment 93 is the method of embodiment 92, wherein the tissue section is a fixed tissue section.

Embodiment 94 is the method of embodiment 93, wherein the fixed tissue section is a formalin-fixed paraffin-embedded tissue section.

Embodiment 95 is the method of any one of embodiments 92-94, wherein the tissue section comprises a tumor region.

Embodiment 96 is the method of any one of embodiments 58-95, wherein the nucleic acid encoding the immune cell receptor comprises RNA.

Embodiment 97 is the method of embodiment 96, wherein the RNA is mRNA.

Embodiment 98 is the method of any one of embodiments 58-95, wherein the nucleic acid encoding the immune cell receptor comprises DNA.

Embodiment 99 is the method of embodiment 98, wherein the DNA is genomic DNA.

Embodiment 100 is the method of any one of embodiments 58-99, wherein the method further comprises, prior to step (b), contacting the biological sample with ribosomal RNA depletion probes and mitochondrial RNA depletion probes.

Embodiment 101 is the method of any one of embodiments 58-100, wherein the method further comprises imaging the biological sample.

Embodiment 102 is the method of any one of embodiments 58-101, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 103 is the method of any one of embodiments 58-102, wherein step (b) comprises determining the presence of the immune cell receptor at a location in the biological sample.

Embodiment 104 is the method of any one of embodiments 58-102, wherein step (b) comprises determining the abundance of the immune cell receptor at a location in the biological sample.

Embodiment 105 is the method of any one of embodiments 58-102, wherein step (b) comprises determining the presence and abundance of the immune cell receptor at a location in the biological sample.

Embodiment 106 is the method of any one of embodiments 58-102, wherein step (b) comprises determining the presence of two or more immune cell receptors at a location in the biological sample.

Embodiment 107 is the method of any one of embodiments 58-102, wherein step (b) comprises determining the abundance of two or more immune cell receptors at a location in the biological sample.

Embodiment 108 is the method of any one of embodiments 58-102, wherein step (b) comprises determining the presence and abundance of two or more immune cell receptors at a location in the biological sample.

Embodiment 109 is the method of any one of embodiments 106-108, wherein the method further comprises comparing the two or more immune cell receptors.

Embodiment 110 is the method of any one of embodiments 106-109, wherein the two or more immune cell clonotypes are each an immune cell receptor of a B cell.

Embodiment 111 is the method of any one of embodiments 106-109, wherein the two or more immune cell clonotypes are each an immune cell receptor of a T cell.

Embodiment 112 is the method of any one of embodiments 106-109, wherein the two or more immune cell clonotypes comprise at least one immune cell receptor of a T cell and at least one immune cell receptor from a B cell.

Embodiment 113 is an array comprising a plurality of capture probes, wherein a capture probe of the plurality of capture probes comprises (i) a spatial barcode and (ii) a capture domain that specifically binds to a nucleic acid encoding an immune cell receptor of an immune cell clonotype.

Embodiment 114 is the array of embodiment 113, wherein the immune cell clonotype is a T cell clonotype.

Embodiment 115 is the array of embodiment 114, wherein the immune cell receptor is a T cell receptor alpha chain.

Embodiment 116 is the array of embodiment 115, wherein the capture domain binds specifically to a nucleic acid sequence encoding a constant region of the T cell receptor alpha chain.

Embodiment 117 is the array of embodiment 114, wherein the immune cell receptor is a T cell receptor beta chain.

Embodiment 118 is the array of embodiment 117, wherein the capture domain binds specifically to a nucleic acid sequence encoding a constant region of the T cell receptor beta chain.

Embodiment 119 is the array of embodiment 113, wherein the immune cell clonotype is a B cell clonotype.

Embodiment 120 is the array of embodiment 119, wherein the immune cell receptor is an immunoglobulin kappa light chain.

Embodiment 121 is the array of embodiment 120, wherein the capture domain binds specifically to a nucleic acid sequence encoding a constant region of the immunoglobulin kappa light chain.

Embodiment 122 is the array of embodiment 119, wherein the immune cell receptor is an immunoglobulin lambda light chain.

Embodiment 123 is the array of embodiment 122, wherein the capture domain binds specifically to a nucleic acid sequence encoding a constant region of the immunoglobulin lambda light chain.

Embodiment 124 is the array of embodiment 119, wherein the immune cell receptor is an immunoglobulin heavy chain.

Embodiment 125 is the array of embodiment 124, wherein the capture domain binds specifically to a nucleic acid sequence encoding a constant region of the immunoglobulin heavy chain.

Embodiment 126 is the array of any one of embodiments 113-125, where the capture probe further comprises a cleavage domain, a functional domain, a unique molecular identifier, or any combination thereof.

Embodiment 127. A kit comprising: an array of any one of embodiments 113-126; and one or both of ribosomal RNA depletion probes and mitochondrial RNA depletion probes.

Embodiment 128 is a method for determining the presence and/or abundance of an immune cell clonotype at a location in a biological sample, the method comprising: (a) contacting a biological sample with an array comprising a plurality of capture probes, wherein a capture probe of the plurality of capture probes comprises (i) a spatial barcode and (ii) a capture domain that binds to a nucleic acid encoding an immune cell receptor of the immune cell clonotype; (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Embodiment 129 is the method of embodiment 1, wherein step (b) comprises extending the capture probe using the nucleic acid encoding the immune cell receptor as a template, thereby generating an extended capture probe.

Embodiment 130 is the method of embodiment 129, wherein step (b) comprises extending a 3' end of the capture probe.

Embodiment 131 is the method of embodiment 129 or 130, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 132 is the method of any one of embodiments 128-131, wherein the capture probe further comprises a cleavage domain, a functional domain, a unique molecular identifier, or any combination thereof.

Embodiment 133 is the method of any one embodiments 128-132, wherein the capture domain comprises a poly(T) sequence.

Embodiment 134 is the method of any one of embodiments 128-133, wherein the capture probe further comprises a functional domain.

Embodiment 135 is the method of embodiment 134, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 136 is the method of embodiment 135, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 137 is the method of any one of embodiments 128-136, wherein the immune cell clonotype is a T cell clonotype.

Embodiment 138 is the method of embodiment 137, wherein the immune cell receptor is a T cell receptor alpha chain.

Embodiment 139 is the method of embodiment 138, wherein step (b) comprises determining a sequence encoding CDR3 of the T cell receptor alpha chain.

Embodiment 140 is the method of embodiment 139, wherein step (b) further comprises determining a sequence encoding one or both of CDR1 and CDR2 of the T cell receptor alpha chain.

Embodiment 141 is the method of embodiment 139, wherein step (b) further comprises determining a sequence encoding a full-length variable domain of the T cell receptor alpha chain.

Embodiment 142 is the method of embodiment 137, wherein the immune cell receptor is a T cell receptor beta chain.

Embodiment 143 is the method of embodiment 142, wherein step (b) comprises determining a sequence encoding CDR3 of the T cell receptor beta chain.

Embodiment 144 is the method of embodiment 143, wherein step (b) further comprises determining a sequence encoding one or both of CDR1 and CDR2 of the T cell receptor beta chain.

Embodiment 145 is the method of embodiment 143, wherein step (b) further comprises determining a full-length variable domain of the T cell receptor beta chain.

Embodiment 146 is the method of any one of embodiments 128-136, wherein the immune cell clonotype is a B cell clonotype.

Embodiment 147 is the method of embodiment 146, wherein the immune cell receptor is an immunoglobulin kappa light chain.

Embodiment 148 is the method of embodiment 147, wherein step (b) comprises determining a sequence encoding CDR3 of the immunoglobulin kappa light chain.

Embodiment 149 is the method of embodiment 148, wherein step (b) further comprises determining a sequence encoding one or both of CDR1 and CDR2 of the immunoglobulin kappa light chain.

Embodiment 150 is the method of embodiment 148, wherein step (b) further comprises determining a sequence encoding a full-length variable domain of the immunoglobulin kappa light chain.

Embodiment 151 is the method of embodiment 146, wherein the immune cell receptor is an immunoglobulin lambda light chain.

Embodiment 152 is the method of embodiment 151, wherein step (b) comprises determining a sequence encoding CDR3 of the immunoglobulin lambda light chain.

Embodiment 153 is the method of embodiment 152, wherein step (b) further comprises determining a sequence encoding one or both of CDR1 and CDR2 of the immunoglobulin lambda light chain.

Embodiment 154 is the method of embodiment 152, wherein step (b) further comprises determining a sequence encoding a full-length variable domain of the immunoglobulin lambda light chain.

Embodiment 155 is the method of embodiment 146, wherein the immune cell receptor is an immunoglobulin heavy chain.

Embodiment 156 is the method of embodiment 155, wherein step (b) comprises determining a sequence encoding CDR3 of the immunoglobulin heavy chain.

Embodiment 157 is the method of embodiment 156, wherein step (b) further comprises determining a sequence encoding one or both of CDR1 and CDR2 of the immunoglobulin heavy chain.

Embodiment 158 is the method of embodiment 156, wherein step (b) further comprises determining a sequence encoding a full-length variable domain of the immunoglobulin heavy chain.

Embodiment 159 is the method of any one of embodiments 128-158, wherein the biological sample comprises a tissue sample.

Embodiment 160 is the method of embodiment 159, wherein the tissue sample is a tissue section.

Embodiment 161 is the method of embodiment 160, wherein the tissue section is a fixed tissue section.

Embodiment 162 is the method of embodiment 161, wherein the fixed tissue section is a formalin-fixed paraffin-embedded tissue section.

Embodiment 163 is the method of any one of embodiments 160-162, wherein the tissue section comprises a tumor region.

Embodiment 164 is the method of any one of embodiments 128-163, wherein the nucleic acid encoding the immune cell receptor comprises RNA.

Embodiment 165 is the method of embodiment 164, wherein the RNA is mRNA.

Embodiment 166 is the method of any one of embodiments 128-163, wherein the nucleic acid encoding the immune cell receptor comprises DNA.

Embodiment 167 is the method of embodiment 166, wherein the DNA is genomic DNA.

Embodiment 168 is the method of any one of embodiments 128-167, wherein the method further comprises, prior to step (b), contacting the biological sample with ribosomal RNA depletion probes and mitochondrial RNA depletion probes.

Embodiment 169 is the method of any one of embodiments 128-168, wherein the method further comprises imaging the biological sample.

Embodiment 170 is the method of any one of embodiments 128-169, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 171 is the method of any one of embodiments 128-170, wherein step (b) comprises determining the presence of the immune cell clonotype at a location in the biological sample.

Embodiment 172 is the method of any one of embodiments 128-171, wherein step (b) comprises determining the abundance of the immune cell clonotype at a location in the biological sample.

Embodiment 173 is the method of any one of embodiments 128-172, wherein step (b) comprises determining the presence and abundance of the immune cell clonotype at a location in the biological sample.

Embodiment 174 is the method of any one of embodiments 128-173, wherein step (b) comprises determining the presence of two or more immune cell clonotypes at a location in the biological sample.

Embodiment 175 is the method of any one of embodiments 128-174, wherein step (b) comprises determining the abundance of two or more immune cell clonotypes at a location in the biological sample.

Embodiment 176 is the method of any one of embodiments 128-174, wherein step (b) comprises determining the presence and abundance of two or more immune cell clonotypes at a location in the biological sample.

Embodiment 177 is the method of any one of embodiments 174-176, wherein the method further comprises comparing the two or more immune cell clonotypes.

Embodiment 178 is the method of any one of embodiments 174-177, wherein the two or more immune cell clonotypes are each a B cell clonotype.

Embodiment 179 is the method of any one of embodiments 174-177, wherein the two or more immune cell clonotypes are each a T cell clonotype.

Embodiment 180 is the method of any one of embodiments 174-177, wherein the two or more immune cell clonotypes comprise at least one T cell clonotype and at least one B cell clonotype.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition section headings, the materials, methods, and examples are illustrative only and not intended to be limiting.

What is claimed is:

1. A method for determining a location of an immune cell receptor in a biological sample, the method comprising:

(a) contacting the biological sample with an array comprising a plurality of capture probes, wherein a capture probe of the plurality of capture probes comprises: (i) a spatial barcode and (ii) a capture domain that hybridizes to a nucleic acid encoding the immune cell receptor;

(b) hybridizing the capture domain of the capture probe to the nucleic acid encoding the immune cell receptor;

(c) extending the capture probe using the nucleic acid encoding the immune cell receptor as a template, thereby generating an extended capture probe;

(d) hybridizing one or more enrichment probes to the extended capture probe, or a complement thereof, in a portion encoding a constant region of the immune cell receptor;

(e) enriching the extended capture probe, or the complement thereof, via the one or more enrichment probes, thereby generating an enriched extended capture probe, or a complement thereof; and (f) determining (i) the sequence of the spatial barcode or a complement thereof, and (ii) all or a portion of the sequence of the enriched extended capture probe or a complement thereof, and using the determined sequences of (i) and (ii) to determine the location of the immune cell receptor in the biological sample.

2. The method of claim 1, wherein the one or more enrichment probes comprises a binding moiety capable of binding a capture moiety, wherein the binding moiety comprises biotin and the capture moiety comprises streptavidin, and wherein the enriching is performed via an interaction between the binding moiety in the one or more enrichment probes and the capture moiety.

3. The method of claim 1, wherein the immune cell receptor comprises a T cell receptor alpha chain and the one or more enrichment probes hybridizes to a nucleic acid sequence encoding a constant region of the T cell receptor alpha chain, or a complement thereof.

4. The method of claim 3, wherein step (f) comprises determining a sequence encoding one or more of CDR1, CDR2, and CDR3 of the T cell receptor alpha chain, and optionally, determining a sequence encoding a full-length variable domain of the T cell receptor alpha chain.

5. The method of claim 1, wherein the immune cell receptor comprises a T cell receptor beta chain and the one or more enrichment probes hybridizes to a nucleic acid sequence encoding a constant region of the T cell receptor beta chain, or a complement thereof.

6. The method of claim 5, wherein step (f) comprises determining a sequence encoding one or more of CDR1, CDR2, and CDR3 of the T cell receptor beta chain, and optionally, determining a sequence encoding a full-length variable domain of the T cell receptor beta chain.

7. The method of claim 1, wherein the immune cell receptor comprises a B cell receptor kappa light chain, and the one or more enrichment probes hybridizes to a nucleic acid sequence encoding a constant region of the B cell receptor kappa light chain, or a complement thereof.

8. The method of claim 7, wherein step (f) comprises determining a sequence encoding one or more of CDR1, CDR2, and CDR3 of the B cell receptor kappa light chain, and optionally, determining a sequence encoding a full-length variable domain of the B cell receptor kappa light chain.

9. The method of claim 1, wherein the immune cell receptor comprises a B cell receptor lambda light chain, and the one or more enrichment probes hybridizes to a nucleic acid sequence encoding a constant region of the B cell receptor lambda light chain, or a complement thereof.

10. The method of claim 9, wherein step (f) comprises determining a sequence encoding one or more of CDR1, CDR2, and CDR3 of the B cell receptor lambda light chain, and optionally, determining a sequence encoding a full-length variable domain of the B cell receptor lambda light chain.

11. The method of claim 1, wherein the immune cell receptor comprises a B cell receptor heavy chain, and the one or more enrichment probes hybridizes to a nucleic acid sequence encoding a constant region of the B cell receptor heavy chain, or a complement thereof.

12. The method of claim 11, wherein step (f) comprises determining a sequence encoding one or more of CDR1, CDR2, and CDR3 of the B cell receptor heavy chain, and optionally, determining a sequence encoding a full-length variable domain of the B cell receptor heavy chain.

13. The method of claim 1, wherein the capture domain comprises a poly(T) sequence and/or the capture probe further comprises a cleavage domain, one or more functional domains, a unique molecular identifier, or combinations thereof.

14. The method of claim 1, further comprising generating the complement of the extended capture probe using the extended capture probe as a template, wherein the complement of the extended capture probe comprises: (i) a sequence that is complementary to the spatial barcode, and (ii) a sequence that corresponds to all or a portion of the sequence of the nucleic acid encoding the immune cell receptor.

15. The method of claim 14, wherein the step of generating the complement of the extended capture probe comprises use of a template switch oligonucleotide.

16. The method of claim 1, wherein extending the capture probe comprises reverse transcription.

17. The method of claim 1, wherein step (f) comprises sequencing all or a portion of the enriched extended capture probe, or the complement thereof, to determine (i) the sequence of the spatial barcode, or the complement thereof, and (ii) all or a portion of the sequence of the enriched extended capture probe, or the complement thereof.

18. The method of claim 1, wherein the biological sample is a fresh-frozen tissue section or a fixed tissue section.

19. The method of claim 1, wherein the method further comprises staining and/or imaging the biological sample.

20. The method of claim 1, wherein the capture probe further comprises an adaptor domain and the method further comprises after step (e), performing a polymerase chain reaction using i) a first primer complementary to the adaptor domain of the enriched extended capture probe, and ii) a second primer complementary to the nucleic acid encoding the immune cell receptor in a region 5' to a sequence encoding CDR3 of the immune cell receptor.

21. The method of claim 20, wherein the immune cell receptor is a T cell receptor.

22. A method for determining a location of a T cell receptor in a biological sample, the method comprising:

(a) contacting the biological sample with an array comprising a plurality of capture probes, wherein a capture probe of the plurality of capture probes comprises: (i) an adaptor domain, (ii) a spatial barcode, and (iii) a capture domain that hybridizes to a nucleic acid encoding the T cell receptor;

(b) hybridizing the capture domain of the capture probe to the nucleic acid encoding the T cell receptor;

(c) extending the capture probe using the nucleic acid encoding the T cell receptor as a template, thereby generating an extended capture probe;

(d) performing an enrichment polymerase chain reaction using i) the extended capture probe, or a complement thereof, as a template; ii) a first primer complementary to the adaptor domain of the capture probe; and iii) a second primer complementary to the nucleic acid encoding the T cell receptor in a region encoding a variable region of the T cell receptor, thereby generating an enriched extended capture probe or a complement thereof; and (e) determining (i) the sequence of the spatial barcode or a complement thereof, and (ii) all or a portion of the sequence of the enriched extended capture probe or a complement thereof, and using the determined sequences of (i) and (ii) to determine the location of the T cell receptor in the biological sample.

23. The method of claim 22, wherein the second primer is complementary to a sequence 5' to a sequence encoding CDR3 of the T cell receptor.

24. The method of claim 22, further comprising generating the complement of the extended capture probe using the extended capture probe as a template, wherein the complement of the extended capture probe comprises: (i) a sequence that is complementary to the spatial barcode, and (ii) a sequence that corresponds to all or a portion of the sequence of the nucleic acid encoding the T cell receptor.

25. The method of claim 24, wherein generating the complement of the extended capture probe comprises use of a template switch oligonucleotide.

26. The method of claim 22, wherein the nucleic acid encoding the T cell receptor comprises mRNA and extending the capture probe comprises reverse transcription.

27. The method of claim 22, wherein the determining in step (e) comprises sequencing the enriched extended capture probe or the complement thereof.

28. The method of claim 22, wherein the capture domain comprises a poly(T) sequence.

29. The method of claim 22, wherein the biological sample is a fresh-frozen tissue section or a fixed tissue section.

30. The method of claim 22, wherein the method further comprises staining and/or imaging the biological sample.

* * * * *